United States Patent
Cook et al.

(10) Patent No.: US 11,981,885 B2
(45) Date of Patent: May 14, 2024

(54) SYSTEM, DEVICE AND METHOD FOR PRODUCTION OF BIOPRODUCT INCLUDING HIGH DENSITY CELL RESPIRATOR (HDCR) FOR INTENSIFIED PRODUCTION OF ADENO-ASSOCIATED VIRUSES (AAV) AND CELL-BASED PRODUCTION

(71) Applicants: City of Hope, Duarte, CA (US); California Institute of Technology, Pasadena, CA (US)

(72) Inventors: Colin Andrew Cook, Pasadena, CA (US); Yuman Fong, La Canada, CA (US); Yu-Chong Tai, Pasadena, CA (US); Saswati Chatterjee, Altadena, CA (US)

(73) Assignee: City of Hope, Duarte, CA (US)

( * ) Notice: Subject to any disclaimer, the term of this patent is extended or adjusted under 35 U.S.C. 154(b) by 556 days.

(21) Appl. No.: 17/098,259

(22) Filed: Nov. 13, 2020

(65) Prior Publication Data
US 2021/0147779 A1 May 20, 2021

Related U.S. Application Data

(60) Provisional application No. 62/936,308, filed on Nov. 15, 2019.

(51) Int. Cl.
*C12M 1/00* (2006.01)
*C12M 1/04* (2006.01)
(Continued)

(52) U.S. Cl.
CPC ............ *C12M 23/34* (2013.01); *C12M 23/08* (2013.01); *C12M 23/10* (2013.01); *C12M 23/24* (2013.01);
(Continued)

(58) Field of Classification Search
CPC ...... C12M 23/34; C12M 23/08; C12M 23/10; C12M 23/24; C12M 23/38; C12M 23/58; C12M 25/34; C12M 25/04; C12M 29/04
(Continued)

(56) References Cited

U.S. PATENT DOCUMENTS 4,937,196 A   6/1990   Wrasidlo et al.
5,714,384 A   2/1998   Wilson et al.
(Continued)

FOREIGN PATENT DOCUMENTS

EP   2955220 A1   12/2015
EP   3546561 A1   10/2019
(Continued)

OTHER PUBLICATIONS

Kumar et al., Large scale industrialized cell expansion: producing the critical raw material for biofabrication processes (Year: 2015).*
(Continued)

*Primary Examiner* — Michael L Hobbs
*Assistant Examiner* — Lenora A Abel
(74) *Attorney, Agent, or Firm* — Mintz Levin Cohn Ferris Glovsky and Popeo, P.C.

(57) ABSTRACT

A cell cultivation apparatus for cultivating microorganisms and growing cells at high density is provided. The apparatus includes a membrane comprising multiple surface features on a first side of the membrane for cell placement. The surface features comprising one or more compartments within which a cell can be located. The membrane includes a material that is at least partially permeable to gas. A second side of the membrane defines a gas region. The second side of the membrane is separated from the first side of the membrane by the membrane. The apparatus further includes a media region for receiving media. The compartments are configured to at least partially reduce media flow shear
(Continued)

forces on one or more cells in the compartments. The surface features may be ridges, protrusions, fins, wells, and/or posts.

21 Claims, 71 Drawing Sheets

(51) Int. Cl.
    *C12M 1/12*     (2006.01)
    *C12M 1/22*     (2006.01)
    *C12M 1/24*     (2006.01)
    *C12N 5/071*     (2010.01)

(52) U.S. Cl.
    CPC ............ *C12M 23/38* (2013.01); *C12M 23/58* (2013.01); *C12M 25/04* (2013.01); *C12M 25/06* (2013.01); *C12N 5/0602* (2013.01)

(58) Field of Classification Search
    USPC ........................................................ 435/289.1
    See application file for complete search history.

(56) References Cited

U.S. PATENT DOCUMENTS

| | | | |
|---|---|---|---|
| 6,194,191 B1* | 2/2001 | Zhang .................... | C12N 15/86 |
| | | | 435/235.1 |
| 6,759,245 B1 | 7/2004 | Toner et al. | |
| 2005/0106717 A1 | 5/2005 | Wilson et al. | |
| 2011/0250585 A1 | 10/2011 | Ingber et al. | |
| 2014/0212967 A1* | 7/2014 | Das ..................... | C12N 5/0068 |
| | | | 264/494 |
| 2014/0315296 A1 | 10/2014 | Wilson | |
| 2019/0002813 A1 | 1/2019 | Tai et al. | |
| 2020/0172847 A1 | 6/2020 | Turkki | |
| 2022/0389361 A1 | 12/2022 | Cook et al. | |

FOREIGN PATENT DOCUMENTS

| | | |
|---|---|---|
| WO | 01/92462 A1 | 12/2001 |
| WO | WO-2016/069892 A1 | 5/2016 |
| WO | WO-2021/097366 A1 | 5/2021 |

OTHER PUBLICATIONS

Riehl et al., Mechanical Stretching for Tissue Engineering: Two-Dimensional and Three-Dimensional Constructs (Year: 2012).*
Large scale industrialized cell expansion: producing the critical raw material for biofabrication processes (Year: 2015).*
Mechanical Stretching for Tissue Engineering: Two-Dimensional and Three-Dimensional Constructs (Year: 2012).*
International Search Report dated Mar. 16, 2021, for PCT Application No. PCT/US2020/060606, filed Nov. 13, 2020, 6 pages.
Invitation to Pay Additional Fees and, Where Applicable, Protest Fees mailed on Jan. 21, 2021, for PCT Application No. PCT/US2020/060606, filed Nov. 13, 2020, 4 pages.
Kumar, A. et al. (Nov. 2015). "Large Scale Industrialized Cell Expansion: Producing the Critical Raw Material for Biofabrication Processes," *Biofabrication* 7(4): 33 pages.
Written Opinion dated Mar. 16, 2021, for PCT Application No. PCT/US2020/060606, filed Nov. 13, 2020, 7 pages.
Extended European Search Report mailed on Jan. 9, 2024, for EP Patent Application No. 20886989.1, 8 pages.

* cited by examiner

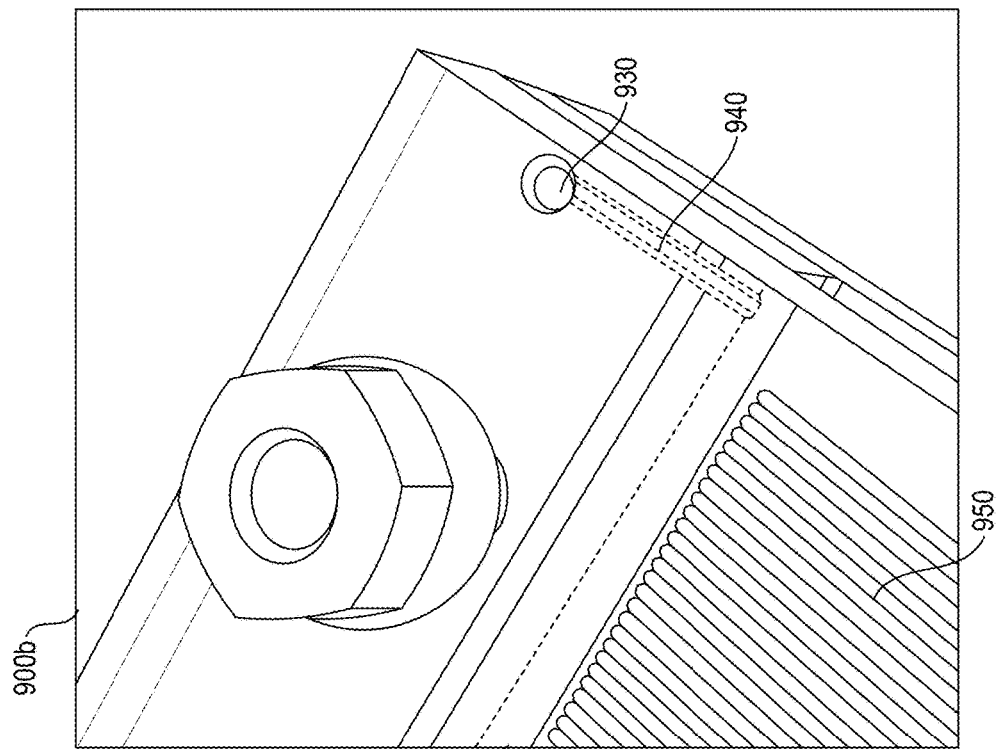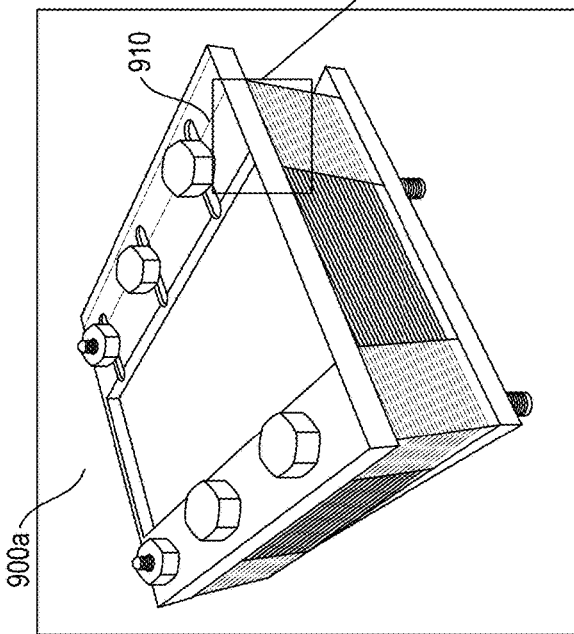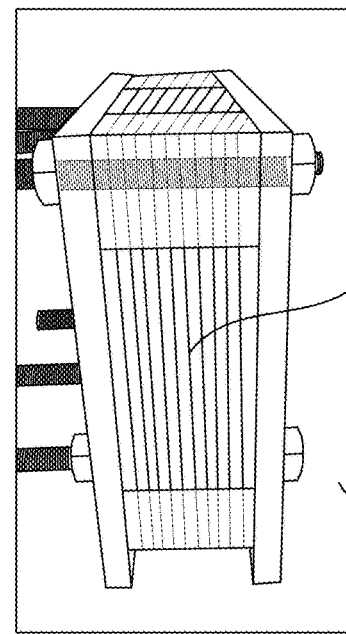

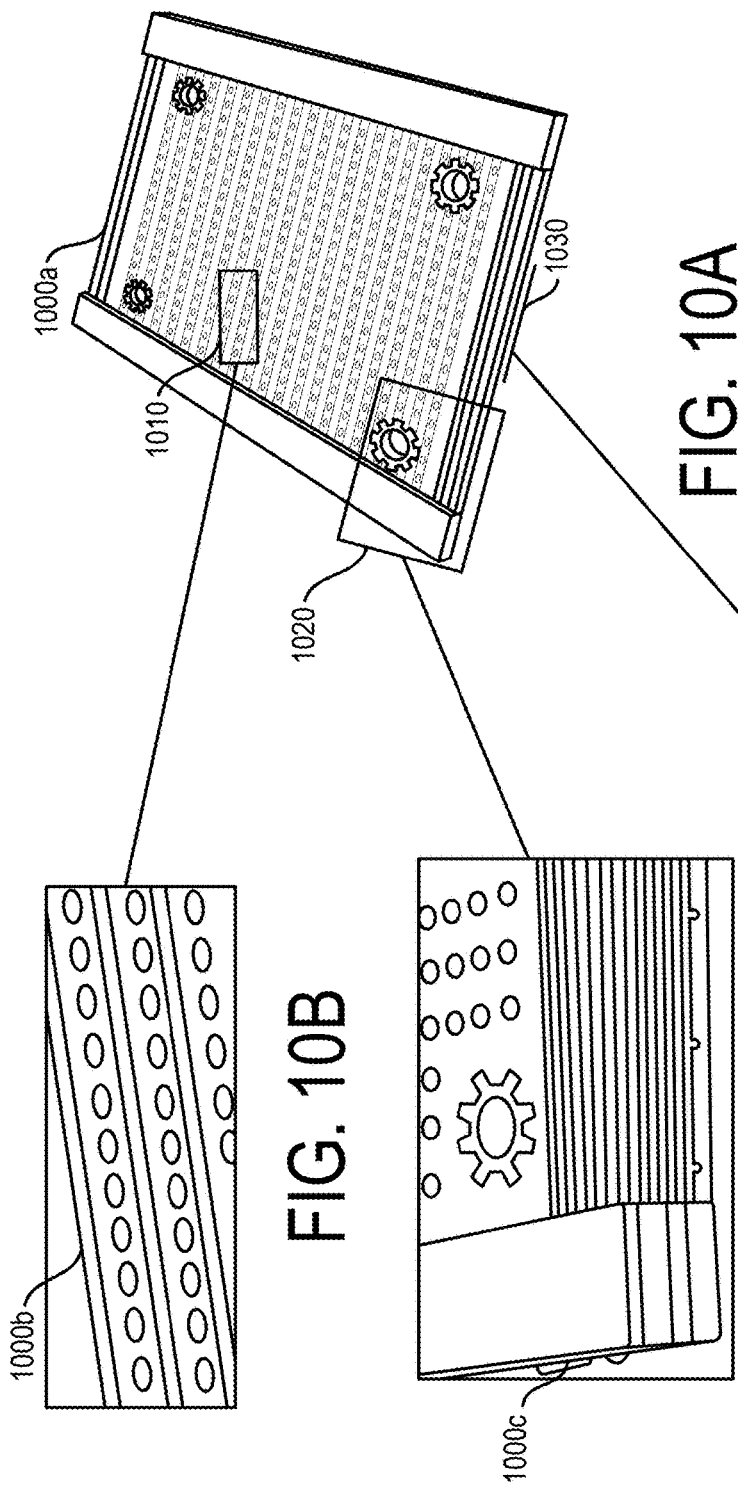
FIG. 10A
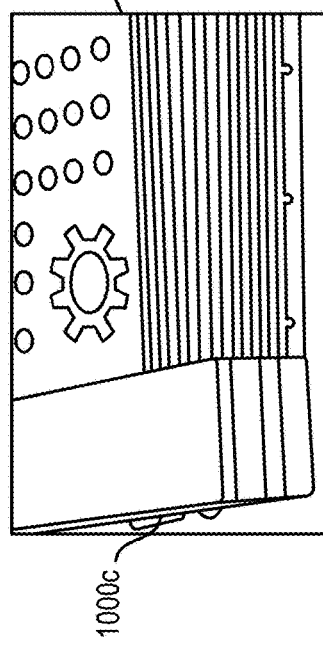
FIG. 10B
FIG. 10C
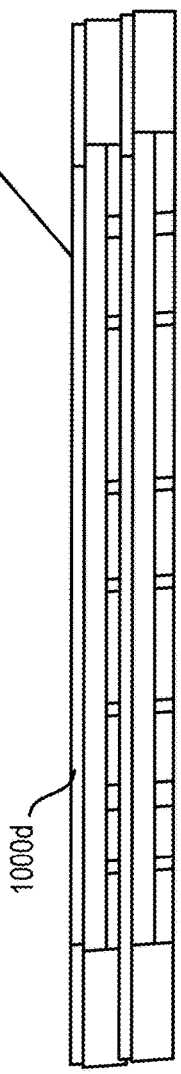
FIG. 10D

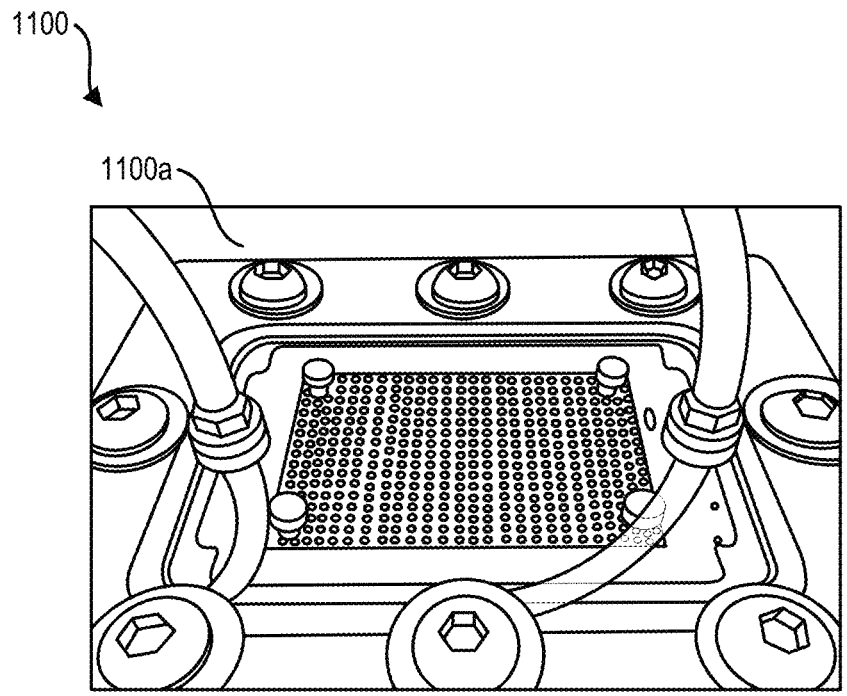
FIG. 11A
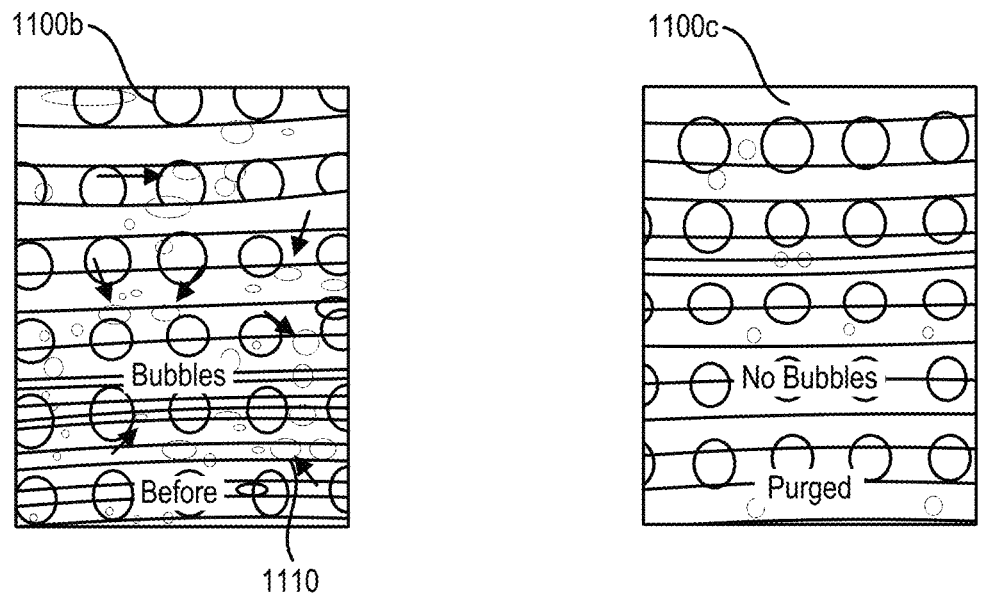
FIG. 11B
FIG. 11C

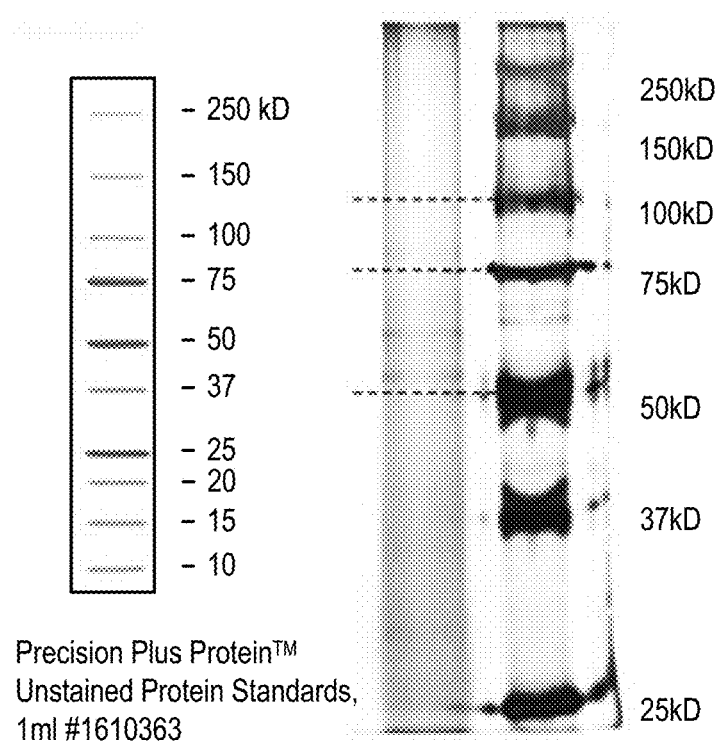
FIG. 37
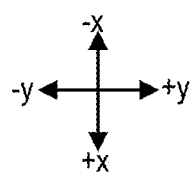
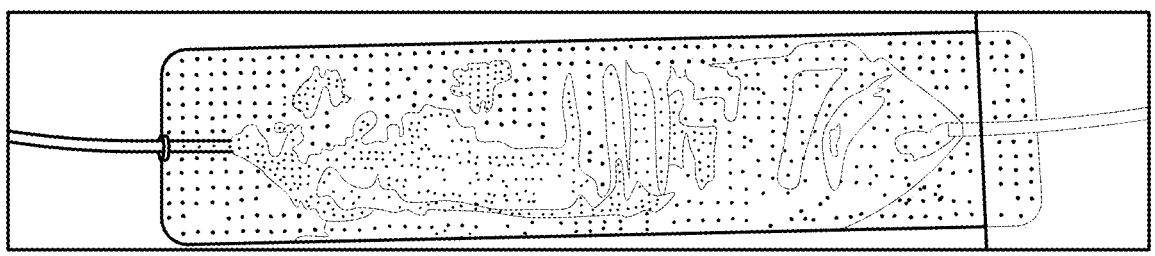
FIG. 38

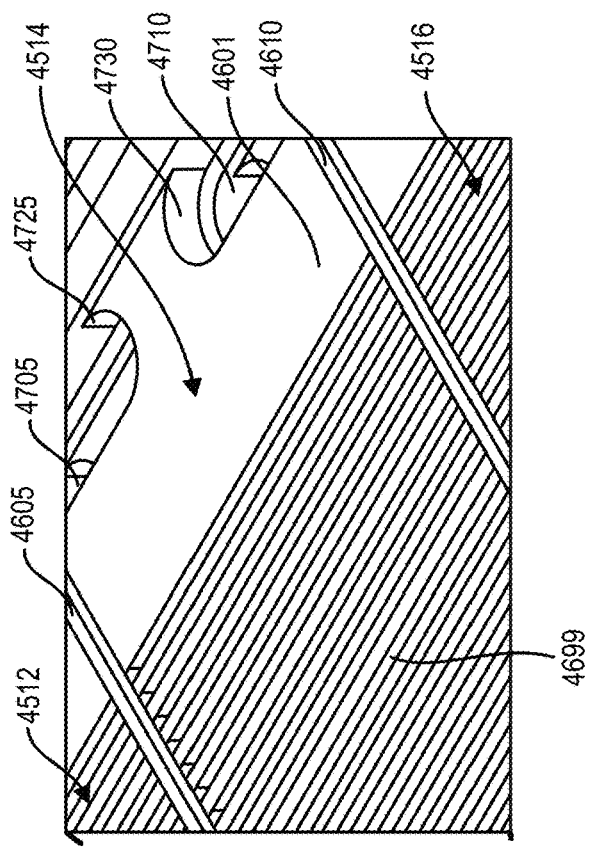
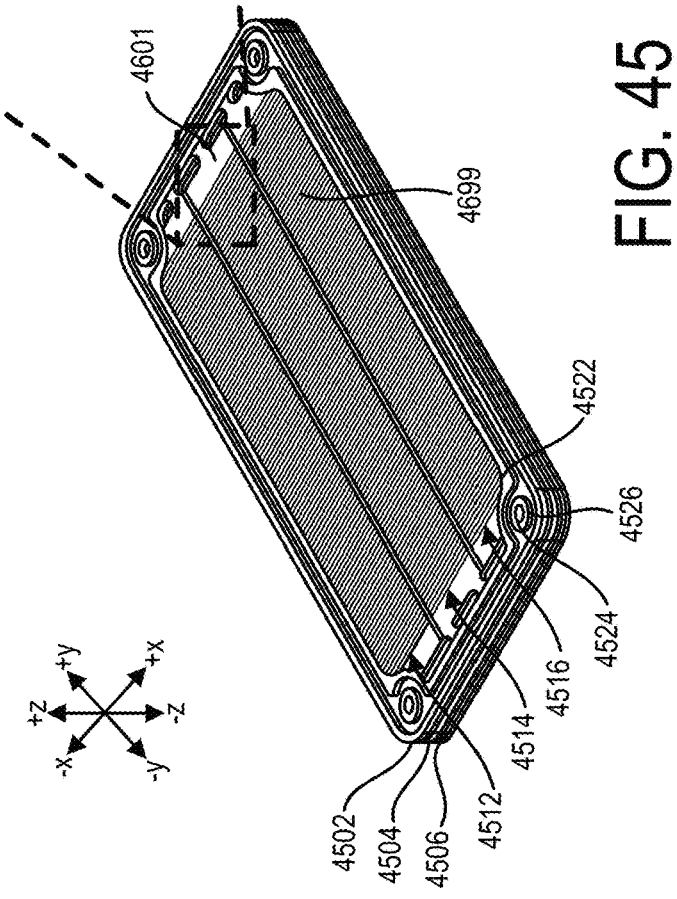
FIG. 46
FIG. 45

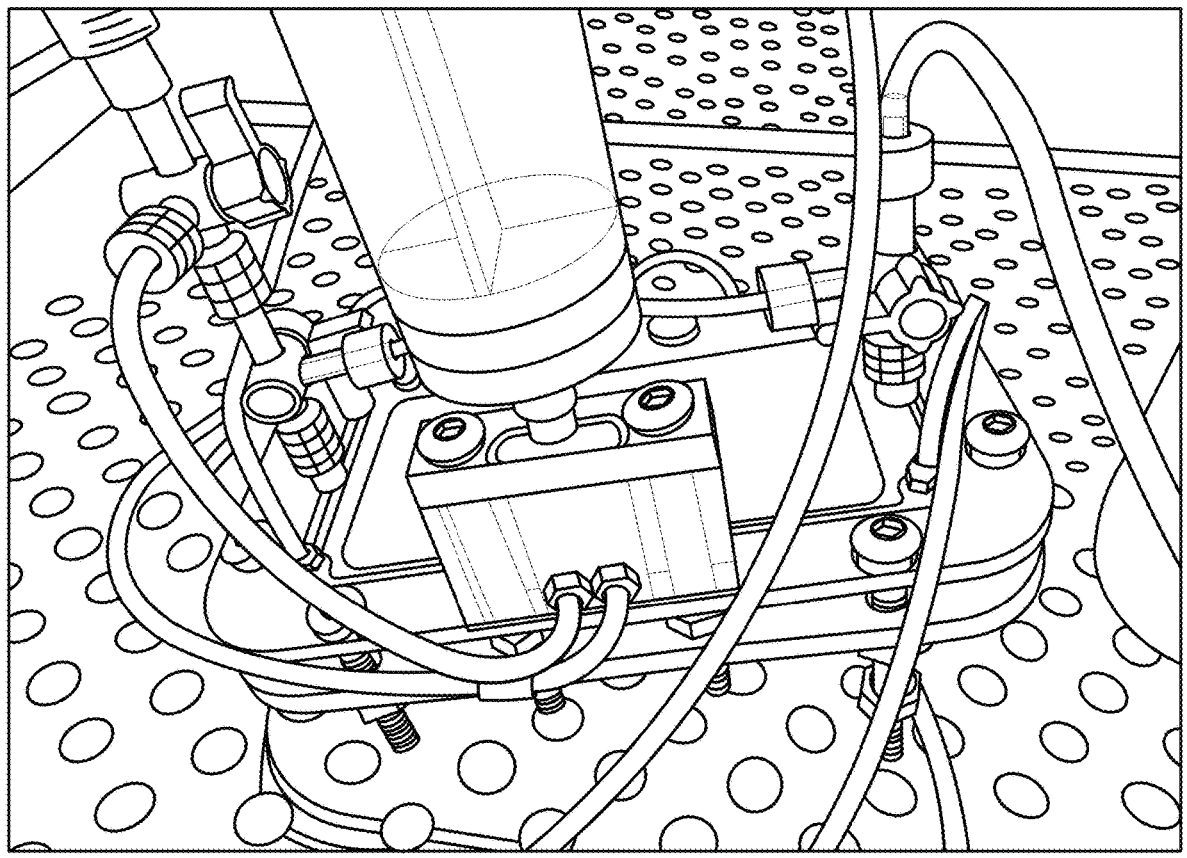
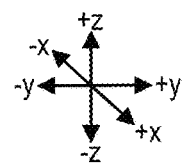
FIG. 56

Aspect Ratio
Membrane Orientation
Cell Expansion Volume
High
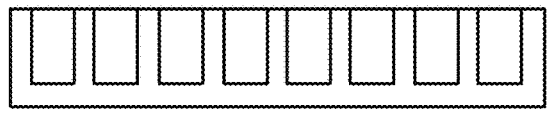
FIG. 68
FIG. 69
Low
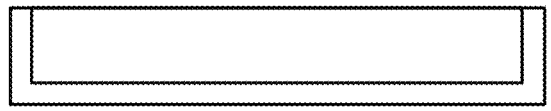
Horizontal
FIG. 70
FIG. 71
High
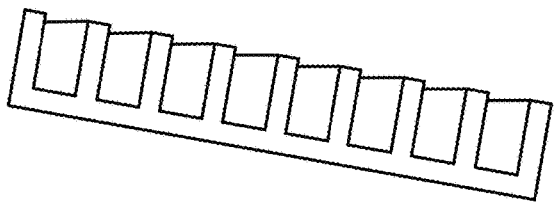
FIG. 72
FIG. 73
Low
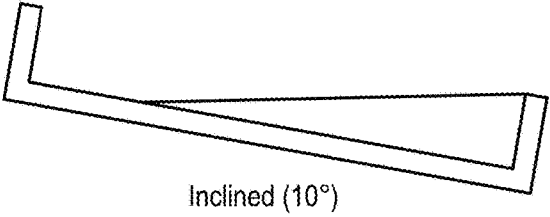
Inclined (10°)
FIG. 74
FIG. 75
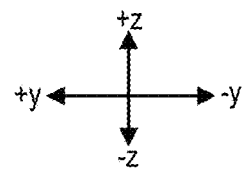

SYSTEM, DEVICE AND METHOD FOR PRODUCTION OF BIOPRODUCT INCLUDING HIGH DENSITY CELL RESPIRATOR (HDCR) FOR INTENSIFIED PRODUCTION OF ADENO-ASSOCIATED VIRUSES (AAV) AND CELL-BASED PRODUCTION

PRIORITY

This application claims the benefit of priority to U.S. Provisional Patent Application No. 62/936,308, entitled "HIGH DENSITY CELL RESPIRATOR FOR PRODUCTION OF BIOPRODUCT", filed on Nov. 15, 2019, which is hereby incorporated by reference herein in its entirety.

FIELD

Embodiments of the disclosed technology generally relate to systems, devices and methods, including a respirator, for producing, cultivating and/or growing bioproduct including microorganisms, tissue and cells. In some exemplary embodiments, the respirator is a high density cell respirator (HDCR). The HDCR may be a bioreactor. The systems, devices and methods of the present disclosure, including the HDCR bioreactor, are effective platforms for intensified production of wide varieties of biomatter including adeno-associated viruses (AAV), oncolytic viruses, and other forms of cell-based production. The HDCR system, device and method brings down the at times prohibitively high cost of goods associated with treatments such as AAV thus making such treatments more widely available to greater numbers of individuals in need without excess cash expenditures.

BACKGROUND

Gene therapy adopted inefficient cell factories and stirred tank reactors (STRs) for scaling up production of bioproduct. However, as has been repeatedly acknowledged in the literature, demands for AAV for systemic therapy vastly exceed the production capability of STRs.

With understanding of the genetic basis of many diseases, the possibility of treatment by gene transfer and gene editing is becoming a clinical reality. Many of these new therapies will depend on viral vectors. Developed cell-based vector production relies on traditional tissue culture technologies whose capacity has plateaued. The high dose of viral particles needed for these applications, combined with the inefficiency of current production methods, results in a staggeringly high cost for these medicines.

Cost and production times are among the largest barriers to clinical investigation of promising approaches at the Phase I and II stages. The high cost is because the quantity of viral vector needed for trials necessitates cell culture at the trillion-cell scale (the $10^{12}$ cell scale). With developed technology, production of sufficient vector for early stage trials may take 9-12 months, and existing manufacturing facilities are already near maximum capacity; the wait time to have vectors produced and into trials is 2-3 years, delaying revolutionary therapies from reaching testing and clinical application.

The high cost and long queues in production are delaying translation of potentially disruptive therapies that may alleviate suffering and preserve life. Some promising approaches may end up being abandoned altogether because of overwhelming financial obstacles.

Even in R&D and preclinical stages, vector development requires cell-culture on the billion-cell scale (the $10^9$ cell scale). Currently, this requires tedious and cumbersome management of dozens of flasks or Petri dishes, occupying valuable operator time and limited incubator space.

A need has arisen for new media-efficient and compact culture systems that can reliably produce viruses to allow many more efforts to be pursued in parallel. Hundreds of candidate viruses are often screened before finding one worth moving forward with, so a need has also arisen for new technologies that facilitate screening and increase laboratory bandwidth, which would accelerate the development of cures for mankind.

Production of vaccines has been a major advance in human public health. Routine vaccination for the most important and common human pathogens has resulted in control of many diseases including influenza, polio, measles, and eradication of some devastating diseases including small pox. Yearly immunization against seasonal and mutable viruses such as influenza requires production of millions of doses of vaccines. The time for production and release of the US flu vaccine supply requires nearly a year. Thus, the viral serotypes most prevalent for the following flu season have to be guessed nearly a year in advance. This is the reason that for some seasons, the vaccine given does not protect against the prevailing strains. Shortening production timelines would allow better determination of the vaccine strain to be produced, and may even permit "last-minute" changes in the event of a new emerging strain. With current technologies, if a pandemic occurs, or worse yet, if a viral bioterror weapon is unleashed, it might take 5-10 years to produce enough doses to vaccinate the world population of more than 7 billion people. Reducing production time by 2-10-fold would save many lives.

Improved understanding of the genetic basis of many diseases make treatment of many diseases by gene transfer and gene editing possible. Development and production of these new treatments depend on trillion-cell scale production of viral vectors and other bioproducts. Existing tissue culture and cultivation technology is inefficient and costly, often resulting in high costs and lengthy delays to produces viral vectors, medicines, vaccines, and other bioproducts.

Cell specific AAV productivity in the literature discuss developed systems, devices and methods only capable of cell density at transfection of about $10^5$-$10^7$ cells/mL with specific productivity of $10^3$-$10^6$ vg/cell.

Embodiments described herein generally relate to improvements in cell and tissue growth production apparatuses and methods. Disclosed herein are systems, devices and methods, which reduce the cost and time of production for viral vectors, facilitating testing and clinical use of promising therapies. Also, the disclosed systems, device and methods achieve significant cost reductions enabling novel therapies and global accessibility. The present systems, devices and methods advance production beyond capabilities of developed technologies including STRs.

SUMMARY

Large and small scale high density cell and tissue culture is important for many biotechnology applications where cells are used to produce specific molecules, proteins, viruses, or other products. Increasing cell density allows for greater production per unit volume, which reduces costs through space savings and more concentrated product.

One challenge of high-density cell growth arises from mass transport limitations particularly with respect to oxygen, nutrients, and waste products. In low-density cell culture systems, passive diffusion of metabolites may be sufficient to meet the metabolic demands of cells; however, in high-density cell culture systems, the metabolic demand of cells exceeds supply from diffusion alone, requiring additional mass transport mechanisms such as convection.

The additional requirement of high-density cell culture is a high surface area to volume ratio, particularly for adherent cell populations. This is because many cells grow in monolayers, and their growth is inhibited once they reach confluence.

Several technologies have been developed to enhance cell density including cell factory systems, wave/stirred bioreactors with microcarriers, and perfused dialysis membrane systems. Numerous disadvantages were determined by the present inventors to be associated with the developed technologies.

Cell factory systems are most similar to conventional flask culture systems except that cell factory systems contain multiple layers of growth substrate within a single flask. The cell density that can be achieved is not very high due to the large spacing between layers, resulting in a low surface-to-volume ratio, and the reliance on diffusive transport for all metabolites.

Wave and stirred bioreactor systems add convection to enhance mass transport by gently mixing cell microcarriers, small neutrally buoyant particles with surface chemistry suitable for cell adhesion and growth, within a container of media. The combination of high surface area afforded by the microcarriers and the convective mixing allows for higher cell densities to be achieved compared to cell factory systems. However, convective mixing causes undesirable shear forces on the cells, which can induce cell death, thereby limiting the degree of mixing and mass transport to cells that can be achieved. Such systems are often shear-limited due to the need to enhance mass transport through mixing rather than surface area limited.

Perfused dialysis membrane systems overcome the shear problem by perfusing gas or oxygenated media through tightly packed semi-permeable dialysis tubes and allowing diffusion to deliver oxygen to cells. However, the geometry of the dialysis tubes prevents very high surface areas to volume ratios from being achieved. Furthermore, there are challenges with cell removal from the highly porous membranes on which the cells grow.

Thus, some challenges of high density cell growth include: 1) achieving high growth surface area to volume ratio; 2) maintaining adequate metabolite transport within the system; and 3) maintaining shear forces experienced by cells below growth inhibiting or lethal levels. While existing technologies have attempted to overcome these challenges, there remains extensive room for improvement of the art. Described herein are various improved system, devices and methods for cell culture, tissue culture and microorganism cultivation.

One feature is a cell cultivation apparatus. The apparatus includes a membrane. The membrane includes surface features on a first side of the membrane. The surface features include one or more compartments within which one or more cells can be confined. The membrane includes a material that is at least partially permeable to gas. A second side of the membrane defines one boundary of a gas region. The membrane is configured so that a gas can pass through the second side of the membrane to the first side of the membrane. The apparatus further includes a media region having one boundary on the first side of the membrane. The media region is configured for passing media over the first side of the membrane. The one or more compartments are configured to at least partially reduce media flow shear forces within the compartments.

Another feature is a petri dish. The petri dish includes a bottom surface and a sidewall that form a dish. The bottom surface includes an at least partially gas permeable material. The bottom surface includes a first side and a second side. The first side includes multiple structures extending from a base of the first side and forms one or more cell niche regions (compartments) below the top surface of the multiple structures. The sidewall is connected to the bottom surface. The sidewall forms a continuous and substantially vertical wall around a perimeter of the bottom surface.

Another feature is a multi-well cell growth device. The device includes multiple wells. The wells include a bottom surface that includes a first side in contact with the interior of the wells and a second side in contact with the exterior of the multi-well cell growth device. The first side includes a topography that provides multiple cell growth compartments. The bottom surface includes a material that is at least partially permeable to a gas. The bottom surface is configured such that a gas from the exterior of the multi-well growth device can pass from the exterior into the interior of the wells and can contact one or more of the multiple cell growth compartments and/or a gas from within the one or more cell growth compartments can pass from the first side to the second side.

Another feature is a cell cultivation apparatus. The apparatus includes a membrane. The membrane includes multiple fin structures running substantially parallel to each other. The substantially parallel fin structures define grooves between adjacent fin structures. At least one groove on a first side of the membrane provides at least a compartment for cell placement. The membrane includes a material that is at least partially permeable to gas. A second side of the membrane defines a gas region. The second side of the membrane is separated from the first side of the membrane by the membrane. A gas is capable of passing through the membrane. A media region on the first side of the membrane is configured for receiving media including one or more cells depositable in the compartment.

Another feature is a cell respirator apparatus. The apparatus includes one or more membranes. At least one membrane from the one or more membranes has a plurality of fins including at least a first fin and a second fin protruding from a first surface of the membrane to form a first compartment of a plurality of compartments configured for retaining a plurality of cells. The membrane is formed of material that is gas-permeable and transmissive to facilitate delivering gas to the plurality of compartments through one or more channels formed under the first surface of the membrane below the fins. At least a first channel of the one or more channels is configured to directly deliver the gas to the first compartment.

Another feature is a method of culturing biological cells. The method includes providing an apparatus according to any of the above features. The method further includes introducing biological cells into the apparatus. The method further includes providing a cell media into the first side of the apparatus such that the cell media is in contact with the biological cells.

A cell cultivation apparatus may include: a membrane, which may include a plurality of surface features on a first side of the membrane, the surface features, which may include one or more compartments within which one or more cells can be confined; the membrane, which may include a material that is at least partially permeable to gas;

a second side of the membrane defining one boundary of a gas region, in which the membrane is configured so that a gas can pass through the second side of the membrane to the first side of the membrane; and a media region having one boundary on the first side of the membrane and configured for passing media over the first side of the membrane, in which the one or more compartments are configured to at least partially reduce media flow shear forces within the compartments.

The apparatus may include one or more media inlets and one or more media outlets fluidically connected to the media region, the one or more media inlets configured to facilitate introduction of media into the media region on the first side of the membrane, the one or more media outlets configured to facilitate removal of media from the media region.

The apparatus, in which at least one of the one or more media inlets is fluidly connected to at least one of the media outlets to facilitate reintroduction of media into the media region on the first side of the membrane.

The apparatus, in which the apparatus is configured to minimize media flow shear forces in the one or more compartments upon introduction or removal of media from the media region.

The apparatus, further, which may include one or more gas inlets and one or more gas outlets in fluid contact with the gas region, the one or more gas inlets configured to introduce a gas into the gas region, and the one or more gas outlets configured for the removal of a gas from the gas region.

The apparatus, which may include one or more channels formed on the second side of the membrane, at least a first channel of the one or more channels configured to deliver gas to the at least one of the compartments via the membrane by way of membrane permeation and diffusion.

The apparatus, which may include an enclosure disposed above the first side of the membrane.

The apparatus, in which the enclosure defines a second boundary of the media region.

The apparatus, in which the apparatus is configured to be stacked with at least a second cell cultivation apparatus.

The apparatus, in which one more of the media or gas inlets or media or gas outlets are configured so that upon stacking, one or more of the media or gas inlets or media or gas outlets are in fluid communication with an inlet or outlet of an immediately adjacent apparatus.

The apparatus, in which one or more of the media or gas inlets is configured so that upon stacking, media or gas introduced into the apparatus is combined into a combined inlet line for transmission to a plurality of the membranes.

The apparatus, in which one or more of the media or gas outlets is configured so that upon stacking, media or gas removed from the apparatus is combined into a combined outlet line for transmission from a plurality of the membranes.

The apparatus, which may include a liquid-tight container for retaining the apparatus.

The apparatus, in which the membrane includes pores having a size permitting permeation and diffusion of oxygen to pass through the membrane.

The apparatus, in which the one or more compartments support tissue-level cell densities such that the volume of cells occupies at least about 10% of the volume of the one or more compartments within which one or more cells can be confined.

The apparatus, in which a negative pressure causes a bottom surface of at least one compartment of the one or more compartments to deform downwards, drawing liquid media in to the at least one compartment via an opening at the top of the at least one cell niche, and/or in which a positive pressure causes the bottom surface of the at least on cell niche of the one or more cell niches to deform upwards, pushing the liquid media out of the at least one compartment via the opening at the top of the at least one compartment.

The apparatus, in which a mechanical stretching of the membrane widens at least one compartment of the one or more compartments to facilitate the release of one or more cells from the at least one cell niche through an opening at the top of the at least one compartment.

The apparatus, which may include a plurality of microdiffusers configured to rectify pulsatile pressure into net flow perpendicular to the first surface of the membrane.

The apparatus, which may include at least one porous wick configured to transport the fluid media to the one or more compartments.

The apparatus, in which the membrane includes a micropatterned architecture with a plurality of compartments that are engineered to provide a substantially high gas-exchange area to volume ratio to maximize oxygen transmission rate to the compartments formed in the membrane.

The apparatus, in which the membrane is configured to expand or contract in response to changes in pressure or flow associated with the gas.

The apparatus, in which the membrane is configured to expand or contract in response to changes in pressure or flow associated with the liquid media.

The apparatus, in which the membrane is configured to expand or contract, in response to changes in pressure or flow associated with at least one of the gas and the liquid media, to promote uniform dispersal of reagents or cells in the one or more compartments.

The apparatus, in which the membrane is configured to expand or contract in response to changes in pressure or flow associated with at least one of the gas and the liquid media in order to facilitate efficient cultivation or harvesting of cells located in the one or more compartments in the membrane.

The apparatus, in which the fluidic path for the media is gravitationally supported with one or more flow regulators regulating the liquid media flow over the first side of the membrane.

The apparatus, which may include a plurality of microcarriers to which cells can adhere.

The apparatus, in which the plurality of surface features include a plurality of fin structures running substantially parallel to each other, the substantially parallel fin structures defining grooves between adjacent fin structures, at least one groove on a first side of the membrane providing at least one of the one or more compartments for cell location, a longitudinal direction of the at least one groove corresponding to a longitudinal direction of the one or more compartments.

The apparatus, in which the one or more media inlets are configured to introduce media into the media region creating a media flow that is not parallel to a longitudinal direction of the grooves.

The apparatus, in which the one or more media inlets are configured to introduce media into the media region creating a media flow that is substantially perpendicular to the grooves.

The apparatus, in which the one or more media inlets are configured to introduce media into the media region creating a media flow that is substantially aligned with the grooves.

The apparatus, in which an opening at the top of one or more of the one or more cell niches is narrower than a width below the opening.

The apparatus, in which the plurality of fins protrude from a base of the membrane to retain and protect one or more of the cells in the one or more cell niches from media flow shear forces generated by the media delivery.

The apparatus, in which the membrane has a multilayered monolithic construction such that the one or more channels for delivery of the gas are formed at a first layer of the membrane and the compartments are formed between the plurality of fins at a second layer of the membrane above the first layer.

The apparatus, in which a dedicated space is provided above the plurality of compartments formed between the plurality of fins to support a fluidic path for the liquid media flowing above and substantially perpendicular to the plurality of fins.

The apparatus, in which a dedicated space is provided above the plurality of compartments formed between the plurality of fins to support a fluidic path for the liquid media flowing above and substantially aligned with the plurality of fins.

The apparatus, in which the fluidic path has a relatively lower resistance against the liquid media flowing above the plurality of fins, thereby eliminating or reducing a need for use of pumps to regulate the liquid media flow.

The apparatus, in which the surface features include a plurality of well structures, at least one of the plurality of well structures providing at least one of the one or more compartments for cell placement.

The apparatus, in which an opening at the top of at least one of the well structures includes a narrower width of diameter than the width of diameter of the well structure below the opening.

The apparatus, in which one or more of the well structures include an opening that is circular, oval, square, rectangular, hexagonal, or octagonal.

The apparatus, in which the well structure protects the one or more cells in the one or more cell niches of the well structure from shear forces generated by the media delivery.

The apparatus, in which the membrane has a multilayered monolithic construction such that the one or more channels for delivery of the gas are formed at a first layer of the membrane and the compartment are formed within well structures at a second layer of the membrane above the first layer.

The apparatus, in which a dedicated space is provided above the plurality of well structures to support a fluidic path for the liquid media flowing above the plurality of well structures.

The apparatus, in which the fluidic path has a relatively lower resistance against the liquid media flowing above the plurality of well structures, thereby eliminating or reducing a need for use of pumps to regulate the liquid media flow.

The apparatus, in which a dedicated space is provided above the plurality of well structures to support a fluidic path for the liquid media flowing above the plurality of well structures.

The apparatus, in which at least one well structure has a circular opening.

The apparatus, in which at least one well structure has a polygonal opening.

The apparatus, in which at least one well structure has a curved opening.

The apparatus, in which the surface structures include a plurality of post structures, at least one post structure providing at least one of the plurality of compartments for cell placement.

The apparatus, in which cells adhere to the at least one post structures.

The apparatus, in which the membrane has a multilayered monolithic construction such that the one or more channels for delivery of the gas are formed at a first layer of the membrane and the cell niches are formed proximal to post structures at a second layer of the membrane above the first layer.

The apparatus, in which a dedicated space is provided above the plurality of post structures to support a fluidic path for the liquid media flowing above the plurality of post structures.

The apparatus, in which the fluidic path has a relatively lower resistance against the liquid media flowing above the plurality of post structures, thereby eliminating or reducing a need for use of pumps to regulate the liquid media flow.

The apparatus, in which a dedicated space is provided above the plurality of post structures to support a fluidic path for the liquid media flowing above the plurality of post structures.

The apparatus in which at least one post structure has a circular cross section.

The apparatus, in which at least one well post has a polygonal cross section.

The apparatus, in which at least one post structure has a curved, chevron, crescent, or U-shaped cross section.

The apparatus, which may include a petri dish configured to house the membrane.

The apparatus, in which the membrane forms a bottom surface of the petri dish.

The apparatus, which may include tension rings configured to keep the membrane taut and add rigidity.

The apparatus, which may include spacing pillars projecting from a second surface of the membrane opposite the first surface, the spacing pillars configured to allow gas exchange to the cell niches through the membrane.

A petri dish, which may include a bottom surface and a sidewall that form a dish: the bottom surface, which may include an at least partially gas permeable material, the bottom surface, which may include a first side and a second side, the first side, which may include a plurality of structures extending from a base of the first side and forming one or more cell niche regions below the top surface of the plurality of structures; and the sidewall connected to the bottom surface and forming a continuous and substantially vertical wall around a perimeter of the bottom surface.

The petri dish, in which the bottom surface and the sidewall include the same material.

The petri dish, in which the bottom surface and the sidewall include the at least partially gas permeable material.

The petri dish, in which the sidewall includes at least one material that is different from the bottom surface.

The petri dish, which may include one or more retention elements that provide support to the sidewall.

The petri dish, in which the bottom surface of the petri dish that is exposed to the exterior environment includes the at least partially gas permeable material such that a gas from the exterior environment can pass through the at least partially as permeable membrane to the first side, and/or gas from the first side can pass from the first side through the at least partially gas permeable membrane to the exterior environment.

The petri dish, in which the bottom surface of the petri dish is placed on a mesh, cloth, or other open pore material to allow gas from the exterior environment to exchange with the membrane.

The petri dish, in which the bottom surface of the petri dish that is exposed to the exterior environment includes one or more variations in its geometry that permits gas to at least partially pass below the bottom surface when the dish is placed on a flat surface.

The petri dish, in which the geometry includes pillars, channels, grooves, bumps, protrusions, or legs.

The petri dish, in which the geometry includes one or more spacing pillars.

The petri dish, which may include a top surface, the top surface, which may include a sealed membrane.

The petri dish, in which the top surface includes a silicone based membrane.

The petri dish, which may include a sealable port for transferring media to or from the petri dish.

A multi-well cell growth device, which may include multiple wells, the wells, which may include a bottom surface that includes a first side in contact with the interior of the wells and a second side in contact with the exterior of the multi-well cell growth device; in which the first side includes a topography that provides a plurality of cell growth compartments; in which the bottom surface includes a material that is at least partially permeable to a gas; and in which the bottom surface is configured such that a gas from the exterior of the multi-well growth device can pass from the exterior into the interior of the wells and can contact one or more of the plurality of cell growth compartments and/or a gas from within the one or more cell growth compartments can pass from the first side to the second side.

The multi-well cell growth device, in which the topography of the first side includes one or more of fins, sub-wells, and pillars, the fins, sub-wells and pillars at least partially defining the plurality of cell growth compartments.

The multi-well cell growth device, in which the sidewalls of the multiple wells at least partially includes a gas permeable material.

The multi-well cell growth device, in which the second side includes one or more variations in its geometry that permits gas to at least partially pass below the bottom surface when on a flat surface.

The multi-well cell growth device, in which the geometry includes pillars, channels, grooves, bumps, protrusions, or legs.

The multi-well cell growth device, in which the geometry includes one or more spacing pillars.

A cell cultivation apparatus, which may include: a membrane, which may include a plurality of fin structures running substantially parallel to each other, the substantially parallel fin structures defining grooves between adjacent fin structures, at least one groove on a first side of the membrane providing at least a compartment for cell placement; the membrane, which may include a material that is at least partially permeable to gas; a second side of the membrane defining a gas region, the second side of the membrane being separated from the first side of the membrane by the membrane, a gas capable of passing through the membrane; and a media region on the first side of the membrane configured for receiving media including one or more cells depositable in the compartment.

A cell respirator apparatus, which may include: one or more membranes, at least one membrane from the one or more membranes having a plurality of fins including at least a first fin and a second fin protruding from a first surface of the membrane to form a first compartment of a plurality of compartments configured for retaining a plurality of cells, the membrane being formed of material that is gas-permeable and transmissive to facilitate delivering gas to the plurality of compartments through one or more channels formed under the first surface of the membrane below the plurality of fins, at least a first channel of the one or more channels is configured to directly deliver the gas to the first compartment.

A method of culturing biological cells—which may include, providing any of the apparatuses noted above, and introducing biological cells into the apparatus, providing a cell media into the first side of the apparatus such that the cell media is in contact with the biological cells.

The method, which may include providing a gas to the second side of the membrane.

The method, which may include flowing media over one or more cell compartments.

The method, in which the flowing of media includes introducing media through an inlet and removing media through an outlet.

The method, which may include flowing gas into the second side of the membrane.

The method, in which the flowing of gas includes introducing gas through an inlet and removing gas through an outlet.

The method, which may include flowing media, biological cells or another material into the one or more cell compartments by creating a negative pressure in the one or more compartments.

The method, which may include maintaining cells in the one or more compartments by creating a negative pressure in the one or more compartments.

The method, which may include flowing media, biological cells or another material out of the one or more cell compartments by creating a positive pressure in the one or more compartments.

The method, which may include directing cells out of the one or more compartments by creating a positive pressure in the one or more compartments.

The method, which may include mixing one or more of the biological cells within the one or more compartments by creating a positive pressure and/or a negative in the one or more compartments.

The method, in which the positive and/or negative pressure is created by flowing gas into the gas region, flowing media into the media region, flowing both gas and media into their respective regions, preventing the flow of gas into the gas region, and/or preventing the flow of media into the media region, thereby creating a pressure differential between the two regions.

The method, in which the biological cells may be selected from any one or more of the group consisting of human, non-human mammalian, insect, bacterial, fungal, yeast, hybridoma, producer cells, inducible producer cells, CAR-T, 3T3-L1, 4T1, 9L, A20, A172, A253, A431, A549, A2780, A2780ADR, A2780cis, AB9, AHL-1, ALC, B16, B35, BCP-1, BEAS-2B, bEnd.3, BHK-21, BOSC23, BT-20, BxPC-3, C2C12, C3H-10T1/2, C6, C6/36, Caco-2, Cal-27, Calu-3, CAP, CGR8, CHO, CML T1, CMT12, COR-L23, COR-L23/5010, COR-L23/CPR, COR-L23/R23-, COS-7, COV-434, CT26, D17, DAOY, DH82, DU145, DuCaP, E14Tg2a, vEL4, EM-2, EM-3, vEMT6/AR1, EMT6/AR10.0, FM3, GL261, H1299, HaCaT, HCA2, HEK 293, HEK 293T, HeLa, Hep G2, Hepa1 c1 c7, High Five, HL-60, HT-29, HT-1080, J558L, Jurkat, JY, K562, KBM-7, KCL-22, KG1, Ku812, KYO-1, L243, L1210, LNCaP, MA-104, Ma-Mel, MA2.1, MC-38, MCF-7, MCF-10A, MDA-MB-157, MDA-MB-231, MDA-MB-361, MDA-MB-468, MDCK II, MG63, MIA PaCa-2, Mono-Mac-6, MOR/0.2R, MRC-5, MTD-1A, MyEnd, NALM-1, NCI-H69, NCI-H69/CPR, NCI-H69/LX4, NCI-H69/LX10, NCI-H69/LX20, Neuro-2a, Neuro2a, NIH-3T3, NK-92, NTERA-2, NW-145, OK, OPCN/OPCT cell lines, P3X63Ag8, PANC-1, PC-3, PC12, Peer, PNT1A, PNT2, Pt K2, Raji, RBL-1, RenCa, RIN-5F, RMA-S, S2, SaOS-2, Sf9, Sf21, SH-SYSY, SiHa, SK-BR-3, SK-N-SH, SK-OV-3, T-47D, T2, T84, T98G, THP-1, U2OS, U87, U373, U937, VCaP, Vero, VG-1, WM39, WT-49, YAC-1, and YAR cells, and the like.

The method, in which the gas is selected from the group consisting of oxygen, carbon dioxide, nitrogen, carbon monoxide, nitrous oxide, hydrogen sulfide, ethylene oxide, ozone, chlorine dioxide, and nitrogen dioxide.

The method, in which the media is selected from the group consisting of DMEM, FCS, 293 SFM II, AEM, CDM4HEK293, SFM4HEK293, Ex-Cell 293, SFM4Transfx-293, Freestyle 293, ESF SFM, CDM4CHO, CHO medium, MEM, MEM Alpha, RPMI, F-10, F-12, IMDM, Medium 199, Leibovitz L-15, McCoy's 5A, MCDB media, William's media, CMRL media, OptiMEM, OptiPro, AIM V, OptiPEAK T Lymphocyte, ExCellerate Human T Cell Expansion Media, StemXVivo Serum-Free Human T Cell Base Media, ExpiSf CD Medium, Sf-900 SFM, and TC-100 Insect Medium.

The method, in which other material is selected from the group consisting of waste material, a material secreted from the cell, material internal to the cell, cellular debris, and gas.

The method, which may include introducing a freezing agent into the gas region to freeze cells and cell components in the plurality of compartments, the freezing agent having a temperature below zero ° C., the freezing agent being in a gas state or a liquid state.

The apparatus, where at least one of the surface features has a height between about 400 μm and about 1000 μm, a width between about 300 μm and about 500 μm, and a pitch between about 200 μm and about 500 μm.

The apparatus, where the at least one of the surface features has a height between about 700 μm and about 1000 μm.

The apparatus, where the at least one of the surface features has a height of about 700 μm.

The apparatus, where at least one of the surface features has a ratio of height to width to pitch of about 4-10 to about 3-5 to about 2-5.

The apparatus, where the ratio of height to width to pitch is about 7-10 to about 3-5 to about 2-5.

The apparatus, where the ratio of height to width to pitch is about 7 to about 3-5 to about 2-5.

The petri dish, where at least one of the plurality of structures has a height between about 400 μm and about 1000 μm, a width between about 300 μm and about 500 μm, and a pitch between about 200 μm and about 500 μm.

The petri dish, where the at least one of the plurality of structures has a height between about 700 μm and about 1000 μm.

The petri dish, where the at least one of the plurality of structures has a height of about 700 μm.

The petri dish, where at least one of the plurality of structures has a ratio of height to width to pitch of about 4-10 to about 3-5 to about 2-5.

The petri dish, where the ratio of height to width to pitch is about 7-10 to about 3-5 to about 2-5.

The petri dish, where the ratio of height to width to pitch is about 7 to about 3-5 to about 2-5.

The multi-well cell growth device of, where at least one of the plurality of cell growth compartments has a height between about 400 μm and about 1000 μm, a width between about 300 μm and about 500 μm, and a pitch between about 200 μm and about 500 μm.

The multi-well cell growth device, where the at least one of the plurality of cell growth compartments has a height between about 700 μm and about 1000 μm.

The multi-well cell growth device, where the at least one of the plurality of cell growth compartments has a height of about 700 μm.

The multi-well cell growth device, where at least one of the plurality of cell growth compartments has a ratio of height to width to pitch of about 4-10 to about 3-5 to about 2-5.

The multi-well cell growth device, where the ratio of height to width to pitch is about 7-10 to about 3-5 to about 2-5.

The multi-well cell growth device, where the ratio of height to width to pitch is about 7 to about 3-5 to about 2-5.

The cell cultivation apparatus, where at least one of the plurality of fin structures has a height between about 400 μm and about 1000 μm, a width between about 300 μm and about 500 μm, and a pitch between about 200 μm and about 500 μm.

The cell cultivation apparatus, where the at least one of the plurality of fin structures has a height between about 700 μm and about 1000 μm.

The cell cultivation apparatus, where the at least one of the plurality of fin structures has a height of about 700 μm.

The cell cultivation apparatus, where at least one of the plurality of fin structures has a ratio of height to width to pitch of about 4-10 to about 3-5 to about 2-5.

The cell cultivation apparatus, where the ratio of height to width to pitch is about 7-10 to about 3-5 to about 2-5.

The cell cultivation apparatus, where the ratio of height to width to pitch is about 7 to about 3-5 to about 2-5.

The cell respirator apparatus, where at least one of the plurality of fins has a height between about 400 μm and about 1000 μm, a width between about 300 μm and about 500 μm, and a pitch between about 200 μm and about 500 μm.

The cell respirator apparatus, where the at least one of the plurality of fins has a height between about 700 μm and about 1000 μm.

The cell respirator apparatus, where the at least one of the plurality of fins has a height of about 700 μm.

The cell respirator apparatus, where at least one of the plurality of fins has a ratio of height to width to pitch of about 4-10 to about 3-5 to about 2-5.

The cell respirator apparatus, where the ratio of height to width to pitch is about 7-10 to about 3-5 to about 2-5.

The cell respirator apparatus, where the ratio of height to width to pitch is about 7 to about 3-5 to about 2-5.

The method, where the apparatus includes at least one surface feature having a height between about 400 μm and about 1000 μm, a width between about 300 μm and about 500 μm, and a pitch between about 200 μm and about 500 μm.

The method, where the apparatus includes at least one surface feature having a height between about 700 μm and about 1000 μm.

The method, where the apparatus includes at least one surface feature having a height of about 700 μm.

The method, where the apparatus includes at least one surface feature having a ratio of height to width to pitch of about 4-10 to about 3-5 to about 2-5.

The method, where the ratio of height to width to pitch is about 7-10 to about 3-5 to about 2-5.

The method, where the ratio of height to width to pitch is about 7 to about 3-5 to about 2-5.

A bioreactor is provided. The bioreactor may include one or more of a gas inlet; a gas outlet; a gas path connected between the gas inlet and the gas outlet; a media inlet; a media outlet; a media path connected between the media inlet and the media outlet; and a membrane separating the gas supply path and the media supply path, where the membrane includes a cell protection region, where the cell protection region is in liquid communication with the media path, where the cell protection region is fluidically distinct from the media path, where the cell protection region is in gaseous communication with the gas path across the membrane, and where the cell protection region is configured to reduce an impact of shear forces of media flowing in the media path on cells produced in the cell protection region.

The bioreactor, where the bioreactor is configured to produce a cell density at transfection of between about $10^7$ cells per milliliter (cells/mL) to about $10^9$ cells/mL and a productivity of between about $10^{15}$ adeno-associated viral genomes per liter (AAV vg/L) and about $10^{16}$ AAV vg/L.

The bioreactor, where a velocity of the media at the media inlet is between about 1 μm/sec and about 1 m/sec.

The bioreactor, where the velocity of the media at the media inlet is about 100 μm/sec, and where the bioreactor has a length of about 40 cm and produces about $10^8$ cells/mL.

The bioreactor of any of claims 135-138, where the velocity of the media at the media inlet is about 1 μm/sec, and where the bioreactor produces about $10^6$ cells/mL.

Any of the apparatus, the petri dish, the multi-well cell growth device, the cell cultivation apparatus, the cell respirator apparatus, and the method, where the apparatus is configured to produce a cell density at transfection of between about $10^7$ cells per milliliter (cells/mL) to about $10^9$ cells/mL and a productivity of between about $10^{15}$ adeno-associated viral genomes per liter (AAV vg/L) and about $10^{16}$ AAV vg/L.

Any of the apparatus, the cell cultivation apparatus, the cell respirator apparatus, and the method, where a velocity of the media at the media inlet is between about 1 μm/sec and about 1 m/sec.

Any of the apparatus, the cell cultivation apparatus, the cell respirator apparatus, and the method, where the velocity of the media at the media inlet is about 100 μm/sec, and where the apparatus has a length of about 40 cm and produces about $10^8$ cells/mL.

Any of the apparatus, the cell cultivation apparatus, the cell respirator apparatus, and the method, where the velocity of the media at the media inlet is about 1 μm/sec, and where the apparatus produces about $10^6$ cells/mL.

Any of the petri dish and the multi-well cell growth device having a length of about 40 cm and configured to produce between about $10^6$ cells/mL and about $10^8$ cells/mL.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The accompanying drawings, which are incorporated in and constitute a part of this specification, show certain features of the subject matter disclosed herein and, together with the description, help explain some of the principles associated with the disclosed implementations. In the drawings.

FIG. 6 further illustrates removal of material from the keystone shaped grooves by either stretching or inverting the membrane in accordance with an exemplary embodiment;

FIG. 9A illustrates an example of an open membrane high capacity cell respirator device with ten stacked membranes in accordance with an exemplary embodiment; FIG. 9B illustrates a close-up plan, perspective view of a corner of the example of the open membrane high capacity cell respirator device of FIG. 9A in accordance with an exemplary embodiment; and FIG. 9C illustrates a side, perspective view of a corner of the example of the open membrane high capacity cell respirator device of FIG. 9A in accordance with an exemplary embodiment;

FIG. 10A illustrates a prototype of a high density cell respirator with integrated cell retaining niches (compartments), spacing pillars, gas-perfusion space, and gas manifolds in accordance with an exemplary embodiment; FIG. 10B illustrates a first close-up portion of the prototype of FIG. 10A in accordance with an exemplary embodiment;

FIG. 10C illustrates a second close-up portion of the prototype of FIG. 10A in accordance with an exemplary embodiment; and FIG. 10D illustrates a cross-section of the prototype of FIG. 10A in accordance with an exemplary embodiment;

FIG. 11A illustrates a high density cell respirator in accordance with an exemplary embodiment; FIG. 11B illustrates a cross-section of the respirator of FIG. 11A before purging bubble and air spaces by perfusing liquid through the media compartment above the membrane of the high density cell respirator in accordance with an exemplary embodiment; and FIG. 11C illustrates the cross-section of the respirator of FIG. 11A after purging bubble and air spaces by perfusing liquid through the media compartment above the membrane of the high density cell respirator in accordance with an exemplary embodiment;

FIG. 37 is an image of an unstained protein standard (at left) alongside AAV2-mCherry HDCR vector (at right) according to an exemplary embodiment;

FIG. 38 is a plan view image of a small-scale HDCR platform having a volume on the order of about 5 mL and a cell density on the order of about $10^{12}$ vg according to an exemplary embodiment;

FIG. 45 is a top perspective view of the HDCR cartridge of FIG. 44 according to an exemplary embodiment;

FIG. 46 is a zoomed-in portion of the top perspective view of FIG. 45 of the HDCR cartridge according to an exemplary embodiment;

FIG. 56 is a back perspective view of the 4-stack demo-scale HDCR of FIG. 55 according to an exemplary embodiment;

FIG. 68 is a schematic side cross-sectional view of an uninclined, high aspect ratio HDCR membrane filled with media according to an exemplary embodiment;

FIG. 69 is a representation of a cell expansion volume of the uninclined, high aspect ratio HDCR membrane filled with media according to an exemplary embodiment;

FIG. 70 is a schematic side cross-sectional view of an uninclined, low aspect ratio HDCR membrane filled with media according to an exemplary embodiment;

FIG. 71 is a representation of a cell expansion volume of the uninclined, low aspect ratio HDCR membrane filled with media according to an exemplary embodiment;

FIG. 72 is a schematic side cross-sectional view of an inclined, high aspect ratio HDCR membrane filled with media according to an exemplary embodiment;

FIG. 73 is a representation of a cell expansion volume of the inclined, high aspect ratio HDCR membrane filled with media according to an exemplary embodiment;

FIG. 74 is a schematic side cross-sectional view of an inclined, low aspect ratio HDCR membrane filled with media according to an exemplary embodiment;

FIG. 75 is a representation of a cell expansion volume of the inclined, low aspect ratio HDCR membrane filled with media according to an exemplary embodiment;

FIG. 47) according to an exemplary embodiment;

When practical, similar reference numbers denote similar structures, features, or elements.

Figure 1:
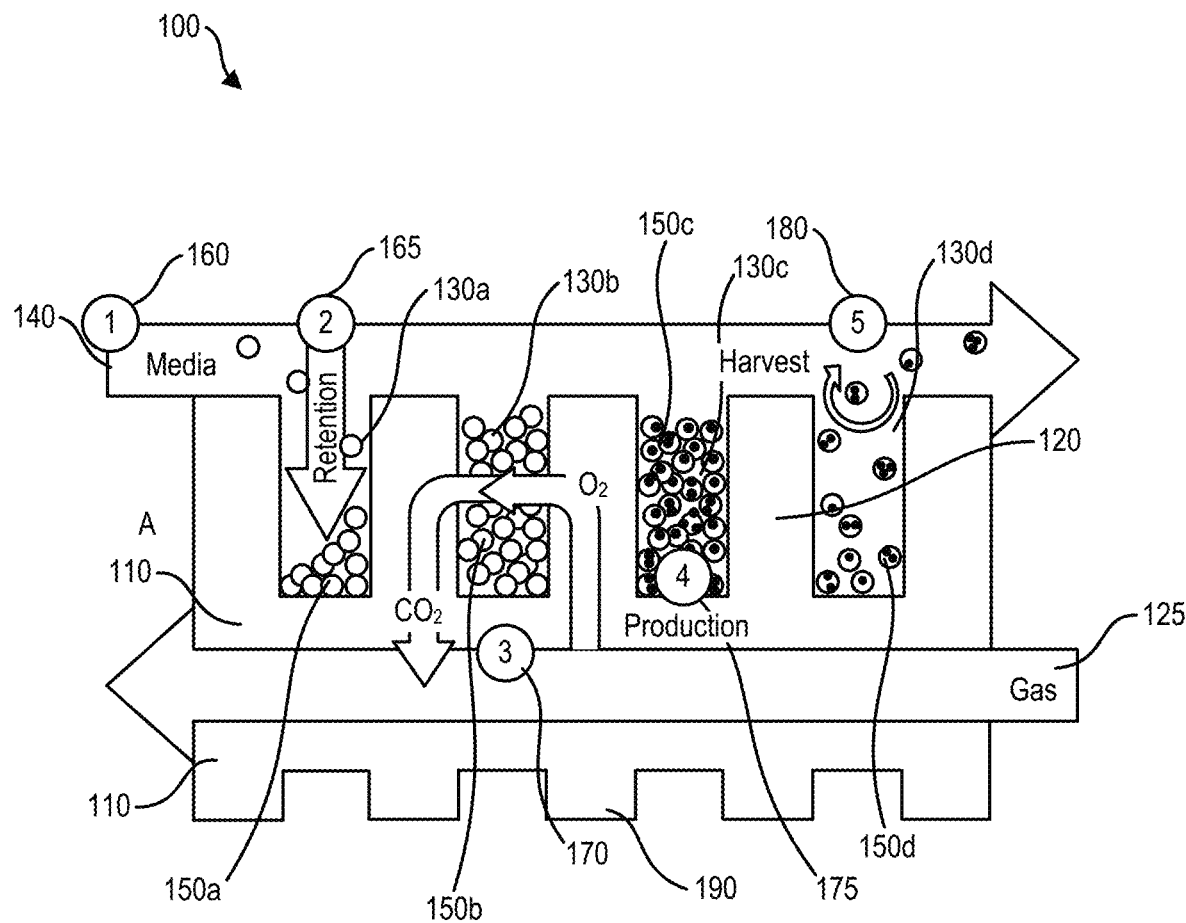
FIG. 1 is a functional overview of a high density cell respirator device, including, for example, fin-like structures, in accordance with various exemplary embodiments.

In the following detailed description, reference is made to the accompanying drawings, which form a part of the present disclosure. In the drawings, similar symbols typically identify similar components, unless context dictates otherwise. The illustrative embodiments described in the detailed description, drawings, and claims are not meant to be limiting. The detailed description is intended as a description of exemplary embodiments and is not intended to represent the only embodiments which may be practiced. The term "exemplary," as used herein, means "serving as an example, instance, or illustration," and should not necessarily be construed as preferred or advantageous over other embodiments. Other embodiments may be utilized, and other changes may be made, without departing from the spirit or scope of the subject matter presented herein. It will be readily understood that the features of the present disclosure, as generally described herein and illustrated in the Figures, can be arranged, substituted, combined, and designed in a wide variety of different configurations, all of which are explicitly contemplated by and form part of this disclosure.

DETAILED DESCRIPTION

The present system, device and method increase cell density while maintaining metabolically effective producer cells or packaging cells. By increasing cell density while maintaining metabolically effective producer cells or packaging cells, space-time productivity are improved in terms of per-cell productivity.

As used herein, the term "high density" (and the like) on the context of high density cell culture may have a specific meaning including the following. Most developed processes for AAV production achieve cell densities of about $10^6$ cells/mL, which is about 0.1% by volume or a single cell in every nL of media. Moving up to $10^7$ and $10^8$ cells/mL, cell densities are 1% and 10% occupancy by volume, respectively. Cell densities of $10^9$ correspond with tissue level densities. The present inventors then focused on what limits cells densities in bioreactors to the $10^6$ cell/mL range.

To a first approximation, it was determined that gas exchange demands limit cells densities in bioreactors to the $10^6$ cell/mL range. From a standpoint of the metabolic needs of the cell, the necessary volumetric mass-transfer coefficients for oxygen may be calculated and compared to glucose, for example. For $10^6$ cells/mL, oxygen needs to be replaced in the media about once an hour; for $10^7$ cells/mL, oxygen needs to be replaced in the media about 8 times per hour; and for $10^8$ cells/mL, oxygen needs to be replaced in the media about once a minute. In contrast, considering the volumetric mass-transfer coefficients for glucose, exchange rates are 100× less compared to oxygen exchange, and the same holds largely for waste elimination and other nutrients. As such, developed bioreactors (STR and fixed-bed) are operating under mixing/perfusion regimes driven by a need to oxygenate cells, but 100× in excess for soluble nutrients. Ultimately, limits on shear forces cap possible oxygen exchange. By de-coupling the exchange of gases from soluble nutrients, perfusion/mixing requirements were drastically reduced, and higher density nodes were achieved.

The present high density cell respirator (HDCR) systems, devices and methods, and their reasonable variants, decouple gas and nutrient exchange, reduce perfusion/mixing requirements, and achieve higher density notes than in the developed art.

Applications and Need

The high density cell respirator (HDCR) embodiments described herein may be used to generate bioproducts for a wide variety of applications, including vectors such as adeno associated virus (AAV) for gene transfer and editing for inborn errors of metabolism and neurologic diseases such as hemophilia, sickle cell anemia, thalassemia, Parkinson's disease, Alzheimer, among others; oncolytic viruses for cancer killing and immunotherapy; stem cell growth and gene editing for replacement of damaged tissues including liver failure, artificial skin, and HIV infection, among others; antibodies and therapeutic proteins; metabolites and other cell-based products.

As used herein, the term "bioproduct" and variants may refer to viruses, virus-like particles, bacteriophages, proteins, recombinant proteins, antibodies, metabolites, cells, eukaryotic cells, bacterial cells, algae, organelles, vacuoles, mitochondria, lipids, exosomes, DNA, RNA, plasmids, antibiotics, and the like.

As used herein, the term "virus" and variants may refer to native, modified, chimeric, and recombinant viruses and virus-like particles based on: Adeno-associated virus, Aichi virus, Australian bat lyssavirus, BK polyomavirus, Banna virus, Barmah forest virus, Bunyamwera virus, Bunyavirus La Crosse, Bunyavirus snowshoe hare, Cercopithecine herpesvirus, Chandipura virus, Chikungunya virus, Cosavirus A, Cowpox virus, Coxsackievirus, Crimean-Congo hemorrhagic fever virus, Dengue virus, Dhori virus, Dugbe virus, Duvenhage virus, Eastern equine encephalitis virus, Ebolavirus, Echovirus, Encephalomyocarditis virus, Epstein-Barr virus, European bat lyssavirus, GB virus C/Hepatitis G virus, Hantaan virus, Hendra virus, Hepatitis A virus, Hepatitis B virus, Hepatitis C virus, Hepatitis E virus, Hepatitis delta virus, Horsepox virus, Human adenovirus, Human astrovirus, Human coronavirus, Human cytomegalovirus, Human enterovirus 68, 70, Human herpesvirus 1, Human herpesvirus 2, Human herpesvirus 6, Human herpesvirus 7, Human herpesvirus 8, Human immunodeficiency virus, Human papillomavirus 1, Human papillomavirus 2, Human papillomavirus 16,18, Human parainfluenza, Human parvovirus B19, Human respiratory syncytial virus, Human rhinovirus, Human SARS coronavirus, Human spumaretrovirus, Human T-lymphotropic virus, Human torovirus, Influenza A virus, Influenza B virus, Influenza C virus, Isfahan virus, JC polyomavirus, Japanese encephalitis virus, Junin arenavirus, KI Polyomavirus, Kunjin virus, Lagos bat virus, Lake Victoria marburgvirus, Langat virus, Lassa virus, Lordsdale virus, Louping ill virus, Lymphocytic choriomeningitis virus, Machupo virus, Mayaro virus, MERS coronavirus, Measles virus, Mengo encephalomyocarditis virus, Merkel cell polyomavirus, Mokola virus, Molluscum contagiosum virus, Monkeypox virus, Mumps virus, Murray valley encephalitis virus, New York virus, Nipah virus, Norwalk virus, O'nyong-nyong virus, Orf virus, Oropouche virus, Pichinde virus, Poliovirus, Punta toro phlebovirus, Puumala virus, Rabies virus, Rift valley fever virus, Rosavirus A, Ross river virus, Rotavirus A, Rotavirus B, Rotavirus C, Rubella virus, Sagiyama virus, Salivirus A, Sandfly fever sicilian virus, Sapporo virus, SARS coronavirus 2, Semliki forest virus, Seoul virus, Simian foamy virus, Simian virus 5, Sindbis virus, Southampton virus, St. louis encephalitis virus, Tick-borne powassan virus, Torque teno virus, Toscana virus, Uukuniemi virus, Vaccinia virus, Varicella-zoster virus, Variola virus, Venezuelan equine encephalitis virus, Vesicular stomatitis virus, Western equine encephalitis virus, WU polyomavirus, West Nile virus, Yaba monkey tumor virus, Yaba-like disease virus, Yellow fever virus, Zika virus, and the like.

The use of AAV vectors for gene therapy and editing is under intense investigation and becoming clinical therapy, including cures for inborn errors of metabolism and genetic engineering of stem cells. Even for Phase I/II trials, greater than about $10^{17}$ vector genomes (vg) may be needed. The capacity and cost of AAV vector production present the largest obstacles for widespread use of AAV gene therapy. Similarly, production of sufficient vector and allied costs are major hurdles for cancer-fighting immuno-oncolytic viruses becoming affordable to all mankind. An immuno-oncolytic virus was recently approved for use in the US and EU for treatment of melanoma, with additional viruses reaching the approval stage. The disclosed technology enables cell culture platforms that may disrupt existing vector production methodologies for genetic vectors and immuno-oncolytic viruses, two fields that have yielded clinical products in the 21st century, with substantially increased efficiency, and decreases in both the time (2-10×) and costs (10×) of producing vectors for therapy.

Viruses and viral vectors have become very important not only as experimental agents but also as medicines for gene therapy and cancer therapy, and as vaccines for infectious diseases. AAV vectors serve as effective gene transfer and gene editing tools that hold the promise of cure for many inherited and acquired diseases. AAV vectors, for example, are under intense investigation as treatment for inborn errors of metabolism, defective structural and secretory protein production, and may become agents of cure for diverse diseases such as hemophilia, thalassemia, sickle cell anemia, mucopolysaccharidosis, cystic fibrosis and muscular dystrophies. One AAV-based therapeutic (Glybera, uniQure, N.V., Amsterdam) has already been approved by the European Union for the treatment of lipoprotein lipase deficiency. Another was approved in 2017 for the treatment of a hereditary form of blindness (Spark Therapeutics). Because of Glybera's $10^{16}$ recombinant AAV viral particle dose it carries with it a $1.2 million per patient charge. Similarly, Spark's Luxturna for blindness costs about $850,000 per patient. Novartis' AAV Zolgensma for SMA is costing $2.1M for a dose. This is partly due to the cost of virus production. The success of recent trials is leading to an exponential growth in the demand for high-quality, functionally active vector. A common problem for this entire field is producing enough viral vector for clinical trials. Even for a Phase I/II trial, about $10^{17}$-$10^{18}$ viral particles are needed, usually costing millions of dollars and taking a year or more to be achieved. A single contaminant in this long production process may doom an entire program or company. The success of recent trials is driving an exponential growth in the demand for high-quality, functionally active vector and this is expected to continue for decades to come. Thus, designing a more rapid and inexpensive production methodology would allow many more products into trials, and allow gene-editing tools proven in trials to be affordable for society.

Immuno-oncolytic viral therapy consists of treating cancer with viruses that are not only capable of directly infecting and killing cancer, but may reduce recurrence by eliciting sustained immunologic memory. An immuno-oncolytic herpes virus (T-VEC, Amgen, Thousand Oaks, CA) has been approved for use in melanoma in the USA and in Europe. An adenovirus (Oncorine, SunwayBio, Shanghai, China) has been approved for use in China for head and neck cancer. Many other viruses are under clinical testing both as single agents and in combination with other immunostimulatory molecules, with promising results. These and most viruses under testing cost thousands of dollars a dose. It has been challenging to produce the many promising viral constructs for trials. It has also been challenging to keep the cost of the viral agents sufficiently low to have these agents be available to cancer patients in poor countries. Thus, having a method to increase production efficiency or decrease cost will greatly help save lives. Development of production process for orthopoxviruses also doubles as proof-of-concept for rapid vaccine development in response to pandemics or bioterrorism.

AAV is a replication defective, nonpathogenic, parvovirus with a single stranded DNA genome that infects both dividing and non-dividing cells. Over the past two decades, there has been intense focus on developing gene therapy vectors based on AAVs to treat inherited diseases, because of their ability to safely and efficiently transduce liver, heart, muscle, and other organs. The therapeutic benefits of AAV gene therapy appear to be sustained. Clinical gene therapy trials of AAV have produced very promising results, especially in spinal muscular atrophy (SMA), hemophilia and several forms of blindness. More recently, AAV vectors are also being used as delivery agents for components of genome editing platforms, and have been shown to be effective and efficient especially when used in vivo. Thus, AAV vectors are likely to play an important role in clinical genome editing. They can also be vectors for gene engineering of stem cells for therapy.

Despite the great promise that AAV vectors hold for genetic medicines, the single biggest limitation to widespread use is the inability to manufacture sufficient quantities of AAV vectors in a timely manner and at low cost. Clinical GMP grade AAV is currently manufactured in a few commercial and academic facilities worldwide.

However, due to the relative inefficiency of production and the use of labor-intensive processes, there is widespread inability to meet the current demand. As a result, there is currently an approximate two-year wait for clinical grade AAV. This is exacerbated by the acquisition of AAV-producing CMOs by major pharmaceutical companies seeking to speed up their own timelines. The ability to rapidly produce high-titer AAV vectors at low cost would be transformational to the fields of gene therapy and genome editing. Many discoveries may never be translated if we cannot increase production capacity and democratize the ability to produce AAV vectors.

Greater than about $10^{17}$ vector genomes are needed even for Phase II clinical trials. Production and cost of vector are major obstacles for these vectors becoming affordable by mankind, since at present these medicines costs hundreds of thousands of dollars to over a million dollars. These staggering numbers are not sustainable as worldwide therapeutic agents. There is a need to speed up production by about 2-10×, and increase efficiency and yield by about 10×. Accomplishing these goals would allow many more candidates into trials and should allow products to be much more affordable and accessible.

The HDCR embodiment described herein could also be used for virus and vaccine production. Enhanced virus production would be useful for the growing field of oncolytic viral therapies. Oncolytic viruses are viruses that have been engineered to specifically infect, replicate within, and kill cancer cells. These viruses can also carry genetic payloads that can lead to production of proteins at the sites of cancer that stimulate the host's immune system to have an immunologic reaction to cancer that is robust, systemic, and lasting. Two such viruses, one based on adenovirus and one based on herpes simplex virus have been approved for use in man as cancer treatments. Many other viruses, including ones based on vaccinia, myxoma, vesicular stomatitis virus, and measles, among others, are currently under investigation. Trials combining oncolytic viruses and immune checkpoint inhibitors are also showing great promise as potential human cancer therapy. Cost is also a consideration in oncolytic virus production. The cost for a 6-month course of oncolytic viral therapy using TVEC is currently about $65,000. Reducing production cost would increase worldwide affordability. Shortening virus production times would also lower the barrier to trials for new agents.

Improved virus production technology would also impact vaccine development. Vaccinia, VSV, measles, and HSV are among the viruses produced routinely for vaccines. Flu vaccines at present are made via egg-based production processes. Current issues associated with egg-based vaccine production include virus strain mutation and low immunogenicity of vaccine, which contributes to low vaccine efficacy, and allergy to eggs, which restricts the number of people receiving protection. The HDCR described herein may optimize virus production to surpass the efficiency of current egg-based production methods, to allow higher yield, more rapid production, and access to vaccines for all of humanity.

Cost and volume pressures have driven the evolution of cell-based production of viral vectors from Petri dishes to flasks, roller bottles, cell factories, stirred-tank reactors, and finally perfusion-based reactors (e.g., hollow fiber), where the art has remained for several decades. These systems rely on transporting nutrients, growth factors, waste, and oxygen/carbon dioxide via culture media. Maximum cell density in bioreactor systems has historically been limited by gas exchange due to the low solubility of gases in media combined with the high oxygen uptake rates of cells. Efforts to increase oxygen delivery through mixing or gas sparging are ultimately limited by the negative effects of shear forces on cell viability. At about $10^6$ cells/mL, a common density in many systems, only about 0.1-1% of reactor space (v/v) is occupied by cells. Recent attempts at high-density cell culture for vaccine production using perfused bioreactors have overcome previous density limitations of continuous and batch-fed cultures; however, associated costs have not decreased significantly, partly due to increased specific media usage and reductions of virus yields in these particular systems.

HDCRs

The disclosed technology advances the art of bioproduction by decoupling gas and soluble nutrient delivery in a unique design that increases oxygen supply, protects cells from shear forces, and efficiently utilizes media, to achieve markedly improved space-time productivity. The embodiments include high density cell respirators (HDCRs) composed of stackable, cell-retaining membranes that are gas-perfusable and highly transmissive allowing for direct oxygenation of the cell niche via membrane permeation and diffusion. Direct oxygenation is important because molecular oxygen (02) may be the most limiting metabolite for cell growth due to its low solubility in cell media. By separating gas convective delivery from other nutrient delivery, it is possible to significantly increase oxygen delivery to cells without increasing detrimental shear forces. The HDCR cartridge is bathed in an independently perfusable media stream allowing for soluble nutrients or reagents delivery, waste removal, and bioproduct harvesting. These designs can support tissue-level cell densities of >about $10^8$ cells/mL in the compartments, or a Vcell/Vbioreactor ratio of about 10%-25%, which corresponds to a 100-fold improvement over conventional bioreactors. Intensification of cell based production processes allows for more efficient use of expensive and limited good manufacturing practice ("GMP") space.

Various implementation described herein include the integration of surface features into the membrane design. For example, the surface features may be fins, wells, or posts. These surface features serve two key functions.

First, the surface features create shear-protected compartments in which adherent, suspension, or microcarrier-attached cells can expand. For some embodiments, adjacent fins form grooves corresponding to compartments. In other embodiments, wells correspond to compartments. In still other embodiments, posts form compartments for cells that adhere to the posts. These compartments are integral to virus production due to loss of cell adhesion during virus production (cytopathic effect ("CPE")), which leads to wash-out in conventional systems. There are repeated calls in the literature for new means of cell retention in high density cell culture systems due to the expense and complication of existing methods, including acoustic filters, tangential flow filtration ("TFF"), and continuous centrifuges.

Second, the surface features facilitate gas exchange around/into the cell niche since they are highly gas permeable. This increases the volumetric mass transfer coefficient for oxygen (i.e., kLa) allowing higher cell densities to be achieved. Furthermore, the surface features constrain the size of cell aggregates, ensuring all cells are able to receive necessary amounts of oxygen (i.e., they are not diffusion-limited). Overcoming gas/nutrient gradients is a major challenge in the literature; the disclosed overcomes this challenge.

Terms

A "compartment," as used herein, is a portion of a membrane structure having the ability to spatially confine one or more cells (or similarly sized materials including viruses, cell organelles, liposomes, carriers (such as beads, etc.) and the like) to a portion of the membrane surface relative to the entire surface of the membrane. Compartments may include a variety of structures and geometries including, but not limited to fins, posts, wells, channels, cages, and combinations of these features. The compartments can have any shape, structure, geometry or architecture, including those described herein. For example, the compartments can include a circular, oval, eliptical, square, rectangular, pentagonal, hexagonal, heptagonal, octagonal, irregular or other geometric shape, opening, side, bottom, etc.

A "gas permeable" or "semipermeable" material, such as a membrane, includes that which allows a gas to permeate through but prevent liquid water from permeating, or as otherwise applicable and known in the art. Permeability can be measured at standard room temperature (i.e., 25° C.) and atmospheric pressure or other applicable temperatures and pressures. For example a standard temperature for cultures of mammalian cells is 37° C. For thermophiles, temperatures can go up to 122° C. Pressures can be adjusted to more or less than standard atmospheric pressure, such as with hydrostatic pressure from being submerged. A gas may be molecular oxygen, carbon dioxide, carbon monoxide, nitrogen, common air, carbon monoxide, nitrous oxide, hydrogen sulfide, ethylene oxide, ozone, chlorine dioxide, nitrogen dioxide, or as otherwise applicable.

A "fin" includes a long and thin raised structure that protrudes above a surface. The fin may have a substantially constant, polygonal and/or curved, cross sectional shape along the length of the fin.

An "array of fins" includes a series of fins that protrude above a surface, with a substantially constant spacing along the length of the fins between neighboring fins in the series of fins. The array of fins may be aligned and substantially parallel to each other.

A "groove" is a long and thin recess formed by neighboring fins. The cross sectional shape of the groove may be defined by the shape of the walls of the neighboring fins that define the groove and the portion of the surface from which the neighboring fins protrude. The neighboring fin walls and the portion of the surface may form three sides of a cross section of the groove. The groove may have an opening opposite to the surface. The opening may be narrower or wider than the width of the groove between the walls of the neighboring fins that form the groove. If the surface is horizontal, and the fins protrude upwards, then the opening is at the top of the groove.

An "array of grooves" includes a series of grooves formed by neighboring fins of an array of fins. The grooves may have a substantially constant spacing along the length of the grooves between neighboring grooves in the series of grooves. The array of grooves may be aligned and substantially parallel to each other.

A "pillar" or "micropillar" includes a column or other structure that extends perpendicularly from a surface, or as otherwise known in the art. A "micropillar" includes a pillar that is small and is not limited to pillars that are on the scale of micrometers (microns) or micro-inches.

An "array of spacers" includes a geometrically regular or irregular pattern of micropillars or other spacers with a height and center-to-center spacing of the spacers configured to keep the sheets at a fixed distance from one another, or as otherwise known in the art.

A "collapse resistant bag" includes a bag that has spacers inside it such that internal surfaces of opposite sides are prevented from touching each other in normal operation.

An "expansion resistant bag" includes a bag that has internal weld points, connected spacers, or other connections that prevent the bag from becoming shaped like a balloon when pressurized, or as otherwise known in the art. An expansion resistant bag may lay substantially flat. It may have convex and concave recesses and curves.

"Hermetically sealed" simply means sealed to be airtight, or at least not permeable to liquid but perhaps permeable to gas, or as otherwise known in the art.

In embodiments, there are provided cell cultivation apparatuses comprising a membrane comprising a plurality of surface features on a first side of the membrane, the surface features comprising one or more compartments within which one or more cells can be confined, the membrane comprising a material that is at least partially permeable to gas, a second side of the membrane defining one boundary of a gas region, wherein the membrane is configured so that a gas can pass through the second side of the membrane to the first side of the membrane; and a media region having one boundary on the first side of the membrane and configured for passing media over the first side of the membrane, wherein the one or more compartments are configured to at least partially reduce media flow shear forces within the compartments.

In embodiments, an apparatus may further comprise one or more media inlets and one or more media outlets fluidically connected to the media region, the one or more media inlets configured to facilitate introduction of media into the media region on the first side of the membrane, the one or more media outlets configured to facilitate removal of media from the media region.

In embodiments, at least one of the one or more media inlets is fluidly connected to at least one of the media outlets to facilitate reintroduction of media into the media region on the first side of the membrane.

In embodiments, the media introduced into the media region is in a liquid state.

In embodiments, the media removed from the media region comprises at least one of a plurality of cells, spent media, cellular waste, secretions, and biomaterial from the plurality of cells.

In embodiments, the apparatus is configured to minimize media flow shear forces in the one or more compartments upon introduction or removal of media from the media region.

In embodiments, the apparatus further comprises one or more gas inlets and one or more gas outlets in fluid contact with the gas region, the one or more gas inlets configured to introduce a gas into the gas region, and the one or more gas outlets configured for the removal of a gas from the gas region.

In embodiments, the apparatus further comprises one or more channels formed on the second side of the membrane, at least a first channel of the one or more channels configured to deliver gas to the at least one of the compartments via the membrane by way of membrane permeation and diffusion.

In embodiments, the apparatus further comprises an enclosure disposed above the first side of the membrane.

In embodiments, the enclosure defines a second boundary of the media region.

In embodiments, the apparatus is configured to be stacked with at least a second cell cultivation apparatus.

In embodiments, one more of the media or gas inlets or media or gas outlets are configured so that upon stacking, one or more of the media or gas inlets or media or gas outlets are in fluid communication with an inlet or outlet of an immediately adjacent apparatus.

In embodiments, one or more of the media or gas inlets is configured so that upon stacking, media or gas introduced into the apparatus is combined into a combined inlet line for transmission to a plurality of the membranes.

In embodiments, one or more of the media or gas outlets is configured so that upon stacking, media or gas removed from the apparatus is combined into a combined outlet line for transmission from a plurality of the membranes.

In embodiments, the liquid media and the gas are independently perfused over each membrane of the stacked cultivation apparatuses by way of separate gas delivery tubes and media delivery tubes connected to a liquid-tight container for containing the stackable membranes.

In embodiments, the apparatus further comprises a liquid-tight container for retaining the apparatus.

In embodiments, the membrane comprises pores having a size permitting permeation and diffusion of oxygen to pass through the membrane.

In embodiments, liquid media perfusion over the first surface of the membrane introduces cells to the one or more compartments.

In embodiments, media perfusing over a first surface of the membrane delivers nutrients or reagents to the one or more compartments.

In embodiments, media perfusion over a first surface of the membrane allows for waste removal from the one or more compartments.

In embodiments, media perfusion over a first surface of the membrane allows for harvesting bio-products from the one or more compartments.

In embodiments, the one or more compartments support tissue-level cell densities of greater than about $10^8$ cells per milliliter or tissue-level cell densities greater than about 10%-25% Vcell/Vbioreactor, where Vcell is the volume of cells and Vbioreactor is the volume of reactor space cell expansion.

In embodiments, at least one of the plurality of surface features is formed of microfabricated silicone to facilitate gas exchange occurring via membrane permeation around the one or more compartments.

In embodiments, the silicone surface features are configured to facilitate gas exchange occurring via membrane permeation into one or more compartments.

In embodiments, a negative pressure causes a bottom surface of at least one compartment of the one or more compartments to deform downwards, drawing liquid media in to the at least one compartment via an opening at the top of the at least one cell niche, and/or wherein a positive pressure causes the bottom surface of the at least on cell niche of the one or more cell niches to deform upwards, pushing the liquid media out of the at least one compartment via the opening at the top of the at least one compartment.

In embodiments, a mechanical stretching of the membrane widens at least on compartment of the one or more compartment to facilitate the release of one or more cells from the at least one cell niche through an opening at the top of the at least one compartment.

In embodiments, the apparatus further comprises a plurality of microdiffusers configured to rectify pulsatile pressure into net flow perpendicular to the first surface of the membrane.

In embodiments, the apparatus further comprises at least one porous wick configured to transport the fluid media to the one or more compartments.

In embodiments, the membrane comprises a micro-patterned architecture with a plurality of compartments that are engineered to provide a substantially high gas-exchange area to volume ratio to maximize oxygen transmission rate to the compartments formed in the membrane.

In embodiments, the membrane is configured to expand or contract in response to changes in pressure or flow associated with the gas.

In embodiments, the membrane is configured to expand or contract in response to changes in pressure or flow associated with the liquid media.

In embodiments, the membrane is configured to expand or contract, in response to changes in pressure or flow associated with at least one of the gas and the liquid media, to promote uniform dispersal of reagents or cells in the one or more compartments.

In embodiments, the membrane is configured to expand or contract in response to changes in pressure or flow associated with at least one of the gas and the liquid media in order to facilitate efficient cultivation or harvesting of cells located in the one or more compartments in the membrane.

In embodiments, the fluidic path for the media is gravitationally supported with one or more flow regulators regulating the liquid media flow over the first side of the membrane.

In embodiments, further comprising a plurality of microcarriers to which cells can adhere.

In embodiments, the plurality of surface features comprise a plurality of fin structures running substantially parallel to each other, the substantially parallel fin structures defining grooves between adjacent fin structures, at least one groove on a first side of the membrane providing at least one of the one or more compartments for cell location, a longitudinal direction of the at least one groove corresponding to a longitudinal direction of the one or more compartments.

In embodiments, the one or more media inlets are configured to introduce media into the media region creating a media flow that is not parallel to a longitudinal direction of the grooves.

In embodiments, wherein the one or more media inlets are configured to introduce media into the media region creating a media flow that is substantially perpendicular to the grooves.

In embodiments, wherein the one or more media inlets are configured to introduce media into the media region creating a media flow that is substantially aligned with the grooves.

In embodiments, an opening at the top of one or more of the one or more cell niches is narrower than a width below the opening.

In embodiments, the plurality of fins protrude from a base of the membrane to retain and protect one or more of the cells in the one or more cell niches from media flow shear forces generated by the media delivery.

In embodiments, the membrane has a multilayered monolithic construction such that the one or more channels for delivery of the gas are formed at a first layer of the membrane and the compartments are formed between the plurality of fins at a second layer of the membrane above the first layer.

In embodiments, a dedicated space is provided above the plurality of compartments formed between the plurality of fins to support a fluidic path for the liquid media flowing above and substantially perpendicular to the plurality of fins.

In embodiments, a dedicated space is provided above the plurality of compartments formed between the plurality of fins to support a fluidic path for the liquid media flowing above and substantially aligned with the plurality of fins.

In embodiments, the fluidic path has a relatively lower resistance against the liquid media flowing above the plurality of fins, thereby eliminating or reducing a need for use of pumps to regulate the liquid media flow.

In embodiments, the surface features comprise a plurality of well structures, at least one of the plurality of well structures providing at least one of the one or more compartments for cell placement.

In embodiments, an opening at the top of at least one of the well structures comprises a narrower width of diameter than the width of diameter of the well structure below the opening.

In embodiments, one or more of the well structures comprise an opening that is circular, oval, square, rectangular, hexagonal, or octagonal.

In embodiments, the well structure protects the one or more cells in the one or more cell niches of the well structure from shear forces generated by the media delivery.

In embodiments, the membrane has a multilayered monolithic construction such that the one or more channels for delivery of the gas are formed at a first layer of the membrane and the compartment are formed within well structures at a second layer of the membrane above the first layer.

In embodiments, a dedicated space is provided above the plurality of well structures to support a fluidic path for the liquid media flowing above the plurality of well structures.

In embodiments, the fluidic path has a relatively lower resistance against the liquid media flowing above the plurality of well structures, thereby eliminating or reducing a need for use of pumps to regulate the liquid media flow.

In embodiments, a dedicated space is provided above the plurality of well structures to support a fluidic path for the liquid media flowing above the plurality of well structures.

In embodiments, at least one well structure has a circular opening.

In embodiments, at least one well structure has a polygonal opening.

In embodiments, at least one well structure has a curved opening.

In embodiments, the surface structures comprise a plurality of post structures, at least one post structure providing at least one of the plurality of compartments for cell placement.

In embodiments, cells adhere to the at least one post structures.

In embodiments, the membrane has a multilayered monolithic construction such that the one or more channels for delivery of the gas are formed at a first layer of the membrane and the cell niches are formed proximal to post structures at a second layer of the membrane above the first layer.

In embodiments, a dedicated space is provided above the plurality of post structures to support a fluidic path for the liquid media flowing above the plurality of post structures.

In embodiments, the fluidic path has a relatively lower resistance against the liquid media flowing above the plurality of post structures, thereby eliminating or reducing a need for use of pumps to regulate the liquid media flow.

In embodiments, a dedicated space is provided above the plurality of post structures to support a fluidic path for the liquid media flowing above the plurality of post structures.

In embodiments, at least one post structure has a circular cross section.

In embodiments, at least one well post has a polygonal cross section.

In embodiments, at least one post structure has a curved, chevron, crescent, or U-shaped cross section.

In embodiments, further comprising a petri dish configured to house the membrane.

In embodiments, the membrane forms a bottom surface of the petri dish.

In embodiments, further comprising tension rings configured to keep the membrane taut and add rigidity.

In embodiments, further comprising spacing pillars projecting from a second surface of the membrane opposite the first surface, the spacing pillars configured to allow gas exchange to the cell niches through the membrane.

In embodiments, there are provided petri dishes comprising a bottom surface and a sidewall that form a dish: the bottom surface comprising an at least partially gas permeable material, the bottom surface comprising a first side and a second side, the first side comprising a plurality of structures extending from a base of the first side and forming one or more cell niche regions below the top surface of the plurality of structures; and the sidewall connected to the bottom surface and forming a continuous and substantially vertical wall around a perimeter of the bottom surface.

In embodiments, the bottom surface and the sidewall comprise the same material.

In embodiments, the bottom surface and the sidewall comprise the at least partially gas permeable material.

In embodiments, the sidewall comprises at least one material that is different from the bottom surface.

In embodiments, further comprising one or more retention elements that provide support to the sidewall.

In embodiments, the bottom surface of the petri dish that is exposed to the exterior environment comprises the at least partially gas permeable material such that a gas from the exterior environment can pass through the at least partially as permeable membrane to the first side, and/or gas from the first side can pass from the first side through the at least partially gas permeable membrane to the exterior environment.

In embodiments, the bottom surface of the petri dish is placed on a mesh, cloth, or other open pore material to allow gas from the exterior environment to exchange with the membrane.

In embodiments, the bottom surface of the petri dish that is exposed to the exterior environment comprises one or more variations in its geometry that permits gas to at least partially pass below the bottom surface when the dish is placed on a flat surface.

In embodiments, the geometry comprises pillars, channels, grooves, bumps, protrusions, or legs.

In embodiments, the geometry comprises one or more spacing pillars.

In embodiments, the petri dish comprises a top surface, the top surface comprising a sealed membrane.

In embodiments, the top surface comprises a silicone based membrane.

In embodiments, the petri dish comprises a sealable port for transferring media to or from the petri dish.

In embodiments, there are provided membranes comprising a plurality of surface features on a first side of the membrane, the surface features comprising one or more compartments within which one or more cells can be confined, the membrane comprising a material that is at least partially permeable to gas.

In embodiments, there are provided multi-well cell growth devices comprising multiple wells, the wells comprising a bottom surface that comprises a first side in contact with the interior of the wells and a second side in contact with the exterior of the multi-well cell growth device; wherein the first side comprises a topography that provides a plurality of cell growth compartments; wherein the bottom surface comprises a material that is at least partially permeable to a gas; and wherein the bottom surface is configured such that a gas from the exterior of the multi-well growth device can pass from the exterior into the interior of the wells and can contact one or more of the plurality of cell growth niches and/or a gas from within the one or more cell growth niches can pass from the first side to the second side.

In embodiments, the topography of the first side comprises one or more of fins, sub-wells, and pillars, the fins, sub-wells and pillars at least partially defining the plurality of cell growth compartments.

In embodiments, the sidewalls of the multiple wells at least partially comprises a gas permeable material.

In embodiments, the second side comprises one or more variations in its geometry that permits gas to at least partially pass below the bottom surface when on a flat surface.

In embodiments, the geometry comprises pillars, channels, grooves, bumps, protrusions, or legs.

In embodiments, the geometry comprises one or more spacing pillars.

In embodiments, there are provided cell cultivation apparatuses comprising: a membrane comprising a plurality of fin structures running substantially parallel to each other, the substantially parallel fin structures defining grooves between adjacent fin structures, at least one groove on a first side of the membrane providing at least a compartment for cell placement; the membrane comprising a material that is at least partially permeable to gas; a second side of the membrane defining a gas region, the second side of the membrane being separated from the first side of the membrane by the membrane, a gas capable of passing through the membrane; and a media region on the first side of the membrane configured for receiving media including one or more cells depositable in the compartment.

In embodiments, there are provided cell respirator apparatus comprising: one or more membranes, at least one membrane from the one or more membranes having a plurality of fins including at least a first fin and a second fin protruding from a first surface of the membrane to form a first compartment of a plurality of compartments configured for retaining a plurality of cells, the membrane being formed of material that is gas-permeable and transmissive to facilitate delivering gas to the plurality of compartments through one or more channels formed under the first surface of the membrane below the plurality of fins, at least a first channel from configured to directly deliver the gas to the first compartment.

In embodiments, there are provided methods of culturing biological cells, comprising, providing an apparatus according to any of claims 1-83, and introducing biological cells into the apparatus, providing a cell media into the first side of the apparatus such that the cell media is in contact with the biological cells.

In embodiments, methods further comprise providing a gas to the second side of the membrane.

In embodiments, methods further comprise flowing media over one or more cell niches.

In embodiments, the flowing of media comprises introducing media through an inlet and removing media through an outlet.

In embodiments, methods further comprise flowing gas into the second side of the membrane.

In embodiments, the flowing of gas comprises introducing gas through an inlet and removing gas through an outlet.

In embodiments, methods further comprise flowing media, biological cells or another material into the one or more cell niches by creating a negative pressure in the one or more compartments.

In embodiments, methods further comprise maintaining cells in the one or more compartments by creating a negative pressure in the one or more compartments.

In embodiments, methods further comprise flowing media, biological cells or another material out of the one or more cell niches by creating a positive pressure in the one or more compartments.

In embodiments, methods further comprise directing cells out of the one or more compartments by creating a positive pressure in the one or more compartments.

In embodiments, methods further comprise mixing one or more of the biological cells within the one or more compartments by creating a positive pressure and/or a negative in the one or more compartments.

In embodiments, the positive and/or negative pressure is created by flowing gas into the gas region, flowing media into the media region, flowing both gas and media into their respective regions, preventing the flow of gas into the gas region, and/or preventing the flow of media into the media region, thereby creating a pressure differential between the two regions.

In embodiments, the biological cells are selected from the group consisting of human, non-human mammalian, insect, bacterial, fungal, yeast, 3T3-L1, 4T1, 9L, A20, A172, A253, A431, A549, A2780, A2780ADR, A2780cis, AB9, AHL-1, ALC, B16, B35, BCP-1, BEAS-2B, bEnd.3, BHK-21, BOSC23, BT-20, BxPC-3, C2C12, C3H-10T1/2, C6, C6/36, Caco-2, Cal-27, Calu-3, CGR8, CHO, CML T1, CMT12, COR-L23, COR-L23/5010, COR-L23/CPR, COR-L23/R23-, COS-7, COV-434, CT26, D17, DAOY, DH82, DU145, DuCaP, E14Tg2a, vEL4, EM-2, EM-3, vEMT6/AR1, EMT6/AR10.0, FM3, GL261, H1299, HaCaT, HCA2, HEK 293, HEK 293T, HeLa, Hep G2, Hepal cic7, High Five, HL-60, HT-29, HT-1080, J558L, Jurkat, JY, K562, KBM-7, KCL-22, KG1, Ku812, KYO-1, L243, L1210, LNCaP, MA-104, Ma-Mel, MA2.1, MC-38, MCF-7, MCF-10A, MDA-MB-157, MDA-MB-231, MDA-MB-361, MDA-MB-468, MDCK II, MG63, MIA PaCa-2, Mono-Mac-6, MOR/0.2R, MRC-5, MTD-1A, MyEnd, NALM-1, NCI-H69, NCI-H69/CPR, NCI-H69/LX4, NCI-H69/LX10, NCI-H69/LX20, Neuro-2a, Neuro2a, NIH-3T3, NK-92, NTERA-2, NW-145, OK, OPCN/OPCT cell lines, P3X63Ag8, PANC-1, PC-3, PC12, Peer, PNT1A, PNT2, Pt K2, Raji, RBL-1, RenCa, RIN-5F, RMA-S, S2, SaOS-2, Sf9, Sf21, SH-SY5Y, SiHa, SK-BR-3, SK-N-SH, SK-OV-3, T-47D, T2, T84, T98G, THP-1, U2OS, U87, U373, U937, VCaP, Vero, VG-1, WM39, WT-49, YAC-1, and YAR cells.

In embodiments, the gas is selected from the group consisting of oxygen, carbon dioxide, nitrogen, carbon monoxide, nitrous oxide, hydrogen sulfide, ethylene oxide, ozone, chlorine dioxide, and nitrogen dioxide.

In embodiments, the media is selected from the group consisting of DMEM, FCS, 293 SFM II, AEM, CDM4HEK293, SFM4HEK293, Ex-Cell 293, SFM4Transfx-293, Freestyle 293, ESF SFM, CDM4CHO, CHO medium, MEM, MEM Alpha, RPMI, F-10, F-12, IMDM, Medium 199, Leibovitz L-15, McCoy's 5A, MCDB media, William's media, CMRL media, OptiMEM, OptiPro, AIM V, OptiPEAK T Lymphocyte, ExCellerate Human T Cell Expansion Media, StemXVivo Serum-Free Human T Cell Base Media, ExpiSf CD Medium, Sf-900 SFM, and TC-100 Insect Medium.

In embodiments, other material is selected from the group consisting of waste material, a material secreted from the cell, material internal to the cell, cellular debris, and gas.

In embodiments, methods further comprise introducing a freezing agent into the gas region to freeze cells and cell components in the plurality of compartments, the freezing agent having a temperature below zero ° C., the freezing agent being in a gas state or a liquid state.

In embodiments, the membranes and devices disclosed herein may be employed in methods for isolating cells. For example, methods of isolating cells may comprise pulsing with media to create turbulence and flow to a collection outlet. Alternatively, methods of isolating cells may comprise creating pressure from the gas region to force a portion of the membrane upward and/or inward from the sides of the one or more compartments to push cells out of the one or more compartments. Further, methods of isolating cells may comprise a combination of pulsing with media to create turbulence and creating pressure from the gas region to force a portion of the membrane upward and/or inward from the sides of the one or more compartments to push cells out of the one or more compartments. In addition, methods of isolating cells may comprise mechanical stretching of the membrane, combined with flowing media across the membrane. Alternatively, methods of isolating cells may comprise mechanical stretching of the membrane and tipping the membrane over to allow the cells to be freed from the one or more compartments.

In embodiments, the membranes and devices disclosed herein may be employed in methods for isolating biological materials other than cells from a culture, such as virus particles, proteins, cell metabolic products and the like. In embodiments, the methods may be used to isolate proteins. In embodiments, the methods may be used to isolate viruses (virus particles). In embodiments, methods may be used to isolate cell metabolic products.

In embodiments, methods for isolating biological materials may comprise flowing media into the one or more compartments to wash the biological materials out of the one or more compartments and flowing media to a collection outlet, while the cells remain in the one or more compartments. For example, methods for isolating biological materials may comprise applying pressure from the gas region of the membrane. Alternatively, methods for isolating biological materials may comprise flowing media into the one or more compartments and applying pressure from the gas region. In embodiments, methods of isolating biologic materials comprises separating the biological material from the cells. For example, methods may comprise continuously separating the biological materials during culturing. Alternatively, methods may comprise separating the biological materials after culturing.

Membranes for HDCRs

FIG. 1 provides a functional overview of a HDCR 100 that separates nutrient and oxygen delivery for high yield of viral vectors. The cell respirator 100 includes a membrane 110, a gas channel 125 that runs through the membrane 110, and surface features in the form of fin structures 120 on a first side of the membrane 110. The first side of the membrane 110 corresponds to the upper side of the membrane in FIG. 1. The fin structures 120 are shown in cross section in FIG. 1, and in perspective in FIG. 7 (see fins 720 in FIG. 7). The fin structures 120 run substantially parallel to each other along the length of the fin structures 120. The substantially parallel fins structures 120 define grooves 130a-d between adjacent fin structures. Grooves 130 between adjacent fin structures provide compartments that may be used for cell placement and production.

The gas channel 125 runs through membrane 110, as illustrated in FIG. 1. Spacing pillars 190 also provide an interface for gas external to the membrane 110 from below. Various exemplary embodiments may include none, one, or more gas channels 125, and/or spacing pillars 190. In some exemplary embodiments, the spacing pillars 190 may be located on a top of the membrane 110, such that, when stacked, there remains a gap for media perfusion. The spacing pillars 190 located on the top of the membrane 110 is an implementation used in cartridge-style HDCR (e.g., FIGS. 8D, 8E and/or 8F). The spacing pillars on the bottom may be used in 24-well and petri-style HDCR devices.

The membrane 110 is formed of material that is permeable to gas, so that oxygen and other gases may be exchanged with the compartments formed by grooves 130a-d. This allows gas exchange from below, and on the sides, of the compartments formed by grooves 130a-d.

The membrane 110 may be permeable to gas, but less permeable, or impermeable, to media in liquid or suspension states. A media region 140 enables the flow of media to the grooves 130a-d. Media flows in a direction substantially perpendicular to the fin structures 120 and grooves 130a-d. In embodiments, for cell harvesting, media may flow in a direction substantially aligned with the fin structures 120. Media flows substantially perpendicular to the fin structures 120 facilitates cell retention within the grooves 130a-d. Media flows substantially aligned with the fin structures 120 facilitates harvesting of cells from the grooves 130a-d.

In a first stage, media containing cells may flow across media region 140 to seed compartments formed by grooves 130a-d. Cells 150a may then flow into the compartments, as illustrated in groove 130a. In order to illustrate a production timeline, five cell production stages are numbered for initial cell flow 160, cell retention 165 in the compartments, gas exchange 170 via the gas permeable membrane 110, production of cells 175, and cell harvesting 180. For clarity, cell retention 165 is illustrated in groove 130a, gas exchange is illustrated in groove 130b, production with media exchange is illustrated in groove 130c, and harvest is illustrated in groove 130d. However, each of these stages occur across all of the grooves 130a-d, in a time sequence. For example, cells are harvested from all of the compartments at substantially the same time, after production.

During initial cell flow 160, media containing cells 150a to be transported to the grooves 130a-d flows through the media region 140. As represented in groove 130a, cells that were transported to the grooves 130a-d are largely retained 165 in the compartments. The media that flows across media region 140 to the compartments in grooves 130a-130d may also supply nutrients or reagents to the cells 150a-d within the compartments.

The media flows in a direction substantially perpendicular to the length of the fin structures 120 and grooves 130a-d. For example, in FIG. 1 the media flows from left to right, through the media region above the first surface of the membrane 110 with fins 120 and grooves 130a-d. This media flow substantially perpendicular to the compartments formed in grooves 130a-d results in less momentum transfer from the media region to the compartments within the grooves 130a-d than would be the case if the media flow was in line with the grooves a-f, or there weren't compartments with depth. Momentum transfer from the media region to the compartments is therefore lower than it would be if the media flowed in a direction in line with the length of the grooves, or if there were not compartments formed by the surface structures on membrane 110. This reduced or minimized momentum transfer and flow to the compartments results in reduced or minimized shear forces on the cells 150a within the compartments formed by the grooves, which reduces the cytopathic impact on the cells 150a in the compartments and prevents cellular washout during the stages of cell or bioproduct production.

While media flows from above via the media region 140, gas exchange 170 occurs via the gas permeable membrane 110 with fins 120, between the compartments. For example oxygen from the gas channel 125 or the pillars 190 may flow into the cell niche in groove 130b to oxygenate the cells 150b, and carbon dioxide waste gas from the cells may flow out of the cell niche in groove 130b into the membrane 110 with fins 120. This gas exchange makes it possible to keep the cells 150b oxygenated while preventing a buildup of carbon dioxide.

Cells expand to high densities and produce or are induced to produce bioproduct (e.g., protein, virus, metabolite) production 175. In addition to gas exchange, cell, virus, and bioproduct production 175 also requires the delivery of nutrients for cell growth, and the removal of waste products. Nutrients for cell growth may be delivered in media via the media region 140 to cells 150c in the cell niche formed by groove 130c. In addition, waste products from the respiration of cells 150c may be carried away in the media via the media region 140.

By separating oxygenation from delivery of soluble nutrients in media, the HDCR 100 may sustain much higher cell densities than current bioreactors. The integrated cell-retaining grooves also protect cells from shear forces, which typically impact cell viability in conventional bioreactors, thus increasing productivity. This may result in higher yield, faster production, and lower cost.

For example, the volume of cells (Vcell) may occupy about 10%-25% of the volume of the reactor available for cell growth (Vbioreactor). The volume of the reactor available for cell growth may correspond to the volume of the grooves 130a-d. For some cells in some embodiments, this may translate to a density of about $10^8$ cells/mL.

Once produced, the bioproduct, such as cells or virus containing cells 150d, may be harvested using trypsin, EDTA, or turbulence.

Membrane 100 may be formed of materials that allow for high gas permeation (a function of solubility and diffusion rate) such as silicones, including polydimethylsiloxane (PDMS).

Gas transmission rates are generally inversely proportional to membrane thickness. At very thin dimensions, the permeability of the material may also increase significantly, such as is observed with thin parylene (<10 μm). Using this fact, polymers that are conventionally thought of as barriers to gases can become suitably transmissive. Porous membrane materials may also be used since the blow point of small pores can be sufficiently high to allow pressure driven flow within the hollow membrane without causing bubbling of gas through the surface. A combination of approaches can also be used to accomplish the desired high gas transmission properties of the membranes.

Surface treatment of the membrane 100 and surface features can facilitate cell adhesion and proliferation. A broadly applicable approach is to coat the membrane with a thin layer of parylene and plasma etch it, using an oxygen plasma treatment and/or an ammonia plasma treatment, to make it hydrophilic and/or to improve cell adhesion.

Additional methods include coating with proteins (e.g., agarose, collagen, fibronectin, fibrin) or other coatings (e.g., lactic acid, laminin, poly-D-lysine, or poly-L-lysine).

HDCRs that include membranes consistent with FIG. 1 have the following features and advantages. First, gas exchange and nutrient delivery are decoupled. In particular, oxygen and carbon dioxide exchange occur via membrane and surface feature (such as fin) permeation at compartments, while media is independently perfused over the compartments. This enables production of cell densities on the order of about $10^8$ cells/mL, or a Vcell/Vbioreactor ratio of about 10%-25%, which enables more efficient media usage than traditional methods of cell production, and eliminates the need for base addition as required in traditional methods of cell production.

Second, the compartments and/or patterned recesses in the HDCR membrane offers integrated cell retention, in which membrane 100 retains cells and protects them from shear forces and washout generated by the perfusion of media over the compartments. This structure for membrane 100 reduces or eliminates the loss of cells due to cytopathic effect. It also eliminates the need for an auxiliary acoustic, TFF, or other auxiliary filtration system. The compartments and/or patterned recesses are suitable for growing cells in suspension, for growing adherent cells, or for growing microcarrier compatible cells.

Third, the membrane 100 offers homogeneous conditions with a micropatterned architecture of HDCR membranes with substantially identical compartments or compartments for cell expansion, engineered to be below both gas and media diffusion limits, even at high-cell density. An extremely high gas-exchange area to volume ratio maximized the oxygen transmission rate, which is often a limiting factor for cell respiration. These membranes allow for uniform conditions throughout an apparatus for cell production. They also offer precise control of oxygen tension, for faster cell expansion and higher viral titers. The homogeneous conditions enable open loop control of oxygen, with, for example, a volumetric mass transfer coefficient of oxygen of kLa>about 40/hr.

The geometry of the cell niche can be adjusted depending on the metabolic needs of the cells and production process. For example, cultures with lower volumetric metabolic rates can use niches with deeper and wider grooves, which offers a higher ratio volume ratio for cell expansion, Vcell/Vbioreactor. Conversely, cultures with higher volumetric metabolic rates (e.g., bacteria) can be accommodated by using shallower, narrower grooves, at the expense of Vcell/Vbioreactor. The optimal tradeoff between niche volume, gas exchange rates, cell retention, and nutrient/waste exchange are carried out using an integrated multiphysics finite element model.

Fourth, the membrane enables space efficient implementations, with a bed length greater than, for example, 40 cm—as compared to 4 cm bed length in existing packed bed designs. This enables generation of more optimal form factors, for increased volumetric productivity of GMP space. Moreover, the membranes 100 may be stacked, packaged, and fit in standard cell incubators. Simulations and preliminary data support the goal of achieving an extremely high density of about $10^8$ cell s/mL or a Vcell/Vbioreactor ratio of about 10%-25%. A yield of about $10^4$-$10^5$ vector genomes per cell (vg/cell), translates to $10^{13}$ vg/ml production. Thus, production of an about $10^{16}$-$^{17}$ vg batch of cGMP vector may be possible in about 1-10 liters of media rather than the about 500-1000 liters required with current methods. What previously required rooms of production space will be produced in a single incubator. At such high efficiency, the embodiments described herein may decrease cost and speed production, disrupting the fields of virus, vector, and vaccine production with increases in volumetric yields by about 10× and speed production by about 2-10×.

Fifth, membrane 100 has a mass-producible, scalable design that is compatible with, for example, liquid silicone rubber (LSR) injection molding. The membranes easily scale, and may be stacked. Therefore, the membranes 100 may be produced at low cost in established production ecosystems. They may be implemented in expandable batch sizes up to clinical scale.

Sixth, the membranes 100 offer low fluidic resistance, with a dedicated media space above the compartments that enable a low resistance fluidic path. This eliminates the need for expensive or power pumps. Cartridges with membranes 100 may have media gravity fed, with a flow regulator.

Seventh, the membranes 100 are configured to expand and contract in response to variations or pulsing of gas or fluidic pressure to induce mixing in compartments. Such mixing enables a more uniform dispersal of reagents or virus in compartments. Such mixing capability may also facilitate harvesting of cells.

Modeling High Density Cell Regulators

Figure 2:
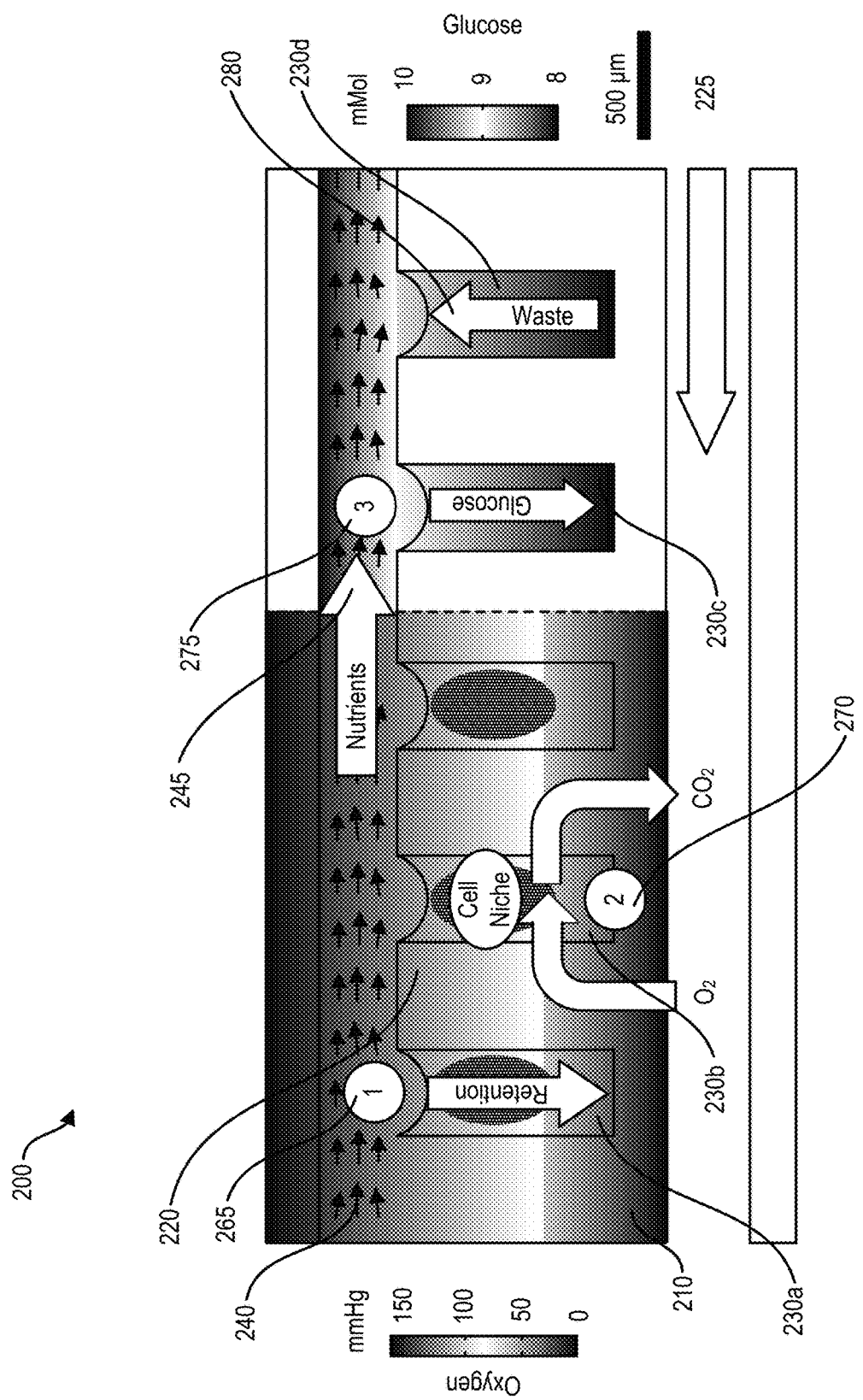
FIG. 2 is a model of the high density cell respirator device of FIG. 1.

FIG. 2 illustrates a model of the HDCR device of FIG. 1. Development of a multiphysics finite element model (FEM) (Comsol Inc, MA, USA) enables an understanding of the interrelations between cell growth, nutrient and gas transport, cell retention, perfusion rates, and pressure drop in the HDCR device 200 of FIG. 2. The HDCR 200 includes a membrane 210 with fins 20, with compartments in grooves 230a-d.

At 240, liquid media flows through a media region above the membrane 210. At 265, cells in the liquid media settle into, and are retained, in the cell niche in groove 230a. The thin solid line (U-shaped, meniscus descending towards a bottom of the cell niche) over the niche indicates a fluidic boundary where an upward component of a flow velocity is less than a settling velocity of cells (i.e., a washout boundary). Therefore, cells below the boundary will be retained. This experiment assumed an about 100 μm/sec inlet velocity for media. The device and system may be configured for media inlet velocity on the order of between about 1 μm/sec and about 1 m/sec. The relatively low speed operation velocities may correspond with a fluidic steady state (i.e., a retention mode) in the compartment(s). The relatively high speed operation velocities may correspond with a fluidically turbulent state (i.e., a flushing mode) in the compartment(s). The 100 μm/sec inlet velocity for media was sufficient to promote, relative to the compartment(s), laminar or near laminar nutrient flow in a primary media path, glucose input, cell growth and retention, waste output, sufficient mixing, without excess cell loss. Note, during the expansion process, there is increased cell-cell and cell-substrate adhesion, so the "true" washout boundary may be higher. The length of the arrows in the perfused media compartment are proportional to the flow velocity; thus, smaller arrows correspond with lesser flow velocity.

There is considerable freedom to operate at different media velocities because of provision of a dedicated media path. Flow may be as low as about 1 μm/sec, up to several cm/sec, and as high as about 1 m/sec. Additionally, the media perfusion can be pulsatile or intermittent (i.e., a bolus of fresh media is fed into the system and then stopped, consumed, and displaced with a fresh bolus of media and so on). The media flow rate may be set such that, upon exiting the reactor, the media has lost about 50% of a glucose content of the media. Flow rate may be feedback controlled. When cell densities are relatively low, a need for perfusion may be proportionally lower. For example, a velocity of about 100 μm/sec was determined to be sufficient for a bioreactor having a length (in the y-axis) of about 40 cm to produce about $10^8$ cells/mL. Also, for a seeding step, a velocity of about 1 μm/s was determined to be sufficient to produce about $10^6$ cells/mL (i.e., a reasonable seeding density).

At 225, gas perfuses from a gas channel under the surface of the membrane 210 through the membrane 210 with fins 220, to and from the cell niche (compartment) in groove 230b. At 270, this enables the delivery of oxygen to and the removal of carbon dioxide from, the cell niche in groove 230b. At 245, soluble nutrients including glucose are delivered from the media stream to the cell niche in groove 230c by diffusion. At 280, soluble waste products are removed from the cell niche in groove 230 to the media stream by diffusion. For clarity of presentation these steps 265, 270, 275, and 280 are illustrated as taken place in individual compartments in grooves 230a, 230b, 230c, and 230d, respectively, but in embodiments, as well as the finite element model, these steps take place across multiple compartments in grooves across the membrane 210.

The finite element model models each of the cell delivery and retention 265, gas exchange 270, nutrient delivery 275, and waste removal 280 operations for the high density gas respirator 200. The model makes it possible to adjust dimensions, flows, concentrations, orientations, and pressures to help design membranes for different applications.

For example, an embodiment includes a design that supports system cell densities of about $2 \times 10^8$ cells/cm$^3$ with a media flow rate of about 0.1 mm/s. This media flow rate is slow enough for single cell retention, and can deliver membranes exceeding about 40 cm in length. This embodiment requires a pressure head of only about 5 Pa, and ensures all cells experience an oxygen tension greater than a typical cellular Michaelis-Menten constant for oxygen (KM,O2=about 1 μM).

Membranes for this embodiment may be fabricated using a mold making process via CNC machining, which enables precise membrane structures via silicone casting or LSR injection molding. This allows for integration of pillars, connectors, niches, and manifolds directly into the membranes at high yield and low cost. Chemical vapor deposition and plasma processes may be used to render membrane surfaces hydrophilic/wettable, and enable cell adhesion.

The membranes for this embodiment may be connected and stacked to create a HDCR cartridge, such as the cartridge described below with respect to FIGS. 8A-8F.

Dynamic Features of Membranes

Figure 3:
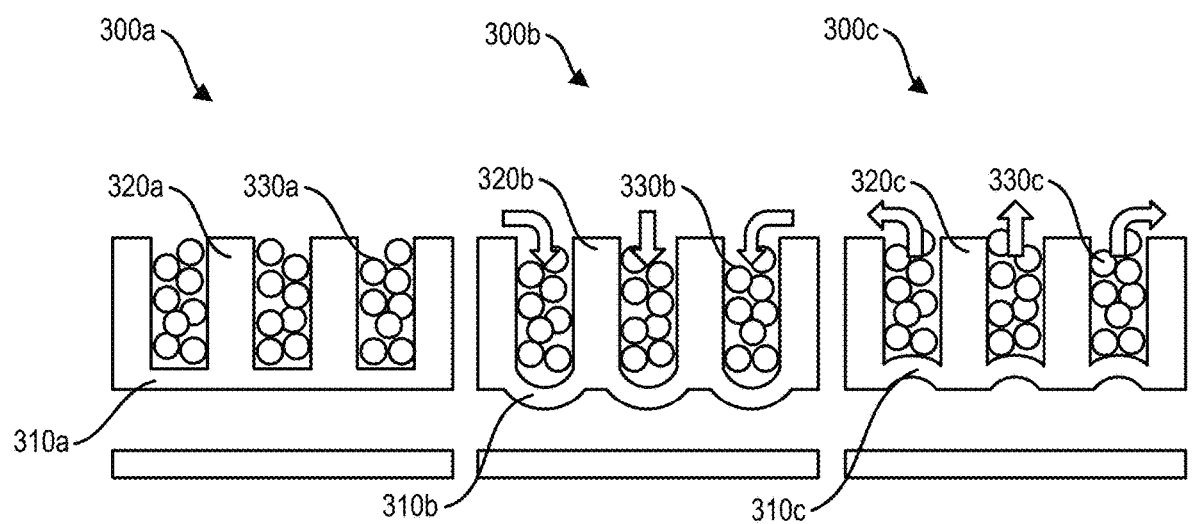
FIG. 3 illustrates deformations of the membrane of FIG. 1 in the presence of pressure variations, resulting in media flows to and from compartments of the high density cell respirator device of FIG. 1.

FIG. 3 illustrates deformations of the membrane of FIG. 1 in the presence of pressure variations, resulting in media flows to and from compartments of the HDCR device of FIG. 1. In general, the membrane can deform in response to changes in pressure. For example, it can deform upwards or down, towards or away from pressure.

In 300a of FIG. 3, membrane 310a is at neutral pressure. Therefore, membrane 310a with fins 320a and grooves 330a is not deformed. Cells, nutrients or waste in media flowing above membrane 310a may diffuse between grooves 330a and the media stream above the grooves, but cells or other liquids are neither being drawn in to the grooves 330a or expelled from the grooves 330a, due to a pressure variation.

In 300b of FIG. 3, membrane 310b is at negative pressure. Therefore the lower surface of membrane 310b, in the region of grooves 330b between fins 320b, is deformed downwards due to the negative pressure exerted on the membrane 310b. Cells, nutrients, or other matter are drawn into grooves 330b due to the deformation of membrane 310b and the negative pressure (in a downwards direction in FIG. 3).

In 300c of FIG. 3, membrane 310c is at positive pressure. Therefore the lower surface of membrane 310c, in the region of grooves 330c between fins 320c, is deformed upwards due to the positive pressure exerted on the membrane 310c. Cells, waste, or other matter are drawn out of grooves 330b due to the deformation of membrane 310c and the positive pressure (in an upwards direction in FIG. 3).

Pressure can be varied, cycled, or pulsed between the neutral pressure, negative pressure, and positive pressure states of 300a, 300b, and 300c. This variation, cycling, or pulsing may enable cyclical or pulsing movement as illustrated by the stages of 300a, 300b, and 300c. Such variation, cycling, or pulsing can be used to mix the contents of the compartments in the grooves 330a-c.

Figure 4:
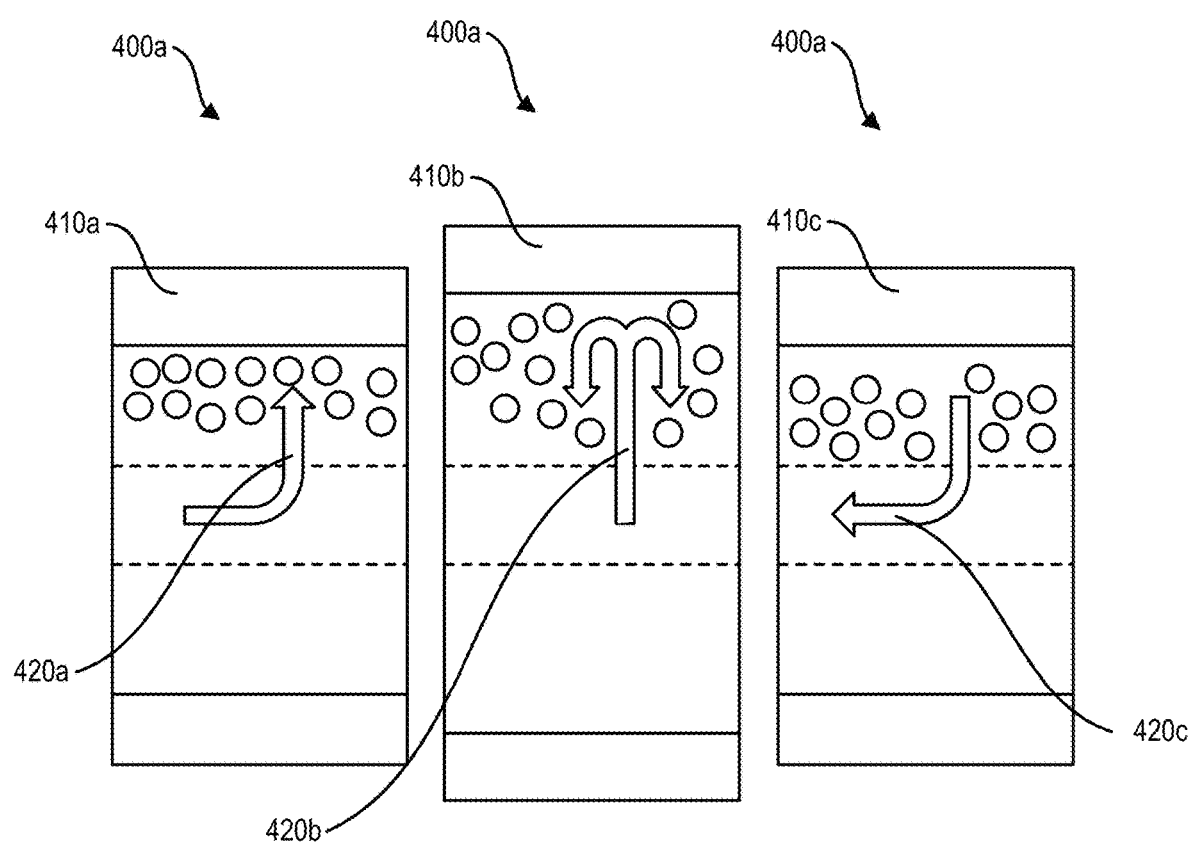
FIG. 4 illustrates the use of pulsatile flow to enhance mixing and nutrient transport in accordance with various exemplary embodiments of the disclosed technology.

FIG. 4 illustrates the use of pulsatile flow to enhance mixing and nutrient transport in accordance with various exemplary embodiments of the disclosed technology. Periodic pulsing of fluidic pressure through/across a membrane can induce expansion and media mixing or jetting in cell compartments to enhance nutrient and oxygen transport. A planar (sheet) membrane may incorporate microdiffusers to rectify pulsatile pressure into net flow perpendicular to a main flow path. Stages of periodic pulsing are illustrated in stages 400a, 400b, and 400c. In 400a, membrane 410a is in a neutral state, and fluid pressure is increasing, so that the flow 420a is flowing towards upwards. Pressure increased in 400b, so that membrane 410b expand in size, causing fluid to flow 420b upwards with greater intensity, causing more mixing. Pressure then decreases in 400c, causing fluid to flow downwards 420, reducing pressure on the top edge of the membrane, and reducing the size back to the size of the membrane in 410a. These stages 400a, 400b, and 400c may repeat, resulting in mixing in a cell niche.

Membrane Architectures and Surface Features

Figure 5:
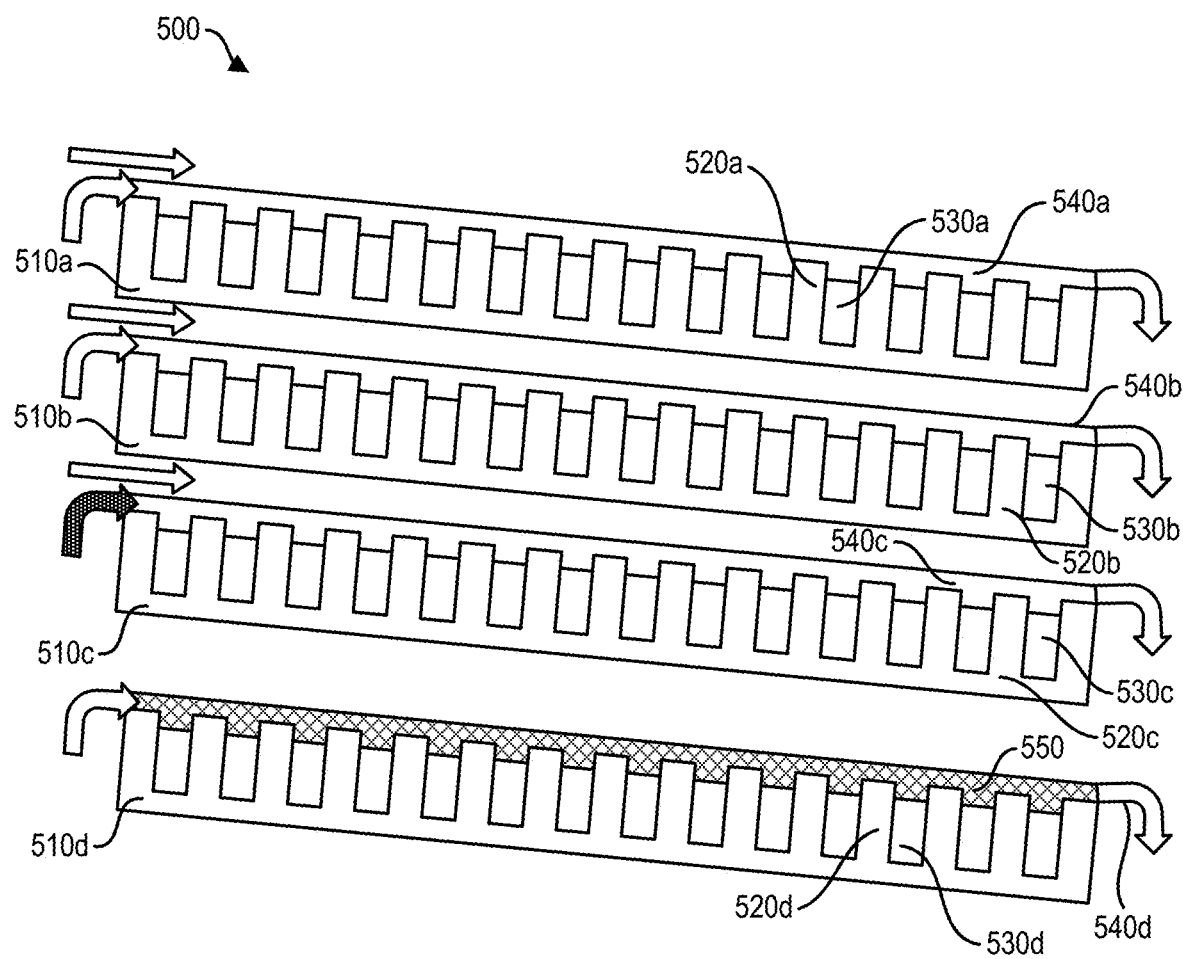
FIG. 5 illustrates open membrane architectures, in which cells settle into and are retained in grooves that form compartments, media flows over the cells, the flow of media draws air into the compartments, and, in various exemplary embodiments, a porous and/or fibrous membrane that wicks media over compartments.

FIG. 5 illustrates open membrane architectures.

Membrane 510a has fins 520a and compartments in grooves 530a between the fins 520a. Media flows through media region 540a. Cells from the media settle in the grooves 530a. Fluidic manifolds supply media to the media region 540a. Media can be collected, recirculated, or discarded.

Membrane 510b has fins 520b and compartments in grooves 530b between the fins 520b. Media flows through media region 540b. The membrane is disposed at an angle so that media flow is gravity-driven, as media flows downhill. Fluidic manifolds supply media to the media region 540b. Media can be collected, recirculated, or discarded.

Membrane 510c has fins 520c and compartments in grooves 530c between the fins 520c. Media flows through media region 540b. The membrane is disposed at an angle so that media flow is gravity-driven, as media flows downhill. The flow of media acts to draw air in. Fluidic manifolds supply media to the media region 540b. Media can be collected, recirculated, or discarded.

Membrane 510d has fins 520d and compartments in grooves 530d between the fins 520d. Media flows through a porous or fibrous membrane 550, in media region 540d. The porous or fibrous membrane 550 acts as a wick to draw fluid in and deliver it to or from the grooves 530d. The membrane is disposed at an angle so that media flow is gravity-driven, as media flows downhill. The flow of media acts to draw air in. Fluidic manifolds supply media to the media region 540b. Media can be collected, recirculated, or discarded.

Figure 6:
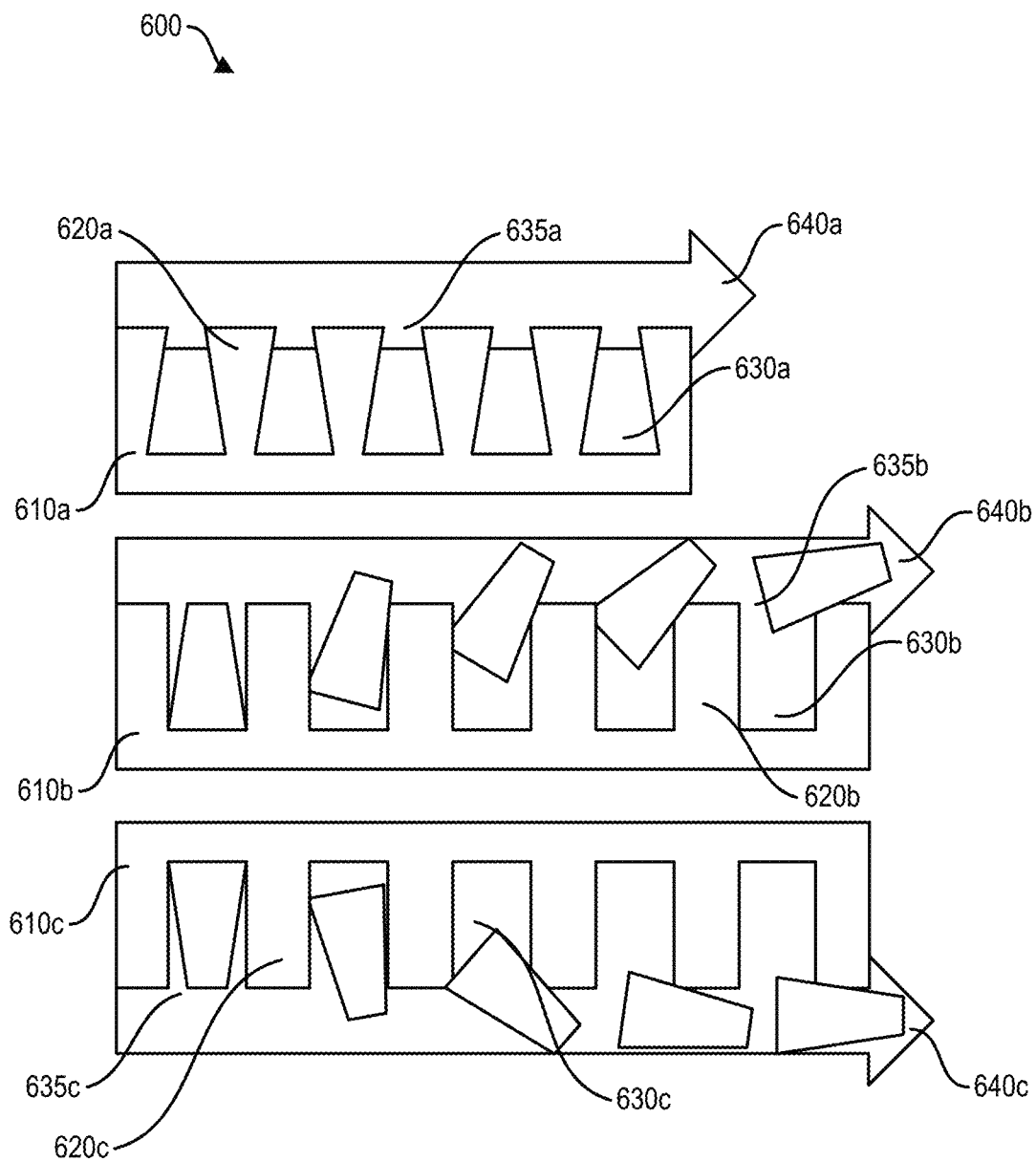
FIG. 6 illustrates a membrane with fins with a keystone shape that form grooves with an opening at the top of the groove that is narrower than at least some points closer to the surface of the membrane.

FIG. 6 illustrates a membrane 610a with fins 620a with a key stone shape that form grooves 630a in which an opening 635a at the top of a groove 630a is narrower than at least some points closer to the surface of the membrane 610a. This keystone fin geometry differs from the fin geometry of the fins pictured in FIGS. 1, 2, 3, and 5.

Other fin shapes are possible. The fins may be tapered, curved to form grooves with a teardrop shape, be prismatic, or have any other shape that forms compartments that protect cells within the niche from shear. One feature of the keystone shape, that applies to some other shapes, such as a teardrop shape, is that the opening at the top of the groove may be narrower than the cross sectional width at a lower elevation, closer to the surface of the membrane. Such narrow openings may afford further protection to the cells from shear, and may improve the ability to retain expanding cells.

Mechanical stretching of membrane 610b causes the length of the membrane 610 to stretch in a direction along the cross sections of the fins 620b and grooves 630b. This results a widening of the opening 635b at the top of groove 630b, making it easier to remove the contents of groove 630b, as illustrated in FIG. 6.

In addition to mechanical stretching, a membrane 610c may be inverted, so that fins 620c and corresponding grooves 630c are inverted (point down instead of up). Groove 630c has an opening 635c that points downwards, so that the contents of groove 630c fall out by the force of gravity. Membrane 610c can be stretched and/or inverted.

Figure 7:
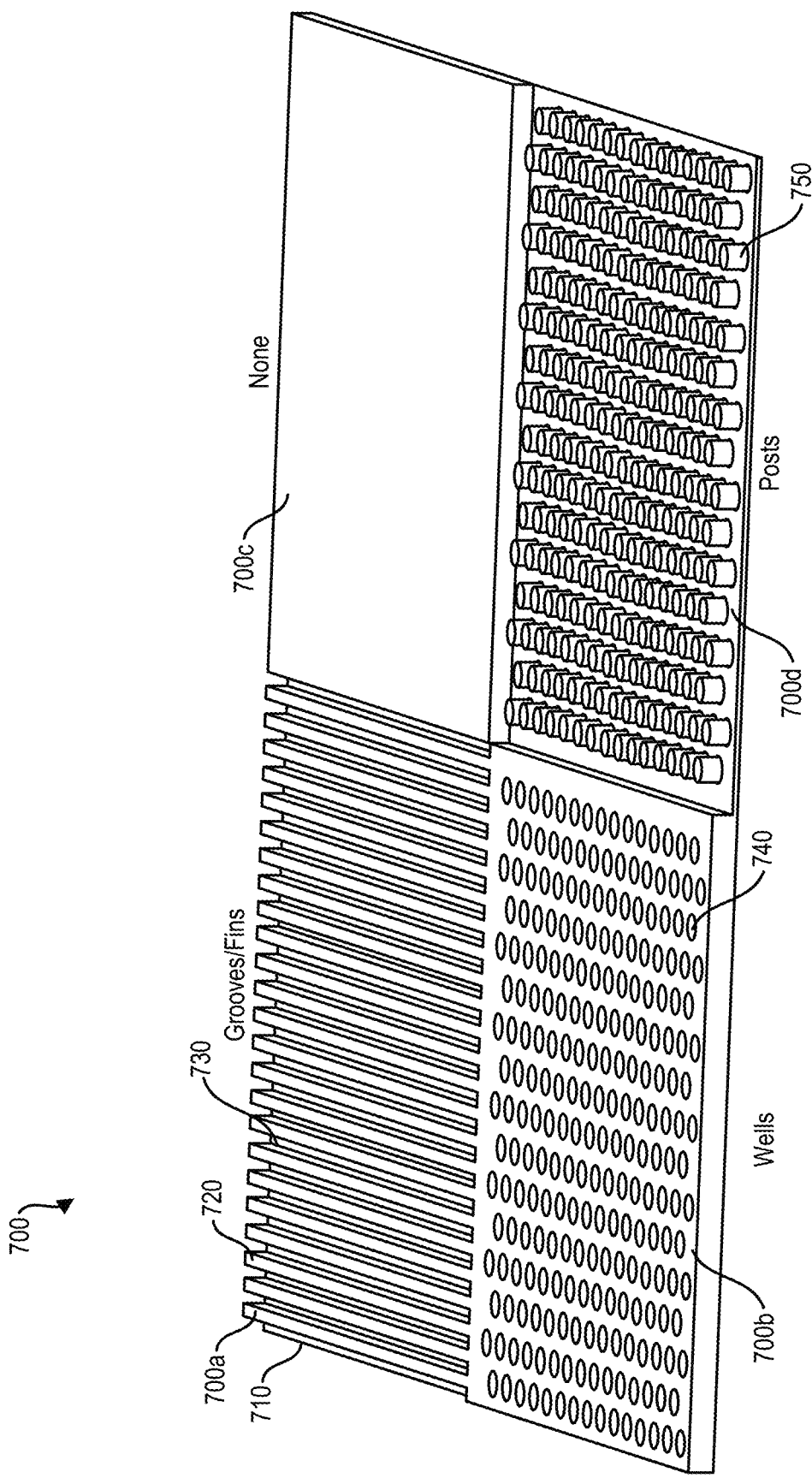
FIG. 7 illustrates membranes with no surface features, with fins and grooves, with wells, and with posts in accordance with an exemplary embodiment.

FIG. 7 illustrates a variety of membranes corresponding to different embodiments.

Membrane 700a includes a flat surface 710 with protruding fins 720. The fins 720 are substantially parallel. Grooves 730 are formed between adjacent fins 720. The fins 720 have a rectangular or prismatic cross section, as do the grooves 730 formed between the fins. As noted with regard to FIG. 6, other fin cross sectional shapes are possible, such as keystone, teardrop, prismatic, tapered, polygonal, or curved. Some fins 720 may be shaped with a narrower opening than a width of a cross section at a lower elevation (closer to surface 710). The membrane 710 and fins 720 are gas permeable, so that gas may perfuse through the membrane and/or fins to compartments within the grooves 730. Media may flow across the top of the fins 720 and grooves 730, in a direction that is not parallel to the length of the grooves 730. Instead, the media may flow in a direction substantially perpendicular to the length of the fins 720 and grooves 730, to lessen shear forces on cells within compartments within the fins.

Membrane 700b includes a two dimensional array of wells 740. The wells 740 serve a similar function as the grooves 720, in that the form protective compartments that protect cells from shear as media flows over the surface. The membrane 700b is gas permeable, so that gas perfuses to and from the wells via the membrane and well walls.

Membrane 700c does not include surface features. In embodiments without surface features, the membrane 700c is gas permeable.

Membrane 700d includes an array of posts 750. The posts 750 form compartments proximate to the posts. Posts with a crescent, chevron, or U-shape may provide better protection in one direction of flow than posts with other shapes. These compartments are more open than the niches within wells 740 or grooves 730, but they do offer some protection to adherent cells that may adhere to the posts 750. The posts 750 are gas permeable, so that gas perfuses to and from cells adhered to, or proximate to, the posts 750.

The fins 720, wells 740, and posts 750 are examples of surface features that protrude from, or are recessed into a membrane. The surface features all may be gas permeable.

HDCRs may use one, or a combination of, membranes with fins 700a and grooves, membranes with wells 700b, membranes without surface features 700c and or membranes with posts 700d.

HDCR Cartridges

Figure 8A:
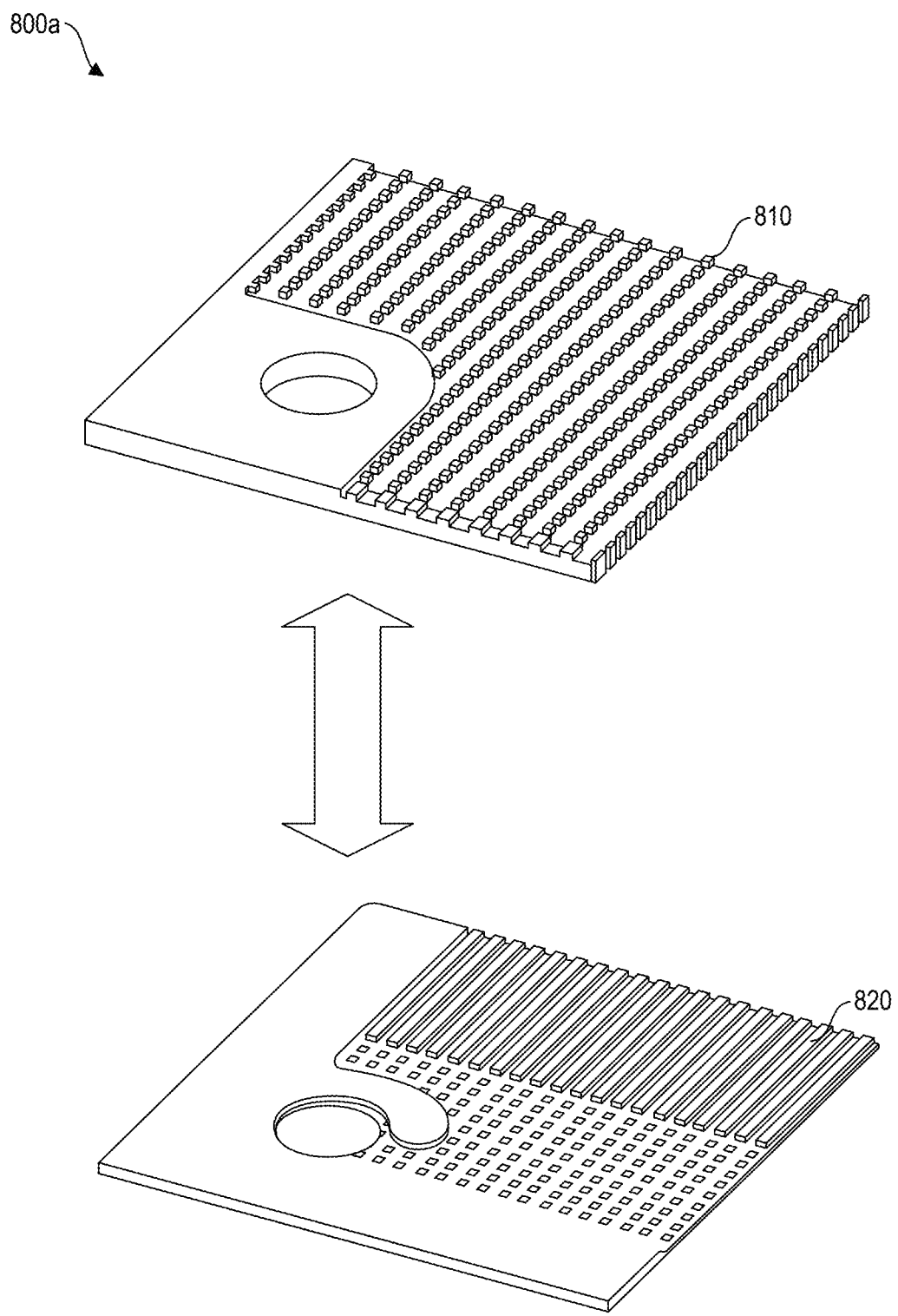
FIG. 8A illustrates the structure and formation of a high density cell respirator device formed of a media layer bonded to a gas layer in accordance with an exemplary embodiment.

FIG. 8A illustrates the structure and formation of a HDCR device. FIG. 8A shows a quarter view of a media layer 810, which is bonded to a gas layer 820. The media layer 810 and gas layer 820. The gas layer 820 is bonded to and below the media layer 810, so that gas exchange and oxygenation from below is physically separate from liquid media perfusion from above. The media layer 810 and gas layer 820 may be formed of polydimethylsiloxane (PDMS).

Figure 8B:
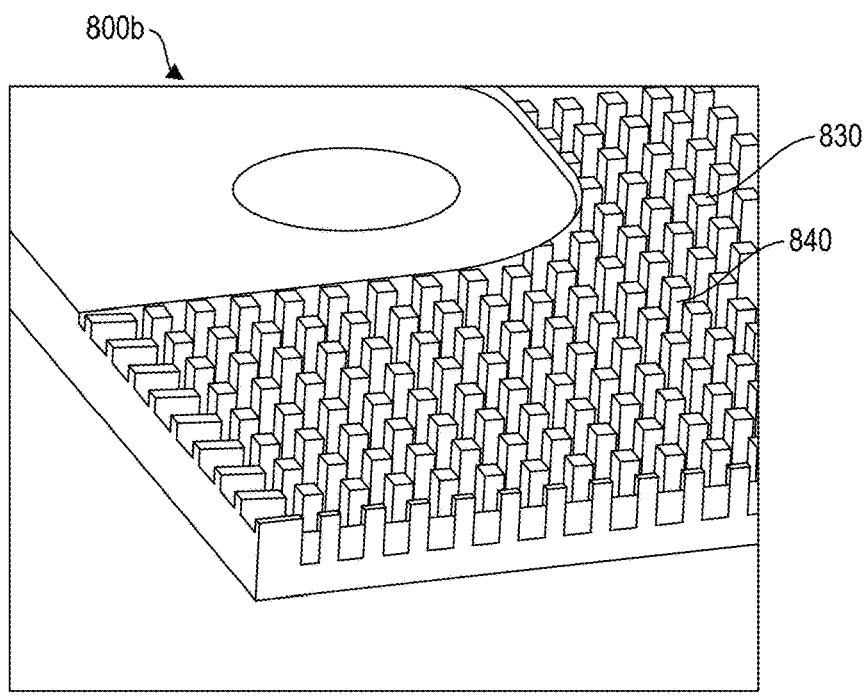
FIG. 8B illustrates spacing pillars defining a space for media perfusion over the cell niches (compartments) formed by surface features of the membrane of FIG. 8A.

FIG. 8B illustrates spacing pillars defining a space for media perfusion (dark) over the compartments formed by surface features of the membrane of FIG. 8A.

Figure 8C:
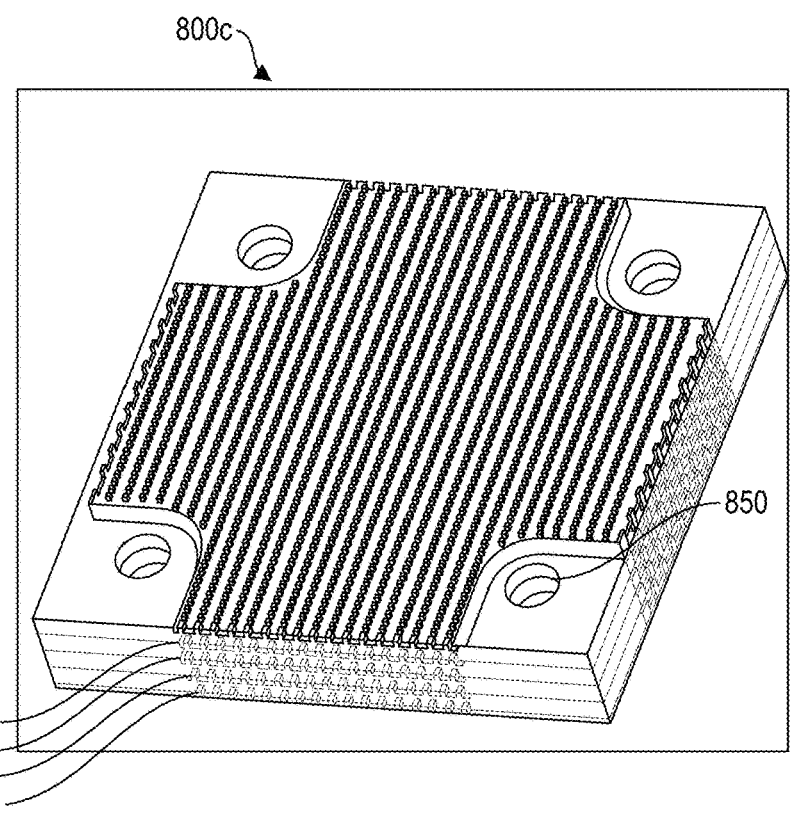
FIG. 8C illustrates multiple membranes stacked together, with a gas manifolds at the corner of the stacked membranes, each of the stacked membrane corresponding a membrane of FIGS. 8A and 8B.

FIG. 8C illustrates multiple membranes 860a, 860b, 860c, and 860d stacked together, with a gas manifolds 850 at the corner of the stacked membranes 860a-d, each of the stacked membranes corresponding a membrane of FIGS. 8A and 8B.

Figure 8D:
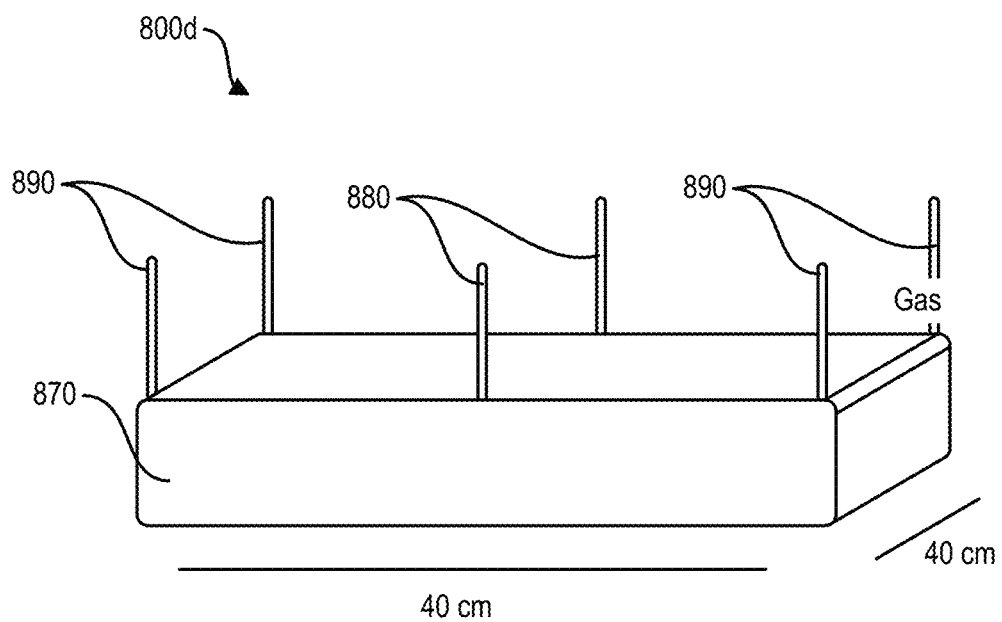
FIG. 8D illustrates an enclosure for housing the stacked membrane of FIG. 8C, with inlets and outlets of gas and media, to form a high density cell respirator cartridge.

FIG. 8D illustrates an enclosure 870 housing the stacked membranes 860a-d of FIG. 8C, with gas access ports 890 and media access ports 880. Each of the gas access ports 890 may function as a gas inlet or a gas outlet. Similarly, each of the media access ports 880 may function as a media inlet or a media outlet. While FIG. 8D shows two media access ports 880 and four gas access ports 890, other embodiments may have a different number of gas access ports and or media access ports.

Figure 8E:
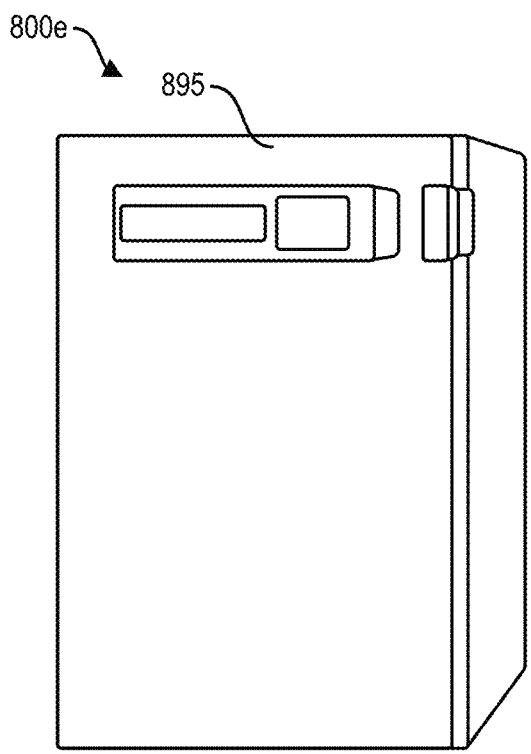
FIG. 8E illustrates an incubator into which the high density cell respirator cartridge of FIG. 8D may be enclosed for incubation of cells.

FIG. 8E illustrates an incubator 895 into which the HDCR cartridge of FIG. 8D may be enclosed for incubation of cells.

Figure 8F:
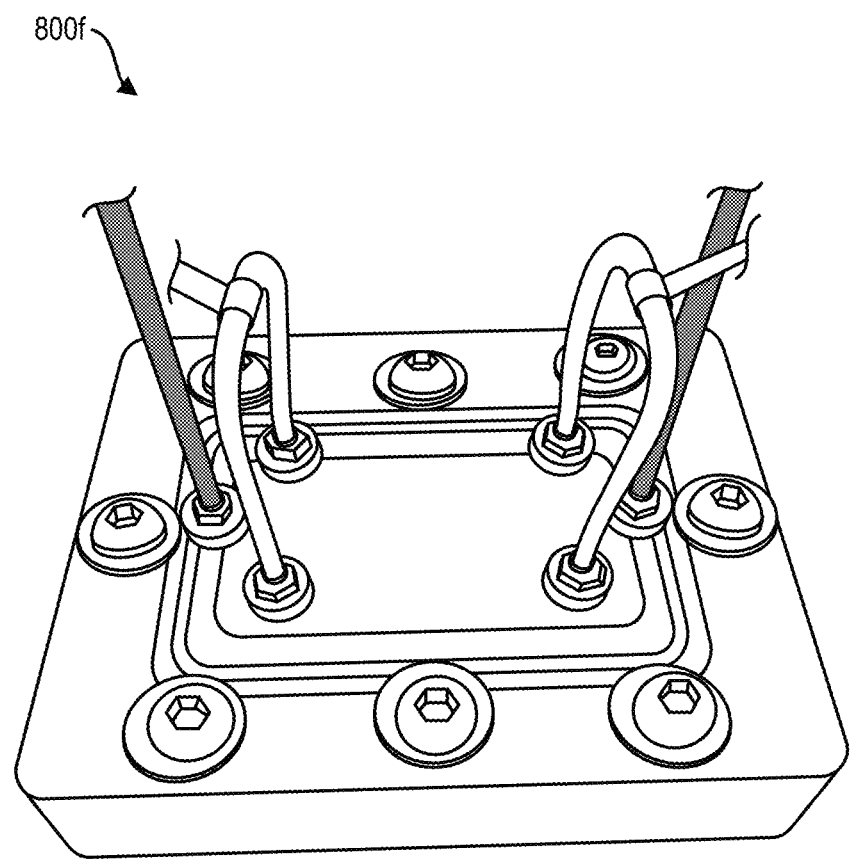
FIG. 8F illustrates an example of a high density cell respirator cartridge in accordance with an exemplary embodiment.

FIG. 8F illustrates an example of a HDCR cartridge including the components described above with respect to FIGS. 8A-8D. The HDCR optimizes the cell expansion niches allowing extremely high densities of production cell lines to be grown. The HDCR is composed of stackable, gas-perfusable and transmissive polydimethylsiloxane (PDMS) membranes bathed in an independently perfusable media compartment. Cells settle into precisely patterned grooves in the membrane that retain and protect them from fluidic shear forces as well as provide ample oxygenation via membrane permeation. Integrated spacing posts maintain a thin media film over the cell niche for delivery of soluble nutrients, reagents, and/or virus as well as waste removal and cell/bioproduct harvesting. The membranes may be inexpensively manufactured in large sheets via industry standard liquid silicone rubber (LSR) injection molding. A coating step renders them hydrophilic and conducive to cell adhesion. Such an apparatus forms the basis of a completely enclosed and autoclavable vector production cartridge. The integrated cell retention technology makes the disclosed designs compatible with both adherent and suspension cells.

The gas perfusable, gas permeable membranes provide a large surface area while delivering sufficient oxygen and gas exchange for high-density cell growth. These membranes can be folded or stacked to achieve high surface area to volume ratios. Cells can be grown directly on the surface of the membranes or on substrates sandwiched between the membranes. The gap between stacked membranes can be perfused with solutions to deliver or remove components into or out of the membrane stacks. The gap and rate of perfusion can be chosen so as to maintain suitable shear rates within the device. A network of tubes or channels can be employed throughout the system to deliver media separately from the gas supply. The tubes or channels may contain pores to allow various sized particles ranging from molecules to cells to pass into or out of the tubing. This is a means by which cells can be seeded within the device and/or virus can be delivered to infect cells. Pores can be formed in the membranes themselves to provide a means of perfusing the stacked membranes normal to their surfaces. In this arrangement the flow induces minimal shear forces on cells because the direction of flow is not parallel to the cells; nutrients then reach the cells through diffusion away from these pores.

The role of oxygen in virus production is well established and reviewed. The so-called "cell density effect" refers to the tendency of cell-specific viral yield to drop in response to limited oxygen or nutrient availability. Interestingly, transient transfection of HEK293 suspension cells with PEI has been demonstrated to be simpler and 2× more efficient at high-density (>about $10^7$ cells/mL) than low-density (about $10^6$ cells/mL). Overcoming metabolite limitations is therefore key to unlocking improved yield. For example, in volume-expanded-fed processes, where the production volume is increased with fresh media at the viral infection stage to provide an abundance of oxygen and nutrients, up to 40-fold increase in per-cell productivity is reported for Parapoxvirus ovis in adherent bovine kidney cells. Similar improvements are reported for almost all clinically relevant viruses.

Furthermore, oxygen uptake rate increases significantly during viral replication due to increased DNA/protein synthesis. For example, in Sf9 cells infected with baculovirus, oxygen uptake rate increased by 1.3×.

Bioreactors need to accommodate this increased oxygen demands post-infection. In existing perfusion systems (e.g., iCellis), which rely on cell adhesion to a static carrier for retention, increasing flow to maintain oxygenation is not viable as cells are experiencing reduced adhesion due to the cytopathic effect and will detach under the increased shear. The novel decoupling of gas and nutrient supply and integrated cell retention in our high density bioreactor make it optimal for virus production. Based on preliminary results and modeling, our HDCR has significantly improved space efficiency (>10×) compared to the industry leading iCellis bioreactor system, and at a fraction of the cost (<¼×).

FIG. 9A illustrates an example of an open membrane high capacity cell respirator device 900a with ten stacked membranes. FIG. 9B illustrates a close-up plan, perspective view of a corner of the example of the open membrane high capacity cell respirator device of FIG. 9A in accordance with an exemplary embodiment. FIG. 9C illustrates a side, perspective view of a corner of the example of the open membrane high capacity cell respirator device of FIG. 9A in accordance with an exemplary embodiment. A region 910 of 900a is depicted in view 900b of FIG. 9B, which illustrates a fluidic manifold 930 that feeds the membranes 960 with media via media channels 940. Grooves 950 in the membranes serve as compartments to retain and grow cells. View 900c of FIG. 9C shows a side view of the high capacity cell respirator device 900a, with a stack of ten membranes 960.

FIG. 10A illustrates a prototype of a HDCR with integrated cell retaining niches, spacing pillars, gas-perfusion space, and gas manifolds. FIG. 10B illustrates a first close-up portion of the prototype of FIG. 10A in accordance with an exemplary embodiment. FIG. 10C illustrates a second close-up portion of the prototype of FIG. 10A in accordance with an exemplary embodiment. FIG. 10D illustrates a cross-section of the prototype of FIG. 10A in accordance with an exemplary embodiment. View 1000a of FIG. 10A illustrates a top view of the HDCR. View 1000b of FIG. 10B is a close up of region 1010 of 1000a. View 1000b shows detailed views of cell niche grooves and underlying gas compartment ties. The view 1000c of FIG. 10C is a close up of region 1020 of 1000a. The view 1000c shows stackable gas manifolds. View 1000d of FIG. 10D is a close up of the side view corresponding to 1030 of 1000a. This side view 1000d shows cell and media channels, and spacing pillars.

FIG. 11A illustrates the management of bubbles, void space, condensation, and evaporation for HDCR 1100a. Specifically, FIG. 11A illustrates a high density cell respirator in accordance with an exemplary embodiment. FIG. 11B illustrates a cross-section of the respirator of FIG. 11A before purging bubble and air spaces by perfusing liquid through the media compartment above the membrane of the high density cell respirator in accordance with an exemplary embodiment. FIG. 11C illustrates the cross-section of the respirator of FIG. 11A after purging bubble and air spaces by perfusing liquid through the media compartment above the membrane of the high density cell respirator in accordance with an exemplary embodiment. View 1100b of FIG. 11B is based on a photograph taken of a membrane with bubbles 1110. The membrane was placed in an imaging and autoclave compatible enclosure. Purging liquid through the media compartment efficiently eliminated bubbles 1110 and void spaces. Pre-humidifying gases prevents evaporation. Pre-warming gases prevent condensation within the gas compartment. After purging, the membrane no longer has bubbles or voids, as shown in view 1100c of FIG. 11C.

Figure 12:
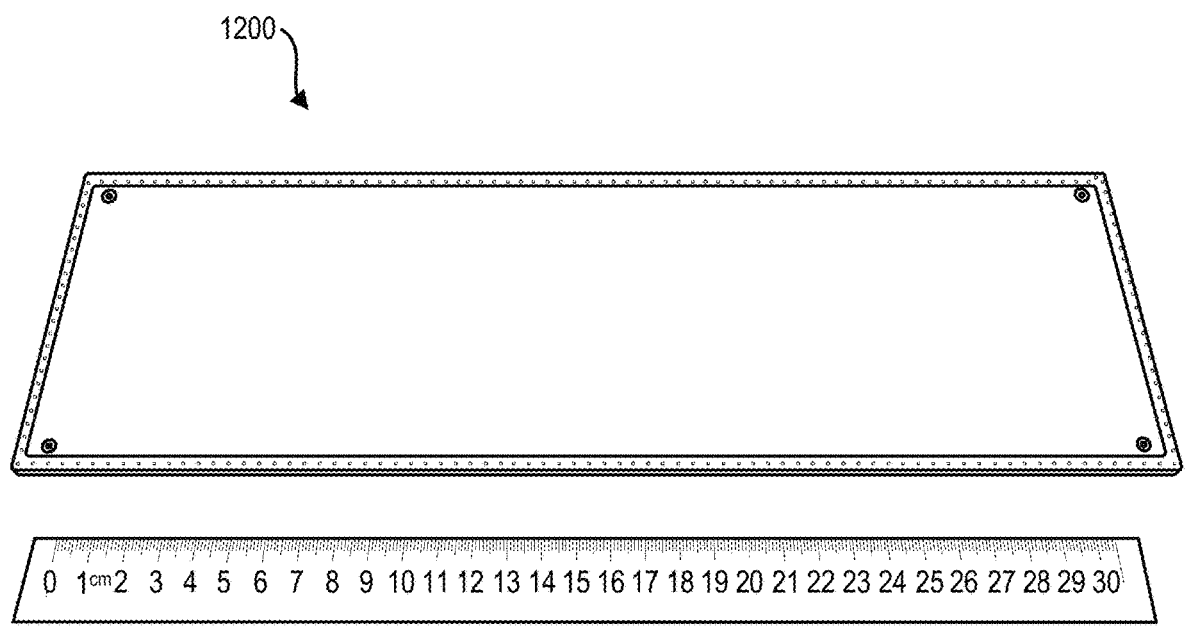
FIG. 12 illustrates membrane prototype for a mid-scale high density cell respirator.
Figure 12A:
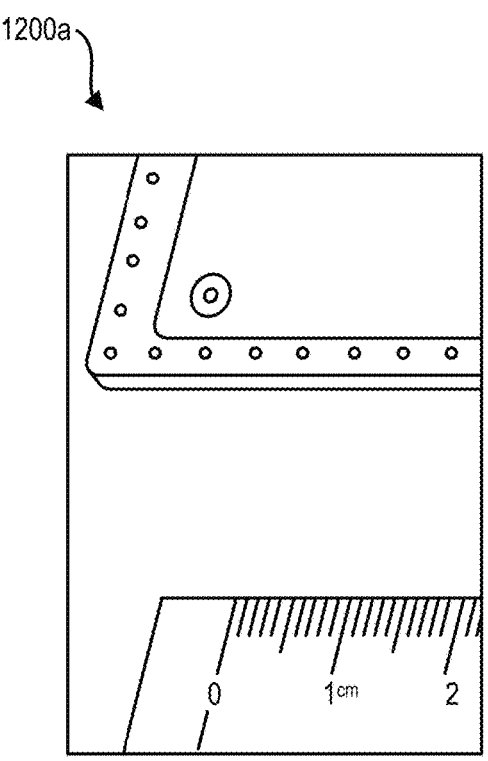
FIG. 12A is a magnified view of a portion of FIG. 12 in accordance with an exemplary embodiment.

FIG. 12 is based on a photograph 1200 of a membrane prototype for a mid-scale HDCR, with a length of about 34 cm and a width of about 10 cm. The prototype was fabricated using injection molding, to de-risk production of the stackable HDCR membranes described herein. FIG. 12A is a magnified view 1200a of a portion of the membrane prototype of FIG. 12.

24-Well Plate HDCRs

Figure 13A:
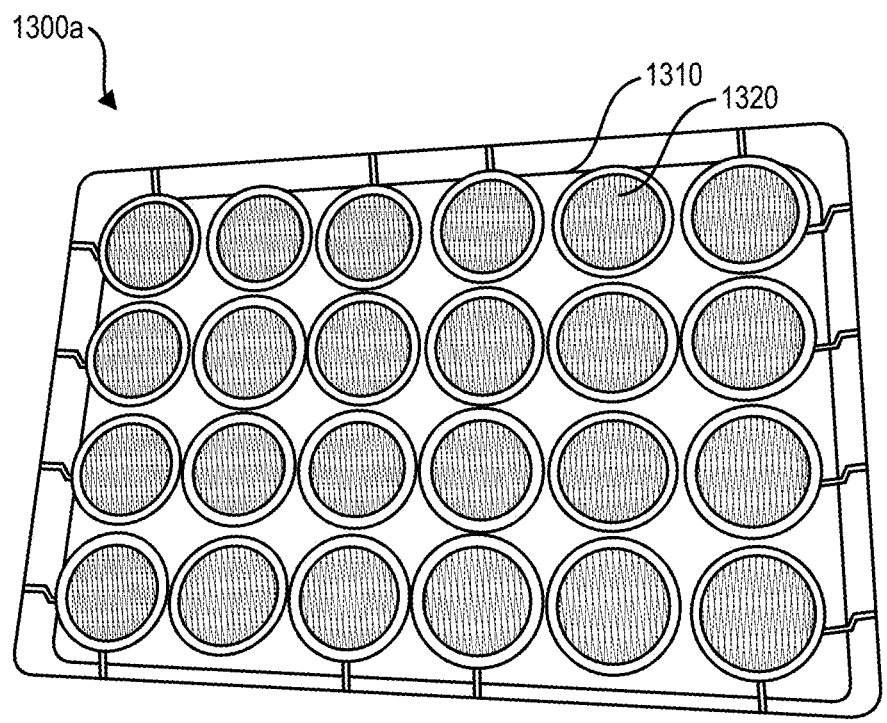
FIG. 13A illustrates a 24 well plate with silicone inserts with pattered grooves glued into each of the well plates.
Figure 13B:
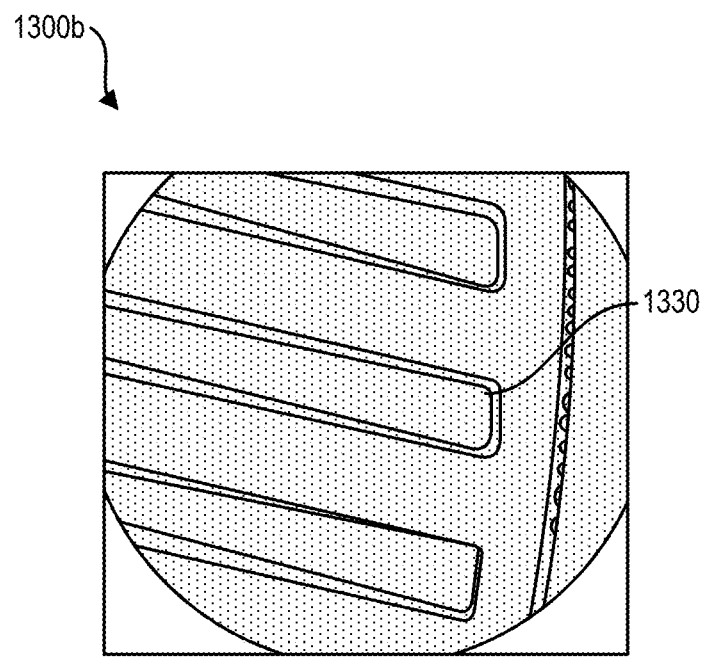
FIG. 13B is a close up of grooves in one of the silicone inserts of FIG. 13A in accordance with an exemplary embodiment.

FIG. 13A illustrates a 24 well plate 1310 with silicone inserts 1320 with pattered grooves glued into each of the well plates. The 24-well plates may be used for million-cell scale cell cultivation. The 24-well plate may be used as a high-throughput screening tool to optimize and experiment with cell seeding density, growth curves, media feed rates, oxygen tension, transfection methods, production/packaging, and other parameters, before scaling up to a billion-cell scale petri dish, or a trillion-cell scale cartridge with stacked membranes. The wells in well-plates are not the same (meaning, for example, dimensions of the groove and/or fin are varied across the wells, so as to identify effective configurations and useful geometries), and are on a much larger scale, when compared to wells 740 of FIG. 7. FIG. 13B is a close up of grooves 1330 in one of the silicone inserts of FIG. 13A.

Petri Dish HDCRs

Figure 14:
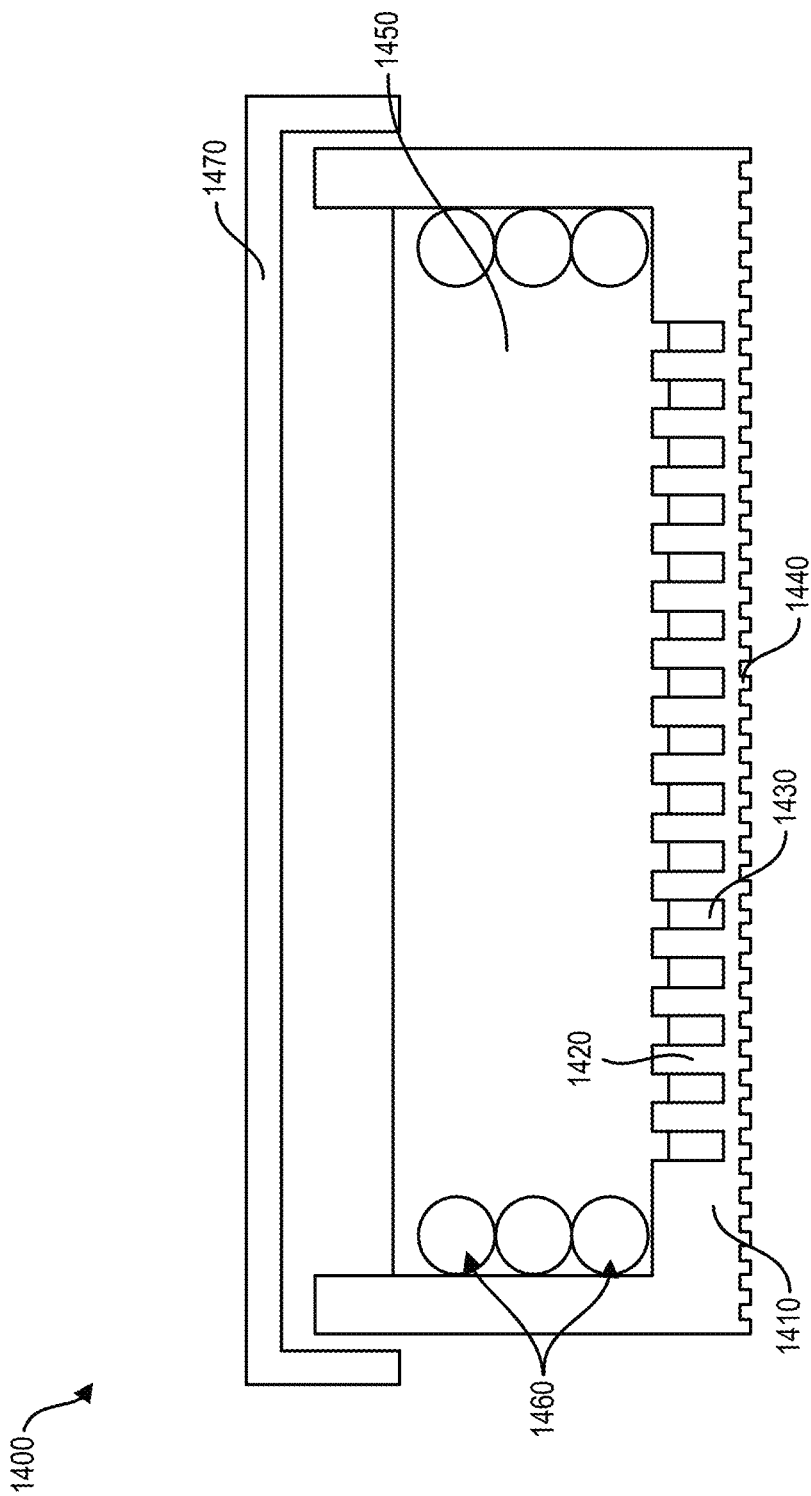
FIG. 14 illustrates a high density cell respirator petri dish, in which a gas permeable membrane forms the bottom surface of the petri dish, gas diffuses from below the membrane, and cells and nutrients are supplies from a deep reservoir above the membrane in accordance with an exemplary embodiment.

FIG. 14 illustrates a HDCR petri dish 1400, in which a gas permeable membrane 1410 with fins 1420 forms the bottom surface of the petri dish 1400, gas diffuses from below the membrane 1410, and cells and nutrients are supplied from a deep reservoir 1450 above the membrane. Spacing pillars 1440 at the bottom of membrane 1410 allow gas to flow under the petri dish 1400. Tension rings 1460 keep the membrane taut and add rigidity to the petri dish 1400. The fins 1420 define compartments in grooves 1430. The membrane 1410 and fins 1420 are gas permeable. For example oxygen may enter the membrane 1410 through the spacing pillars 1440 or the sides of the membrane 1410, and permeate through the membrane 1410 and the fins 1420 to the compartments in grooves 1430. Carbon dioxide may be removed from the compartments in grooves 1430 by permeating through the fins 1420 and membrane 1410, and exit from the membrane 1410 near the spacing pillars 1440 or the sides of the membrane 1410. The reservoir 1450 above the membrane 1410 and compartments in grooves 1430 is deep, to reduce the need to replenish or replace nutrient-rich media. For many applications, it may not be necessary to replenish or replace media in the reservoir 1450.

Figure 15A:
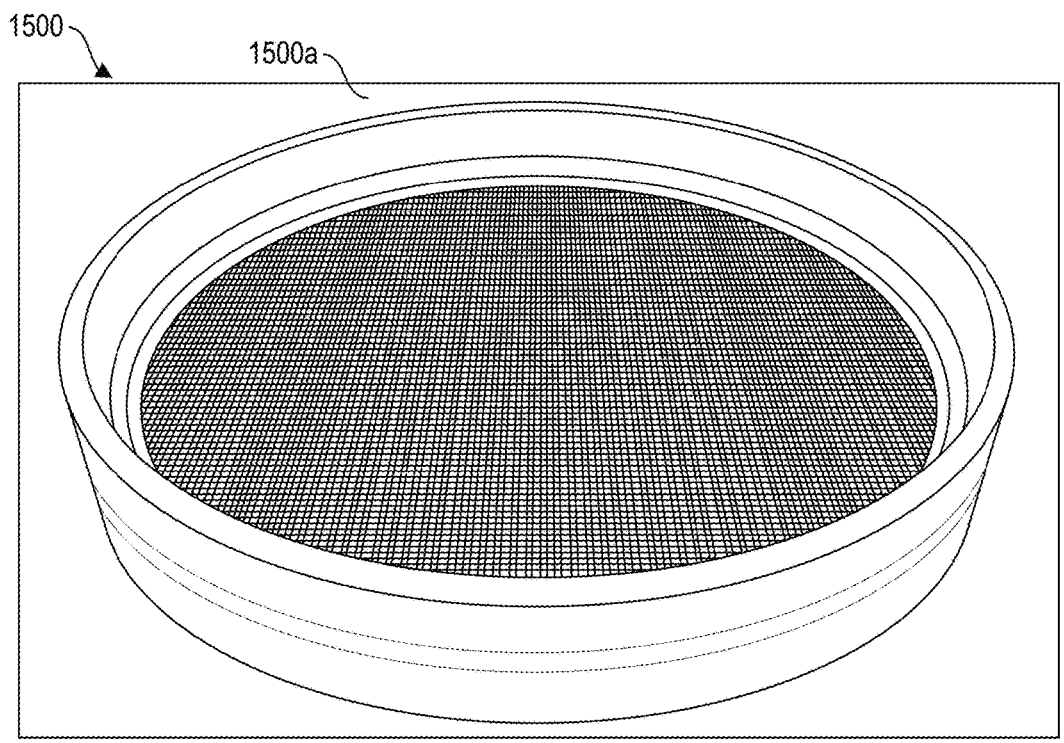
FIG. 15A illustrates an example of a petri dish, corresponding to the petri dish of FIG. 14, in which HEK293 cells were cultivated on microcarriers.
Figure 15B:
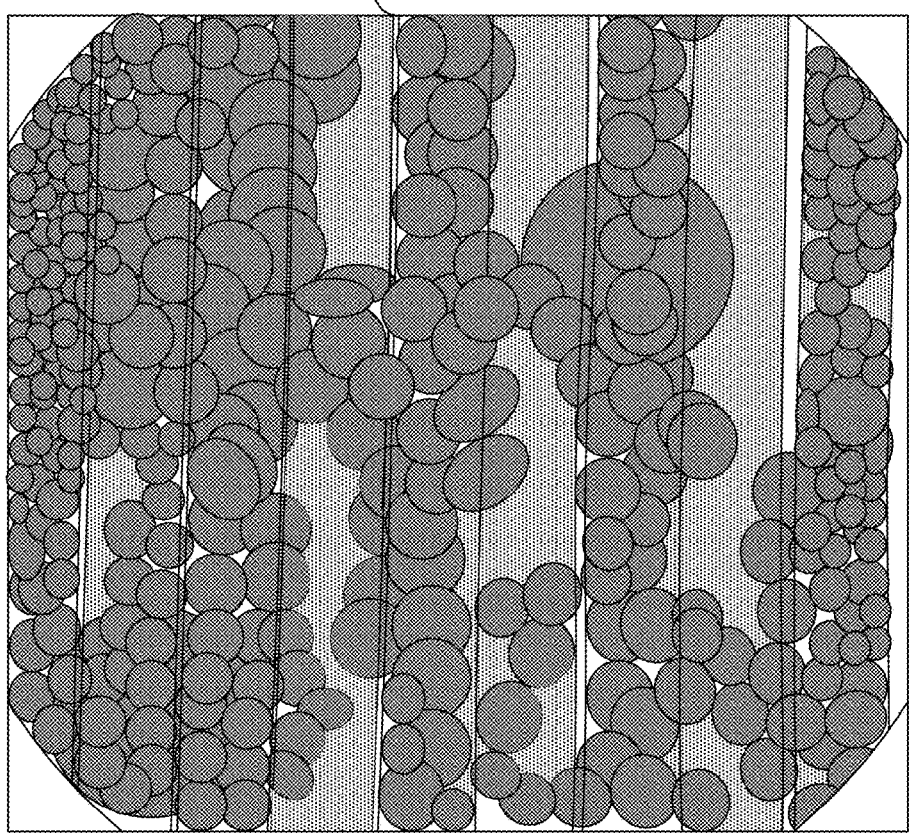
FIG. 15B illustrates a plan view of the petri dish of FIG. 15B highlighting the microcarriers.
Figure 15C:
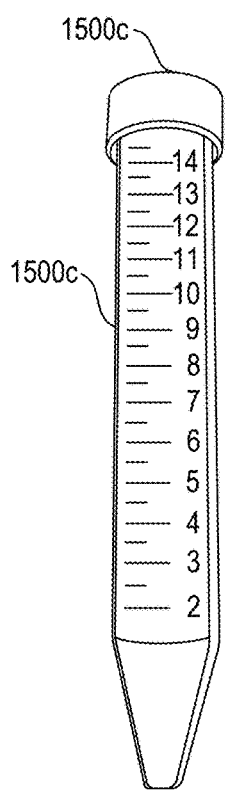
FIG. 15C illustrates cultivation and harvest of about 400 million HEK293 cells from the single HDCR petri dish of FIGS. 15A and 15B.

FIG. 15A illustrates an example of a petri dish 1500a, corresponding to the petri dish of FIG. 14, in which HEK293 cells were cultivated on microcarriers. FIG. 15B illustrates a plan view of the petri dish of FIG. 15B highlighting the microcarriers. FIG. 15C illustrates cultivation and harvest of about 400 million HEK293 cells from the single HDCR petri dish of FIGS. 15A and 15B. Microfabricated grooves and fins provide oxygen optimized niches for cell expansion. In the example of FIG. 15B, HEK293 cells on microcarriers 1500b concentrate in grooves of the petri dish 1500a, resulting in (see, FIG. 15C) the cultivation and harvest of about 400 million HEK293 cells 1500c from a single HDCR petri dish, a much greater volume than is possible from traditional petri dishes. Each HDCR petri dish generates as many cells as 25 petri dishes cultivating cells using traditional methods. This frees incubator space and technician time by an about 25:1 ratio. The plate is autoclavable and reusable.

Silicone Sheet Style Bioreactors

Figures 16A, 16B, 16C:
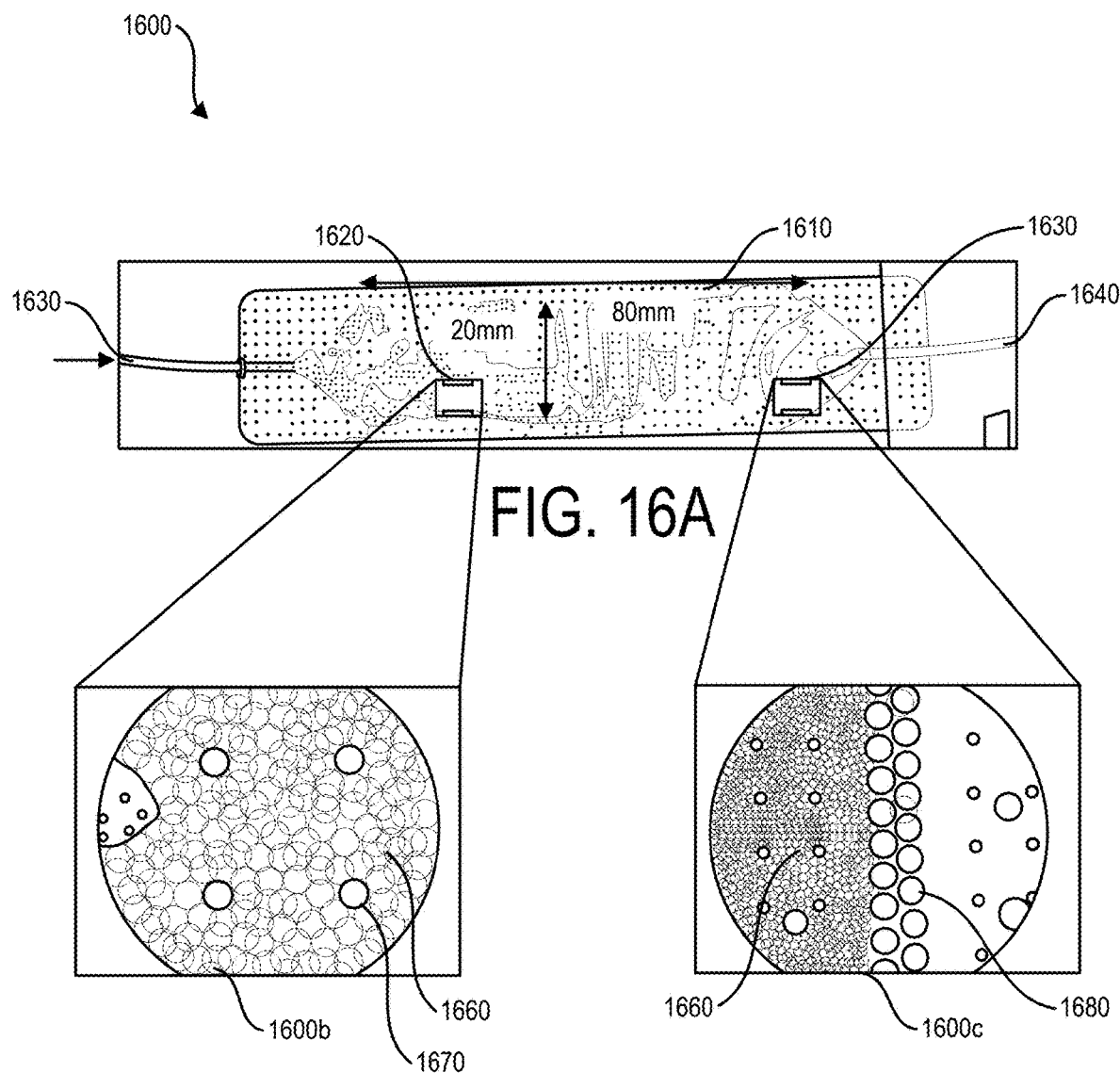
FIG. 16A illustrates a silicone sheet style bioreactor, in which microcarriers flow into the membranes until they are stopped by filter posts at the end of the membrane in accordance with an exemplary embodiment.
FIG. 16B illustrates a plan view of a portion of the bioreactor of FIG. 16A highlighting the microcarriers.
FIG. 16C illustrates a plan view of another portion of the bioreactor of FIG. 16A highlighting the filter posts.

FIG. 16A illustrates a silicone sheet style bioreactor 1600, with a HDCR membrane 1600. Media flows into the membrane 1600 via an inlet 1630, and flows out of the membrane 1640. FIG. 16B illustrates a plan view of a portion of the bioreactor of FIG. 16A highlighting the microcarriers. FIG. 16C illustrates a plan view of another portion of the bioreactor of FIG. 16A highlighting the filter posts. View 1600b of FIG. 16B is based on a close up picture, including microcarriers 1660 upon which cells can grow, and membrane ties 1670 perpendicular to the membranes. The membrane ties 1670 anchor the membrane 1610 in place. As shown in FIG. 16C, filter posts 1680 perpendicular to the membrane provide boundaries or fences that define boundaries of regions accessible to the microcarriers 1660. The filter posts 1680 allow perfusion of media without microcarrier loss, as media will flow more freely in regions of the membrane without the microcarriers, where fluid resistance is lower, and the filter posts 1680 may be arrayed to block microcarriers from travel beyond the filter posts 1680.

Figure 17:
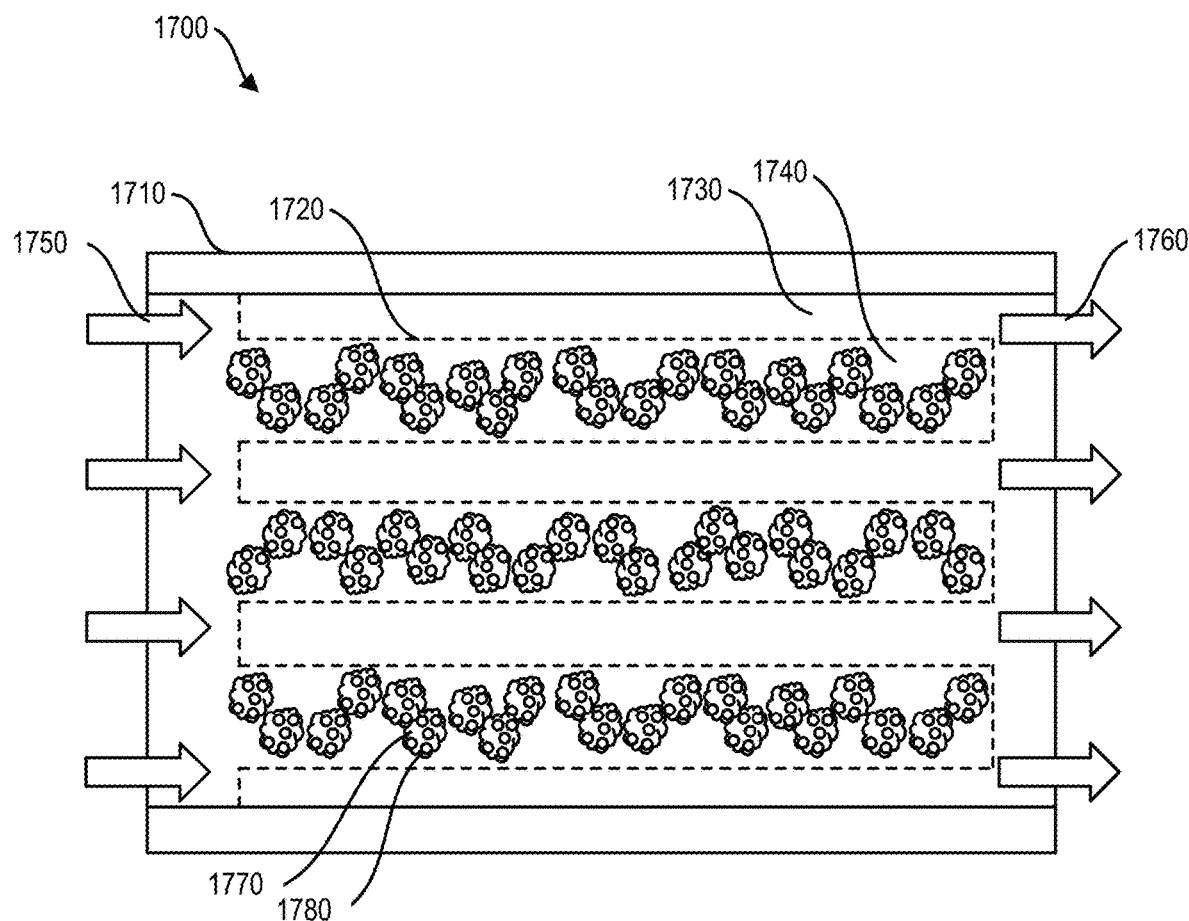
FIG. 17 is a top view of a cross section of a silicone sheet-style bioreactor, illustrating cells on microcarriers in regions delineated by posts in accordance with an exemplary embodiment.
Figure 18:
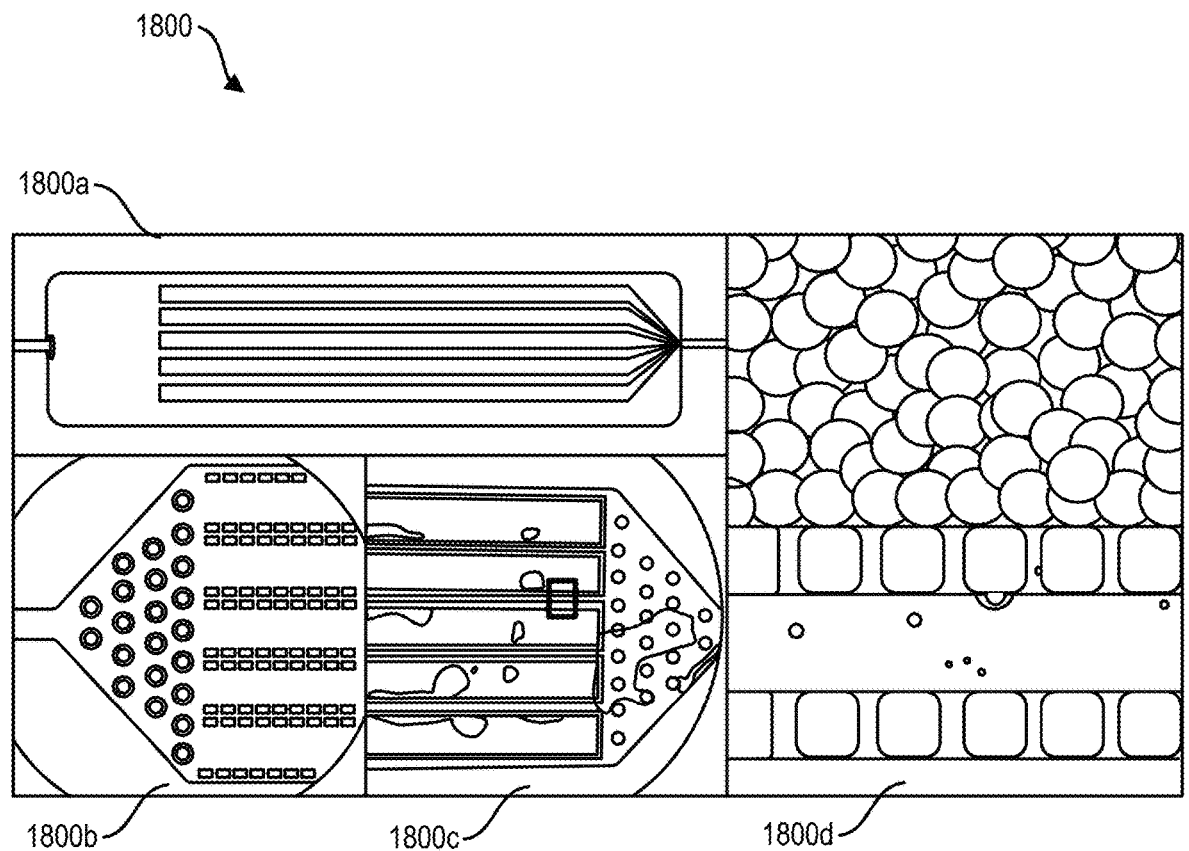
FIG. 18 is a close up view of the silicone sheet style bioreactors of FIGS. 16 and 17.

FIG. 17 is a top view of a cross section of a silicone sheet-style bioreactor 1700, such as the silicone sheet-style bioreactor of FIG. 18. A top view of the membrane 1710 includes an array 1720 of filter posts, similar to the filter posts 1680 of FIG. 16. The filter posts 1720 delineate regions 1740 that are accessible to microcarriers 1770, as well as regions 1730 that are not accessible to microcarriers 1770. This causes the microcarriers 1770, with cells adhered to the microcarriers 1780, to accumulate in the regions 1740. Media flows enter at the arrows 1750, and flows through the membrane 1710 from left to right in FIG. 17 towards the arrows 1760. Media will flow more freely in regions 1730 without microcarriers than in regions 1740 with microcarriers, reducing microcarrier loss. In addition, the microcarriers may be stopped from being washed to the region with arrows 1760, as they are blocked by filter posts 1720 proximate to the arrows 1760.

FIG. 18 depicts close up view of the silicone sheet style bioreactors of FIGS. 16 and 17. View 1800*a* is based on a photograph of a silicone membrane filled with microcarriers and media. View 1800*b* is based on a close up of the entrance to the silicone membrane entrance. View 1800*c* is based on a close up of the silicone membrane exit with microcarriers. View 1800*d* is based on a close up of a filter channel, delineated by filter posts, retaining microcarriers.

Experimental Results

The HDCRs described herein have been used to demonstrate confluent cell growth on a high-surface area membrane bioreactor with a decoupled gas and nutrient supply. CV-1 cells were grown within a perfused HDCR membrane on microcarriers up to densities of about $1.2\times10^8$ cells/mL over a five day expansion. Further, the expansion of A549 (about $0.86\pm0.17$ S.E.M.$\times10^8$ cells/mL), Wagner 39652-1 (about $1.1\pm0.1$ S.E.M.$\times10^8$ cells/mL), and suspension CHO-S (about $0.82\pm0.02$ S.E.M $10^8$ cells/mL) within 24-well HDCR plates. Up to about 500M HEK293 cells were grown in an about 150 mm HDCR petri dish on Cultisphere G microcarriers as well as HEK293-S up to about 250M (at about 30% of niche capacity).

Figure 19:
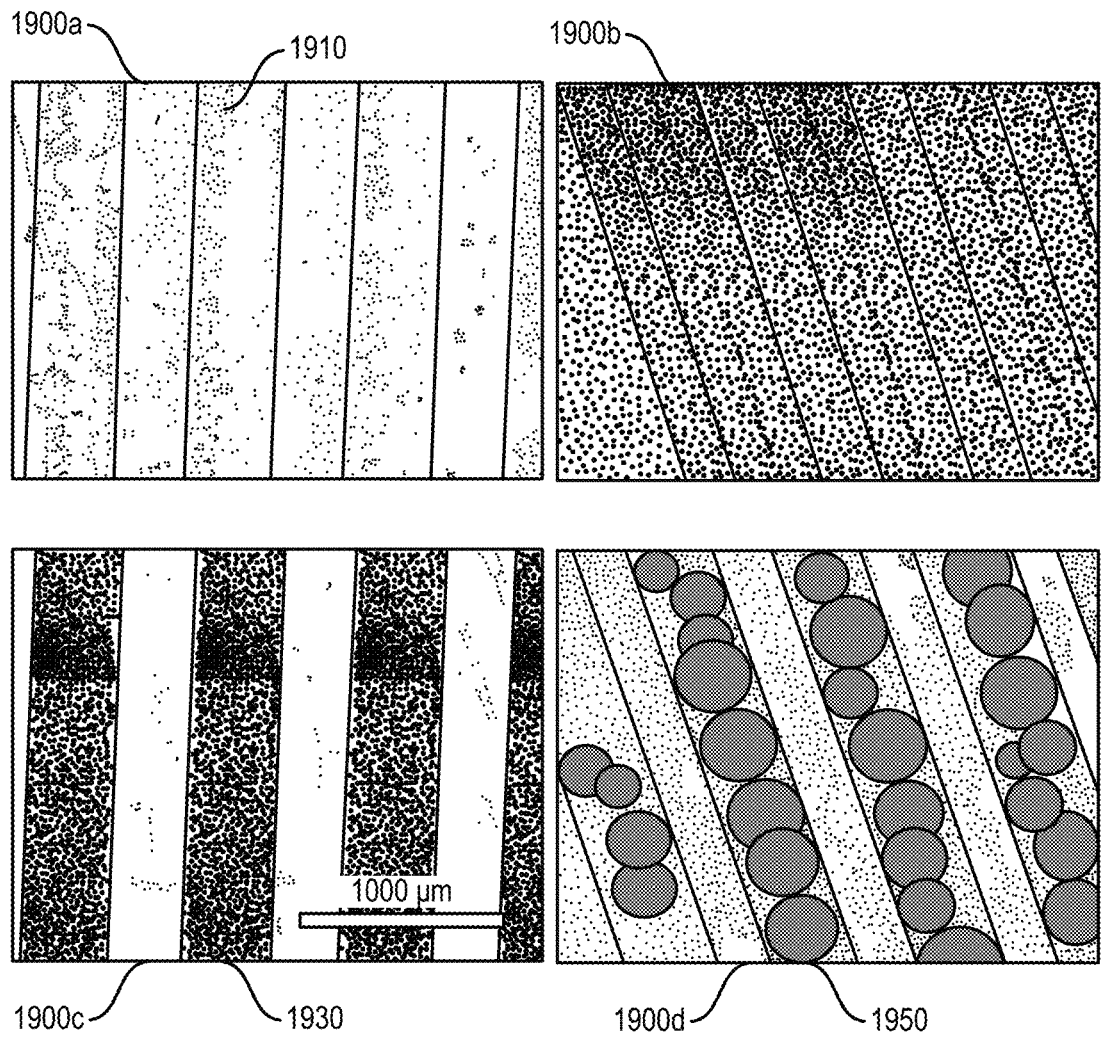
FIG. 19 illustrates an experimental result of growing, in suspension, CHO-S cells, and growing, on microcarriers, Wagner (GFP+) cells, in a 24-well high density cell respirator plate with fins in accordance with an exemplary embodiment.

FIG. 19 illustrates cell expansions in 24-well HDCR plates over 7 days. On the left, 1900*a* illustrates CHO-S cells at the start of an experiment, in which the compartments 1910 are seeded with CHO-S cells. After seven days of growth, in 1900*c*, the compartments 1930 appear dark, as they are full of cells, as shown in 1900*c*. On the right, 1900*b* illustrates adherent GFP+Wagner 39652-1 cells on Cultisphere G microcarriers under fluorescence at the start (day 0) of the experiment. As expected, the field of view for 1900*b* is dark. After 7 days, Wagner 39652 cells on Cultisphere G microcarriers are visible under fluorescence along the compartments 1950 in 1900*d*.

Figure 20:
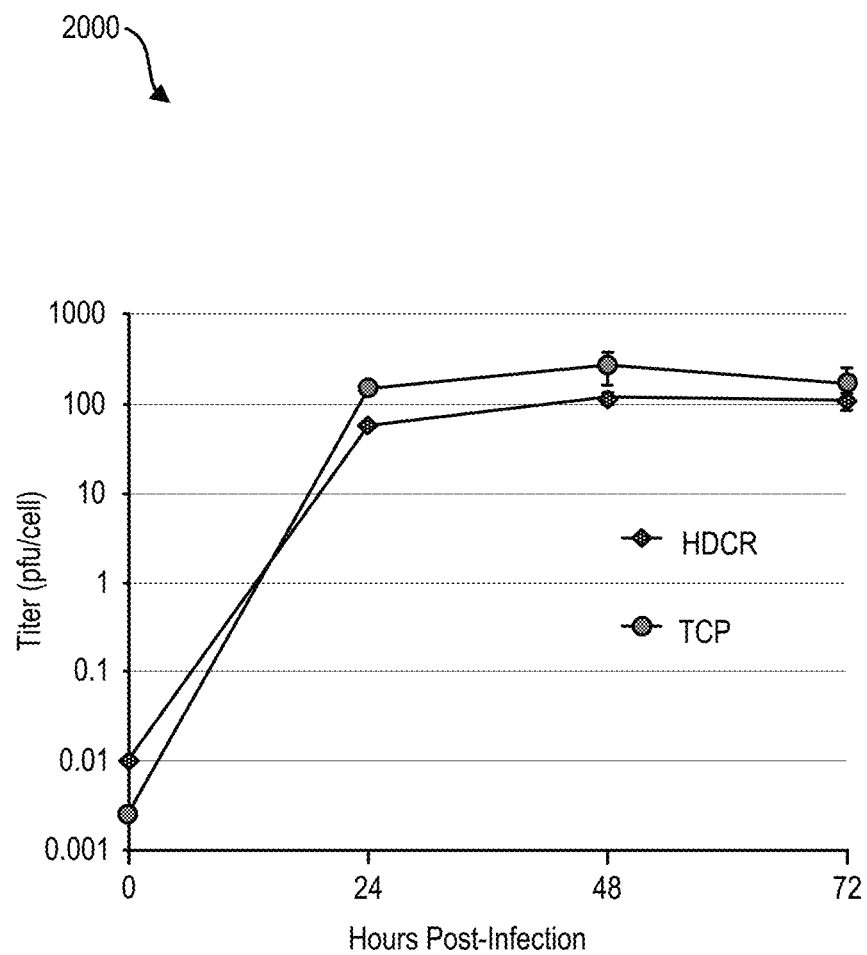
FIG. 20 is a graph of an experimental result of producing orthopoxvirus in A549 in a 24-well high density cell respirator cell plate; and the graph compares per cell production in 24-well high density cell respirator plate with a tissue culture plate in accordance with an exemplary embodiment.
Figure 21:
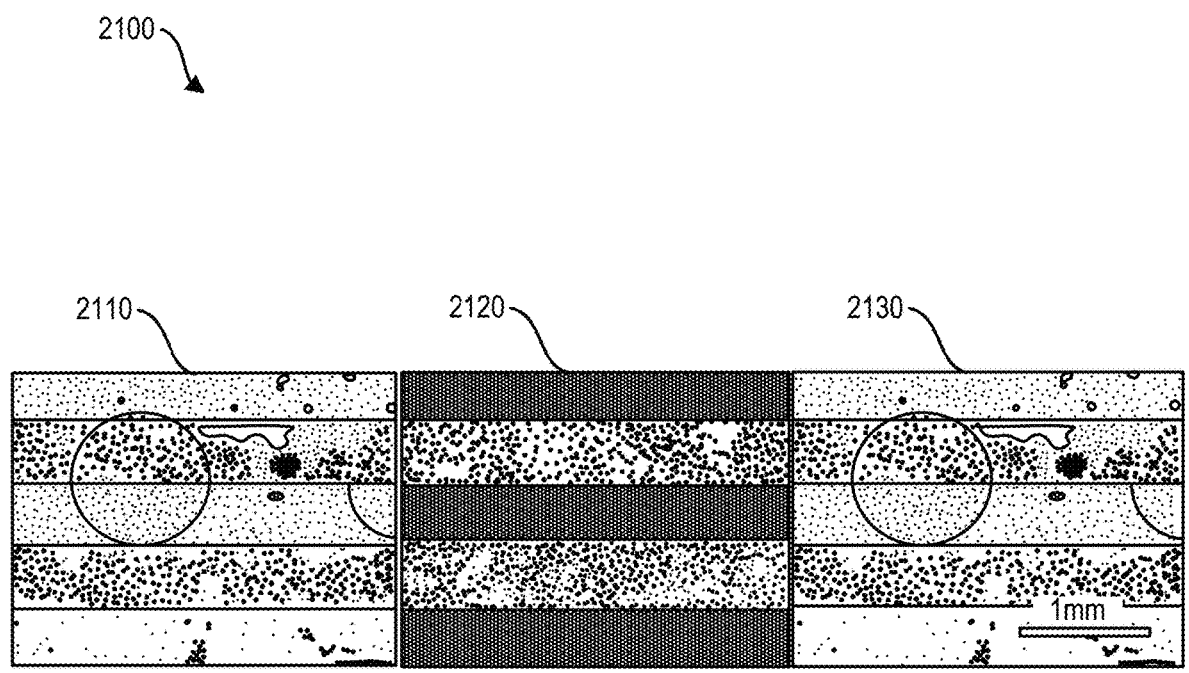
FIG. 21 illustrates the experimental result that HEK293 cells can be transfected at high density using the membrane structures described in the disclosed technology in accordance with an exemplary embodiment.
Figure 22:
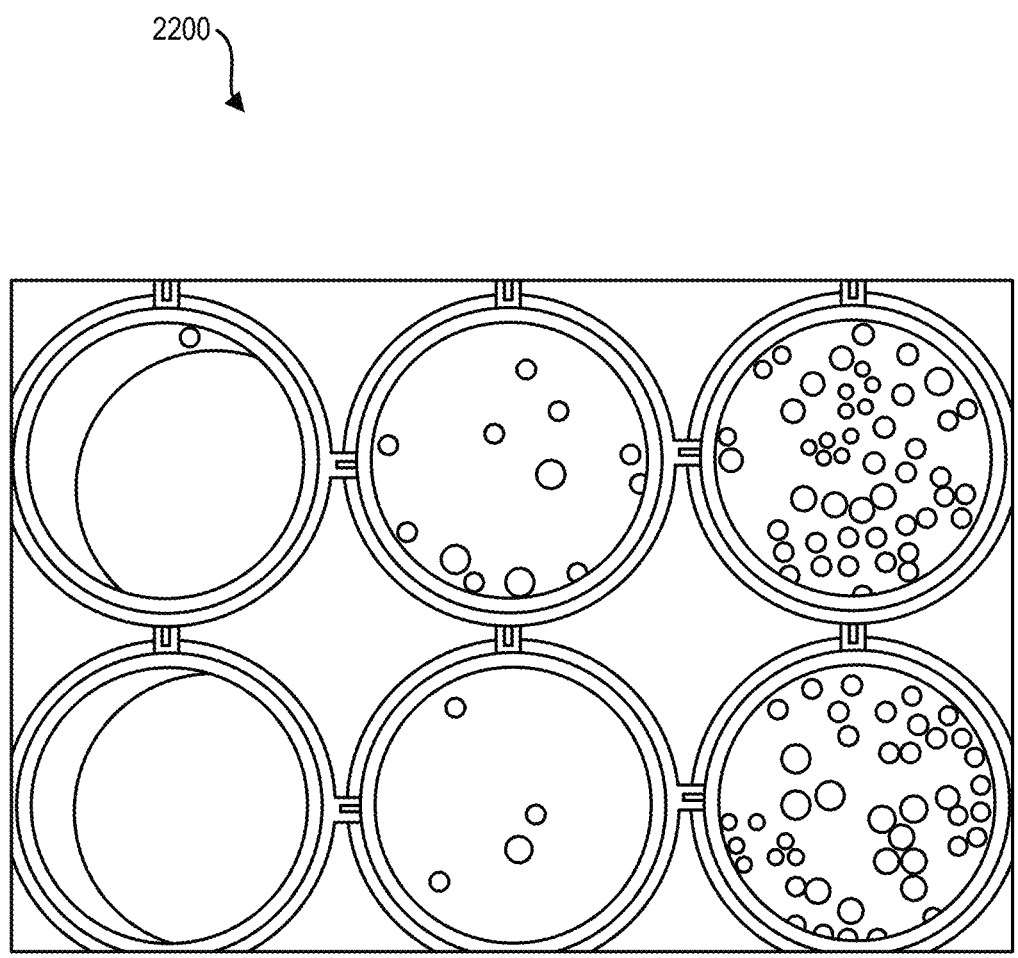
FIG. 22 illustrates the experimental result of titering of orthopox virus (CF33) from high-density A549 cells grown in high density cell respirator membranes in accordance with an exemplary embodiment.
Figure 23:
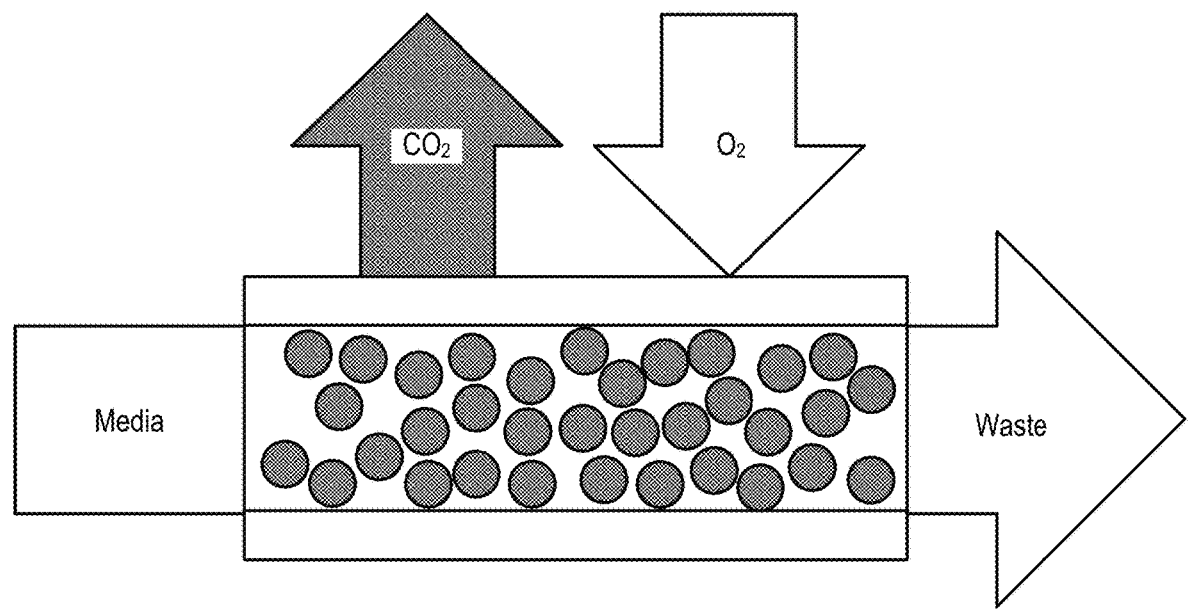
FIG. 23 is a schematic diagram of an HDCR architecture configured to receive media, exchange oxygen for carbon dioxide, and output waste having a static volumetric oxygen exchange rate (kLa) of greater than about 60/hr, e.g., greater than about 63+/−12 (S.E.M.)/hr.

FIG. 20 is a graph of an experimental result of producing orthopoxvirus in A549 cells in a 24-well HDCR plate on Cultisphere microcarriers to a niche density of about $2\times10^7$ cells/mL. Cells were infected with HOV-2 at a multiplicity of infection (MOI) of about 0.01 (about 1 virus particle for every 10 cells) and harvested at about 24, 48, and 72 hours. Measured titers (pfu/cell) were comparable to virus production in A549 cells grown on tissue culture plates (FIG. 20), which alleviates the concern that virus infection could be compromised at high cell densities. This data demonstrates that successful production of orthopoxvirus in the HDCR devices describes herein, with successfully scaled cell expansion from about 5M cells/well in the 24-well HDCR plates to about 500M cells in the about 150 mm HDCR Petri dishes. In addition, A549 cells have been grown in 24-well HDCR plates at cell densities of about $4\times10^7$ cells/mL and achieved per cell yields of about $64\pm9$ pfu/cell of CF33.

FIG. 21 illustrates the experimental result that HEK293 cells can be transfected at high density using the membrane structures described in the disclosed technology. jetPRIME reagent was used to transfect mCherry plasmid into cells at about $2\times10^7$ cells/mL grown directly on HDCR membranes as well as on solid (Cytodex-1 and Cytodex-3) and microcarriers (Cultisphere G). Other embodiments may include different macrocarriers, such as non-porous macrocarriers or macroporous macrocarriers. FIG. 21 shows phase 2110, fluorescence 2120, and overlay 2130 views of transfection of high-density HEK293 cells grown on Cultisphere G microcarriers with RFP plasmid using jetPRIME in 24-well HDCR plates.

FIG. 22 illustrates the experimental result of titering of orthopox virus (CF33) from high-density A549 cells grown in HDCR membranes.

Background

Historically, in the 1940s, deep tank fermentation technology then successfully revolutionized scaled-up production of penicillin. Stirred tank reactors (STRs) were used to produce cells of importance in gene therapy. However, demand for AAV for systemic therapy exceed production capacity offered by STRs.

Much effort to date (e.g., over the last 30 years) has been focused on improving cell-specific productivity, which nominally increases space-time productivity. Cell specific AAV productivity in published literature reveals $10^6$ cells/mL as an upper limit of such productivity. Developed technologies such as flasks, STRs, and fixed bed reactors are reported with the $10^6$ cells/mL regime. Although some developed systems, like fixed bed reactors, have relatively high cell densities locally ($10^8$ cells/mL) in the reactor bed, the relatively large volume of the reactor that is effectively devoid of cells limits the effective system cell density in line with other reactors, certainly within an order of magnitude.

Intensification saves space, labor and cash as a resource. Intensification drives down costs and meets capacity goals. Efficiency of production may be evaluated in terms of a space-time productivity continuum, i.e., how much of a given product in a given volume in a given period can be produced. Space-time productivity is a product of both cell specific productivity of cells and cellular density of bioreactors.

As noted above, the present system, device and method increase cell density while maintaining metabolically effective producer cells or packaging cells. By increasing cell density while maintaining metabolically effective producer cells or packaging cells, space-time productivity are improved in terms of per-cell productivity.

EXAMPLES

FIG. 23 is a schematic diagram of an HDCR architecture configured to receive media, exchange oxygen for carbon dioxide, and output waste having a static volumetric oxygen exchange rate (kLa) of greater than about 60/hr, e.g., greater than about 63+/−12 (S.E.M.)/hr. Specifically, as represented, for example, by the schematic diagram of FIG. 23, the HDCR architecture achieves decoupling by utilizing membrane oxygenation and $CO_2$ exchange, whereby gases permeate the membrane to reach cells, while relying on gentle perfusion of media through the cell expansion niche to provide soluble nutrient and waste exchange. By stacking a plurality of HDCR membranes on top of one another, space is efficiently utilized and the system may be scaled up.

With the HDCR architecture, static volumetric oxygen exchange rates (kLa) of greater than about 60/hr were achieved, compared to flasks, STRs, and fixed beds, which for mammalian cell culture operate on the order of 1-8/hr. Exchange rates of about 60/hr provides sufficient gas exchange to sustain upwards of $10^8$ cells/mL.

As illustrated in FIG. 16, which is a microscope image of an exemplary HDCR membrane, where media perfuses left to right, and gas exchange occurs in and out of the screen. The HDCR membrane is supporting a microcarrier-assisted culture, which may be packed in the HDCR membrane and retained by, for example, a line of filter posts. As a representative example, in a single HDCR membrane of 145 cm$^2$ (i.e., the size of a 15 cm Petri dish), approximately 500M HEK293 cells were grown, which would normally require on the order of about 25×15-cm Petri dishes to culture. That is, the HDCR membrane may achieve intensification of about 25× per unit area.

Figure 24:
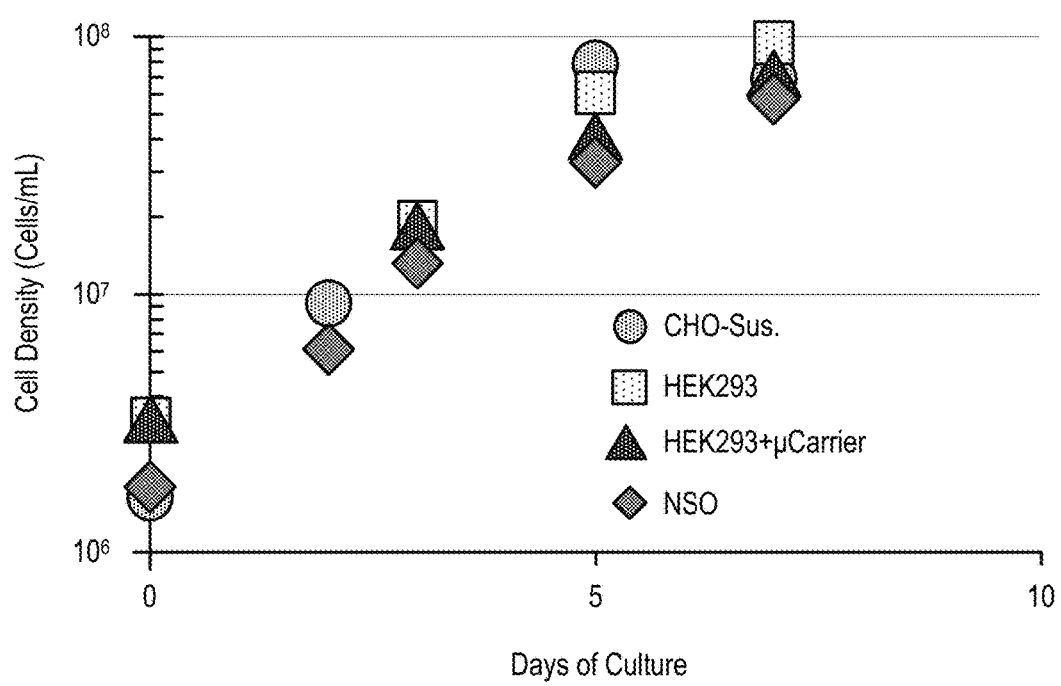
FIG. 24 is a plot of cell density (cells/mL) on the y-axis versus days of culture on the x-axis according to an exemplary embodiments.

The HDCR membrane is effective across cell lines. Using the present systems, devices and methods, HEK293 was cultured for AAV applications, HEK293 cells on microcarriers, CHO suspension cells for protein production applications, NS0 cells for antibody production applications, and A549 cells, CV-1 cells for oncolytic virus production. All of the cells noted above were tested and appeared to grow robustly. Doubling times were comparable to conventional flask culture. The HDCR architecture and platform may be considered universal with relevance for AAV, oncolytic viruses, antibodies, vaccines, and the like. Specifically, FIG. 24 is a plot of cell density (cells/mL) on the y-axis versus days of culture on the x-axis according to exemplary embodiments. In FIG. 24, HEK293 cells cultured for AAV applications are represented by squares, HEK293 cells on microcarriers are represented by filled triangles, CHO suspension cells are represented by filled circles, and NS0 cells are represented by filled diamonds. Using the present HDCR architecture, cell densities were increased from on the order of about $10^6$ to on the order of about $10^8$ in about 2-8 days.

Figure 25:
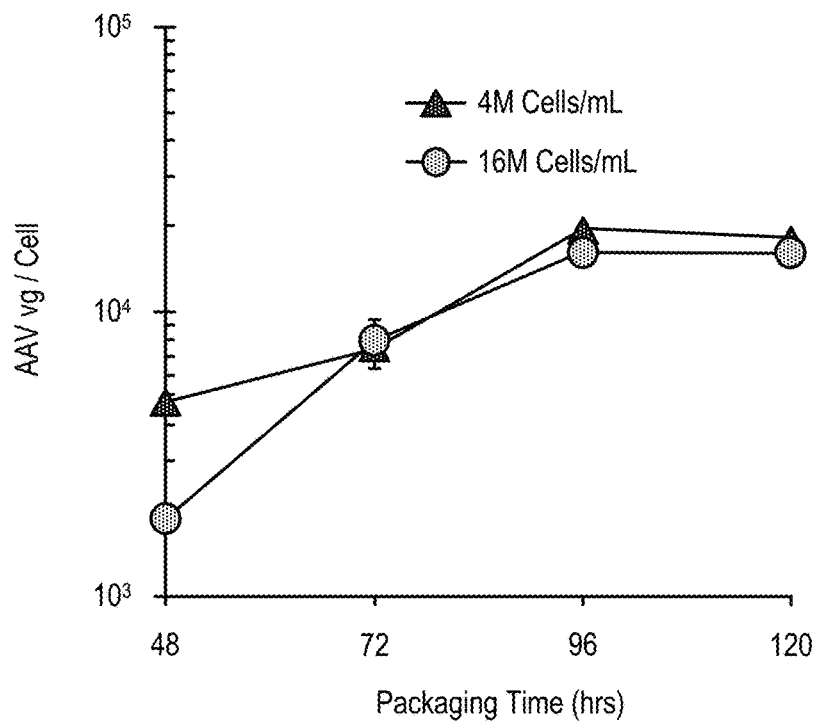
FIG. 25 is a plot of AAV (vg/cell) on the y-axis versus packaging time (in hours) on the x-axis for samples having 4M cells/mL and 16M cells/mL according to an exemplary embodiment.
Figure 26:
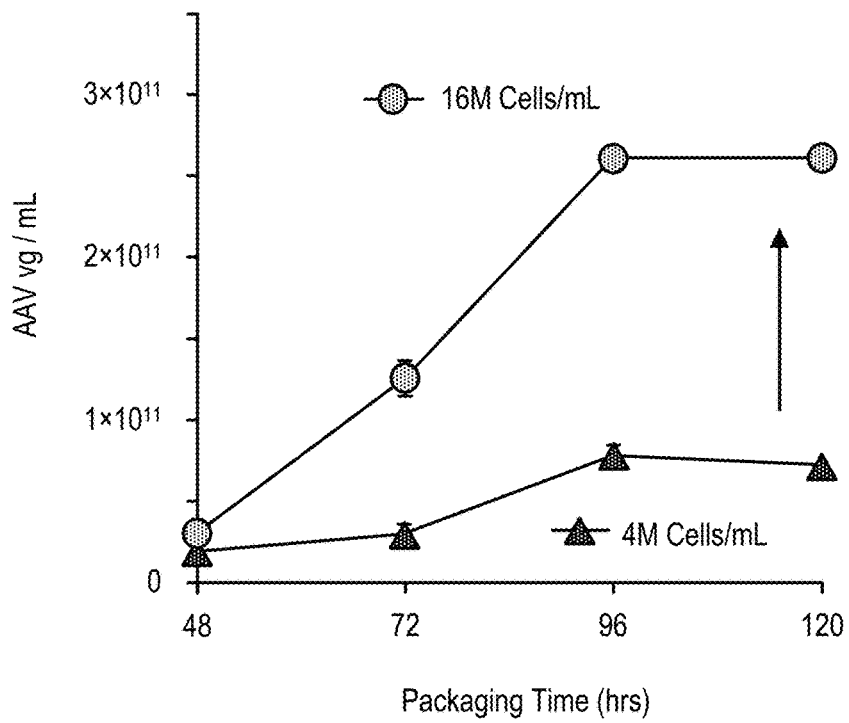
FIG. 26 is a plot of AAV (vg/mL) on the y-axis versus packaging time (in hours) on the x-axis for samples having 4M cells/mL and 16M cells/mL according to an exemplary embodiment.

Growing cells to high density includes AAV production processes using the HDCR system. For example, a 3-plasmid and PEI-based transfection approach was used for proof of concept using an AAV2-mCherry vector (3 PEI:1 DNA, 3 μg DNA/$10^6$ cells, 2 pHelper: 1.5 Rep/Cap: 1 AAV2-CMV-mCherry). DNAse-resistant particles in the resulting crude cell lysate by qPCR were observed. Yields per cell were comparable between conventional and higher cell densities. Thus, in terms of volumetric productivity, multiplicative improvements with increasing cell density are observed using the HDCR architecture. Specifically, FIG. 25 is a plot of AAV (vg/cell) on the y-axis versus packaging time (in hours) on the x-axis for samples having 4M cells/mL and 16M cells/mL according to an exemplary embodiment. FIG. 26 is a plot of AAV (vg/mL) on the y-axis versus packaging time (in hours) on the x-axis for samples having 4M cells/mL and 16M cells/mL according to an exemplary embodiment.

Figure 27:
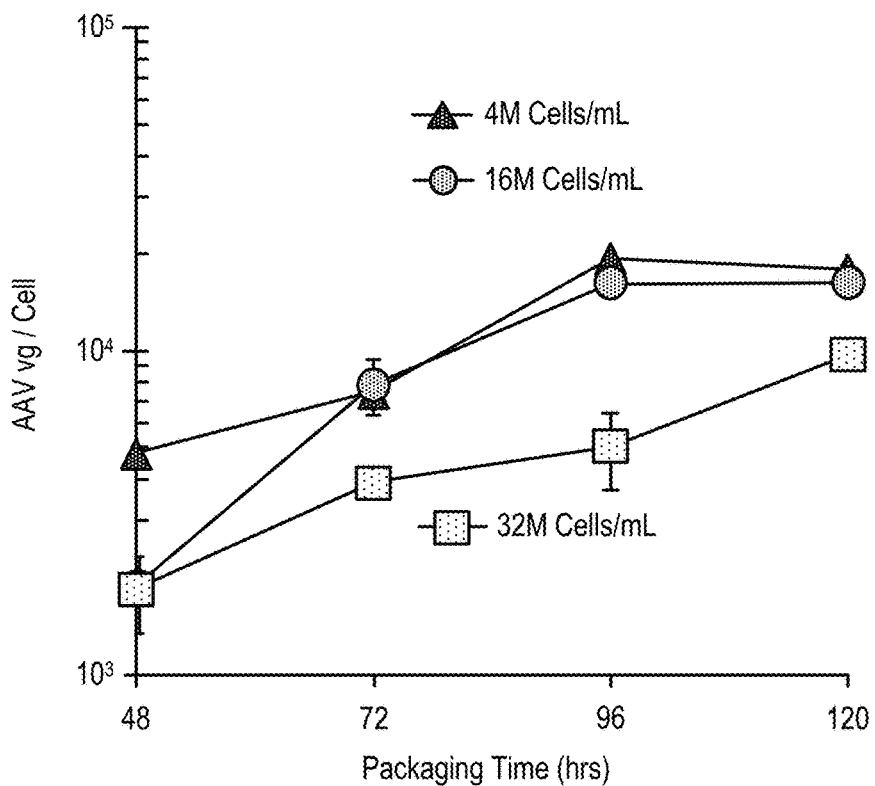
FIG. 27 is a plot of AAV (vg/cell) on the y-axis versus packaging time (in hours) on the x-axis for samples having 4M cells/mL, 16M cells/mL, and 32M cells/mL according to an exemplary embodiment.
Figure 28:
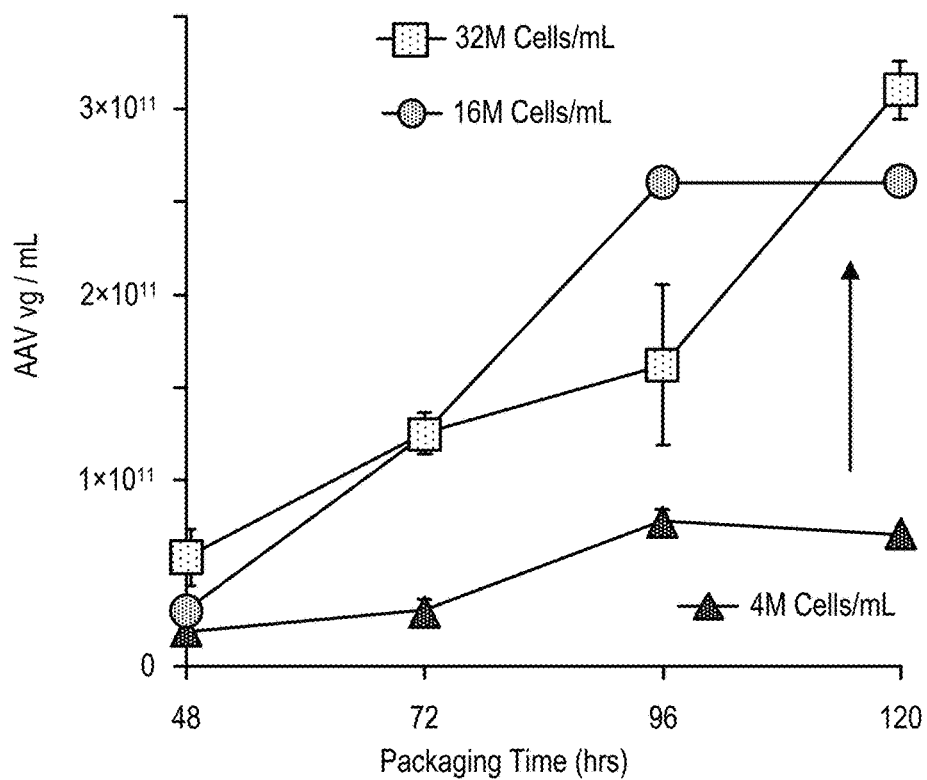
FIG. 28 is a plot of AAV (vg/mL) on the y-axis versus packaging time (in hours) on the x-axis for samples having 4M cells/mL, 16M cells/mL, and 32M cells/mL according to an exemplary embodiment.

Transfection may be a limiting factor. As density was increased, for instance up to 3×$10^7$ cells/mL, reductions in per-cell productivity were observed. Consequently, at these higher densities, volumetric productivity achieved diminished returns with increasing cell density. While there are a number of factors to consider, transfection may be the limiting factor. Specifically, FIG. 27 is a plot of AAV (vg/cell) on the y-axis versus packaging time (in hours) on the x-axis for samples having 4M cells/mL, 16M cells/mL, and 32M cells/mL according to an exemplary embodiment. FIG. 28 is a plot of AAV (vg/mL) on the y-axis versus packaging time (in hours) on the x-axis for samples having 4M cells/mL, 16M cells/mL, and 32M cells/mL according to an exemplary embodiment.

Figure 29:
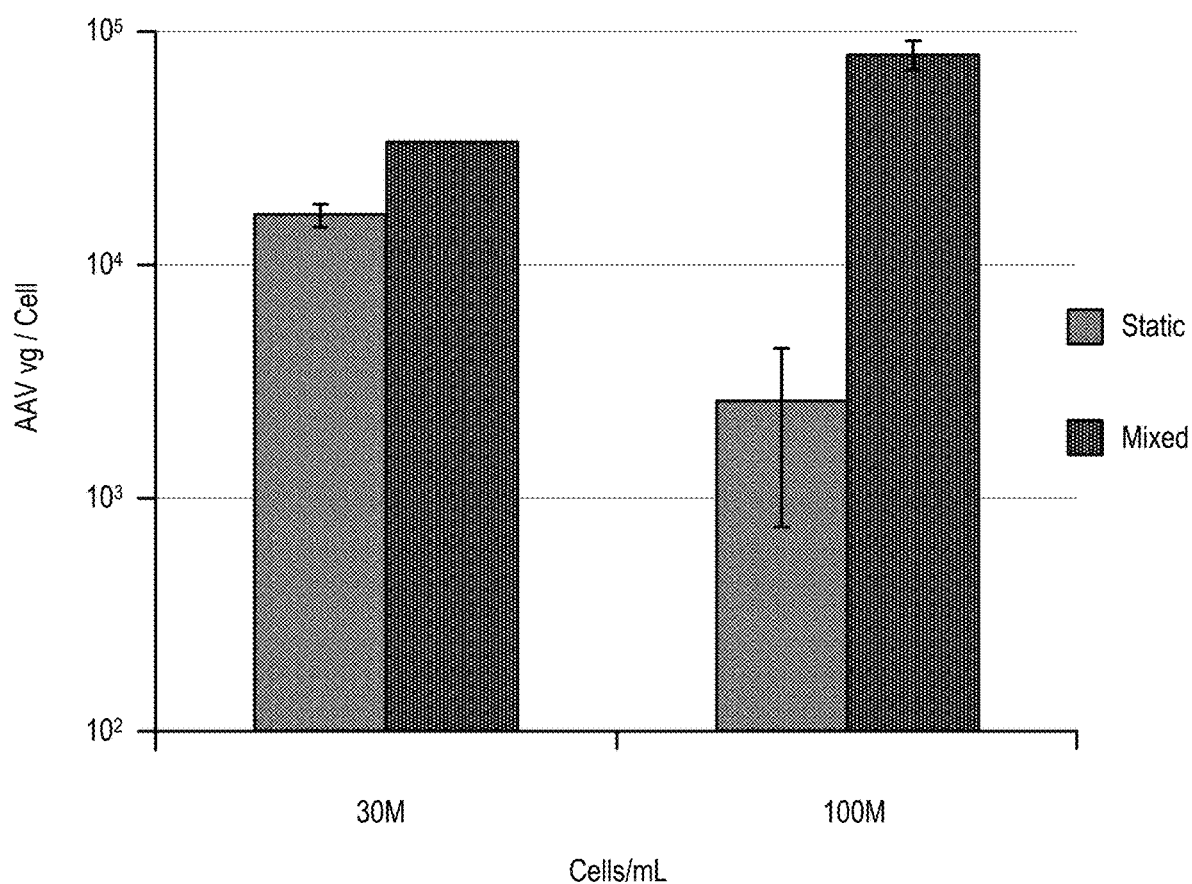
FIG. 29 is a chart of AAV (vg/cell) on the y-axis for samples having 30M and 100M cells/mL and comparing static and mixed modalities according to an exemplary embodiment.
Figure 30:
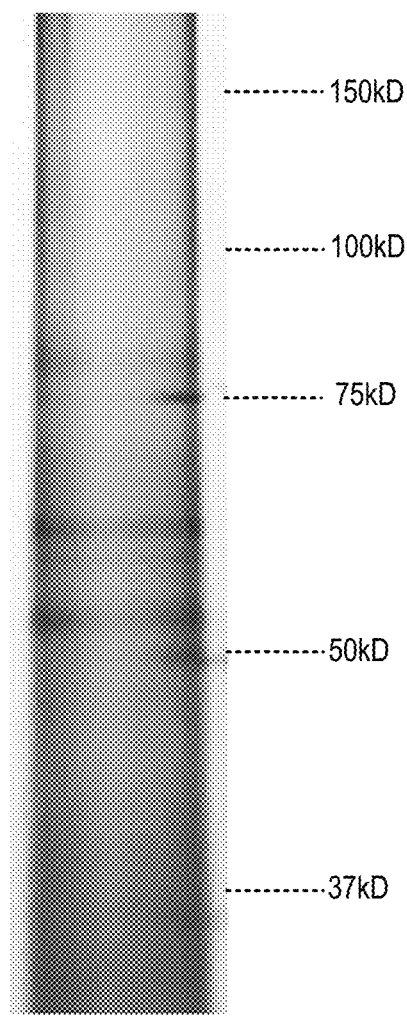
FIG. 30 is an HDCR-produced AAV2 vector scaled from about 37 kD to about 150 kD according to an exemplary embodiment.

A dispersion/mixing step was added to the process during transfection, which improved per-cell yields, notably at higher cell densities. Plasmid complexes may not interact with all cells due to the relatively high density; therefore, the lower per-cell productivity may be the result of an averaging of a normally producing cell population and a non-producing cell population. Specifically, FIG. 29 is a chart of AAV (vg/cell) on the y-axis for samples having 30M and 100M cells/mL and comparing static and mixed modalities according to an exemplary embodiment. A dispersion/mixing step markedly improved AAV (vg/cell). FIG. 30 is an HDCR-produced AAV2 vector scaled from about 37 kD to about 150 kD according to an exemplary embodiment.

Figure 31:
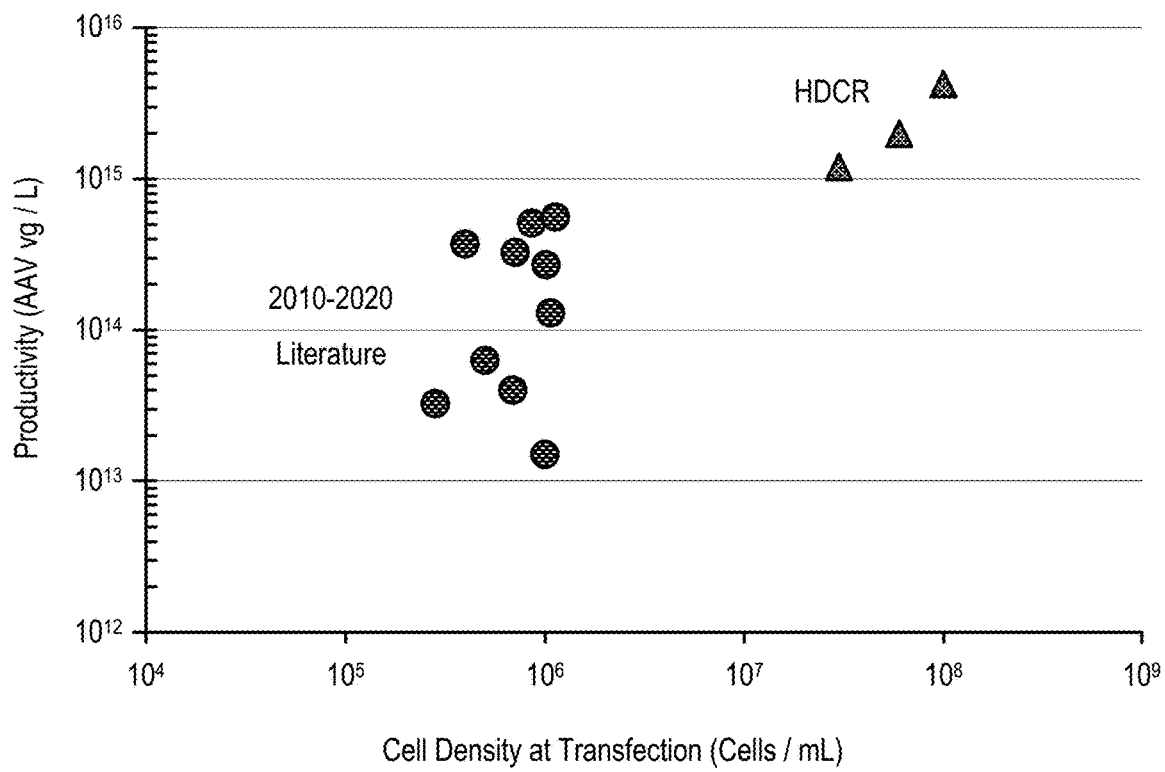
FIG. 31 is a plot of productivity (AAV vg/L) on the y-axis versus cell density at transfection (cells/mL) on the x-axis as reported in 2010-2020 literature and compared to the present HDCR-produced cells according to an exemplary embodiment.

FIG. 31 is a plot of productivity (AAV vg/L) on the y-axis versus cell density at transfection (cells/mL) on the x-axis as reported in 2010-2020 literature and compared to the present HDCR-produced cells according to an exemplary embodiment. Productivity in the 2010-2020 literature was reported between about $10^{13}$ and about $10^{15}$ AAV (vg/L), and cell density at transfection was reported between about $10^5$ and about $10^6$ (cells/mL). Whereas, productivity with the HDCR architecture is between about $10^{15}$ and about $10^{16}$ AAV (vg/L), and cell density at transfection is reported between about $10^7$ and about $10^8$ (cells/mL). In summary, HDCR boosts AAV volumetric productivity to a $10^{15}$ vg/L regime.

Figure 32:
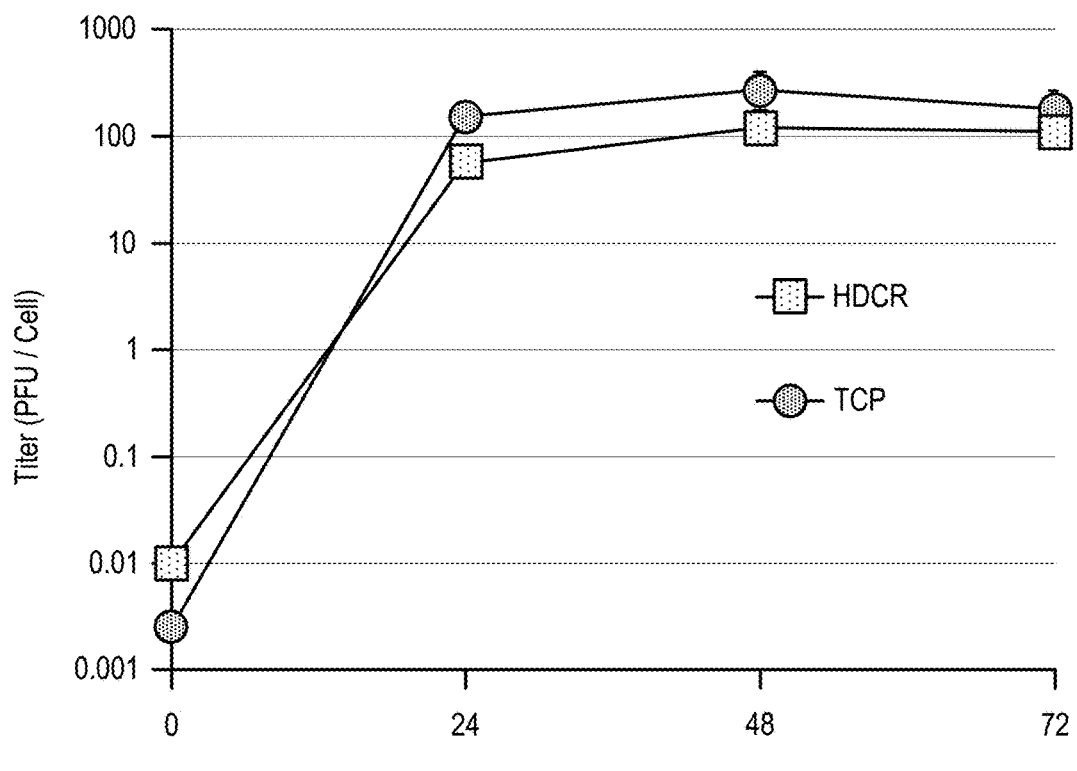
FIG. 32 is a plot of titer (PFU/cell) on the y-axis versus hours post-infection on the x-axis and comparing tissue culture (flask) production (TCP) versus HDCR production according to an exemplary embodiment.

HDCR supports CF33-hNIS orthopox production. Oncolytic virus production in the HDCR was proven. For example, CF33-hNIS, a replication competent chimeric orthopox virus with efficacy against colon cancers, was produced. A549 cells were grown up in the HDCR to 2×$10^7$ cells/mL and infected with CF33 at an MOI of 0.01. FIG. 32 is a plot of titer (PFU/cell) on the y-axis versus hours post-infection on the x-axis and comparing tissue culture (flask) production (TCP) versus HDCR production according to an exemplary embodiment. FIG. 32 demonstrates comparable per-cell CF-33 production in the HDCR compared to conventional production in tissue culture (flask) production (TCP). As above, increases in cell density translate into multiplicative improvements in volumetric productivity. (Please note, HOV-2 orthopoxvirus is a chimeric poxvirus encoding a human sodium iodide symporter (hNIS) at a redundant tk locus, aka CF33-hNIS. Also, HOV-2 titers (pfu per cell) from production in A549 cells were grown in 24 well HDCR plates at high cell density (2×$10^7$ cells/mL) versus standard monolayer production. Further, cells were harvested at 24, 48, and 72 hours post-infection.)

Therefore, decoupling of gas and media supplies in the HDCR architecture is useful for supporting high density cell cultures and has application to AAV and oncolytic virus production.

Additional Examples

Figures 33, 34:
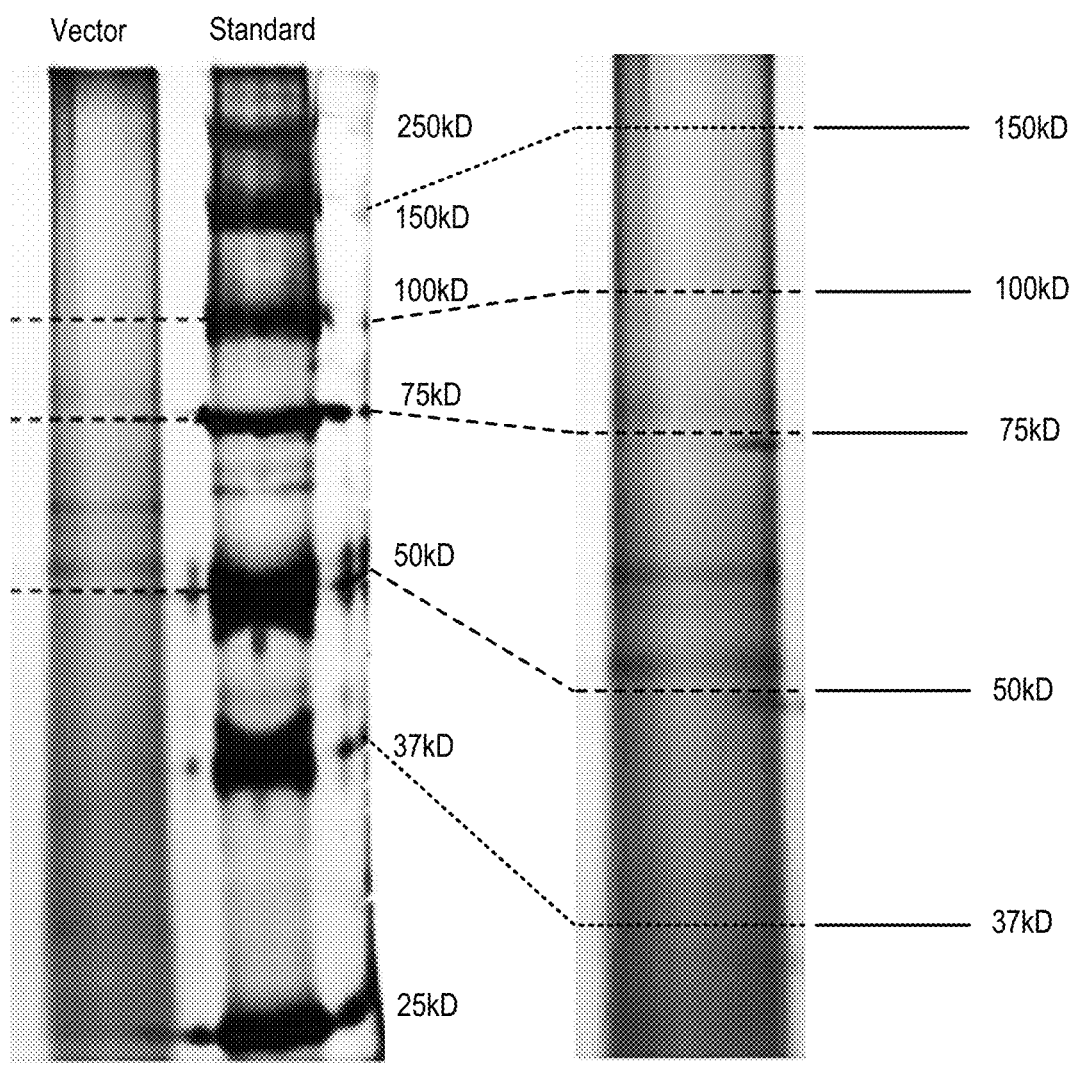
FIG. 33 is a side-by-side comparison of an AAV2-mCherry HDCR vector versus standard scaled from about 25 kD to about 250 kD according to an exemplary embodiment.
FIG. 34 is an HDCR-produced AAV2 vector scaled from about 37 kD to about 150 kD according to an exemplary embodiment.

FIG. 33 is a side-by-side comparison of an AAV2-mCherry HDCR vector versus standard scaled from about 25 kD to about 250 kD according to an exemplary embodiment.

FIG. 34 is an HDCR-produced AAV2 vector scaled from about 37 kD to about 150 kD according to an exemplary embodiment.

Figure 35:
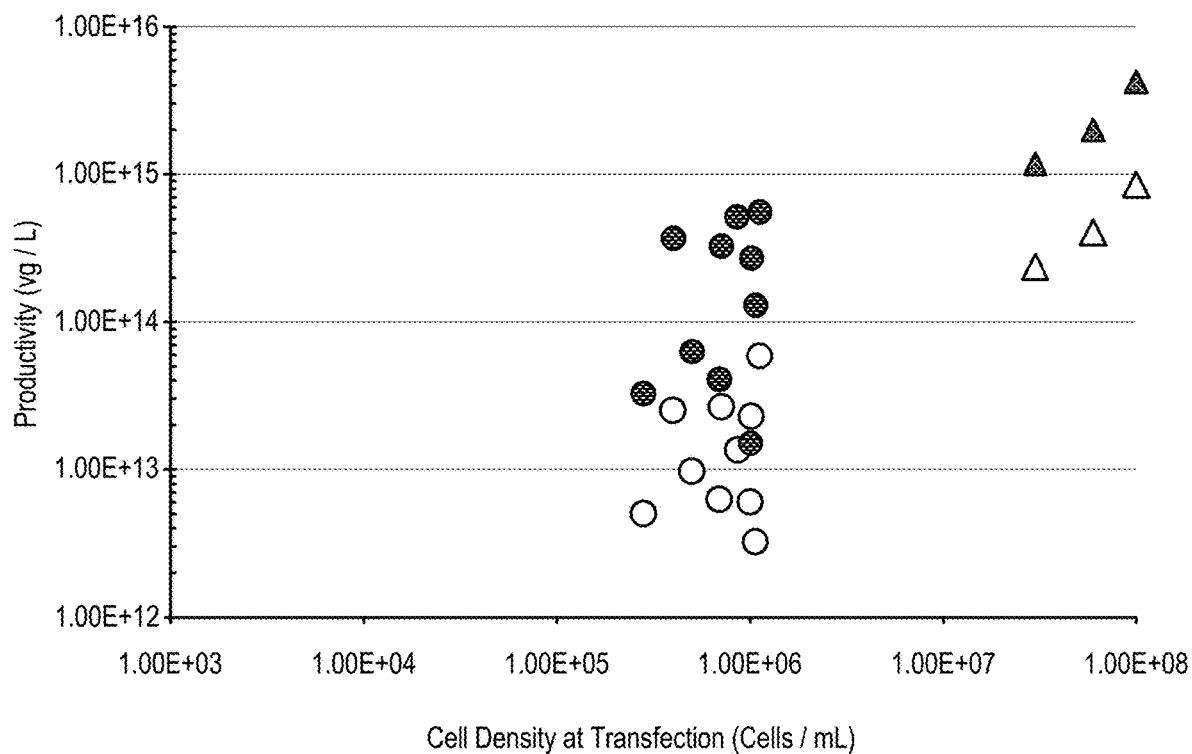
FIG. 35 is another plot (inclusive of the data in FIG. 31) of productivity (AAV vg/L) on the y-axis versus cell density at transfection (cells/mL) on the x-axis as reported in 2010-2020 literature and compared to the present HDCR-produced cells further including results at relatively lower productivities according to an exemplary embodiment.

FIG. 35 is another plot (inclusive of the data in FIG. 31) of productivity (AAV vg/L) on the y-axis versus cell density at transfection (cells/mL) on the x-axis as reported in 2010-2020 literature and compared to the present HDCR-produced cells further including results at relatively lower productivities according to an exemplary embodiment.

Figure 36:
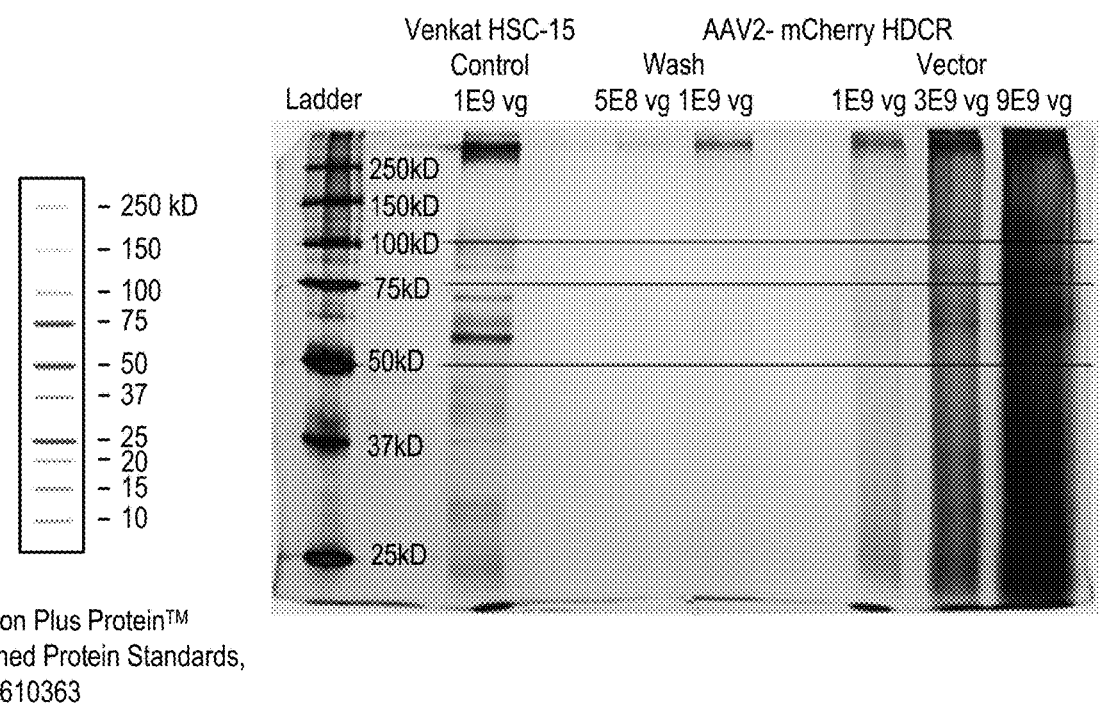
FIG. 36 is an image of an unstained protein standard (at left) alongside AAV2 from HDCR (at right) according to an exemplary embodiment.

FIG. 36 is an image of an unstained protein standard (at left) alongside AAV2 from HDCR (at right) according to an exemplary embodiment.

FIG. 37 is an image of an unstained protein standard (at left) alongside AAV2-mCherry HDCR vector (at right) according to an exemplary embodiment.

Figure 80:
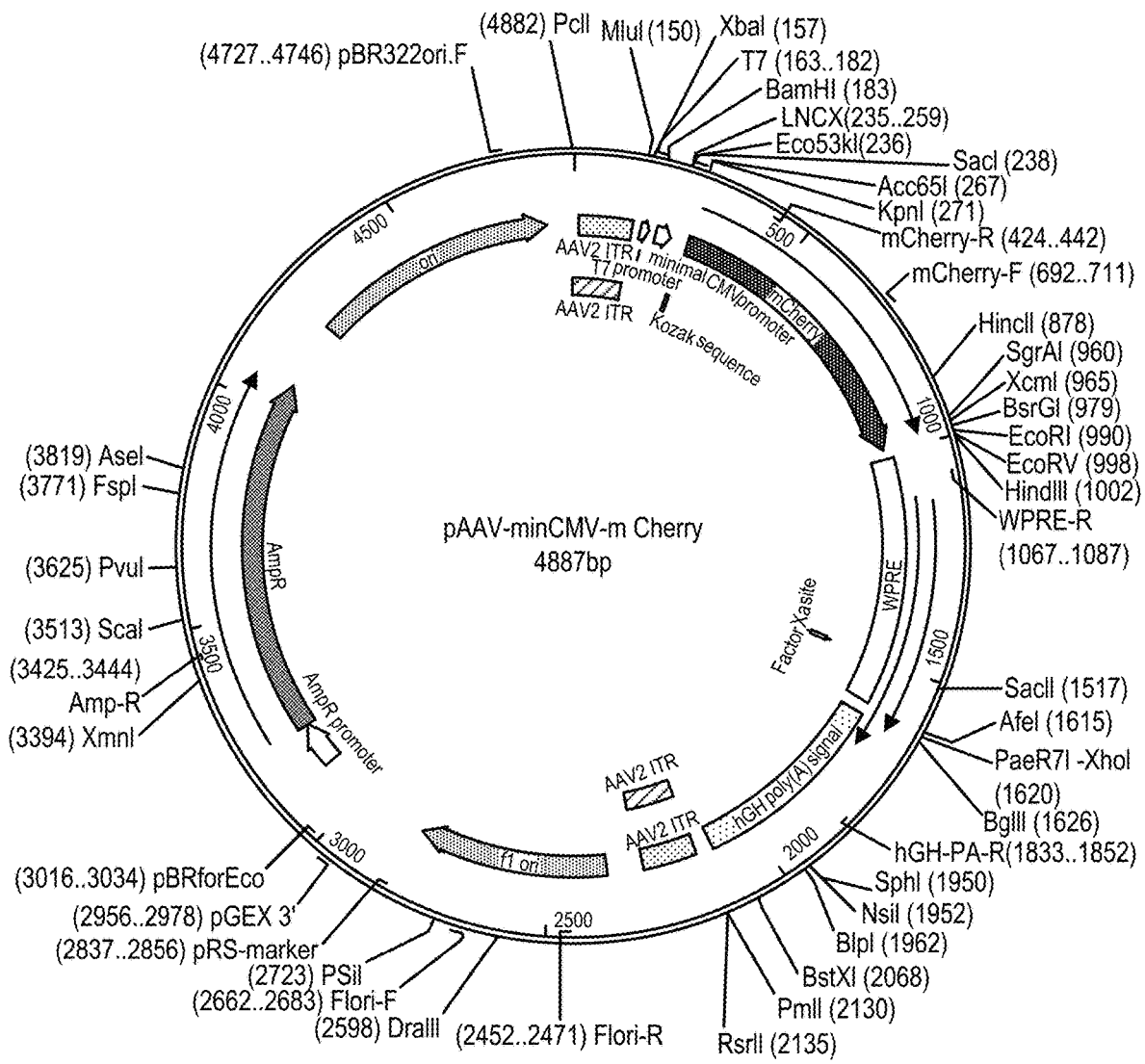
FIG. 80 is a schematic representation of pAAV-minCMV-mCherry as reported in the prior art.

FIG. 80 is a schematic representation of pAAV-minCMV-mCherry as reported by Zhang et al., in "Efficient construction of sequence-specific TAL effectors for modulating mammalian transcription", in Nat Biotechnol, on Jan. 19, 2011.

FIG. 80 is a schematic representation of pAAV-RC as reported in the prior art. Related to FIG. 80, the following Table 1 summarizes features and their corresponding nucleotide positions:

| Feature | Nucleotide Position |
| --- | --- |
| adenovirus E2A gene | 1-5336 |
| adenovirus E4 gene | 5337-8537 |
| adenovirus VA gene | 8538-9280 |
| pUC origin of replication | 9367-10034 |
| ampicillin resistance (bla) ORF | 10182-11042 |
| f1 origin of ss-DNA replication | 11305-11600 |

Figure 81:
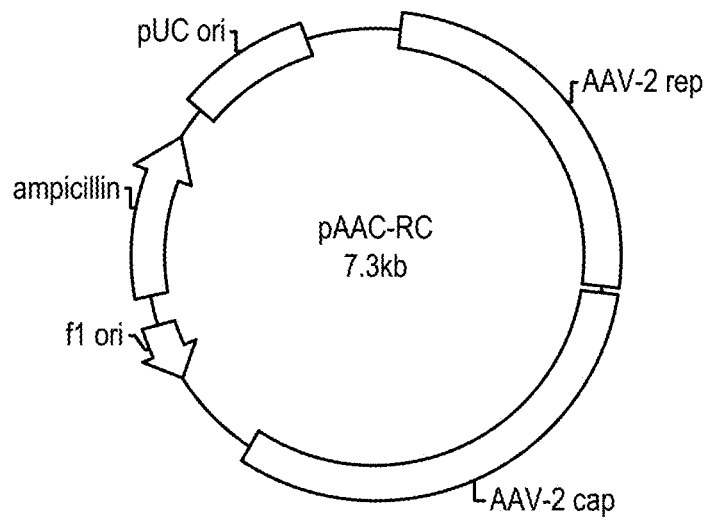
FIG. 81 is a schematic representation of pAAV-RC as reported in the prior art.
Figure 82:
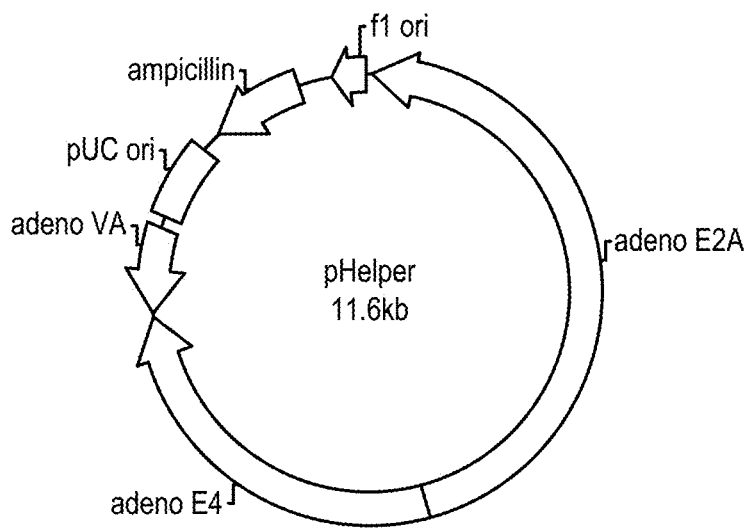
FIG. 82 is a schematic representation of pHelper as reported in the prior art.

FIG. 81 is a schematic representation of pHelper as reported in the prior art. Related to FIG. 81, the following Table 2 summarizes features and their corresponding nucleotide positions:

| Feature | Nucleotide Position |
| --- | --- |
| AAV-2 rep gens | 131-1996 |
| AAV-2 cap gene | 2013-4346 |
| f1 origin of ss-DNA replication | 4838-5143 |
| ampicillin resistance (bla) ORF | 5292-6149 |
| pUC origin of replication | 6300-6967 |

Overview of Exemplary Embodiments

Initially, it is noted that FIGS. 38, 40-45, 54-56, 61, 65-75 and 79 include an exemplary coordinate axis for convenience. The directions are not intended to be limiting. As seen, for example, in FIG. 40, a width of the device may be provided in an x-axis direction where "into the page" is a −x direction and "out of the page" is a +x direction; a length of the device may be provided in a y-axis direction where page-left is a −y direction and page-right is a +y direction; and a height of the device may be provided in a z-axis direction where page-up is a +z direction and page-down is a −z direction. FIGS. 38, 40-45, 54-56, 61, 65-75 and 79 use similar conventions rotated and labeled as appropriate for the Figure.

FIG. 38 is a plan view image of a small-scale HDCR platform having a volume on the order of about 5 mL and a cell density on the order of about $10^{12}$ vg according to an exemplary embodiment. The small-scale HDCR may be suitable for research and development applications.

Figure 39:
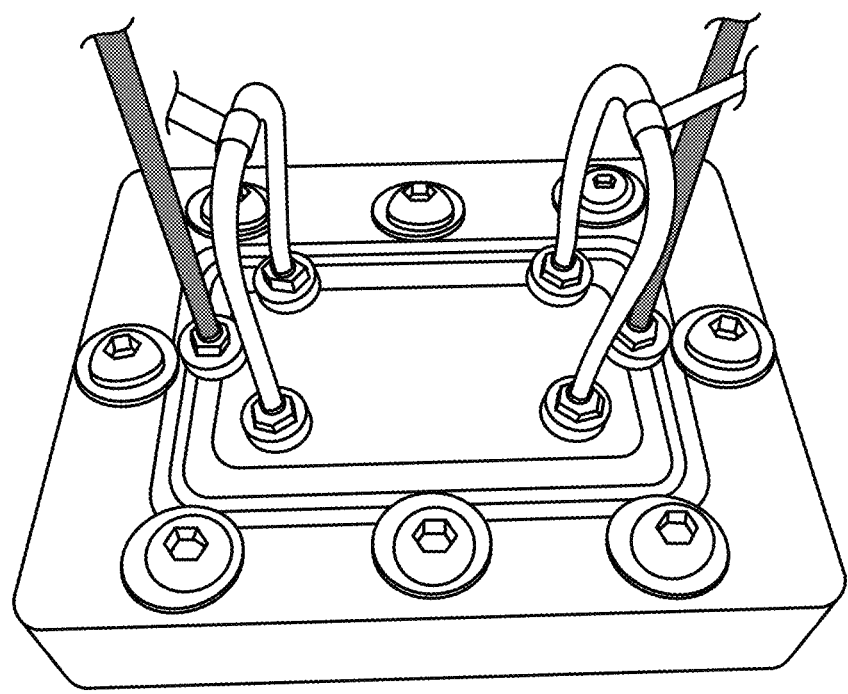
FIG. 39 is a perspective view image of a medium-scale HDCR platform having a volume on the order of about 500 mL and a cell density on the order of about $10^{14}$ vg according to an exemplary embodiment.

FIG. 39 is a perspective view image of a medium-scale HDCR platform having a volume on the order of about 500 mL and a cell density on the order of about $10^{14}$ vg according to an exemplary embodiment. The medium-scale HDCR may be suitable for animal study applications.

Figure 40:
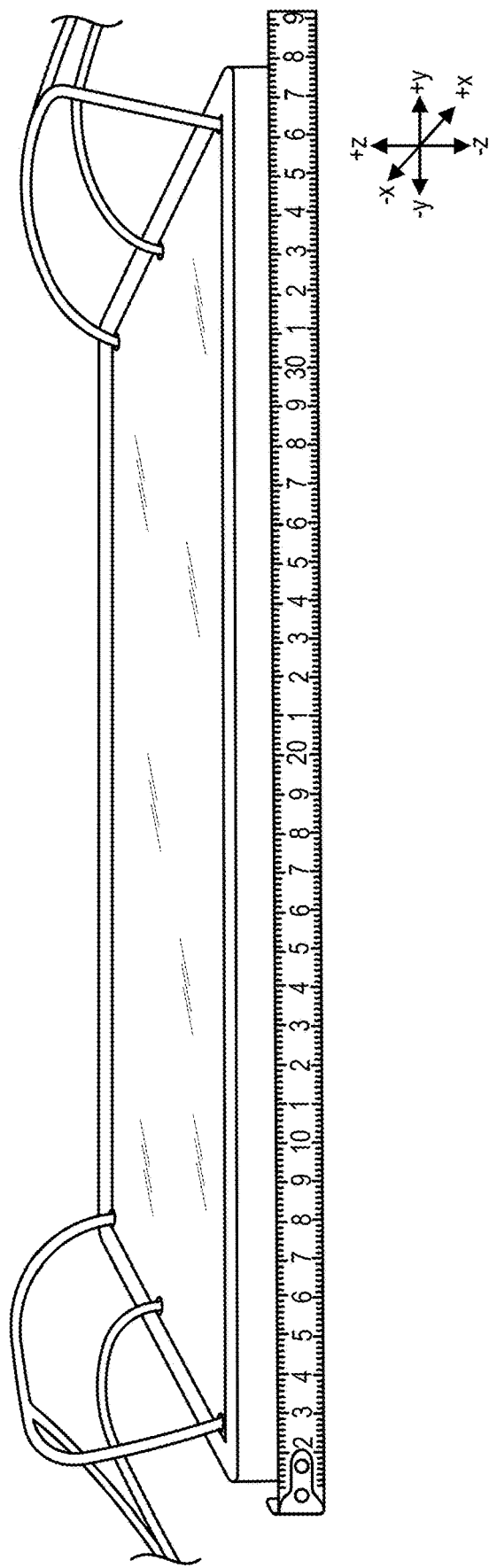
FIG. 40 is a perspective view image of a large-scale HDCR platform having a volume on the order of about 50 L and a cell density on the order of about $10^{16-17}$ vg according to an exemplary embodiment.

FIG. 40 is a perspective view image of a large-scale HDCR platform having a volume on the order of about 50 L and a cell density on the order of about $10^{16.47}$ vg according to an exemplary embodiment. In this exemplary embodiment, the plate extends about 15 inches from inlet to outlet. The large-scale HDCR may be suitable for clinical applications.

Some embodiments of the present systems, devices and methods include gas perfusable microfabricated membranes for high density cell culture. Oxygen may be the most limiting nutrient and was observed to be about 155 times more limiting than the next most limiting nutrient (i.e., GLN). Some embodiments of the present systems, devices and methods provide oxygen directly from gas perfusable membranes on which the cells are grown to overcome oxygen delivery limitations in traditional culture systems. With translation in mind, the membranes may be composed only of medical grade, relatively inexpensive materials to mitigate contaminant leaching concerns.

Exemplary Embodiments

Figure 41:
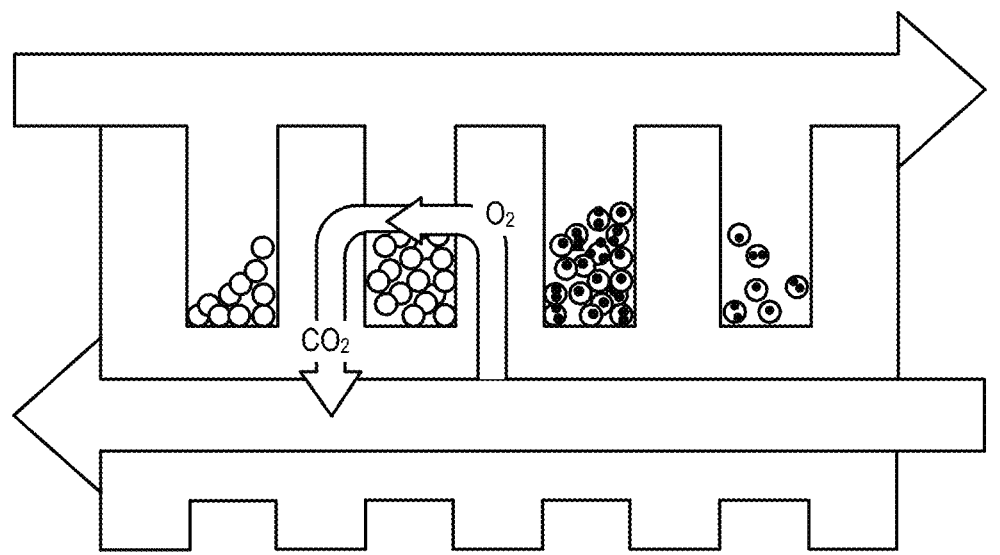
FIG. 41 is a schematic side view of an HDCR platform having spaced fins configured to supply oxygen and receive carbon dioxide according to an exemplary embodiment.

FIG. 41 is a schematic side view of an HDCR platform having spaced fins configured to supply oxygen and receive carbon dioxide according to an exemplary embodiment.

Figure 42:
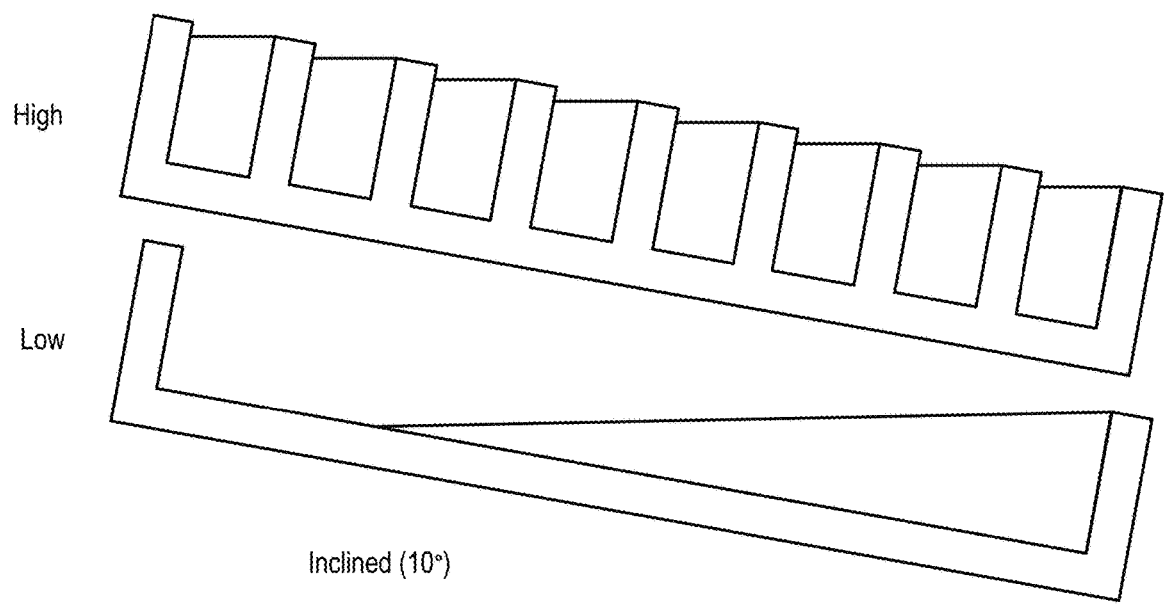
FIG. 42 is a schematic side view of inclined HDCR platforms according to an exemplary embodiment.

FIG. 42 is a schematic side view of inclined HDCR platforms according to an exemplary embodiment. The upper portion of FIG. 42 is a high density embodiment of the inclined HDCR platform having 7 fins between ends of the device. The lower portion of FIG. 42 is a low density embodiment of the inclined HDCR platform having no fins between ends of the device. Both the high density and low density embodiments are inclined at an angle of about 10 degrees. See FIGS. 70-78, inclusive, for an analysis of impacts of various angles of incline.

Figure 43:
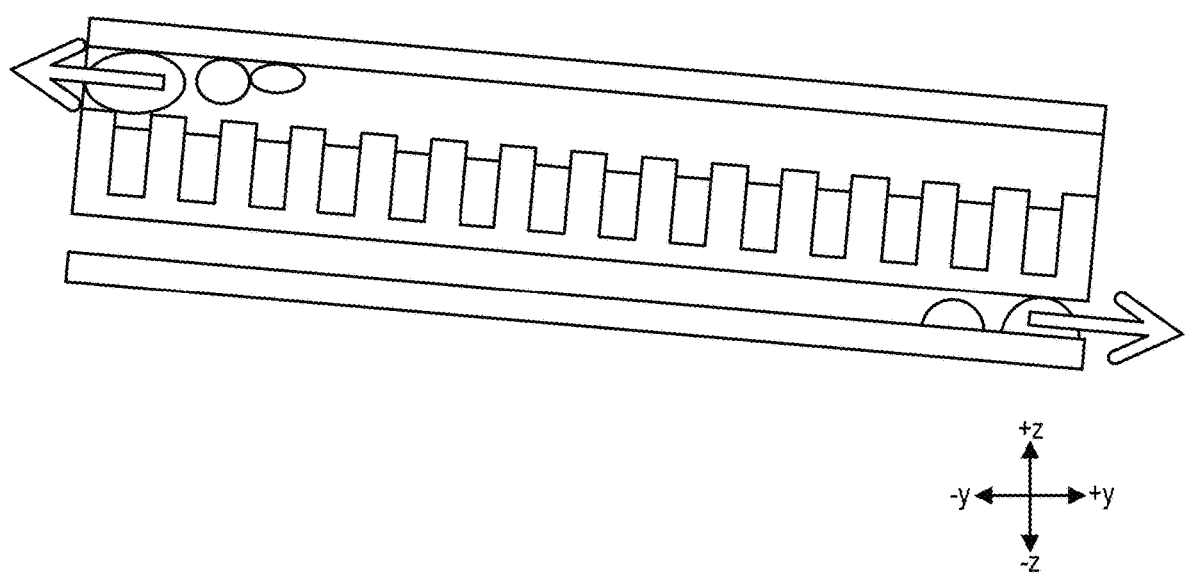
FIG. 43 is a schematic side view of an inclined HDCR platform configured to promote removal of gas bubbles (above) and condensation (below) according to an exemplary embodiment.

FIG. 43 is a schematic side view of an inclined HDCR platform configured to promote removal of gas bubbles (above) and condensation (below) according to an exemplary embodiment.

FIGS. 44-47, 52-54 and 79 illustrate an exemplary embodiment of an HDCR device according to an exemplary embodiment.

Figure 44:
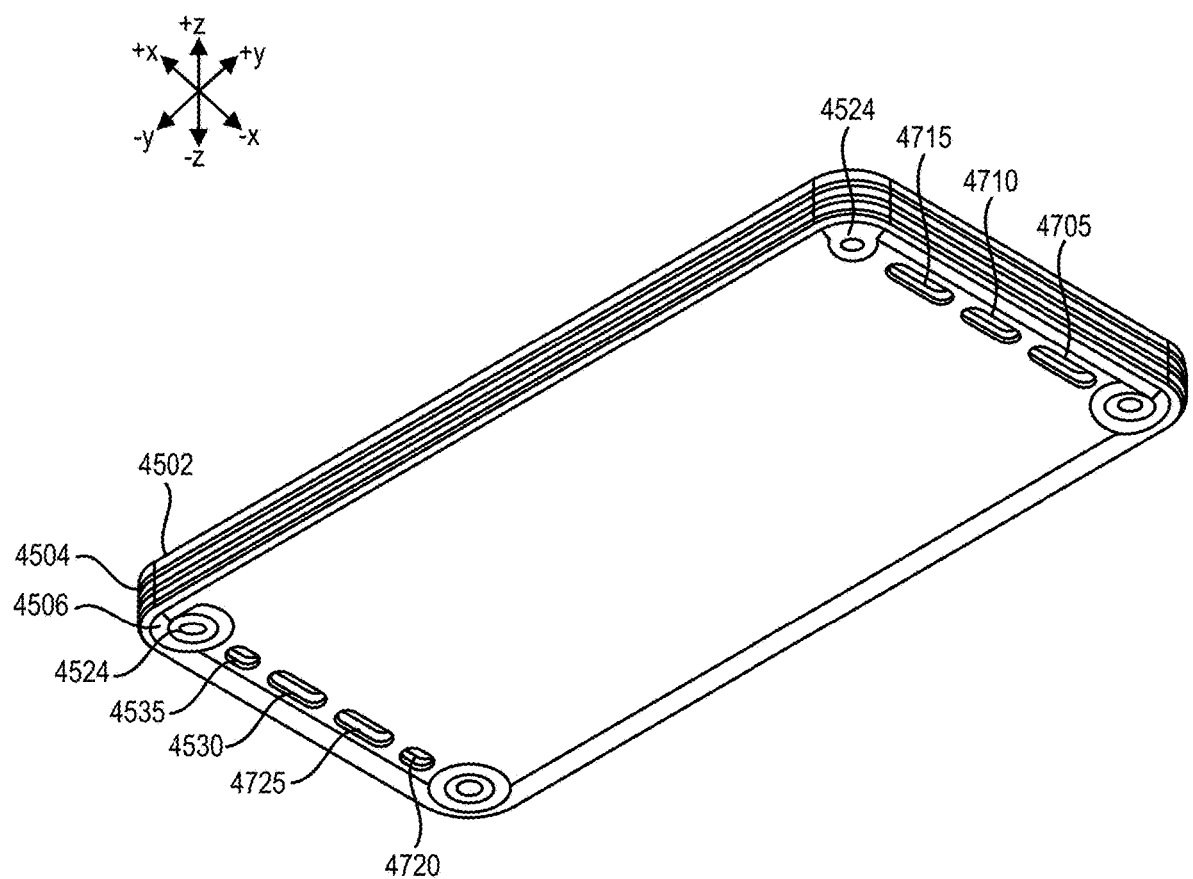
FIG. 44 is a bottom perspective view of an HDCR cartridge according to an exemplary embodiment.

FIG. 44 is a bottom perspective view of an HDCR cartridge according to an exemplary embodiment.

FIG. 45 is a top perspective view of the HDCR cartridge of FIG. 44 according to an exemplary embodiment. The HDCR device may have a plurality of stacked plates configured to stack one on another. In FIG. 45, a stack of three plates 4502, 4504, 4506 is provided. Each plate 4502, 4504, 4506 may have one or more channels. In FIG. 45, three channels 4512, 4514, 4516 are provided. The three channels 4512, 4514, 4516 may be bounded by a boundary ridge 4522. The boundary ridge 4522 may include a continuous wall bounding an entirety of a periphery of the three channels 4512, 4514, 4516. The boundary ridge 4522 may have relatively thicker portions in each corner of the plate. Each corner of the plate may have an opening 4524 for permitting a connector (not shown) to pass therethrough. The opening 4524 may be bounded by a circular ridge 4526. Each opening 4524 of each plate may communicate with an opening in an adjacent plate.

FIG. 46 is a zoomed-in portion of the top perspective view of FIG. 45 of the HDCR cartridge according to an exemplary embodiment. The first channel 4512 may be separated from the second channel 4514 with a first ridge 4605. The second channel 4514 may be separated from the third channel 4516 with a second ridge 4610. Each of the first ridge 4605 and the second ridge 4610 may extend continuously across an entirety or a substantial entirety of each plate (e.g., 4502). The first channel 4512 may be separated from the second channel 4514 with a first ridge 4605.

Figure 47:
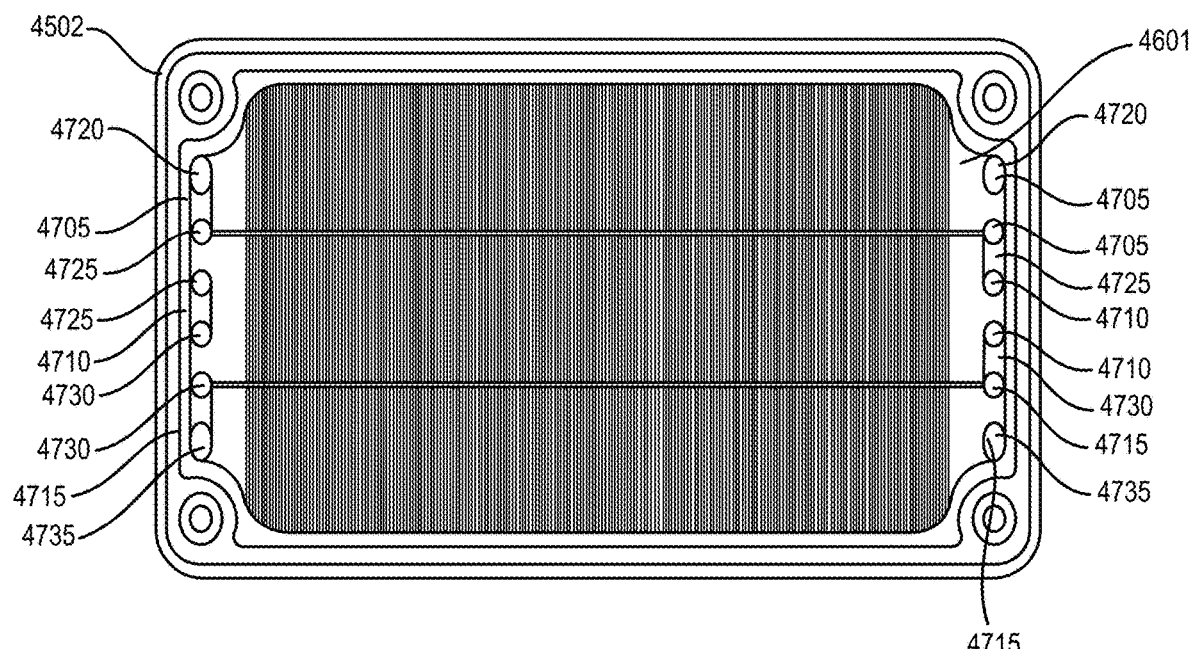
FIG. 47 is a top plan view of the HDCR cartridge of FIGS. 44-46 according to an exemplary embodiment.

FIG. 47 is a top plan view of the HDCR cartridge of FIGS. 44-46 according to an exemplary embodiment. Each plate (e.g., 4502, 4504, 4506) may have a plurality of openings through a base channel surface (e.g., 4601) thereof to communicate with openings located in an adjacent plate or an adjacent structure other than a plate. The openings of one plate may communicate with openings in another plate. A top of one plate may be configured to nest and/or structurally cooperate with a bottom of another plate to form a unitary sandwich construction, such as that shown in detail in FIGS. 52-54, inclusive.

Figure 79:
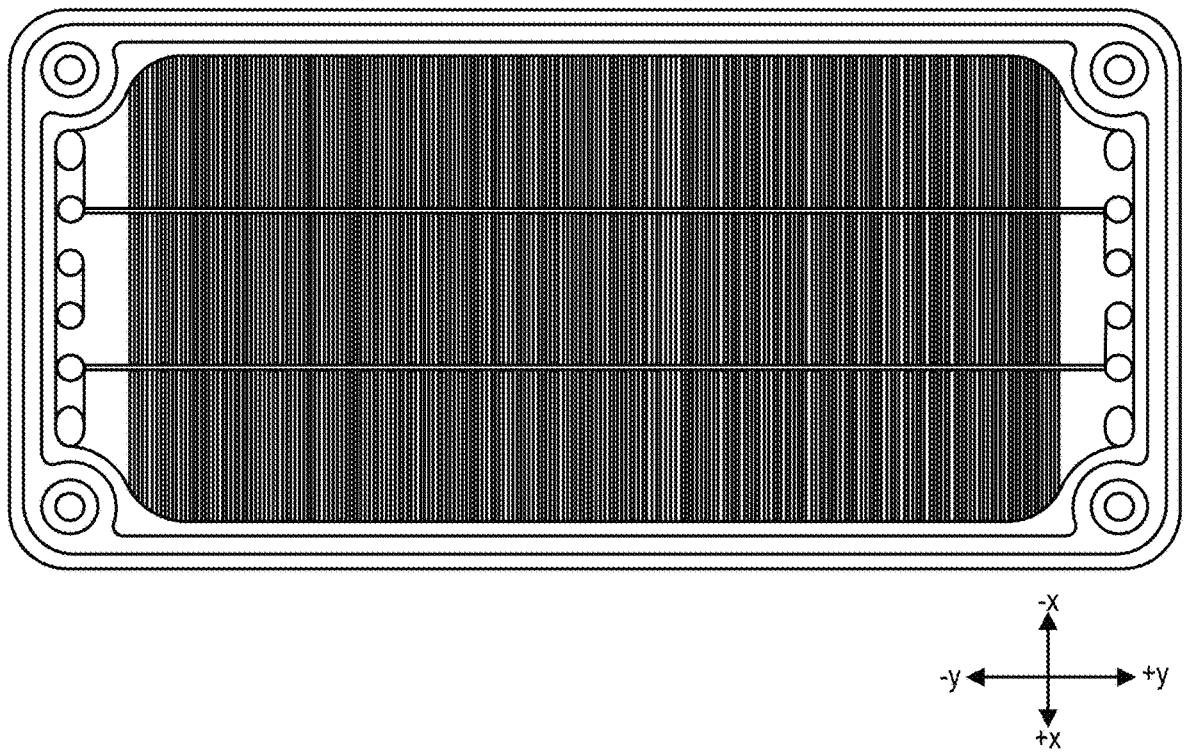
FIG. 79 is an enlarged plan view of an HDCR membrane (cf.

FIG. 79 is an enlarged plan view of an HDCR membrane (cf. FIG. 47) according to an exemplary embodiment. Specifically, 3-stacked 50 $cm^2$ HDCR membranes are provided. Note the asymmetry of the left and right media inlet and outlet channels. In this configuration, the membranes are rotated 180 degrees with respect to the membrane above or below them. This creates a tortuous flowpath that can improve mixing of components added into the bioreactor to achieve better uniformity.

For example, within an area bounded by the boundary region 4522, adjacent to a first end of the first ridge 4605 and a first end of the second ridge 4610, the first plate 4502 may include a first opening 4705, a second opening 4710, and a third opening 4715; and still within the area bounded by the boundary region 4522, adjacent to a second end of the first ridge 4605 and a second end of the second ridge 4610, the first plate 4502 may further include a fourth opening 4720, a fifth opening 4725, a sixth opening 4730, and a seventh opening 4735. The first opening 4705 of the first plate 4502 may communicate with one end of the fourth opening 4720 and one end of the fifth opening 4725 in the second plate 4504 to form a first common fluid passageway through the first plate 4502 and the second plate 4504. The second opening 4710 of the first plate 4502 may communicate with another end of the fifth opening 4725 and one end of the sixth opening 4730 in the second plate 4504 to form a second common fluid passageway through the first plate 4502 and the second plate 4504. The third opening 4715 of the first plate 4502 may communicate with another end of the sixth opening 4730 and the seventh opening 4735 in the second plate 4504 to form a third common fluid passageway through the first plate 4502 and the second plate 4504. The fourth opening 4720 of the first plate 4502 may communicate with one end of the first opening 4705 in the second plate 4504 to form a fourth common fluid passageway through the first plate 4502 and the second plate 4504. The fifth opening 4725 of the first plate 4502 may communicate with another end of the first opening 4705 and one end of the second opening 4710 in the second plate 4504 to form a fifth common fluid passageway through the first plate 4502 and the second plate 4504. The sixth opening 4730 of the first plate 4502 may communicate with another end of the second opening 4710 and one end of the third opening 4715 in the second plate 4504 to form a sixth common fluid passageway through the first plate 4502 and the second plate 4504. The seventh opening 4735 of the first plate 4502 may communicate with another end of the third opening 4715 in the second plate 4504 to form a seventh common fluid passageway through the first plate 4502 and the second plate 4504. The first opening 4705, the second opening 4710, the third opening 4715, the fifth opening 4725, and the sixth opening 4730 may have an approximately similar shape, i.e., they may each be a relatively long slot with rounded ends as shown in FIG. 47. The fourth opening 4720 and the seventh opening 4735 may have an approximately similar shape, i.e., they may each be a relatively short slot with rounded ends as shown in FIG. 47. The overlap of one set of openings with another may effectively form an approximately circular shaped through opening when looking straight down through the plates, as seen best in FIG. 47.

As such, at each end of the first plate 4502, the first channel 4512 of the first plate 4502 may be configured to communicate with the first channel 4512 and the second channel 4512 of the second plate 4504; the second channel 4514 of the first plate 4502 may be configured to communicate with the first channel 4512 and the third channel 4516 of the second plate 4504; and the third channel of the first plate 4502 may be configured to communicate with the second channel 4514 and the third channel 4514 of the second plate 4504.

Each plate (e.g., 4502) may be configured with a plurality of structures in active region 4699, the structures configured to promote oxygen and carbon dioxide exchange and the other features of the HDCR system described herein. The plurality of structures in the active region 4699 may be a series of alternatively protruding ridges and recessed depressions formed on and in the base channel surface 4601 of each plate. A side cross section through various exemplary ridges and depressions is shown in FIGS. 1, 2, 3, 5, 6, FIGS. 14, 41, 42, 43, 66, 67, 68, and 72, inclusive. Other structures may be provided such as the grooves/fins shown in the upper left corner of FIG. 7, the wells shown in the lower left corner of FIG. 7, and/or the posts shown in the lower right corner of FIG. 7. The region 4699 may have a smooth structure such as that shown in the upper right corner of FIG. 7. The structures in the region 4699 may be any suitable shape including pillars, channels, grooves, bumps, protrusions, and/or legs in any suitable combination. Each structure may be substantially similar to others in the region 4699 or different shapes may be provided within the region 4699.

2-Plasmid Transfection in HDCR

In an exemplary embodiment, a demo-scale HDCR bioreactor according to an exemplary embodiment was assembled with a glass bottom for microscope compatibility. About 1.7 mL of blue-stained Cytodex 3 microcarriers were flowed into a membrane of the bioreactor via two about 50 mL syringes depressed to and fro. The bioreactor and components were autoclaved about 15 min on liquid cycle.

On Day 1, final connections with 3-way stopcocks were made under a biohood. A fluid path in the HDCR bioreactor was flushed with 37° C., degassed PBS+1% P/S/A to remove bubbles including loop. The HDCR bioreactor was subsequently flushed with DMEM+10% FBS+1% P/S/A (20 mL) on Day 2. Stopcocks were rotated to purge bubbles within dead volume. 3.6M of P21 HEK293AAV cells were loaded into the bioreactor (3 PM) through gas trap lines and cycled through via peristatlic pump for 3×1 min to evenly seed within the membrane. A flow rate for gas was set to about 0.1 mL/min and media flow was set to about 0.02 mL/min. Bubbles were removed daily from trap by purging through with media.

On Day 5, a transfection cocktail was produced assuming $4 \times 10^7$ cell/mL density with 4 mg DNA/1M cells (232 uL pDP2rs, 52 uL pAAV-ssG FP, 1216 uL DMEM combined with 567 uL PEI, 933 uL DMEM; vortexed about 5 sec, allowed to stand about 10 min at RT). Later on Day 5, the transfection cocktail was injected into the loop and circulated for 3×1 min. The bioreactor was returned to incubator with perfusion off. Media was mixed on loop for about 1 min at 30 min, 60 min, 90 min post-transfection. Media was restarted about 4 hrs post-transfection at 0.05 mL/min.

On Day 8, the membrane was removed and imaged in Petri dish by flooding the gas chamber with PBS to improve light transmission. Cells and supernatant collected for purification from 1 half of the membrane that showed best transfection (other half had low transfection). Cell s/microcarriers were pelleted at 500 g, 5 min and supernatant was removed. Pellet was frozen at 80° C.

Figure 48:
FIG. 48 is an image of GFP (pAAV) 70 hours post-transfection, 4×, according to an exemplary embodiment.
Figure 49:
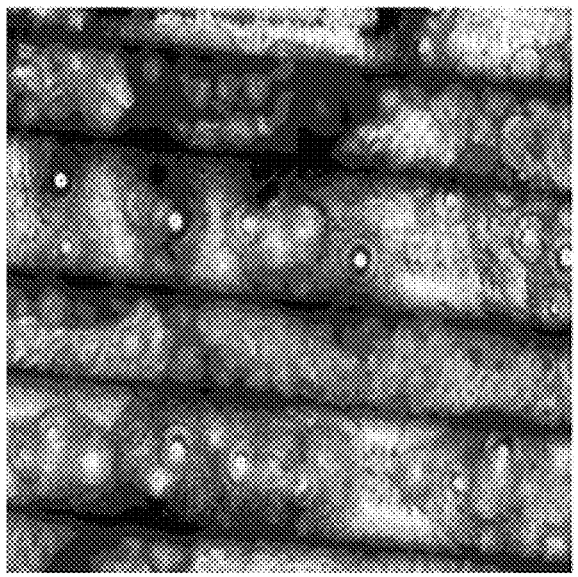
FIG. 49 is an image of Phase 70 hours post-transfection, 4×, according to an exemplary embodiment.
Figure 50:
FIG. 50 is an image of RFP (pHelper+RC) 70 hours post-transfection, 4×, according to an exemplary embodiment.
Figure 51:
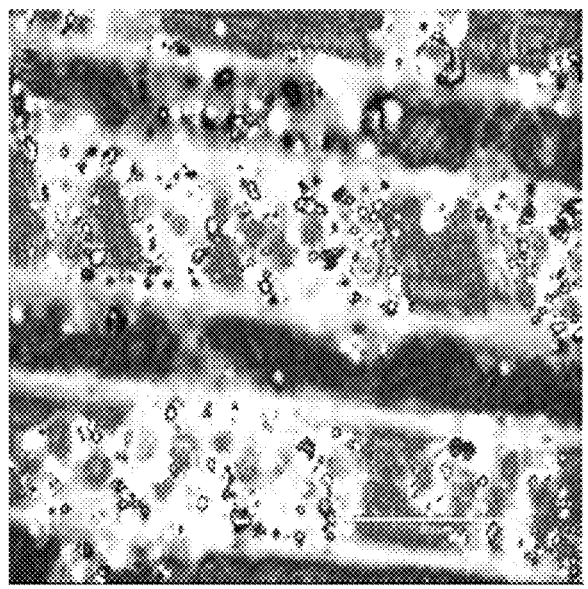
FIG. 51 is an overlay of FIGS. 48, 49 and 50 according to an exemplary embodiment.

Regarding the above trial, FIG. 48 is an image of GFP (pAAV) 70 hours post-transfection, 4×, according to an exemplary embodiment. FIG. 49 is an image of Phase 70 hours post-transfection, 4×, according to an exemplary embodiment. FIG. 50 is an image of RFP (pHelper+RC) 70 hours post-transfection, 4×, according to an exemplary embodiment. FIG. 51 is an overlay of FIGS. 48, 49 and 50 according to an exemplary embodiment.

Integrated O-Ring Seals HDCR Compartments

Figure 52:
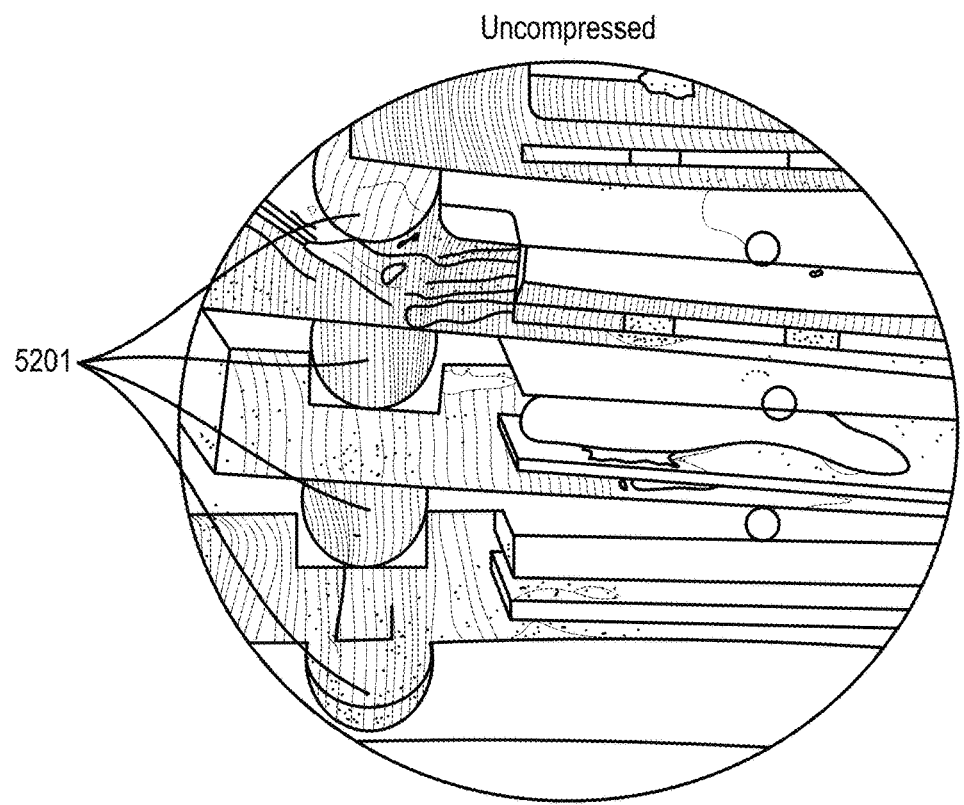
FIG. 52 is a cross-sectional cut through an uncompressed 4-stack of HDCR membranes demonstrating the formation of seal and alignment of membranes according to an exemplary embodiment.
Figure 53:
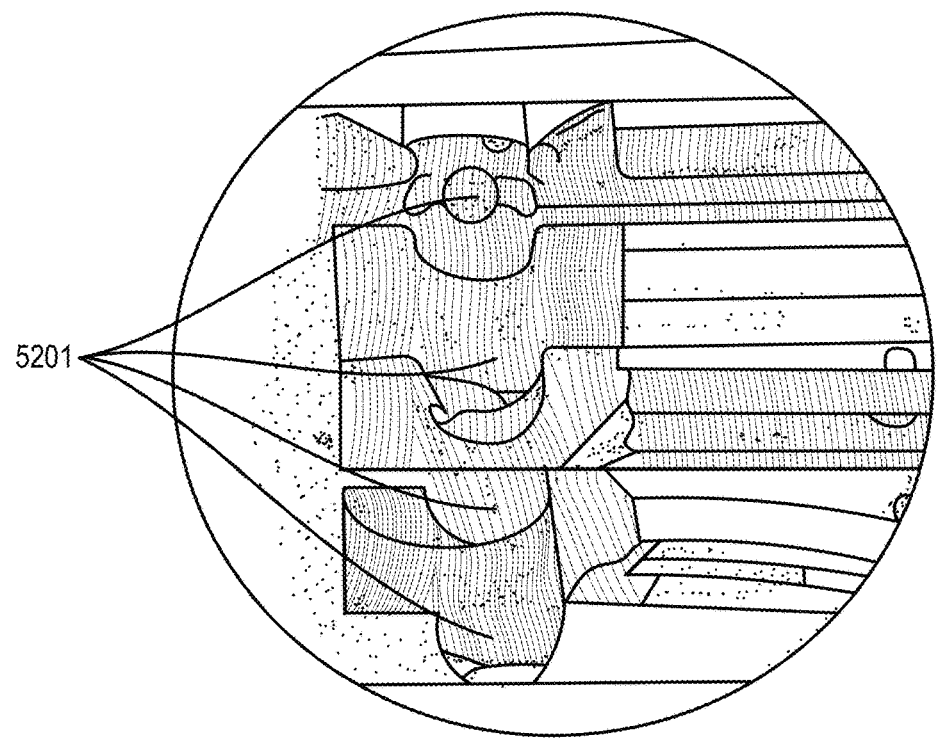
FIG. 53 is a cross-sectional cut through a compressed (40% compression ratio) 4-stack of HDCR membranes according to an exemplary embodiment.
Figure 54:
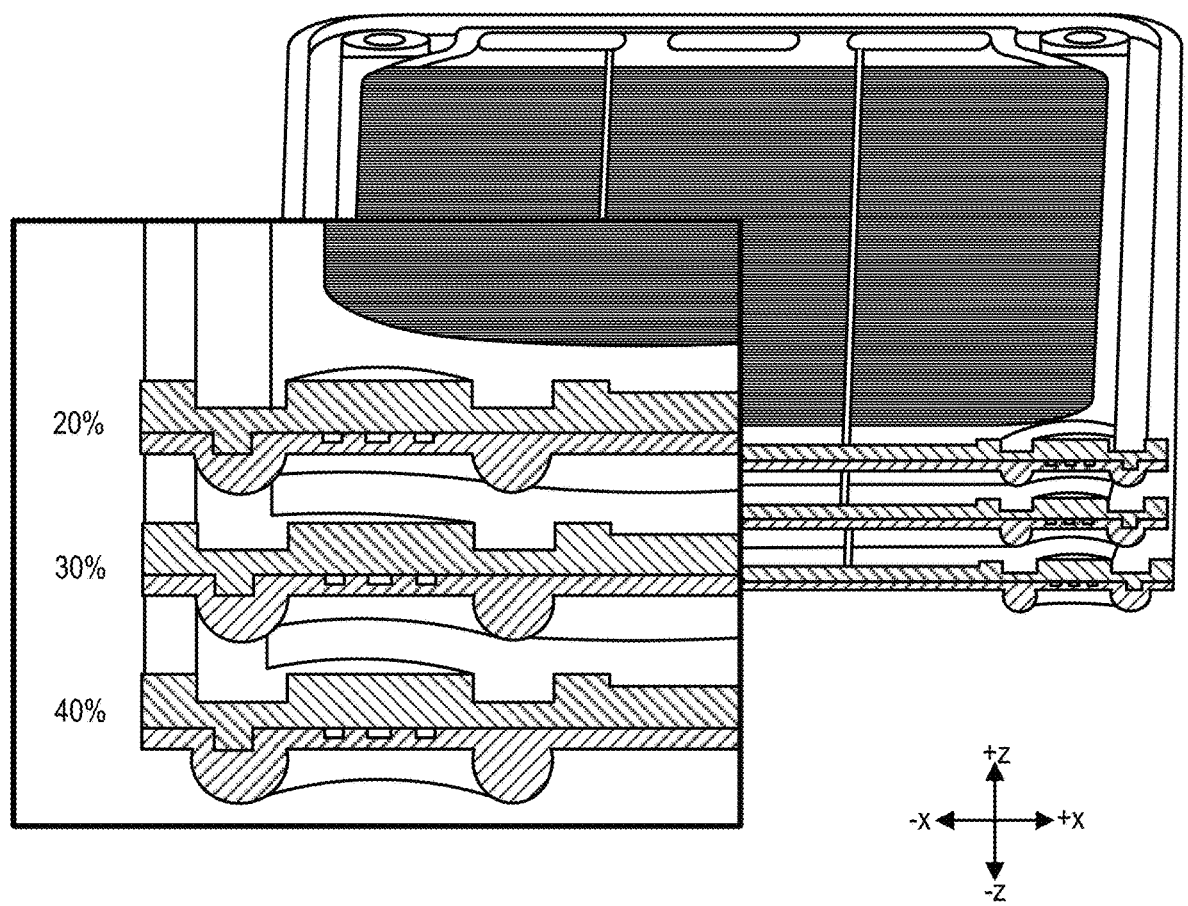
FIG. 54 is a CAD rendering of HDCR membranes with a close-up sectional view (lower-left side) showing gas compartment openings as well as various compression ratios of possible design (i.e., compression ratios of 20%, 30%, 40%) according to an exemplary embodiment.

FIGS. 52-54 include various views of an o-ring seal for HDCR compartments between HDCR plates. In FIG. 52, a peripheral, one or more integrated o-rings 5201 facilitate the alignment and stacking of HDCR membranes, such as plates 4502, 4504, 4506. When compressed, as shown in FIG. 53, the o-rings 5201 seal to form independent gas and fluidic manifolds. Specifically, FIG. 52 is a cross-sectional cut through an uncompressed 4-stack of HDCR membranes demonstrating the formation of seal and alignment of membranes according to an exemplary embodiment. FIG. 53 is a cross-sectional cut through a compressed (40% compression ratio) 4-stack of HDCR membranes according to an exemplary embodiment. FIG. 54 is a CAD rendering of HDCR membranes with a close-up sectional view (lower-left side) showing gas compartment openings as well as various compression ratios of possible design (i.e., compression ratios of 20%, 30%, 40%) according to an exemplary embodiment. The gas compartment openings can be reinforced (e.g., with rigid tubing) to maintain their patency under compressive forces from the o-ring above and below gas compartment openings.

4-Stack Demo-Scale HDCR Run

Figure 55:
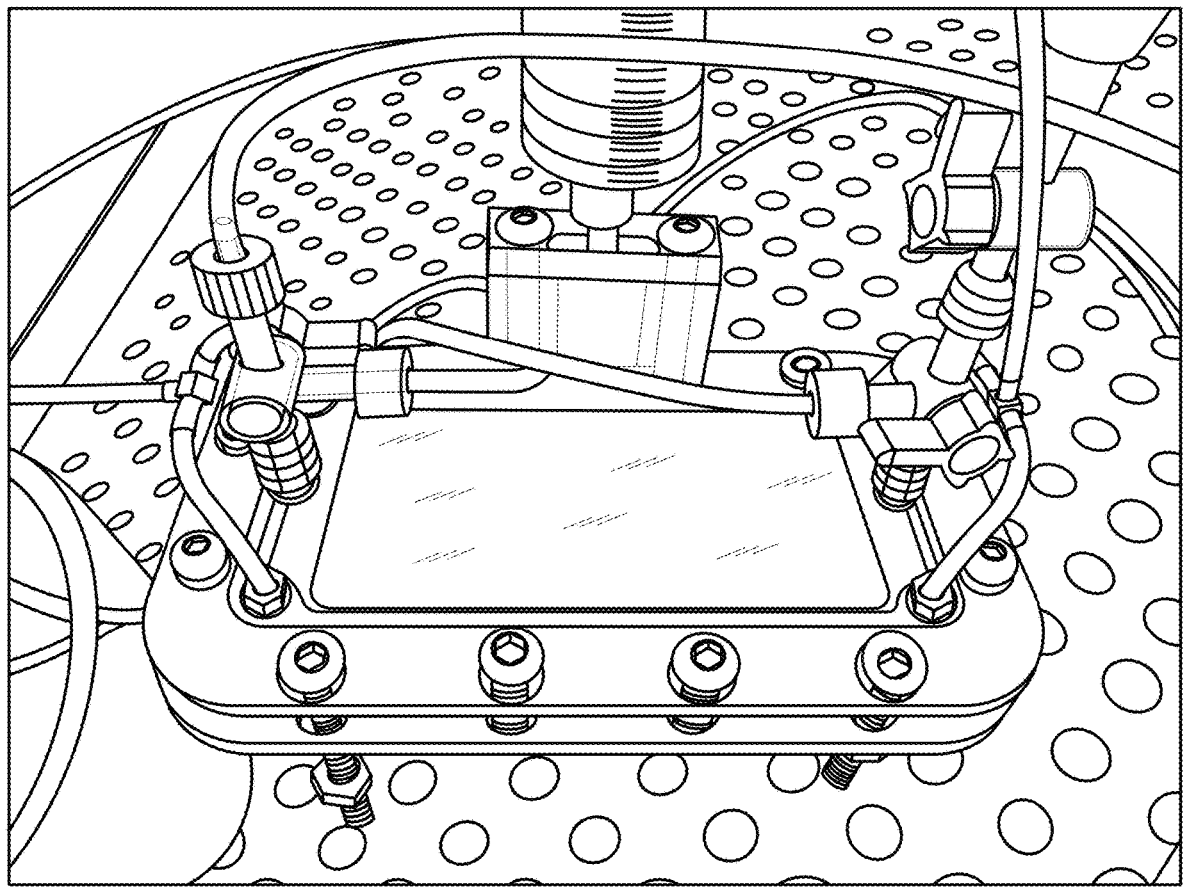
FIG. 55 is a front perspective view of a 4-stack demo-scale HDCR according to an exemplary embodiment.
Figure 57:
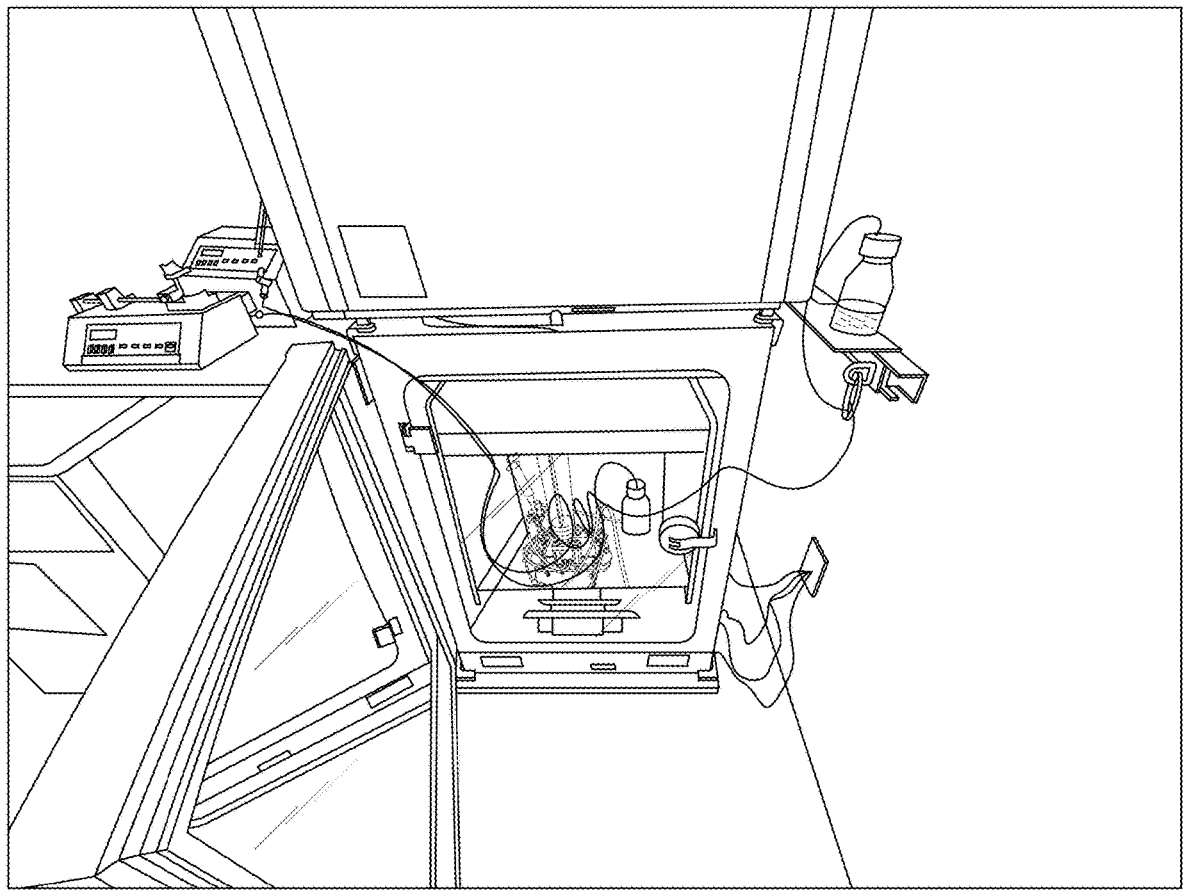
FIG. 57 is a front perspective view of a complete system for the 4-stack demo-scale HDCR of FIGS. 55 and 56 according to an exemplary embodiment.

FIGS. 55-57 depict 4-stack 50 cm² HDCR membranes assembled into a functional bioreactor. Air with 5% $CO^2$ supplement is perfused into the membranes through the gas compartment while media is perfused into the cell-media compartment and waste is disposed of through the media outlet. A mixable loop is formed by tubing connected between the media inlet and outlet with adjustable valves. Connection of the tubing to a peristaltic pump allows for circulation of media within the cell-media compartment, useful for the uniform introduction of cells, microcarriers, virus, transfection agent, or other additives. Rapid perfusion of the fluid through the circulation loop, optionally combined with tilting or inverting the bioreactor, allows for collection of cell or bioproduct from the membranes. A bubble trap can be added to the bioreactor to mitigate the introduction of bubbles into the cell-media compartment and to facilitate their removal. Perfusion of media and gas can be controlled by peristaltic, syringe, or other pumps (e.g., active or passive such as gravity feed). Cytodex-3 microcarriers stained with Trypan blue for visualization were loaded into the membranes prior to seeding A549 cells, which were expanded over 10 days from ~700,000 cells to 100,000,000 cells. Specifically, FIG. 55 is a front perspective view of a 4-stack demo-scale HDCR according to an exemplary embodiment; FIG. 56 is a back perspective view of the 4-stack demo-scale HDCR of FIG. 55 according to an exemplary embodiment; and FIG. 57 is a front perspective view of a complete system for the 4-stack demo-scale HDCR of FIGS. 55 and 56 according to an exemplary embodiment.

Monitoring Metabolism via Glucose

Figure 58:
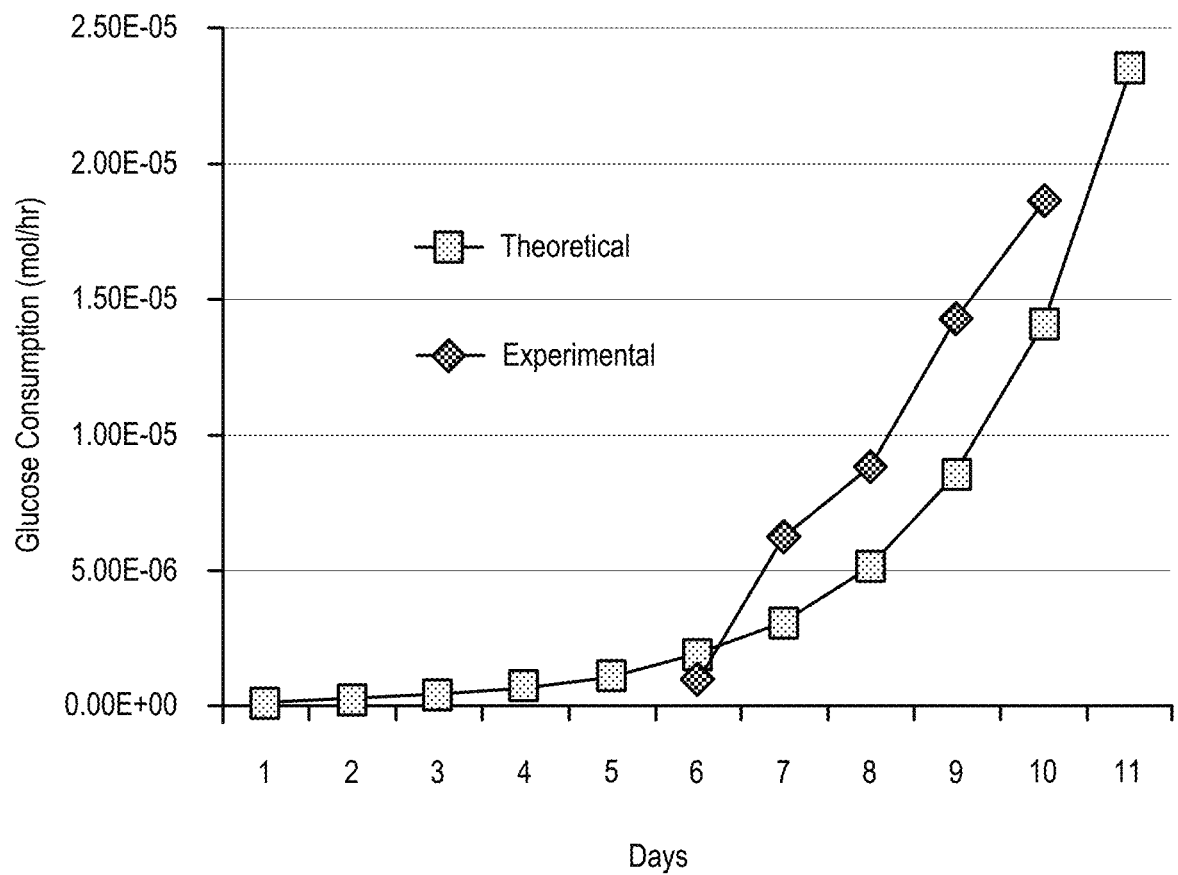
FIG. 58 is a plot of glucose consumption (mol/hr) on the y-axis versus days on the x-axis and comparing theoretical and experimental results according to an exemplary embodiment.
Figure 59:
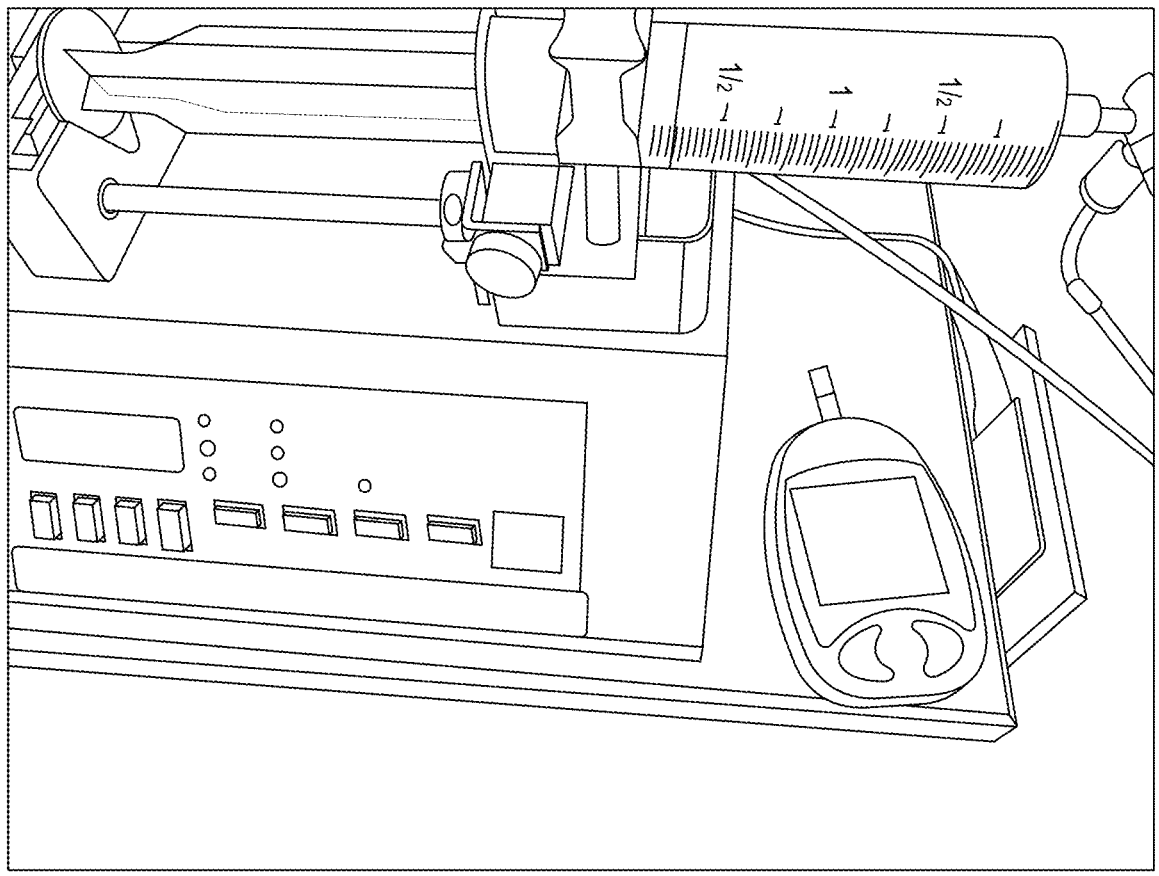
FIG. 59 is a front perspective view of a system for measuring metabolism derived from flow rate and glucose in a waste stream according to an exemplary embodiment.

The glucose consumption of cells within the bioreactor is monitored by sampling the input media stream and outlet media stream using a glucose meter. From the differences in glucose concentration and known perfusion rate, the glucose consumption is determined. The feed rate of the media and gas into the bioreactor can be adjusted to ensure glucose levels are maintained within certain ranges. Specifically, FIG. 58 is a plot of glucose consumption (mol/hr) on the y-axis versus days on the x-axis and comparing theoretical and experimental results according to an exemplary embodiment; and FIG. 59 is a front perspective view of a system for measuring metabolism derived from flow rate and glucose in a waste stream according to an exemplary embodiment.

Figure 60:
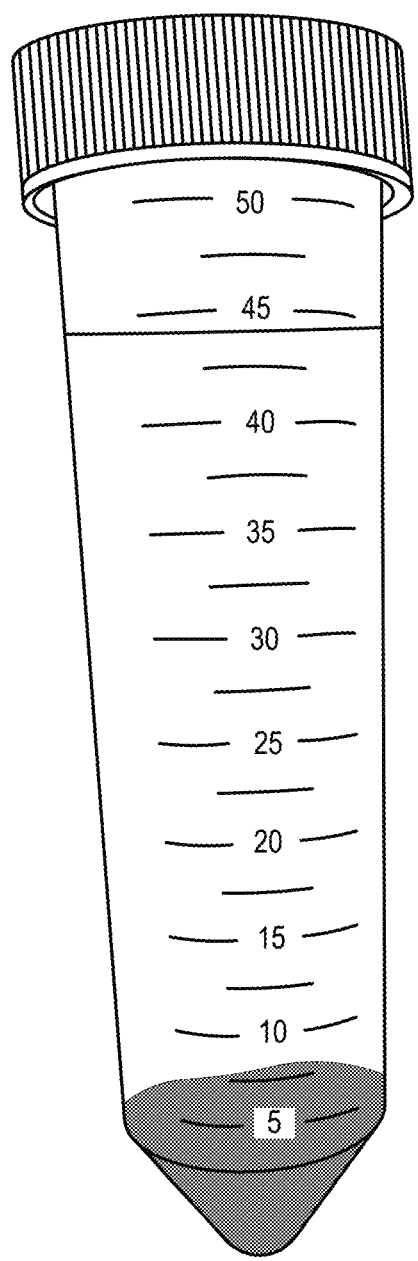
FIG. 60 is a front perspective view of a system for measuring metabolism via glucose by harvesting cells for count by DNA according to an exemplary embodiment.

FIG. 60 is a front perspective view of a system for measuring metabolism via glucose by harvesting cells for count by DNA according to an exemplary embodiment in which collected cells and microcarriers appear at a bottom of a vial following 10 day expansion of A549 cells in the HDCR bioreactor.

Half-Scale (600 cm²) HDCR Run

Figure 61:
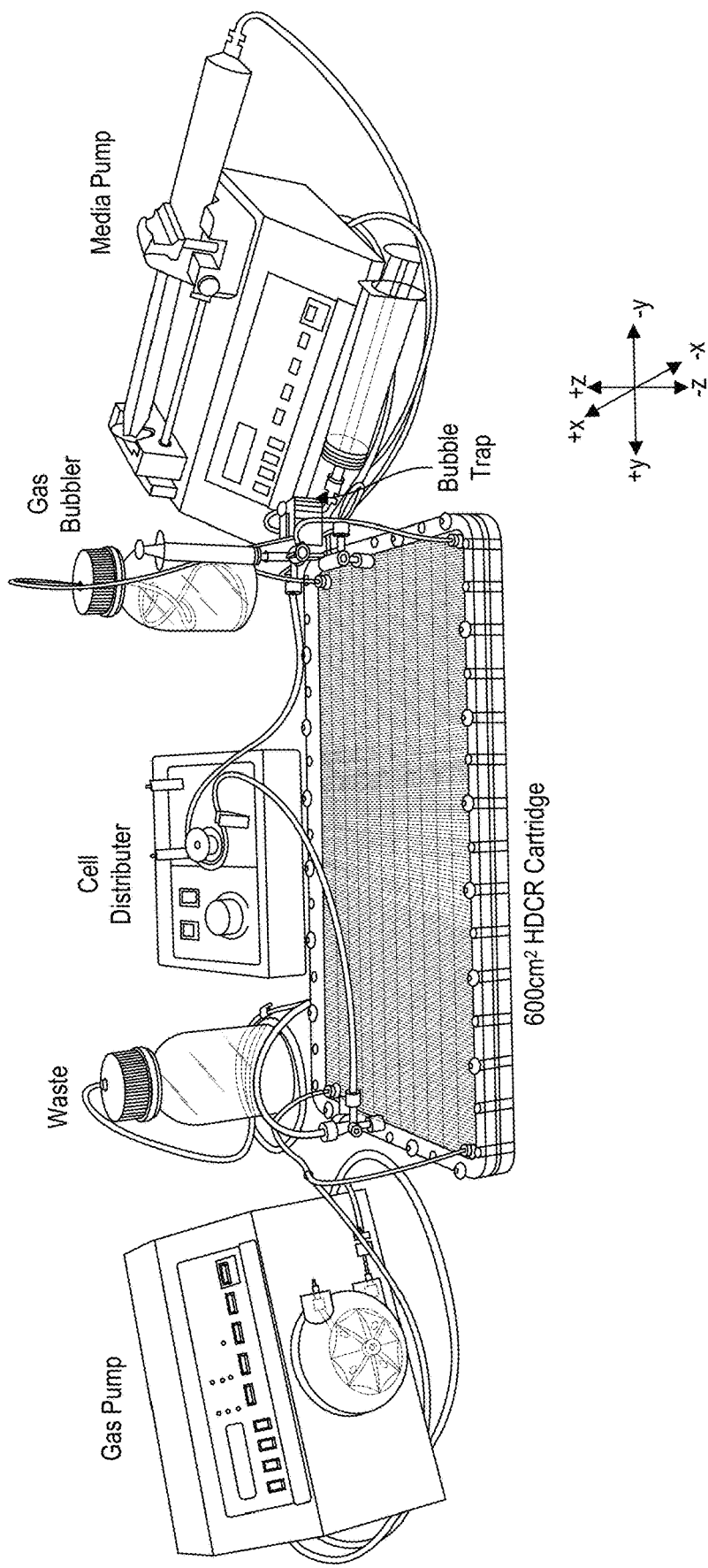
FIG. 61 is a front perspective view of a half-scale HDCR system including, from right to left, a media pump, a bubble trap, a gas bubbler, a 600 cm$^2$ HDCR cartridge, a cell distributer, a waste receptacle, a gas pump according, and associated interconnecting tubing according to an exemplary embodiment.

An HDCR bioreactor system based on a 600 cm² membrane design is provided. The HDCR cartridge includes top and bottom compression plates, fluidic couplings and valves for the media and gas compartments as well as circulation tube, an HDCR membrane, and bolts and spacers. In this example, a syringe pump controls the perfusion of media into the bioreactor. Bubble traps remove bubbles from the perfusion stream and prevent them from entering the system. A peristaltic pump controls the perfusion of gas into the bioreactor. A gas bubbler can also be incorporated to humidify the gas to reduce the pervaporation of water from the media compartment. Spent media is collected in a waste bottle while depleted gas is exhausted to the atmosphere. An additional peristaltic pump and appropriate positioning of the fluid valves can be used to achieve circulation of media though the bioreactor to facilitate seeding, infections/transfection, and harvesting. For example, FIG. 61 is a front perspective view of a half-scale HDCR system including, from right to left, a media pump, a bubble trap, a gas bubbler, a 600 cm² HDCR cartridge, a cell distributer, a waste receptacle, a gas pump according, and associated interconnecting tubing according to an exemplary embodiment.

Production of CF33-GFP

Figure 62:
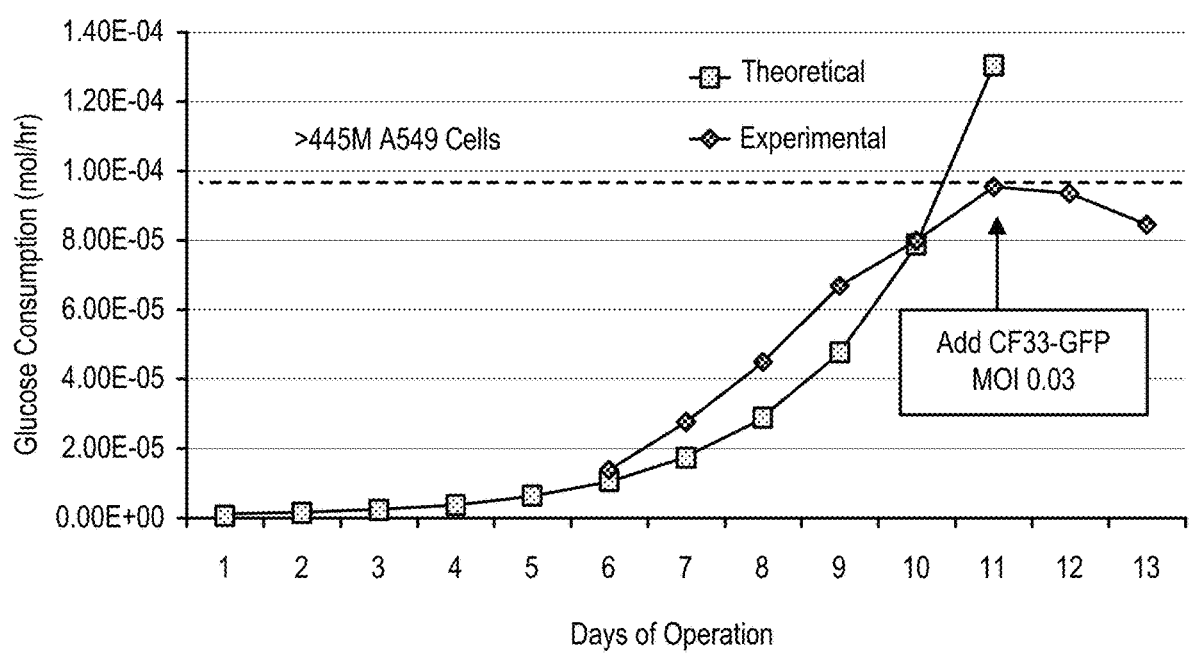
FIG. 62 is a plot of glucose consumption (mol/hr) on the y-axis versus days of operation on the x-axis and comparing theoretical and experimental results according to an exemplary embodiment.
Figure 63:
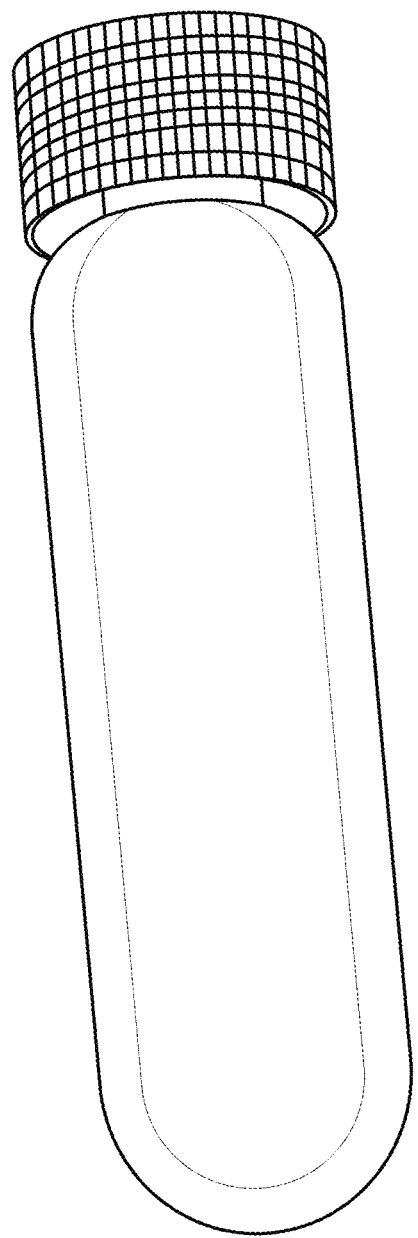
FIG. 63 is a front perspective view of a band of CF33-GFP in a first sucrose gradient according to an exemplary embodiment.

The production of CF33-GFP, an orthopox virus, was carried out in the HDCR bioreactor by expanding A549 cells to approximately ~400M cells/membrane under controlled media and gas perfusion. Theoretical and experimental measurements of glucose consumption over the production run were used to monitor cell expansion. At Day 11, CF33-GFP virus was introduced into the bioreactor at an multiplicity of infection of 0.03 plaque forming units per cell. 3 days post infection, the cell and virus material was harvested from the bioreactor for titration and purification. FIG. 62 is a plot of glucose consumption (mol/hr) on the y-axis versus days of operation on the x-axis and comparing theoretical and experimental results according to an exemplary embodiment. FIG. 63 is a band of CF33-GFP after a first sucrose gradient centrifugation. The Table 3 below presents yields of CF-33 GFP in the 600 cm² HDCR membrane after purification and within the unpurified flow thru media.

| Source | Volume [mL] | Concentration [PFU/mL] | Yield [Total PFU] | Specific Yield [PFU/Cell] |
|---|---|---|---|---|
| Purified CF33-GFP from 600 cm² HDCR Membrane | 2 | 8.00E+08 | 1.60E+09 | 2.67 |
| Flow thru media post-infection | 1000 | 6.75E+07 | 6.75E+10 | 113 |

Exosome Extraction

Figure 64:
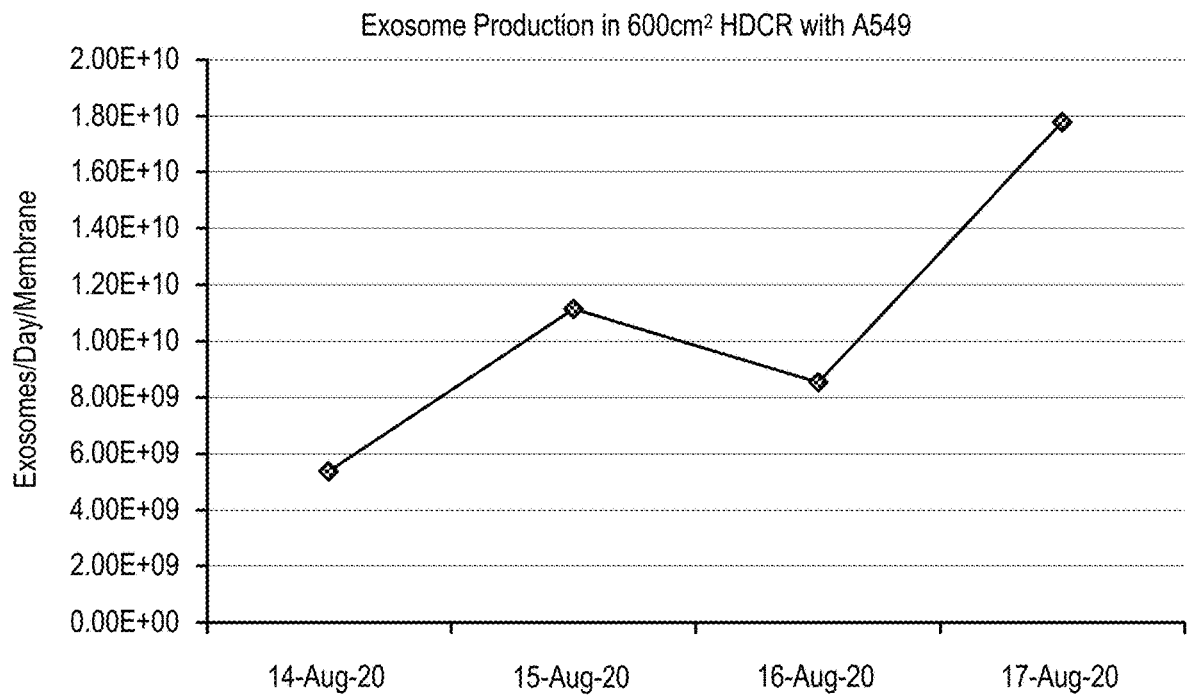
FIG. 64 is a plot of exosomes/day/membrane on the y-axis versus date on the x-axis, i.e., exosome production in a 600 cm$^2$ HDCR with A549 according to an exemplary embodiment.

Spent media from the 600 cm² HDCR bioreactor was collected over the 8th, 9th, 10th, and 11th days of expansion of A549 cells. Exosomes were purified from the spent medium and subsequently quantitated and characterized using nanoparticle tracking analysis. The results demonstrate the considerable quantities of exosomes can be recovered from the medium exiting the HDCR bioreactor. Specifically, FIG. 64 is a plot of exosomes/day/membrane on the y-axis versus date on the x-axis, i.e., exosome production in a 600 cm² HDCR with A549 according to an exemplary embodiment.

5-Stack HDCR

Figure 65:
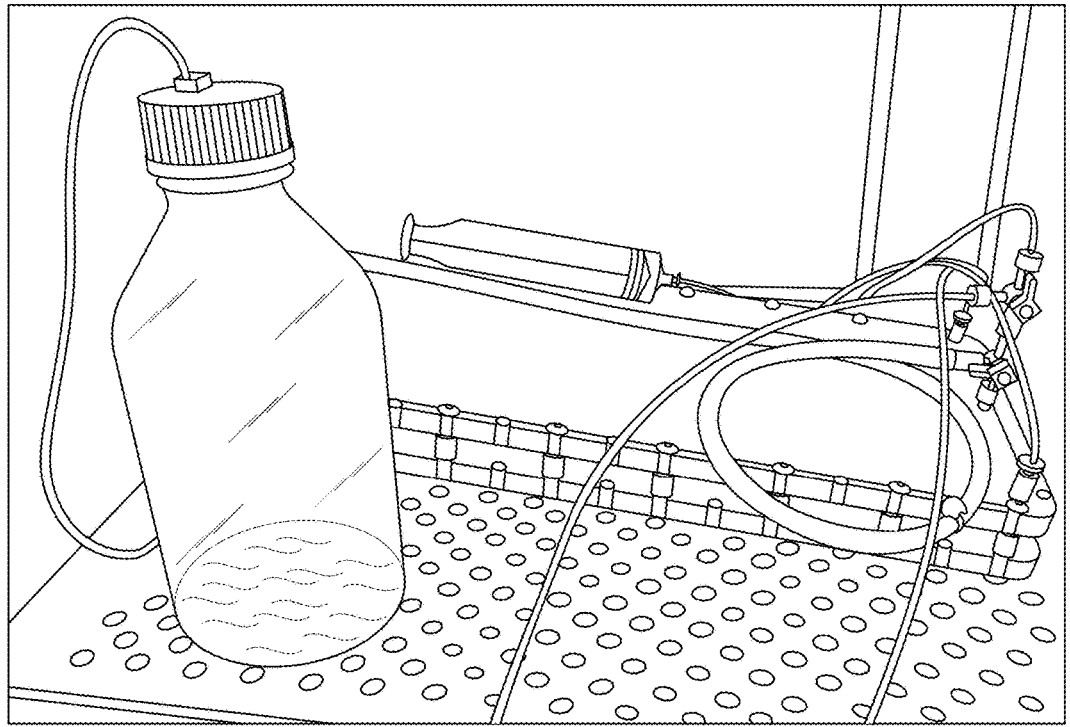
FIG. 65 is a front perspective view of a system including a 5-stack of 600 cm$^2$ HDCR cartridges according to an exemplary embodiment.

An HDCR bioreactor setup including a 5-stack of 600 cm² membranes in operation within a standard cell incubator is provided. Microcarriers stained with trypan blue can be seen uniformly distributed within the membranes. Specifically, FIG. 65 is a front perspective view of a system including a 5-stack of 600 cm² HDCR cartridges according to an exemplary embodiment.

Tilting the HDCR Bioreactor

Figure 66:
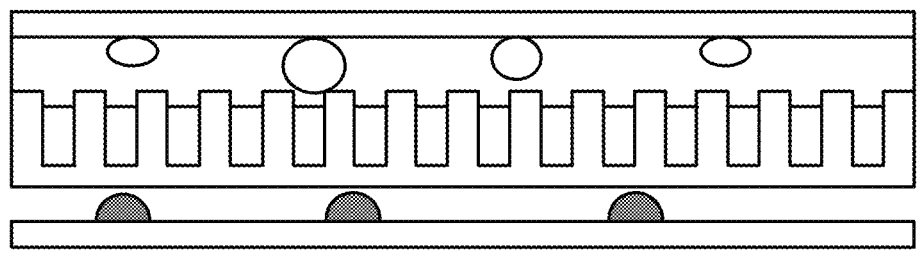
FIG. 66 is a schematic front cross-sectional view of an HDCR membrane including gas bubbles above the membrane and condensation below the membrane according to an exemplary embodiment.
Figure 67:
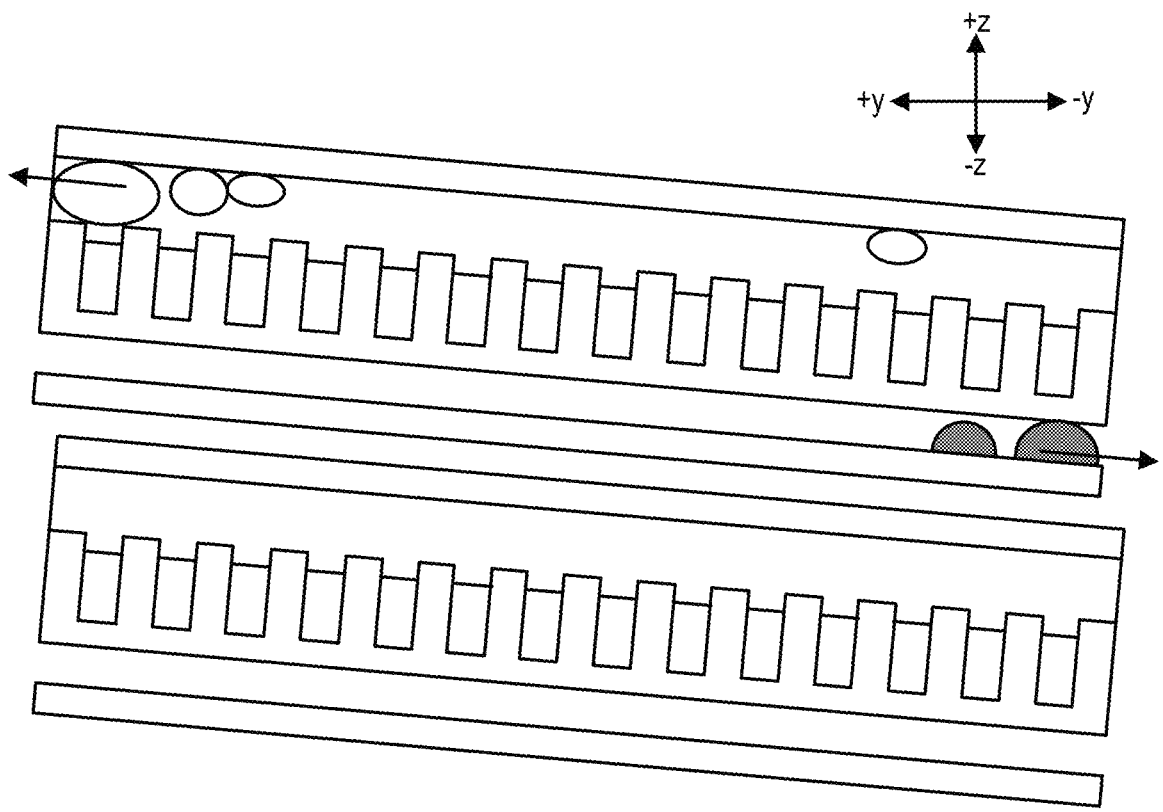
FIG. 67 is a schematic front cross-sectional view of an inclined HDCR membrane highlighting removal of gas bubbles above the membrane and removal of condensation below the membrane (before, above, and after, below) according to an exemplary embodiment.

Positioning the HDCR bioreactor membranes at an angle facilitates removal of gas bubbles from within the cell-media compartment as well as removal of condensation from the gas compartment. Whereas, in a horizontal state, there is only minimal force from the perfusing media to dislodge and sweep out bubbles from the media compartment, in an inclined state the hydrostatic pressure gradient forces the bubbles towards higher elevation where they eventually reach the fluid manifold and are carried out to the waste collection. It is advantageous, though not necessary, to perfuse media into the low-elevation fluid manifold and collect it from the high-elevation fluid manifold as in this arrangement both the fluid and hydrostatic forces on the bubble are in the same direction. Similarly, within the gas compartment condensation and water droplets are more easily removed when the membranes are in an inclined state, due to their tendency to migrate down the gravitational potential gradient. It is advantageous, though not necessary, for the perfusion of gas within the gas compartment to be into the high-elevation fluid manifold and out from the high-elevation fluid manifold, as in this this arrangement both the fluidic and gravitational forces on the droplet are in the same direction. FIG. 66 is a schematic front cross-sectional view of an HDCR membrane including gas bubbles above the membrane and condensation below the membrane according to an exemplary embodiment. In contrast, FIG. 67 is a schematic front cross-sectional view of an inclined HDCR membrane highlighting removal of gas bubbles above the membrane and removal of condensation below the membrane (the before state is shown at the top of FIG. 67, and the after state is shown at the bottom of FIG. 67) according to an exemplary embodiment.

FIGS. 68-75 illustrate membrane architectures that facilitate cell retention. The architectures are configured for operation of a membrane-based bioreactor in non-horizontal orientations due to the tendency of cells to otherwise aggregate or pool in masses too large for efficient mass transport of nutrients and gases. The HDCR membrane integrates such architecture (e.g., wells, grooves, cupules, pillars, overhangs, and the like) on the cell-media facing side the membranes to overcome this problem. Comparison of membranes with high and low aspect ratio architectures in the (FIGS. 68 and 70) horizontal orientation shows how the introduction of cell retaining structures (e.g., fins) reduces the (FIGS. 69 and 71) available volume for cell expansion. However, in the (FIGS. 72 and 74) inclined orientation the lost expansion volume due to the presence of retaining structures is more than compensated by the (FIGS. 73 and 75) increased retention of cells. Specifically, FIG. 68 is a schematic side cross-sectional view of an uninclined, high aspect ratio HDCR membrane filled with media according to an exemplary embodiment. FIG. 69 is a representation of a cell expansion volume of the uninclined, high aspect ratio HDCR membrane filled with media according to an exemplary embodiment. FIG. 70 is a schematic side cross-sectional view of an uninclined, low aspect ratio HDCR membrane filled with media according to an exemplary embodiment. FIG. 71 is a representation of a cell expansion volume of the uninclined, low aspect ratio HDCR membrane filled with media according to an exemplary embodiment. FIG. 72 is a schematic side cross-sectional view of an inclined, high aspect ratio HDCR membrane filled with media according to an exemplary embodiment. FIG. 73 is a representation of a cell expansion volume of the inclined, high aspect ratio HDCR membrane filled with media according to an exemplary embodiment. FIG. 74 is a schematic side cross-sectional view of an inclined, low aspect ratio HDCR membrane filled with media according to an exemplary embodiment. FIG. 75 is a representation of a cell expansion volume of the inclined, low aspect ratio HDCR membrane filled with media according to an exemplary embodiment.

Figure 76:
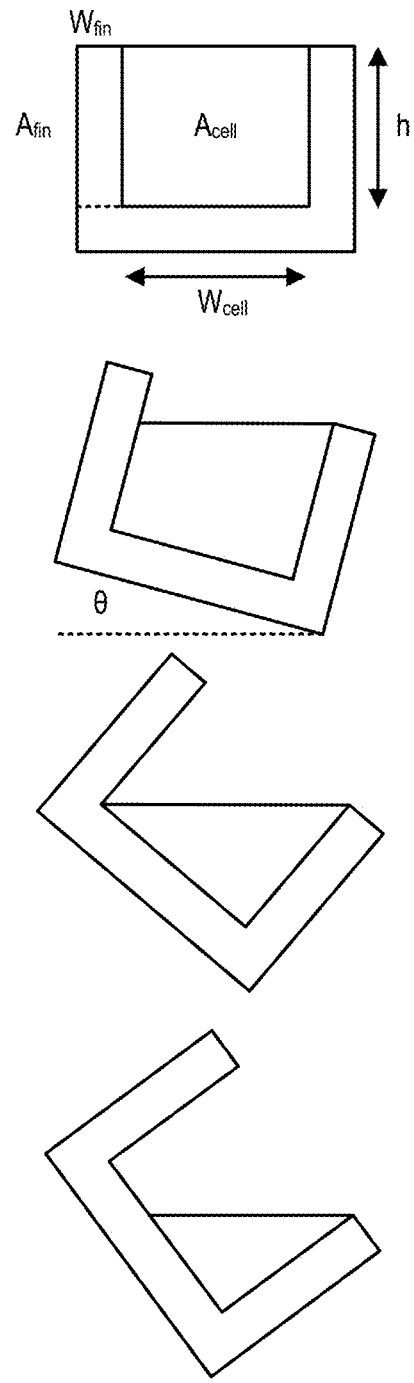
FIG. 76 establishes variables for a geometry of cell retention in a rectangular channel versus incline angle according to an exemplary embodiment.

FIG. 76 establishes variables for a geometry of cell retention in a rectangular channel versus incline angle according to an exemplary embodiment. In the formulas below, Wfin is a width of a fin, Afin is an Area of the fin, h is a height of the fin, Wcell is a width of a cell, Acell is an area of the cell, and theta ($\theta$) is an angle of inclination of the cell.

Relative Cell Retention Efficiency $$E_{retention} = \frac{A_{cell}}{w_{cell} \cdot h}$$

Overall Cell Retention Efficiency $$E_{total} = \frac{A_{cell}}{A_{unit}}$$

Cross-sectional Area of Fin $$A_{fin} = w_{fin} \cdot h$$

Cross-sectional Area of Unit Cell of Architecture $$A_{unit} = (w_{fin} + w_{cell}) \cdot h$$

Cross-sectional Area of Retained Cells

For $\theta < \arctan\left(\frac{h}{w_{cell}}\right)$:

$$A_{cell} = h \cdot w_{cell} - \frac{1}{2}\tan(\theta) \cdot w_{cell}^2$$

For $\theta > \arctan\left(\frac{h}{w_{cell}}\right)$:

$$A_{cell} = \frac{h^2}{2\tan(\theta)}$$

Figure 77:
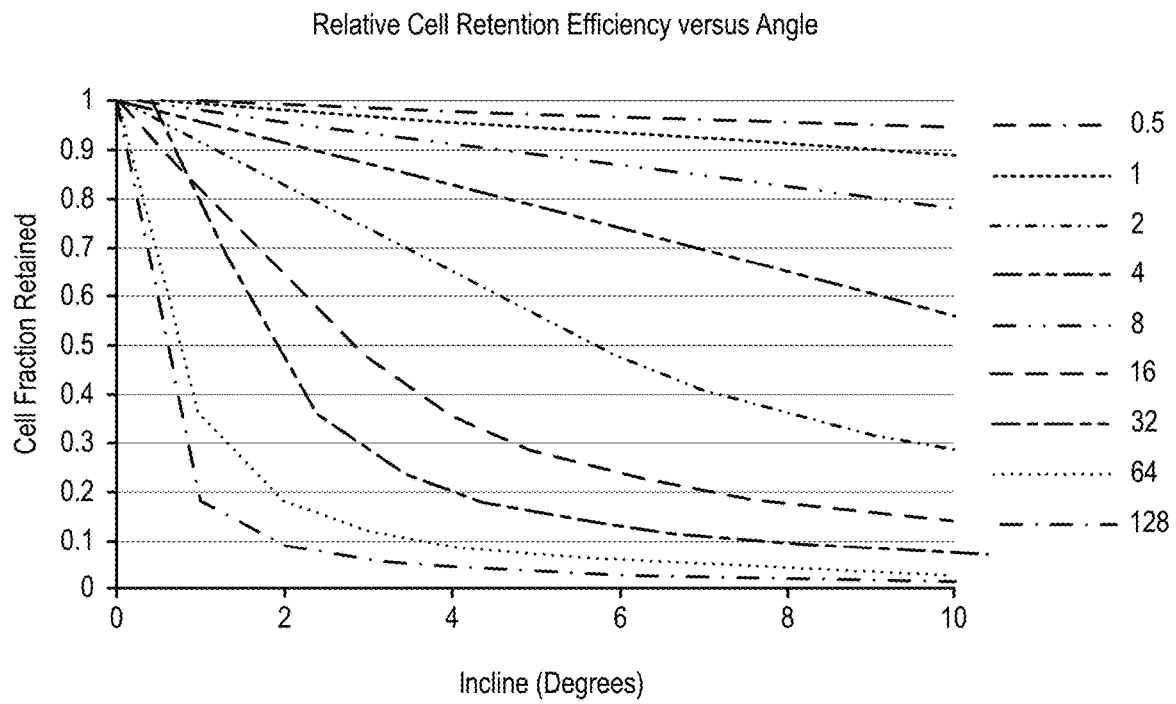
FIG. 77 is a plot of cell fraction retained on the y-axis versus incline (degrees) on the x-axis and comparing different channel widths (legend) according to an exemplary embodiment.

FIG. 77 is a plot of relative cell retention efficiency in 0.8 mm deep rectangular channels of varying widths (mm) as a function of membrane incline angle. The widths range from about 0.5 mm to about 128 mm and increase exponentially.

Figure 78:
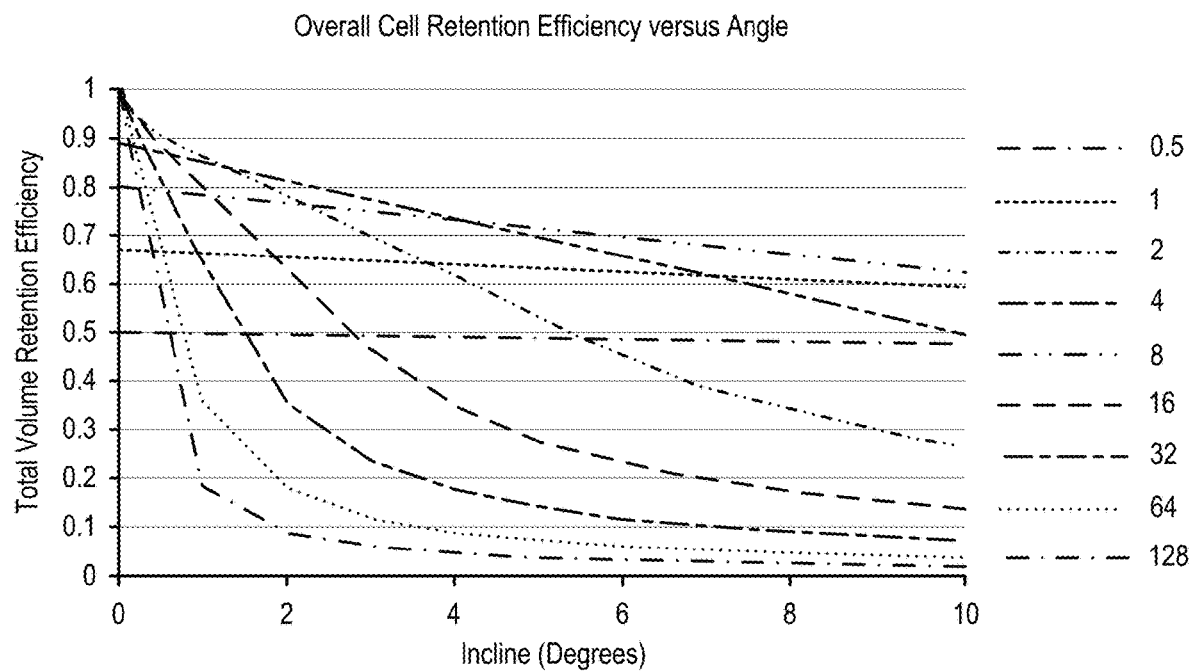
FIG. 78 is a plot of total volume retention efficiency on the y-axis versus incline (degrees) on the x-axis and comparing different channel widths (legend) according to an exemplary embodiment.

FIG. 78 is a plot of overall cell retention efficiency in 0.8 mm deep rectangular channels of varying widths (mm) as a function of membrane incline angle. The widths range from about 0.5 mm to about 128 mm and increase exponentially.

Figure 83:
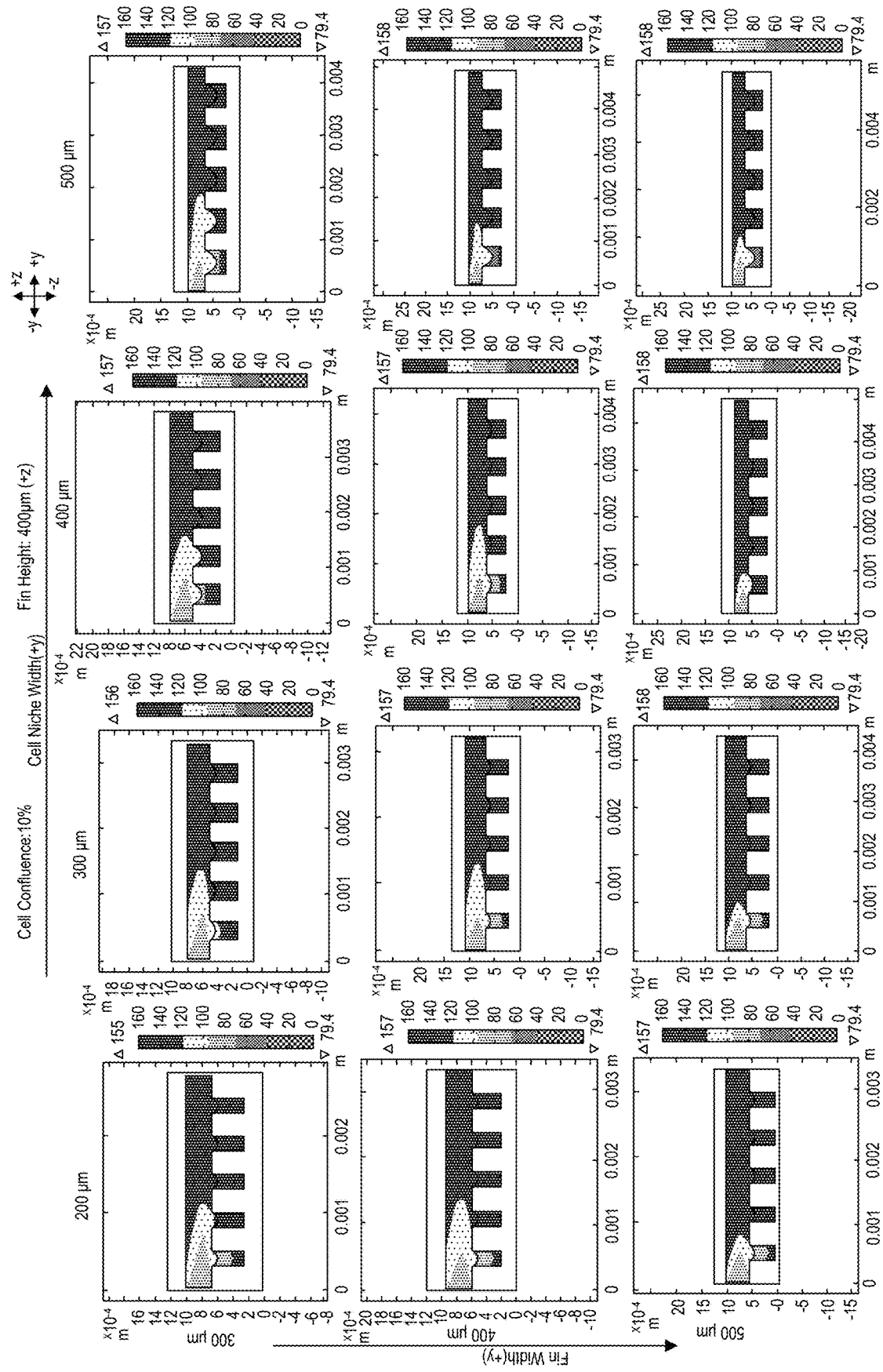
FIG. 83 includes 12 plots of an HDCR simulation of bioreactor cellularity versus architecture for a cell confluence of 10% and a fin height of 400 µm with variation of cell niche width and fin width according to an exemplary embodiment.

FIG. 83 includes 12 plots of an HDCR simulation of bioreactor cellularity versus architecture for a cell confluence of 10% and a fin height of 400 µm with variation of cell niche width and fin width according to an exemplary embodiment.

Figure 84:
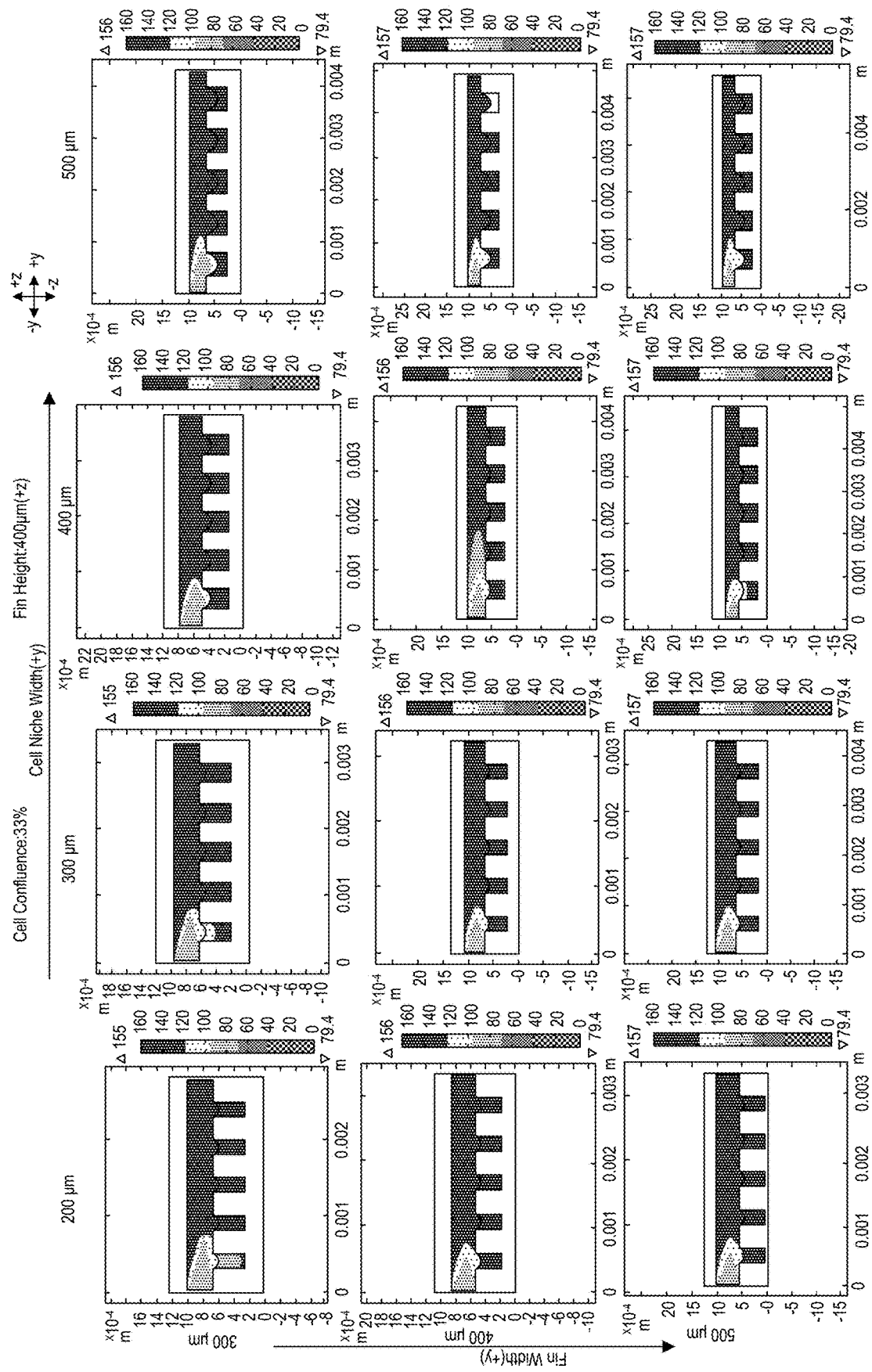
FIG. 84 includes 12 plots of an HDCR simulation of bioreactor cellularity versus architecture for a cell confluence of 33% and a fin height of 400 µm with variation of cell niche width and fin width according to an exemplary embodiment.

FIG. 84 includes 12 plots of an HDCR simulation of bioreactor cellularity versus architecture for a cell confluence of 33% and a fin height of 400 µm with variation of cell niche width and fin width according to an exemplary embodiment.

Figure 85:
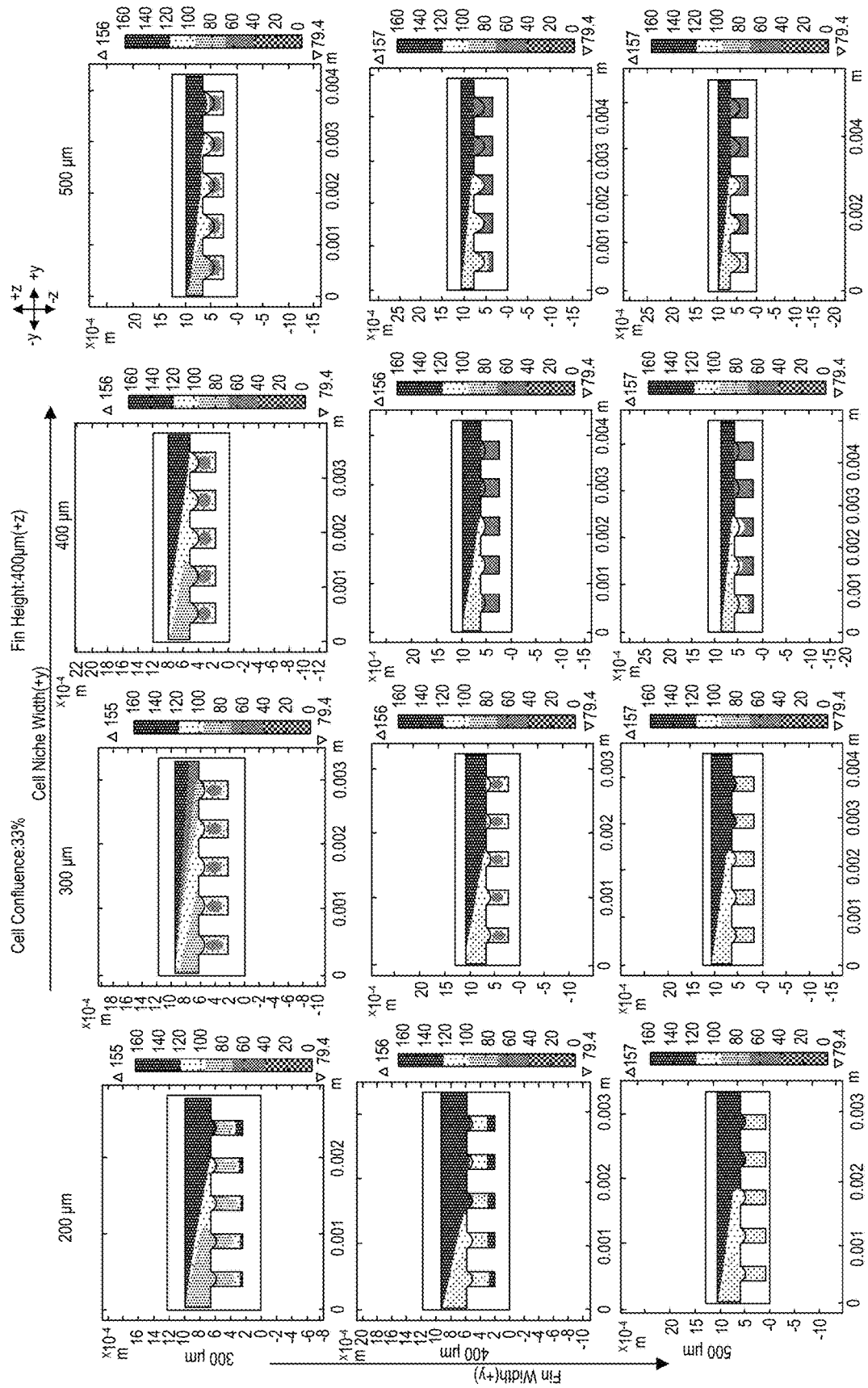
FIG. 85 includes 12 plots of an HDCR simulation of bioreactor cellularity versus architecture for a cell confluence of 100% and a fin height of 400 µm with variation of cell niche width and fin width according to an exemplary embodiment.

FIG. 85 includes 12 plots of an HDCR simulation of bioreactor cellularity versus architecture for a cell confluence of 100% and a fin height of 400 µm with variation of cell niche width and fin width according to an exemplary embodiment.

Figure 86:
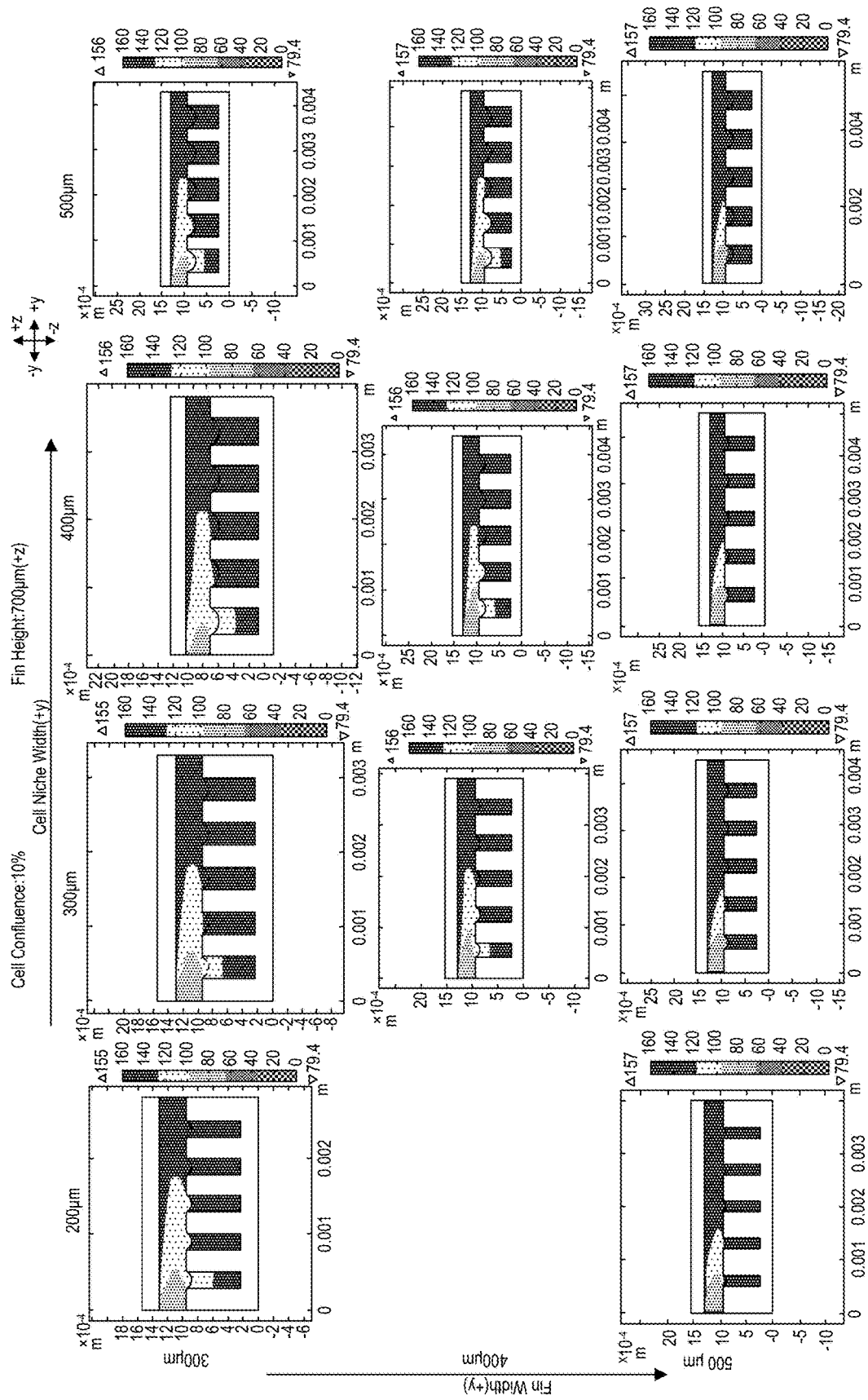
FIG. 86 includes 11 plots of an HDCR simulation of bioreactor cellularity versus architecture for a cell confluence of 10% and a fin height of 700 µm with variation of cell niche width and fin width according to an exemplary embodiment.

FIG. 86 includes 11 plots of an HDCR simulation of bioreactor cellularity versus architecture for a cell confluence of 10% and a fin height of 700 µm with variation of cell niche width and fin width according to an exemplary embodiment.

Figure 87:
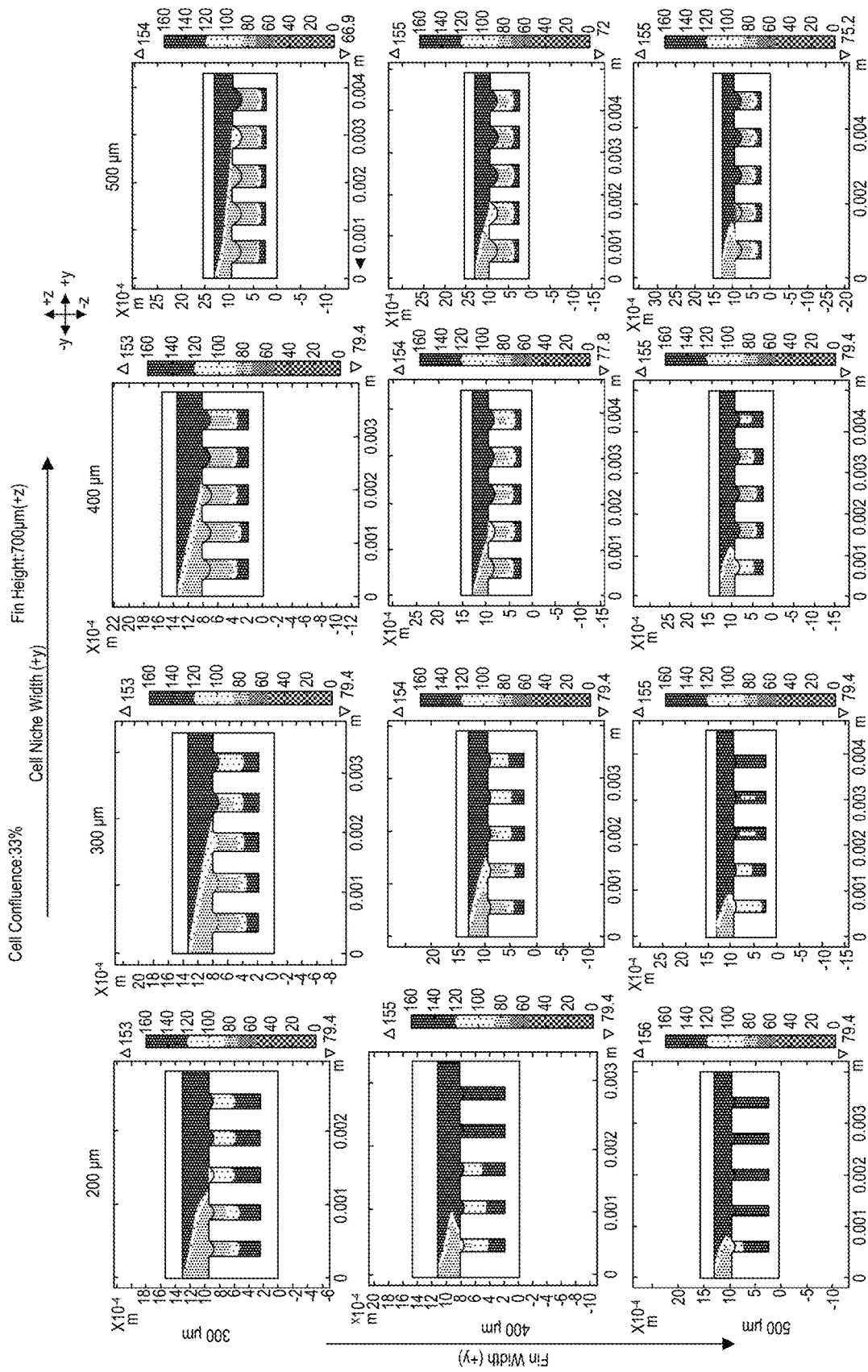
FIG. 87 includes 12 plots of an HDCR simulation of bioreactor cellularity versus architecture for a cell confluence of 33% and a fin height of 700 µm with variation of cell niche width and fin width according to an exemplary embodiment.

FIG. 87 includes 12 plots of an HDCR simulation of bioreactor cellularity versus architecture for a cell confluence of 33% and a fin height of 700 µm with variation of cell niche width and fin width according to an exemplary embodiment.

Figure 88:
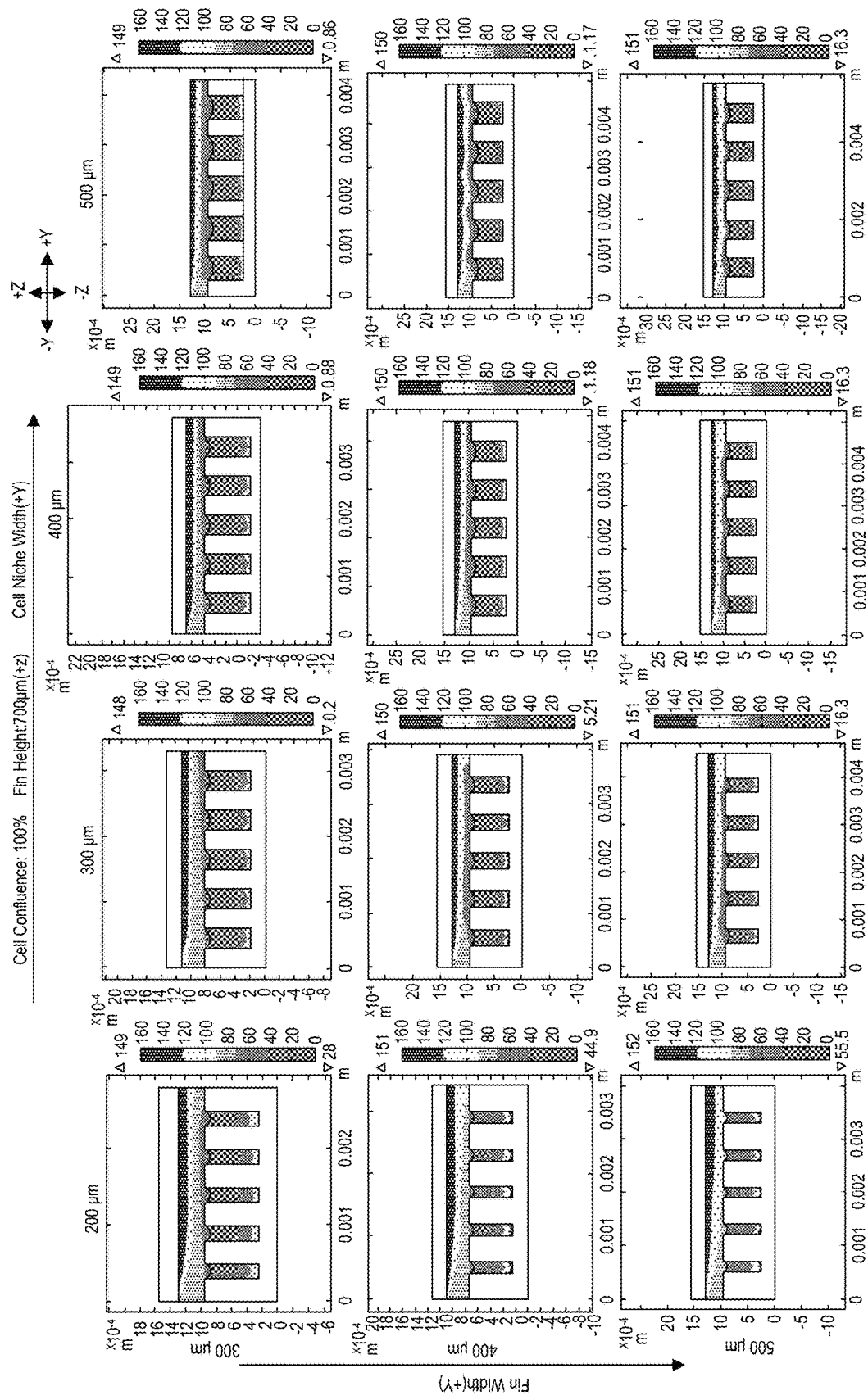
FIG. 88 includes 12 plots of an HDCR simulation of bioreactor cellularity versus architecture for a cell confluence of 100% and a fin height of 700 µm with variation of cell niche width and fin width according to an exemplary embodiment.

FIG. 88 includes 12 plots of an HDCR simulation of bioreactor cellularity versus architecture for a cell confluence of 100% and a fin height of 700 µm with variation of cell niche width and fin width according to an exemplary embodiment.

Figure 89:
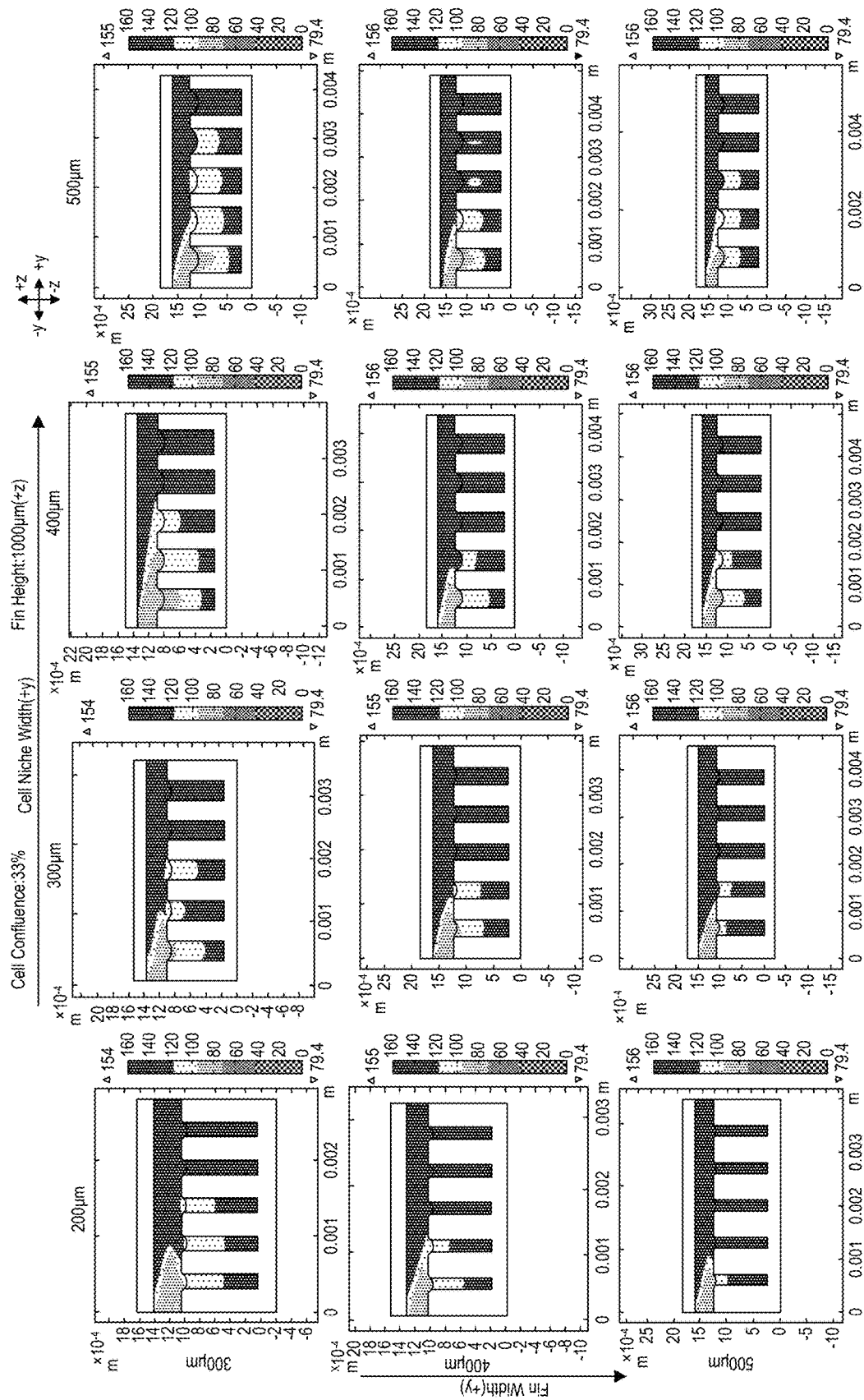
FIG. 89 includes 12 plots of an HDCR simulation of bioreactor cellularity versus architecture for a cell confluence of 10% and a fin height of 1000 µm with variation of cell niche width and fin width according to an exemplary embodiment.

FIG. 89 includes 12 plots of an HDCR simulation of bioreactor cellularity versus architecture for a cell confluence of 10% and a fin height of 1000 µm with variation of cell niche width and fin width according to an exemplary embodiment.

Figure 90:
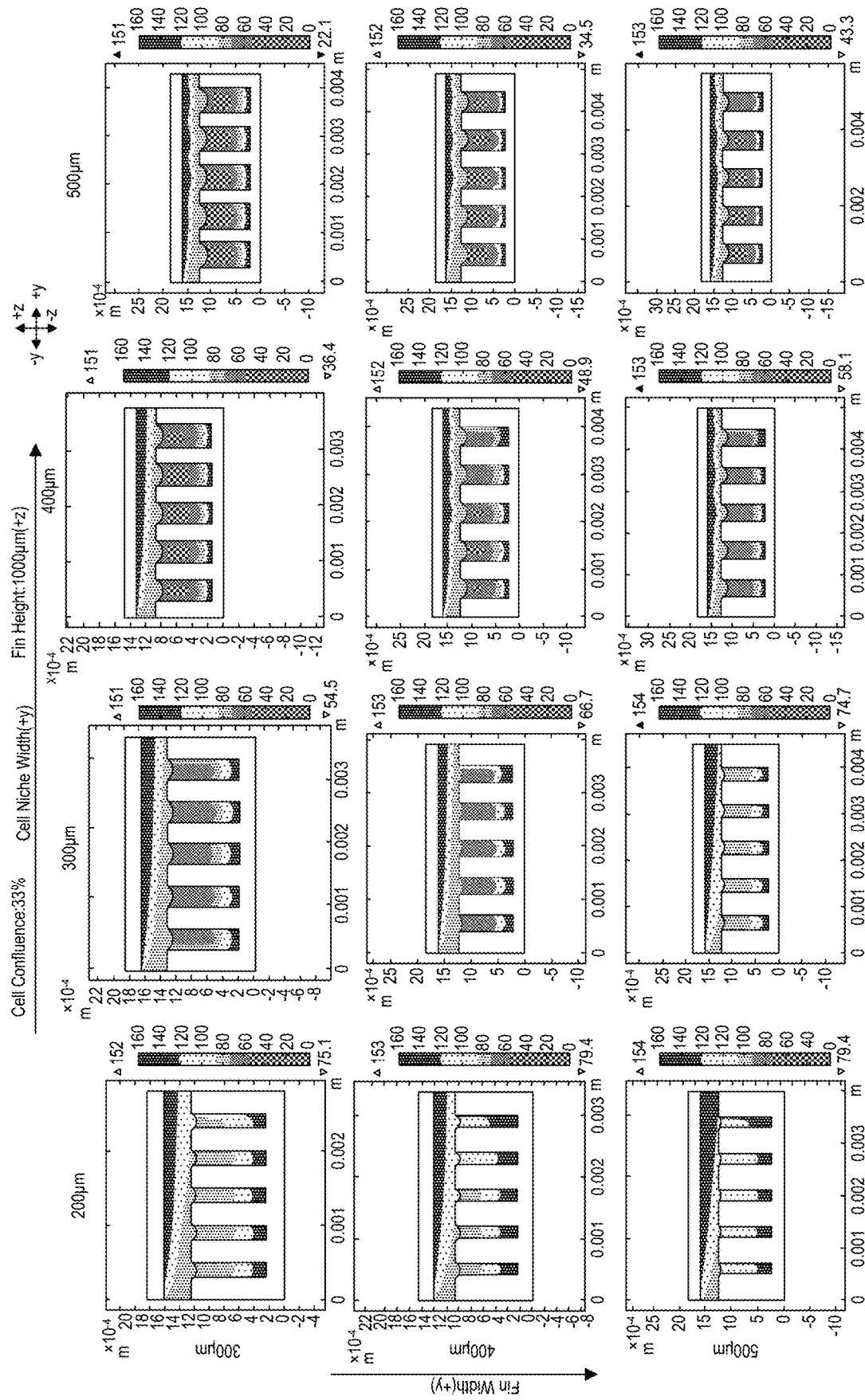
FIG. 90 includes 12 plots of an HDCR simulation of bioreactor cellularity versus architecture for a cell confluence of 33% and a fin height of 1000 µm with variation of cell niche width and fin width according to an exemplary embodiment.

FIG. 90 includes 12 plots of an HDCR simulation of bioreactor cellularity versus architecture for a cell confluence of 33% and a fin height of 1000 µm with variation of cell niche width and fin width according to an exemplary embodiment.

Figure 91:
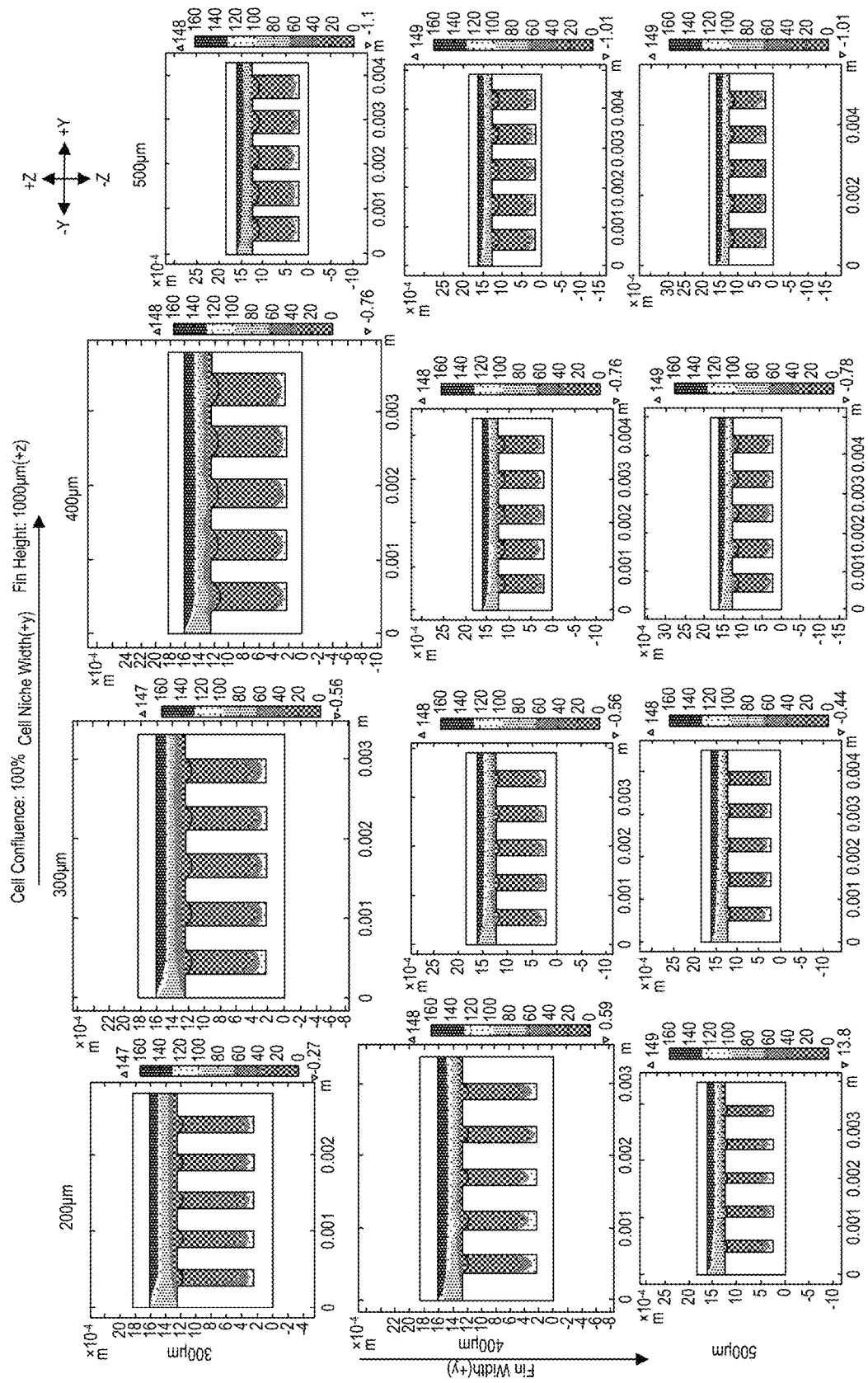
FIG. 91 includes 12 plots of an HDCR simulation of bioreactor cellularity versus architecture for a cell confluence of 100% and a fin height of 1000 µm with variation of cell niche width and fin width according to an exemplary embodiment.

FIG. 91 includes 12 plots of an HDCR simulation of bioreactor cellularity versus architecture for a cell confluence of 100% and a fin height of 1000 µm with variation of cell niche width and fin width according to an exemplary embodiment.

For each of the above-referenced simulations, cell niche width was varied from 200 µm to 500 µm in 100 µm increments, and fin width was varied from 300 µm to 500 µm in 100 µm increments.

The results of the simulations are summarized in Tables 4, 5 and 6, as follows:

| Fin Height (m) | Fin Width (m) | Niche Width (m) | Cell Confluence | Viable Reactor Cellularity per mL | Reactor Length (m) |
|---|---|---|---|---|---|
| 7.00E−04 | 3.00E−04 | 4.00E−04 | 100% | 3.64E+08 | 0.39 |
| 7.00E−04 | 3.00E−04 | 3.00E−04 | 100% | 3.61E+08 | 0.43 |
| 7.00E−04 | 3.00E−04 | 5.00E−04 | 100% | 3.60E+08 | 0.18 |
| 0.001 | 3.00E−04 | 3.00E−04 | 100% | 3.56E+08 | 0.36 |
| 0.001 | 3.00E−04 | 4.00E−04 | 100% | 3.50E+08 | 0.35 |
| 0.001 | 3.00E−04 | 2.00E−04 | 100% | 3.48E+08 | 0.41 |
| 0.001 | 3.00E−04 | 5.00E−04 | 100% | 3.43E+08 | 0.34 |
| 7.00E−04 | 4.00E−04 | 4.00E−04 | 100% | 3.31E+08 | 0.40 |
| 7.00E−04 | 4.00E−04 | 5.00E−04 | 100% | 3.30E+08 | 0.39 |
| 0.001 | 4.00E−04 | 3.00E−04 | 100% | 3.27E+08 | 0.35 |
| 0.001 | 4.00E−04 | 4.00E−04 | 100% | 3.25E+08 | 0.33 |
| 0.001 | 4.00E−04 | 5.00E−04 | 100% | 3.21E+08 | 0.33 |
| 7.00E−04 | 4.00E−04 | 3.00E−04 | 100% | 3.11E+08 | 0.43 |
| 0.001 | 5.00E−04 | 4.00E−04 | 100% | 3.04E+08 | 0.34 |
| 0.001 | 5.00E−04 | 5.00E−04 | 100% | 3.03E+08 | 0.33 |
| 7.00E−04 | 3.00E−04 | 2.00E−04 | 100% | 3.02E+08 | 0.55 |
| 0.001 | 5.00E−04 | 3.00E−04 | 100% | 3.02E+08 | 0.35 |
| 0.001 | 4.00E−04 | 2.00E−04 | 100% | 3.01E+08 | 0.40 |
| 7.00E−04 | 5.00E−04 | 5.00E−04 | 100% | 3.01E+08 | 0.40 |
| 7.00E−04 | 5.00E−04 | 4.00E−04 | 100% | 2.99E+08 | 0.41 |
| 7.00E−04 | 5.00E−04 | 3.00E−04 | 100% | 2.70E+08 | 0.46 |
| 0.001 | 5.00E−04 | 2.00E−04 | 100% | 2.57E+08 | 0.42 |
| 4.00E−04 | 3.00E−04 | 4.00E−04 | 100% | 2.53E+08 | 0.67 |
| 7.00E−04 | 4.00E−04 | 2.00E−04 | 100% | 2.50E+08 | 0.57 |
| 4.00E−04 | 3.00E−04 | 5.00E−04 | 100% | 2.45E+08 | 0.66 |
| 4.00E−04 | 3.00E−04 | 3.00E−04 | 100% | 2.44E+08 | 0.75 |
| 4.00E−04 | 4.00E−04 | 4.00E−04 | 100% | 2.20E+08 | 0.71 |
| 4.00E−04 | 4.00E−04 | 5.00E−04 | 100% | 2.16E+08 | 0.70 |
| 7.00E−04 | 5.00E−04 | 2.00E−04 | 100% | 2.14E+08 | 0.59 |
| 4.00E−04 | 3.00E−04 | 2.00E−04 | 100% | 2.10E+08 | 0.94 |
| 4.00E−04 | 4.00E−04 | 3.00E−04 | 100% | 2.08E+08 | 0.78 |

-continued

| Fin Height (m) | Fin Width (m) | Niche Width (m) | Cell Confluence | Viable Reactor Cellularity per mL | Reactor Length (m) |
|---|---|---|---|---|---|
| 4.00E-04 | 5.00E-04 | 4.00E-04 | 100% | 1.94E+08 | 0.75 |
| 4.00E-04 | 5.00E-04 | 5.00E-04 | 100% | 1.93E+08 | 0.74 |
| 4.00E-04 | 5.00E-04 | 3.00E-04 | 100% | 1.81E+08 | 0.83 |
| 4.00E-04 | 4.00E-04 | 2.00E-04 | 100% | 1.74E+08 | 0.97 |
| 4.00E-04 | 5.00E-04 | 2.00E-04 | 100% | 1.49E+08 | 1.02 |

| Fin Height (m) | Fin Width (m) | Niche Width (m) | Cell Confluence | Viable Reactor Cellularity per mL | Reactor length (m) |
|---|---|---|---|---|---|
| 0.001 | 3.00E-04 | 5.00E-04 | 33% | 1.74E+08 | 0.65 |
| 0.001 | 3.00E-04 | 4.00E-04 | 33% | 1.65E+08 | 0.72 |
| 0.001 | 3.00E-04 | 3.00E-04 | 33% | 1.53E+08 | 0.68 |
| 0.001 | 3.00E-04 | 3.00E-04 | 33% | 1.48E+08 | 0.84 |
| 0.001 | 4.00E-04 | 4.00E-04 | 33% | 1.42E+08 | 0.74 |
| 0.001 | 5.00E-04 | 5.00E-04 | 33% | 1.30E+08 | 0.72 |
| 7.00E-04 | 3.00E-04 | 5.00E-04 | 33% | 1.36E+08 | 0.99 |
| 7.00E-04 | 3.00E-04 | 4.00E-04 | 33% | 1.32E+08 | 1.05 |
| 0.001 | 5.00E-04 | 4.00E-04 | 33% | 1.26E+08 | 0.80 |
| 0.001 | 4.00E-04 | 3.00E-04 | 33% | 1.26E+08 | 0.88 |
| 7.00E-04 | 3.00E-04 | 3.00E-04 | 33% | 1.22E+08 | 1.23 |
| 0.001 | 3.00E-04 | 2.00E-04 | 33% | 1.20E+08 | 1.00 |
| 7.00E-04 | 4.00E-04 | 5.00E-04 | 33% | 1.20E+08 | 1.04 |
| 7.00E-04 | 4.00E-04 | 4.00E-04 | 33% | 1.14E+08 | 1.12 |
| 0.001 | 5.00E-04 | 3.00E-04 | 33% | 1.09E+08 | 0.93 |
| 7.00E-04 | 5.00E-04 | 5.00E-04 | 33% | 1.97E+08 | 1.10 |
| 7.00E-04 | 4.00E-04 | 3.00E-04 | 33% | 1.03E+08 | 1.26 |
| 7.00E-04 | 5.00E-04 | 4.00E-04 | 33% | 1.01E+08 | 1.18 |
| 7.00E-04 | 3.00E-04 | 2.00E-04 | 33% | 9.98E+07 | 1.48 |
| 0.001 | 4.00E-04 | 2.00E-04 | 33% | 9.94E+07 | 1.13 |
| 7.00E-04 | 5.00E-04 | 3.00E-04 | 33% | 8.92E+07 | 1.37 |
| 0.001 | 5.00E-04 | 2.00E-04 | 33% | 8.48E+07 | 1.25 |
| 4.00E-04 | 4.00E-04 | 3.00E-04 | 33% | 8.35E+07 | 1.93 |
| 7.00E-04 | 4.00E-04 | 2.00E-04 | 33% | 8.26E+07 | 1.57 |
| 4.00E-04 | 3.00E-04 | 5.00E-04 | 33% | 8.07E+07 | 2.02 |
| 4.00E-04 | 3.00E-04 | 4.00E-04 | 33% | 8.05E+07 | 2.10 |
| 4.00E-04 | 4.00E-04 | 3.00E-04 | 33% | 7.27E+07 | 2.14 |
| 4.00E-04 | 4.00E-04 | 4.00E-04 | 33% | 7.11E+07 | 2.12 |
| 7.00E-04 | 5.00E-04 | 2.00E-04 | 33% | 7.05E+07 | 1.61 |
| 4.00E-04 | 3.00E-04 | 2.00E-04 | 33% | 6.92E+07 | 2.53 |
| 4.00E-04 | 4.00E-04 | 3.00E-04 | 33% | 6.87E+07 | 2.18 |
| 4.00E-04 | 5.00E-04 | 4.00E-04 | 33% | 6.41E+07 | 2.27 |
| 4.00E-04 | 5.00E-04 | 5.00E-04 | 33% | 6.36E+07 | 2.25 |
| 4.00E-04 | 5.00E-04 | 3.00E-04 | 33% | 6.97E+07 | 2.48 |
| 4.00E-04 | 4.00E-04 | 2.00E-04 | 33% | 5.76E+07 | 2.08 |
| 4.00E-04 | 5.00E-04 | 2.00E-04 | 33% | 4.92E+07 | 2.82 |

| Fin Height (m) | Fin Width (m) | Niche Width (m) | Cell Confluence | Viable Reactor Cellulartiy per mL | Reactor length (m) |
|---|---|---|---|---|---|
| 0.001 | 3.00E-04 | 5.00E-04 | 10% | 5.26E+07 | 1.92 |
| 0.001 | 3.00E-04 | 4.00E-04 | 10% | 4.99E+07 | 2.10 |
| 0.001 | 4.00E-04 | 5.00E-04 | 10% | 4.62E+07 | 2.00 |
| 0.001 | 3.00E-04 | 3.00E-04 | 10% | 4.49E+07 | 2.52 |
| 0.001 | 4.00E-04 | 4.00E-04 | 10% | 4.21E+07 | 2.74 |
| 0.001 | 5.00E-04 | 5.00E-04 | 10% | 4.13E+07 | 2.25 |
| 7.00E-04 | 3.00E-04 | 5.00E-04 | 10% | 4.12E+07 | 2.94 |
| 7.00E-04 | 3.00E-04 | 4.00E-04 | 10% | 4.00E+07 | 1.15 |
| 0.001 | 5.00E-04 | 4.00E-04 | 10% | 3.82E+07 | 2.43 |
| 0.001 | 4.00E-04 | 3.00E-04 | 10% | 3.82E+07 | 2.61 |
| 7.00E-04 | 3.00E-04 | 3.00E-04 | 10% | 3.66E+07 | 3.47 |
| 0.001 | 3.00E-04 | 2.00E-04 | 10% | 3.65E+07 | 3.20 |
| 7.00E-04 | 4.00E-04 | 5.00E-04 | 10% | 3.62E+07 | 3.19 |
| 7.00E-04 | 4.00E-04 | 4.00E-04 | 10% | 3.47E+07 | 3.36 |
| 0.001 | 5.00E-04 | 3.00E-04 | 10% | 3.20E+07 | 2.86 |
| 7.00E-04 | 5.00E-04 | 5.00E-04 | 10% | 3.23E+07 | 3.35 |
| 7.00E-04 | 4.00E-04 | 3.00E-04 | 10% | 3.12E+07 | 3.93 |

-continued

| Fin Height (m) | Fin Width (m) | Niche Width (m) | Cell Confluence | Viable Reactor Cellulartiy per mL | Reactor length (m) |
|---|---|---|---|---|---|
| 7.00E−04 | 5.00E−04 | 4.00E−04 | 10% | 3.06E+07 | 3.56 |
| 7.00E−04 | 3.00E−04 | 2.00E−04 | 10% | 3.02E+07 | 4.48 |
| 0.001 | 4.00E−04 | 2.00E−04 | 10% | 3.02E+07 | 3.32 |
| 7.00E−04 | 5.00E−04 | 3.00E−04 | 10% | 2.70E+07 | 4.06 |
| 0.001 | 5.00E−04 | 2.00E−04 | 10% | 2.57E+07 | 3.09 |
| 4.00E−04 | 3.00E−04 | 4.00E−04 | 10% | 2.53E+07 | 5.98 |
| 7.00E−04 | 4.00E−04 | 2.00E−04 | 10% | 2.50E+07 | 4.70 |
| 4.00E−04 | 3.00E−04 | 5.00E−04 | 10% | 2.45E+07 | 0.08 |
| 4.00E−04 | 3.00E−04 | 3.00E−04 | 10% | 2.44E+07 | 0.45 |
| 4.00E−04 | 4.00E−04 | 4.00E−04 | 10% | 2.20E+07 | 6.47 |
| 4.00E−04 | 4.00E−04 | 5.00E−04 | 10% | 2.16E+07 | 6.42 |
| 7.00E−04 | 5.00E−04 | 2.00E−04 | 10% | 2.14E+07 | 5.20 |
| 4.00E−04 | 3.00E−04 | 2.00E−04 | 10% | 2.10E+07 | 7.96 |
| 4.00E−04 | 4.00E−04 | 3.00E−04 | 10% | 2.08E+07 | 6.87 |
| 4.00E−04 | 5.00E−04 | 4.00E−04 | 10% | 1.94E+07 | 6.80 |
| 4.00E−04 | 5.00E−04 | 5.00E−04 | 10% | 1.93E+07 | 6.91 |
| 4.00E−04 | 5.00E−04 | 3.00E−04 | 10% | 1.82E+07 | 7.54 |
| 4.00E−04 | 4.00E−04 | 2.00E−04 | 10% | 1.74E+07 | 8.39 |
| 4.00E−04 | 5.00E−04 | 2.00E−04 | 10% | 1.49E+07 | 9.15 |

In conclusion, in terms of viable reactor cellularity (VRC) per mL, the highest VRC per mL, i.e., $3.65 \times 10^8$ VRC/mL was observed with a fin height of 700 a fin width of 300 µm, a niche width of 400 µm, a cell confluence of 100%, and a reactor length of 0.39 m. The lowest VRC per mL, i.e., $1.49 \times 10^7$ VRC/mL was observed with a fin height of 400 a fin width of 500 µm, a niche width of 200 µm, a cell confluence of 10%, and a reactor length of 9.15 m. Generally speaking, higher cell density and metabolism may contribute to availability of relatively shorter bioreactor lengths due to the associated consumption of soluble nutrients at higher cell densities and metabolisms.

Example

A 4-stack of 600 cm² HDCR membranes was assembled into a bioreactor cartridge and sterilized. Bioreactor was wetted and loaded with 80 mL of microcarriers. The bioreactor and mixing line were flushed with about 400 mL of media (i.e., F-12K+10% FBS+1% P/S). About 166M A549 cells at passage 22 were seeded into the bioreactor in about 20 mL and gently circulated to allow them to settle into the cell niches of the membranes. The bubble trap line was communicatively coupled with a syringe pump to remove accumulating gas (set to about 1 mL/hr). A flow rate for gas was set to about 0.5 mL/min and a media flow rate was set to about 0.5 mL/hr. On a daily basis, the media coming out of the waste stream was measured for glucose and the flow rate was adjusted to target a concentration of about 100 mg/dL. Gas perfusion was scaled proportionally with media perfusion. Prior to infection with virus, media was switched to about 500 mL of reduced serum (F-12K+2.5% FBS+1% P/S). CF33 hNIS-anti-PDL1 virus was added at 0.1 MOI in about 25 mL of 2.5% FBS+F-12K media, and circulated for about 15 min on loop at about 50 mL/min. The bioreactor was returned to incubator and media perfusion was resumed at about 0.5 mL/min for remaining 48 hours post-infection (F-12K+10% FBS+1% P/S). Following addition of virus, the waste stream was collected and subsequently stored at about 4° C. to analyze viral escape from host cells.

Table 7 summarizes operational parameters for the above-described bioreactor, as follows:

| | | |
|---|---|---|
| Membrane Area (Version: 167 mm × 355 mm × 2.1 mm) | 593 | cm² |
| Number of Membranes | 4 | |
| Cell Niche Volume per Membrane (mm³) | 21 | mL |
| Membrane Inlet Cross-Sectional Area (mm²) | 64 | |
| Targeted Minimum Glucose Concentration (x-Fold over $K_M$) | 2 | |
| Microcarriers Added | 80 | mL |
| Reactor Fluid Volume | 355 | mL |

Table 8 summarizes properties of the A549 cells, as follows:

| Parameter | Value | Unit |
|---|---|---|
| Glutamine Uptake | 8.6E−14 | mol/cell/hr |
| Glucose Uptake | 2.14E−13 | mol/cell/hr |
| Oxygen Uptake | 1.5E−13 | mol/cell/hr |
| Cell diameter | 13 | µm |
| Doubling Time | 33 | hrs |

Table 9 summarizes Ham's F-12K (Kaighn's) key components as follows:

| Parameter | Initial Media Composition | Units |
|---|---|---|
| Glutamine | 2.00E−03 | mol/L |
| Glucose | 7.00E−03 | mol/L |
| Oxygen | 1.79E−04 | mol/L |

Table 10 summarizes Michalis-Menten Concentrations, as follows:

| Parameter | Michalis-Menten Concentration | Units |
|---|---|---|
| Glutamine | 2.09E−04 | mol/L |
| Glucose | 1.61E−03 | mol/L |
| Oxygen | 1.79E−06 | mol/L |
| Lactate Production | 0.02 | mol/L |
| Ammonia Production | 0.0024 | mol/L |

Table 11 summarizes daily observations and calculations, as follows:

| Time | Day | 0 | 1 | 2 | 3 |
|---|---|---|---|---|---|
| Cell Density in Niche | cells/mL | 1.95E+06 | 3.23E+06 | 5.34E+06 | 8.85E+06 |
| Total Cells | cells | 1.67E+08 | 2.77E+08 | 4.58E+08 | 7.58E+08 |
| Glutamine Uptake Rate | mol/hr | 1.44E−05 | 2.38E−05 | 3.94E−05 | 6.52E−05 |
| Glucose Uptake Rate | mol/hr | 3.58E−05 | 5.92E−05 | 9.80E−05 | 1.62E−04 |
| Oxygen Uptake Rate | mol/hr | 2.51E−05 | 4.15E−05 | 6.87E−05 | 1.14E−04 |
| Media Feed Rates Based On C > X*Km (or C < X*Km) | | | | | |
| Glutamine Uptake Rate | mL/hr | 9.09E+00 | 1.50E+01 | 2.49E+01 | 4.12E+01 |
| Glucose Uptake Rate | mL/hr | 9.49E+00 | 1.57E+01 | 2.60E+01 | 4.30E+01 |
| Oxygen Uptake Rate | mL/hr | 1.43E+02 | 2.37E+02 | 3.92E+02 | 6.48E+02 |
| Limiting Rate | mL/min | 1.58E−01 | 2.62E−01 | 4.33E−01 | 7.17E−01 |
| Linear Media Velocity | μm/s | 1.03E+01 | 1.70E+01 | 2.82E+01 | 4.67E+01 |
| Gas Flow Rate | mL/min | 5.72E−02 | 9.47E−02 | 1.57E−01 | 2.60E−01 |

| Time | Day | 4 | 5 | 6 | 7 | 8 |
|---|---|---|---|---|---|---|
| Cell Density | cells/mL | 1.46E+07 | 2.42E+07 | 4.01E+07 | 6.65E+07 | 1.10E+08 |
| Total Cells | cells | 1.26E+09 | 2.08E+09 | 3.44E+09 | 5.70E+09 | 9.43E+09 |
| Glutamine Uptake Rate | mol/hr | 1.08E−04 | 1.79E−04 | 2.96E−04 | 4.90E−04 | 8.11E−04 |
| Glucose Uptake Rate | mol/hr | 2.69E−04 | 4.45E−04 | 7.36E−04 | 1.22E−03 | 2.02E−03 |
| Oxygen Uptake Rate | mol/hr | 1.88E−04 | 3.12E−04 | 5.16E−04 | 8.54E−04 | 1.41E−03 |
| Media Feed Rates Based On C > X*Km (or C < X*Km) | | | | | | |
| Glutamine Uptake Rate | mL/hr | 6.83E+01 | 1.13E+02 | 1.87E+02 | 3.10E+02 | 5.13E+02 |
| Glucose Uptake Rate | mL/hr | 7.13E+01 | 1.18E+02 | 1.95E+02 | 3.23E+02 | 5.35E+02 |
| Oxygen Uptake Rate | mL/hr | 1.07E+03 | 1.78E+03 | 2.94E+03 | 4.87E+03 | 8.06E+03 |
| Limiting Rate | mL/min | 1.19E+00 | 1.97E+00 | 3.25E+00 | 5.39E+00 | 8.92E+00 |
| Linear Velocity | μm/s | 7.73E+01 | 1.28E+02 | 2.12E+02 | 3.51E+02 | 5.81E+02 |
| Gas Flow Rate | mL/min | 4.30E−01 | 7.11E−01 | 1.18E+00 | 1.95E+00 | 3.23E+00 |

| Time | Day | 9 | 10 | 11 | 12 | 13 |
|---|---|---|---|---|---|---|
| Cell Density | cells/mL | 1.82E+08 | 3.02E+08 | 4.99E+08 | 8.26E+08 | 1.37E+09 |
| Total Cells | cells | 1.56E+10 | 2.58E+10 | 4.28E+10 | 7.08E+10 | 1.17E+11 |
| Glutamine Uptake Rate | mol/hr | 1.34E−03 | 2.22E−03 | 3.68E−03 | 6.09E−03 | 1.01E−02 |
| Glucose Uptake Rate | mol/hr | 3.34E−03 | 5.53E−03 | 9.16E−03 | 1.52E−02 | 2.51E−02 |
| Oxygen Uptake Rate | mol/hr | 2.34E−03 | 3.88E−03 | 6.42E−03 | 1.06E−02 | 1.76E−02 |
| Media Feed Rates Based On C > X*Km (or C < X*Km) | | | | | | |
| Glutamine Uptake Rate | mL/hr | 8.49E+02 | 1.41E+03 | 2.33E+03 | 3.85E+03 | 6.38E+03 |
| Glucose Uptake Rate | mL/hr | 8.86E+02 | 1.47E+03 | 2.43E+03 | 4.02E+03 | 6.66E+03 |
| Oxygen Uptake Rate | mL/hr | 1.33E+04 | 2.21E+04 | 3.66E+04 | 6.06E+04 | 1.00E+05 |
| Limiting Rate | mL/min | 1.48E+01 | 2.44E+01 | 4.05E+01 | 6.70E+01 | 1.11E+02 |
| Linear Velocity | μm/s | 9.61E+02 | 1.59E+03 | 2.64E+03 | 4.36E+03 | 7.22E+03 |
| Gas Flow Rate | mL/min | 5.34E+00 | 8.84E+00 | 1.46E+01 | 2.42E+01 | 4.01E+01 |

Table 12 summarizes the implied cell count over time, as follows:

| Serial Time (days) | Flow Rate During (mL/min) | Glucose Measurement (mg/dL) | Consumption Rate (mol/hr) | Flow Rate After (mL/min) | Flow Velocity (μm/s) | Volume Exchanges/hr | Implied Cell Count | Implied Cell Density |
|---|---|---|---|---|---|---|---|---|
| 0.00 | 0.5 | | | 0.5 | 32.55208 | 0.084507 | 1.67E+08 | 1.95E+06 |
| 0.89 | 0.5 | 183 | 6.25E−05 | 0.5 | 32.55208 | 0.084507 | 2.92E+08 | 3.41E+06 |
| 1.82 | 0.5 | 160 | 1.01E−04 | 0.5 | 32.55208 | 0.084507 | 4.71E+08 | 5.50E+06 |
| 2.89 | 0.5 | 120 | 1.68E−04 | 0.6 | 39.06250 | 0.101408 | 7.83E+08 | 9.13E+06 |
| 3.89 | 0.6 | 110 | 2.21E−04 | 0.7 | 45.57292 | 0.118310 | 1.03E+09 | 1.20E+07 |
| 5.74 | 0.7 | 100 | 2.81E−04 | 0.9 | 58.59375 | 0.152113 | 1.31E+09 | 1.53E+07 |

The foregoing description details certain embodiments of the systems, devices, and methods disclosed herein. It will be appreciated, however, that no matter how detailed the foregoing appears in text, the devices and methods can be practiced in many ways. As is also stated above, it should be noted that the use of particular terminology when describing certain features or features of the technology should not be taken to imply that the terminology is being re-defined herein to be restricted to including any specific characteristics of the features or features of the technology with which that terminology is associated. The scope of the disclosure should therefore be construed in accordance with the appended claims and any equivalents thereof.

It will be appreciated by those skilled in the art that various modifications and changes may be made without departing from the scope of the described technology. Such modifications and changes are intended to fall within the scope of the embodiments, as defined by the appended claims. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims are generally intended as "open" terms (e.g., the term "including" should be interpreted as "including but not limited to," the terms "comprising" and "having" should, respectively, be interpreted as "comprising at least" and "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an." In general, "a" and/or "an" should be interpreted to mean "at least one" or "one or more"; the same holds true for the use of definite articles used to introduce claim recitations.

Although at least one exemplary embodiment is described as using a plurality of units to perform the exemplary process, it is understood that the exemplary processes may also be performed by one or plurality of modules.

The use of the terms "first", "second", "third" and so on, herein, are provided to identify various structures, dimensions or operations, without describing any order, and the structures, dimensions or operations may be executed in a different order from the stated order unless a specific order is definitely specified in the context.

Approximating language, as used herein throughout the specification and claims, may be applied to modify any quantitative representation that could permissibly vary without resulting in a change in the basic function to which it is related. Accordingly, a value modified by a term or terms, such as "about" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." The subject matter described herein may be embodied in systems, apparatus, methods, and/or articles depending on the desired configuration. The embodiments set forth in the foregoing description do not represent all embodiments consistent with the subject matter described herein. Instead, they are merely some examples consistent with aspects related to the described subject matter. Although a few variations have been described in detail above, other modifications or additions are possible. In particular, further features and/or variations may be provided in addition to those set forth herein. For example, the embodiments described above may be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other embodiments may be within the scope of the following claims.

The technology disclosed herein has numerous applications and while particular embodiments of the technology have been described in detail, it will be apparent to those skilled in the art that the disclosed embodiments may be modified given the design considerations discussed herein. Therefore, the foregoing description is to be considered exemplary rather than limiting, and the true scope of the invention is that defined in the following claims.

What is claimed is:

1. An apparatus for cell cultivation, the apparatus comprising:
   a membrane having a first side and a second side, the first side being separated from the second side of the membrane by a gas channel that passes through the membrane between the first side and the second side, the first side having a plurality of surface features forming one or more compartments configured to confine one or more cells the second side of the membrane having a permeable interface that allows gas external to the membrane to pass through the permeable interface into the gas channel, the gas channel being configured to pass gas from the second side of the membrane to the first side of the membrane.

2. The apparatus of claim 1, further comprising:
a media region situated over the first side of the membrane, the media region configured to allow media to pass over the first side of the membrane for harvesting;
one or more media inlets and one or more media outlets fluidically connected to the media region, the one or more media inlets configured to facilitate introduction of media into the media region on the first side of the membrane, the one or more media outlets configured to facilitate removal of media from the media region; and
an enclosure disposed above the first side of the membrane,
wherein at least one of the one or more media inlets is fluidly connected to at least one of the media outlets to facilitate reintroduction of media into the media region on the first side of the membrane,
wherein the apparatus is configured to minimize media flow shear forces in the one or more compartments upon introduction or removal of media from the media region,
wherein the one or more compartments are configured to at least partially reduce media flow shear forces within the compartments, and
wherein the enclosure defines a second boundary of the media region.

3. The apparatus of claim 1, further comprising
one or more gas inlets and one or more gas outlets in fluid contact with the gas channel, the one or more gas inlets configured to introduce a gas into the gas channel, and the one or more gas outlets configured for the removal of gas from the gas channel,
one or more channels formed on the second side of the membrane, at least a first channel of the one or more channels configured to deliver gas to the at least one of the compartments via the membrane by way of membrane permeation and diffusion.

4. The apparatus of claim 1, wherein the membrane comprises pores having a size permitting permeation and diffusion of oxygen to pass through the membrane.

5. The apparatus of claim 1, wherein the one or more compartments support tissue-level cell densities such that the volume of cells occupies at least about 10% of the volume of the one or more compartments within which one or more cells can be confined.

6. The apparatus of claim 1, wherein a negative pressure causes a bottom surface of at least one compartment of the one or more compartments to deform downwards, drawing liquid media in to the at least one compartment via an opening at the top of the at least one cell niche, and/or wherein a positive pressure causes the bottom surface of the at least one cell niche of the one or more cell niches to deform upwards, pushing the liquid media out of the at least one compartment via the opening at the top of the at least one compartment.

7. The apparatus of claim 1, wherein a mechanical stretching of the membrane widens at least one compartment of the one or more compartments to facilitate the release of one or more cells from the at least one cell niche through an opening at the top of the at least one compartment.

8. The apparatus of claim 1, wherein the plurality of surface features comprise a plurality of fin structures running parallel to each other, the parallel fin structures defining grooves between adjacent fin structures, at least one groove on the first side of the membrane providing at least one of the one or more compartments for cell location, a longitudinal direction of the at least one groove corresponding to a longitudinal direction of the one or more compartments.

9. The apparatus of claim 8, wherein the plurality of fins protrude from a base of the membrane to retain and protect one or more of the cells in the one or more cell niches from media flow shear forces generated by the media delivery.

10. The apparatus of claim 9, wherein the fluidic path has a relatively lower resistance against the liquid media flowing above the plurality of fins, thereby eliminating or reducing a need for use of pumps to regulate the liquid media flow.

11. The apparatus of claim 1, wherein at least one of the surface features has a height between about 400 μm and about 1000 μm, a width between about 300 μm and about 500 μm, and a pitch between about 200 μm and about 500 μm.

12. The apparatus of claim 1, wherein at least one of the surface features has a ratio of height to width to pitch of about 4-10 to about 3-5 to about 2-5.

13. The apparatus of claim 1, wherein the apparatus is configured to produce a cell density at transfection of between about $10^7$ cells per milliliter (cells/mL) to about $10^9$ cells/mL and a productivity of between about $10^{15}$ adeno-associated viral genomes per liter (AAV vg/L) and about $10^{16}$ AAV vg/L.

14. The apparatus of claim 1, wherein the apparatus is configured to be stacked with at least a second cell cultivation apparatus, wherein one or more of media or gas inlets or media or gas outlets are configured so that upon stacking, one or more of the media or gas inlets or media or gas outlets are in fluid communication with an inlet or outlet of an immediately adjacent apparatus, wherein one or more of the media or gas inlets is configured so that upon stacking, media or gas introduced into the apparatus is combined into a combined inlet line for transmission to a plurality of the membranes, wherein one or more of the media or gas outlets is configured so that upon stacking, media or gas removed from the apparatus is combined into a combined outlet line for transmission from a plurality of the membranes.

15. A method of culturing biological cells, comprising, providing an apparatus comprising:
a membrane having a first side and a second side, the first side being separated from the second side of the membrane by a gas channel that passes through the membrane between the first side and the second side, the first side having a plurality of surface features forming one or more compartments configured to confine one or more cells the second side of the membrane having a permeable interface that allows gas external to the membrane to pass through the permeable interface into the gas channel, the gas channel being configured to pass gas from the second side of the membrane to the first side of the membrane; and
introducing biological cells into the apparatus, providing a cell media into the first side of the apparatus such that the cell media is in contact with the biological cells.

16. The method of claim 15, further comprising providing a gas to the second side of the membrane.

17. The method of claim 15, further comprising flowing media over one or more cell compartments.

18. The method of claim 15, wherein the apparatus comprises at least one surface feature having a height between about 400 µm and about 1000 µm, a width between about 300 µm and about 500 µm, and a pitch between about 200 µm and about 500 µm.

19. The method of claim 15, wherein the apparatus comprises at least one surface feature having a ratio of height to width to pitch of about 4-10 to about 3-5 to about 2-5.

20. The method of claim 15, wherein the method is configured to produce a cell density at transfection of between about 10' cells per milliliter (cells/mL) to about $10^9$ cells/mL and a productivity of between about $10^{15}$ adeno-associated viral genomes per liter (AAV vg/L) and about $10^{16}$ AAV vg/L.

21. A bioreactor comprising:
- a gas inlet;
- a gas outlet;
- a gas path connected between the gas inlet and the gas outlet;
- a media inlet;
- a media outlet;
- a media path connected between the media inlet and the media outlet; and
- a membrane separating the gas supply path and the media supply path,
- wherein the membrane includes a cell protection region,
- wherein the cell protection region is in liquid communication with the media path,
- wherein the cell protection region is fluidically distinct from the media path,
- wherein the cell protection region is in gaseous communication with the gas path across the membrane,
- wherein the cell protection region is configured to reduce an impact of shear forces of media flowing in the media path on cells produced in the cell protection region,
- wherein the bioreactor is configured to produce a cell density at transfection of between about $10^7$ cells per milliliter (cells/mL) to about $10^9$ cells/mL and a productivity of between about $10^{15}$ adeno-associated viral genomes per liter (AAV vg/L) and about $10^{16}$ AAV vg/L, and
- wherein at least one surface feature in the cell protection region has a ratio of height to width to pitch of about 4-10 to about 3-5 to about 2-5.

* * * * *